US009051618B2

(12) United States Patent
Croce et al.

(10) Patent No.: US 9,051,618 B2
(45) Date of Patent: *Jun. 9, 2015

(54) METHODS FOR DIAGNOSING LUNG CANCER USING MICRORNA SIGNATURES

(75) Inventors: Carlo M. Croce, Columbus, OH (US); George A. Calin, Pearland, TX (US); Stefano Volinia, Ferrara (IT)

(73) Assignee: The Ohio State University, Columbus, OH (US)

(*) Notice: Subject to any disclaimer, the term of this patent is extended or adjusted under 35 U.S.C. 154(b) by 375 days.

This patent is subject to a terminal disclaimer.

(21) Appl. No.: 13/407,894

(22) Filed: Feb. 29, 2012

(65) Prior Publication Data
US 2012/0214701 A1 Aug. 23, 2012

Related U.S. Application Data

(62) Division of application No. 12/160,061, filed as application No. PCT/US2007/000159 on Jan. 3, 2007, now Pat. No. 8,148,069.

(60) Provisional application No. 60/756,585, filed on Jan. 5, 2006.

(51) Int. Cl.
| C12Q 1/68 | (2006.01) |
| C12N 15/11 | (2006.01) |
| C12N 15/113 | (2010.01) |
| A61K 31/7105 | (2006.01) |

(52) U.S. Cl.
CPC ............ *C12Q 1/6886* (2013.01); *C12N 15/111* (2013.01); *C12N 15/113* (2013.01); *C12N 2310/14* (2013.01); *C12N 2320/11* (2013.01); *C12N 2320/12* (2013.01); *C12N 2330/10* (2013.01); *C12Q 1/6837* (2013.01); *C12Q 2600/158* (2013.01); *C12Q 2600/178* (2013.01); *A61K 31/7105* (2013.01)

(58) Field of Classification Search
None
See application file for complete search history.

(56) References Cited

U.S. PATENT DOCUMENTS

| 7,888,010 B2 | 2/2011 | Brown et al. |
| 7,919,245 B2 | 4/2011 | Brown et al. |
| 2007/0092882 A1 | 4/2007 | Wang et al. |
| 2009/0131356 A1 | 5/2009 | Bader et al. |
| 2010/0099200 A1 | 4/2010 | Nazabal et al. |
| 2010/0104662 A1 | 4/2010 | Oren et al. |
| 2010/0196426 A1 | 8/2010 | Skog et al. |

FOREIGN PATENT DOCUMENTS

| CA | 2533701 A1 | 2/2005 |
| WO | 2005013901 A3 | 2/2005 |
| WO | 2005079397 A2 | 9/2005 |
| WO | 2005103298 A2 | 11/2005 |
| WO | 2007016548 A2 | 2/2007 |
| WO | 2007112754 A2 | 10/2007 |
| WO | 2008/036168 A2 | 3/2008 |
| WO | 2008073915 A2 | 6/2008 |

OTHER PUBLICATIONS

Tockman et al (Cancer Res., 1992, 52:2711s-2718s).*
Szymanski et al (Biochimica et Biophysica Acta, 2005, 65-75).*
Cheng et al (Nucleic Acids Resarch, 2005, 33(4): 1290-1297).*
Australian Office Action, Application No. 2007205257 dated Dec. 22, 2011.
Australian Office Action, Application No. 2007205234 dated Sep. 20, 2011.
European Communication Pursuant to Article 94(3) EPC, Application No. 07716208.9, dated Sep. 13, 2011.
European Communication Pursuant to Article 94(3)EPC, Application No. 06814375.9 dated Oct. 14, 2011.
European Communication Pursuant to Article 94(3) EPC, Application No. 08799295.4, dated Nov. 18, 2011.
European Search Report, Application No. 09714868.8 dated Aug. 1, 2011.
European Search Report, Application No. 09713926.5 dated Jul. 21, 2011.
European Search Report, Application No. 08770974.4, dated Oct. 21, 2011.
PCT International Preliminary Report on Patentability, PCT/US2010/025173 filed Feb. 24, 2010, dated Sep. 9, 2011.
Aiba, M. "Pathology of the Breast Carcinoma from the Viewpoint of the Proliferative Activity and Grade of Malignancy," JP J Cancer Clin, 2000, pp. 475-181, vol. 46, No. 5.
Li, Z. et al., "Inhibition of PRL-3 Gene Expression in Gastric Cancer Cell Line SGC7901 via MicroRNA Suppressed Reduces Peritoneal Metastasis," Biochemical and Biophysical Research, Sep. 2006, pp. 229-237, vol. 348, No. 1.
Petrocca, F. et al., "MicroRNAs Deregulation in Gastric Cancer," PNAS, Apr. 2006, p. 1338, vol. 47, Abstract # 5690.
Thomson, M., Supplementary data for "A Custon Microarray Platform for Analysis of MicroRNA Gene Expression," Nature Methods, Oct. 2004, pp. 47-53, vol. 1, No. 1.
Wiemer et al., "The Role of MicroRNAs in Cancer: No Small Matter," European Journal of Cancer, Jun. 12, 2007, vol. 43, No. 10, pp. 1529-1544.
Australian Office Action, Application No. 2006291165 dated Feb. 13, 2012.
Canadian Office Action, Application No. 2,617,581, dated Apr. 2, 2012.
Canadian Office Action, Application No. 2,635,616, dated Feb. 27, 20112.
Chinese Office Action, Application No. 20088011920639 dated May 3, 2012.

(Continued)

*Primary Examiner* — Sean Aeder
(74) *Attorney, Agent, or Firm* — MacMillan, Sobanski & Todd, LLC

(57) ABSTRACT

The present invention provides novel methods and compositions for the diagnosis and treatment of solid cancers. The invention also provides methods of identifying inhibitors of tumorigenesis.

8 Claims, 9 Drawing Sheets
(7 of 9 Drawing Sheet(s) Filed in Color)

(56) References Cited

OTHER PUBLICATIONS

Communication Concerning Office Action Received from Japanese Patent Office dated Jan. 30, 2012, Japanese Patent Application No. 2008-531200.
EP Search Report, Application No. 11196190.0 dated Apr. 24, 2012.
EP Search Report, Application No. 11196256.9 dated Feb. 28, 2012.
EP Search Report, Application No. 11196250.2 dated Apr. 24, 2012.
EP Search Report, Application No. 11196254.4 dated Feb. 28, 2012.
EP Search Report, Application No. 11196265.0 dated Mar. 5, 2012.
EP Search Report, Application No. 11196262.7 dated Feb. 28, 2012.
EP Search Report, Application No. 11196261.9 dated Feb. 28, 2012.
EP Search Report, Application No. 11196264-3 dated Feb. 28, 2012.
EP Search Report, Application No. 11196253.6 dated Apr. 24, 2012.
European Communication Pursuant to Article 94(3) EPC, Application No. 06800599.0 dated Nov. 25, 2011.
European Communication Pursuant to Article 94(3) EPC, Application No. 08767439.6, dated Feb. 12, 2011.
European Communication Pursuant to Article 94(3) EPC, Application No. 07717903.4, dated Apr. 25, 2012.
European Communication Pursuant to Article 94(3) EPC, Application No. 07867402.5, dated Apr. 10, 2012.
Japanese Office Action dated Feb. 22, 2012, Japanese Patent Application No. 2008-549549.
Japanese Office Action dated Jan. 4, 2012, Japanese Patent Application No. 2008-5251070.
Japanese Office Action dated Feb. 24, 2012, Japanese Patent Application No. 2008-549532.
Japanese Office Action dated Feb. 24, 2012, Japanese Patent Application No. 2008-549555.
PCT International Search Report and the Written Opinion, PCT/US2012/020911 filed Jan. 11, 2012, dated Apr. 25, 2012.
Braun et al., "p53-Responsive MicroRNAs 192 and 215 are Capable of Inducing Cell Cycle Arrest," Cancer Research, 2008, pp. 10094-10104, vol. 68.
Fujuta, S. et al., "miR-21 Gene Expression Triggered by AP-1 is Sustained Through a Double-Negative Feedback Mechanism," J. Mol. Biol., Abstract, 2008, pp. 492-504, vol. 378.
Gang, M. et al., "Expression of Programmed Cell Death 4 and Its Clinicopathological Significance in Human Pancreatic Cancer," Abstract, 2005, pp. 597-600, vol. 27.
Jazbutyte, V. et al., "MicroNRA-21: From Cancer to Cardiovascular Disease," Current Drug Targets, Abstract, 2010, pp. 926-935, vol. 11.
Nakajima, G. et al., "Non-Coding MicroRNAs HAS-LET-7G and HAS-MIR-181b are Associated with Chemoresponse to S-1 in Colon Cancer," Cancer Genomics & Proteomics, Sep. 2006, pp. 317-324, vol. 3, No. 5.
Pichiorri et al., "Downregulation of p53-Inducible MicroRNAs 192, 194 and 215 Impairs the p53/MDM2 Autoregulatory Loop in Multiple Myeloma Development," Cancer Cell, 2010, pp. 367-381, vol. 18.
Ribas, J. et al., "The Transcriptional Regulation of miR-21, Its Multiple Transcripts, and Their Implication in Prostate Cancer," Cell Cycle, 2010, pp. 923-929, vol. 9.
Rossi, S. et al., "MicroRNA Fingerprinting of CLL Patients with Chromosome 17p Deletion Identify a miR-21 Score that Stratifies Early Survival," Blood, Aug. 2010, pp. 945-952, vol. 116, No. 6.
Ryu, J.K. et al., "Aberrant MicroRNA-155 Expression is an Early Event in the Multistep Progression of Pancreatic Adenocarcinoma," Pancreatology, 2010, pp. 66-73, vol. 10.
Stamatopoulos, B. et al., "MicroRNA-29c and MicroRNA-233 Down-Regulation has In Vivo Significance in Chronic Lymphocytic Leukemia and Improves Disease Risk Stratification," Blood, May 2009, pp. 5237-5245, vol. 113, No. 21.
Vassilev et al., "In Vivo Activation of the p53 Pathway by Small-Molecule Antagonists of MDM2," Science, 2004, pp. 844-848, vol. 303.
Watson, D.I. et al., "MicroRNA Expression Profiles in Barrett's Oesophagus," RACS Annual Scientific Congress, 2007, pp. A45, vol. 77.
Xi, Y. et al., "Prognostic Values of MicroRNAs in Colorectal Cancer," Biomarker Insights, Jan. 2006, pp. 113-121, vol. 1.
Zhao et al., "p53 Mediates the Negative Regulation of MDM2 by Orphan Receptor TR3," The EMBO Journal, 2006, pp. 5703-5715, vol. 25.
EP Search Report, Application No. 12165636.7 dated Jun. 8, 2012.
EP Search Report, Application No. 12165638.3 dated Jun. 12, 2012.
Australian Government, Examiner's First Report, Appln. No. 2007243475, Dated Mar. 30, 2012.
Australian Office Action, Application No. 2008248319 dated Jul. 12, 2012.
Australian Office Action, Application No. 2007272947 dated May 21, 2012.
Australian Office Action, Application No. 2007227423 dated Apr. 13, 2012.
Chinese Office Action, Application No. 200780033066.9 dated Jun. 26, 2012.
Chinese Office Action, Application No. 200880116343.7 dated Jan. 31, 2011.
Chinese Office Action, Application No. 200880112585.9 dated May 24, 2012.
EP Search Report, Application No. 12154321.9 dated Jul. 20, 2012.
EP Search Report, Application No. 12154298.9 dated Jun. 4, 2012.
EP Search Report, Application No. 12154304.5 dated Jun. 26, 2012.
European Communication Pursuant to Article 94(3) EPC, Application No. 08841700.1, dated Jun. 1, 2012.
PCT International Preliminary Report on Patentability, PCT/US2010/057758 filed Nov. 23, 2010, dated Jun. 7, 2012.
PCT International Search Report and the Written Opinion, PCT/US2012/28016 filed Mar. 7, 2012, dated Aug. 3, 2012.
PCT Invitation to Pay Additional Fees, PCT/US2012/028016 filed Mar. 7, 2012, dated May 29, 2012.
Butz, H. et al., "Down-Regulation of Wee1 Kinase by a Specific Subset of MicroRNA Sporadic Pituitary Adenomas," Journal of Clinical Endocrinol Metab, Oct. 2010, pp. E181-E191, vol. 95, No. 10.
Eiriksdottir, G. et al., "Mapping Loss of Heterozygosity at Chromosome 13q: Loss at 13q12-q13 is Associated wit Breast Tumour Progression and Poor Prognosis," European Journal of Cancer, 1998, pp. 2076-2081, vol. 34, No. 13.
Gailiun, M., "Single MicroRNA Causes Cancer in Transgenic Mice," Research Communications, The Ohio State University, Apr. 2006.
Garofalo, M. et al., "MicroRNA Signatures of TRAIL Resistance in Human Non-Small Cell Lung Cancer," Oncogene, 2007, pp. 3854-3855, vol. 27.
Martin, M. et al., "MicroRNA-155 Regulates Human Angiotensin II Type 1 Receptor Expression in Fibroblasts," The Journal of Biological Chemistry, Jul. 2006, pp. 18277-18284, vol. 281, No. 27.
Mazurek, N. et al., "Phosphorylated Galectin-3 Mediates Tumor Necrosis Factor-Related Apoptosis-Inducing Ligand Signaling by Regulating Phosphatase and Tensin Homologue Deleted on Chromosome 10 in Human Breast Carcinoma Cells," The Journal of Biological Chemistry, Jul. 2007, pp. 21337-21348, vol. 282, No. 29.
O'Connell, R. et al., "Inositol Phosphatase SHIP1 is a Primary Target of miR-155," PNAS, Apr. 2009, pp. 7113-7118, vol. 106, No. 17.
Okada, H. et al., "MicroRNAs in Immune Regulation—Opportunities for Cancer Immunotherapy," The International Journal of Biochemistry & Cell Biology, 2010, pp. 1256-1261, vol. 42.

* cited by examiner

SEQUENCE LISTING

<160> NUMBER OF SEQ ID NOS: 498

<210> SEQ ID NO 1
<211> LENGTH: 90
<212> TYPE: RNA
<213> ORGANISM: Homo sapiens

<400> SEQUENCE: 1
cacuguggga ugagguagua gguuguauag uuuuaggguc acacccacca cugggagaua      60 acauacaau cuacugucuu uccuaacgug                                       90

<210> SEQ ID NO 2
<211> LENGTH: 72
<212> TYPE: RNA
<213> ORGANISM: Homo sapiens

<400> SEQUENCE: 2
agguugaggu aguagguugu auaguuuaga auuacaucaa gggagauaac uguacagccu      60
ccuagcuuuc cu                                                         72

<210> SEQ ID NO 3
<211> LENGTH: 74
<212> TYPE: RNA
<213> ORGANISM: Homo sapiens

<400> SEQUENCE: 3
gggugaggua guagguugua uaguuugggg cucugcccug cuaugggaua acauacaau       60 cuacugucuu uccu                                                       74

<210> SEQ ID NO 4
<211> LENGTH: 107
<212> TYPE: RNA
<213> ORGANISM: Homo sapiens

<400> SEQUENCE: 4
gugacugcau gcucccaggu ugagguagua gguuguauag uuuagaauua cacaagggag      60
auaacuguac agccuccuag cuuuccuugg gucuugcacu aaacaac                  107

<210> SEQ ID NO 5
<211> LENGTH: 85
<212> TYPE: RNA
<213> ORGANISM: Homo sapiens

<400> SEQUENCE: 5
ggcgggguga gguaguaggu uguguggguuu cagggcagug auguugcccc ucggaagaua     60 acauacaac cuacugccuu cccug                                            85

<210> SEQ ID NO 6
<211> LENGTH: 84
<212> TYPE: RNA
<213> ORGANISM: Homo sapiens

<400> SEQUENCE: 6 gcauccggu ugagguagua gguuguaugg uuuagaguua cacccuggga guuaacugua       60
caaccuucua gcuuuccuug gagc                                            84

<210> SEQ ID NO 7
<211> LENGTH: 87
<212> TYPE: RNA
<213> ORGANISM: Homo sapiens

```
<400> SEQUENCE: 7
ccuaggaaga gguaguaggu ugcauaguuu uagggcaggg auuugccca caaggaggua      60 acuauacgac cugcugccuu ucuuagg                                         87

<210> SEQ ID NO 8
<211> LENGTH: 85
<212> TYPE: RNA
<213> ORGANISM: Homo sapiens

<400> SEQUENCE: 8
cuaggaagag guaguaguuu gcauaguuu agggcaaaga uuugcccac aaguaguuag       60 cuauacgacc ugcagccuuu uguag                                           85

<210> SEQ ID NO 9
<211> LENGTH: 85
<212> TYPE: RNA
<213> ORGANISM: Homo sapiens

<400> SEQUENCE: 9
cuggcugagg uaguaguuug ugcuguuggu cgguuguga cauugcccgc uguggagaua      60
acugcgcaag cuacugccuu gcuag                                           85

<210> SEQ ID NO 10
<211> LENGTH: 79
<212> TYPE: RNA
<213> ORGANISM: Homo sapiens

<400> SEQUENCE: 10
cccgggcuga gguaggaggu uguauaguug aggaggacac ccaaggagau cacuauacgg     60
ccuccuagcu uuccccagg                                                  79

<210> SEQ ID NO 11
<211> LENGTH: 87
<212> TYPE: RNA
<213> ORGANISM: Homo sapiens

<400> SEQUENCE: 11
ucagagugag guaguagauu guauaguugu ggggauaguga uuuuacccug uucaggagau    60
aacuauacaa ucuauugccu ucccuga                                         87

<210> SEQ ID NO 12
<211> LENGTH: 89
<212> TYPE: RNA
<213> ORGANISM: Homo sapiens

<400> SEQUENCE: 12 cuguggaug agguaguaga uuguauaguu gugggguagu gauuuuaccc uguucaggag      60
auaacuauac aaucuauugc cuucccuga                                       89

<210> SEQ ID NO 13
<211> LENGTH: 85
<212> TYPE: RNA
<213> ORGANISM: Homo sapiens

<400> SEQUENCE: 13 cuguggaug agguaguaga uuguauaguu uuagggucau accccaucuu ggagauaacu      60
auacagucua cugcuuucc cacgg                                            85
```

```
<210> SEQ ID NO 14
<211> LENGTH: 108
<212> TYPE: RNA
<213> ORGANISM: Homo sapiens

<400> SEQUENCE: 14
uugccugauu ccaggcugag guaguaguuu guacaguuug agggucuaug auaccacccg      60
guacaggaga uaacuguaca ggccacugcc uugccaggaa cagcgcgc                 108

<210> SEQ ID NO 15
<211> LENGTH: 85
<212> TYPE: RNA
<213> ORGANISM: Homo sapiens

<400> SEQUENCE: 15
cuggcugagg uaguaguuug ugcuguuggu cggguuguga cauugcccgc uggagaua       60 acugcgcaag cuacugccuu gcuag                                           85

<210> SEQ ID NO 16
<211> LENGTH: 85
<212> TYPE: RNA
<213> ORGANISM: Homo sapiens

<400> SEQUENCE: 16
accuacucag aguacauacu ucuuuaugua cccauaugaa cauacaaugc uauggaaugu     60
aaagaaguau guauuuuugg uaggc                                           85

<210> SEQ ID NO 17
<211> LENGTH: 108
<212> TYPE: RNA
<213> ORGANISM: Homo sapiens

<400> SEQUENCE: 17
cagcuaacaa cuuaguaaua ccuacucaga guacauacuu cuuuauguac ccauaugaac     60
auacaaugcu auggaaugua aagaaguaug uauuuuuggu aggcaaua                108

<210> SEQ ID NO 18
<211> LENGTH: 85
<212> TYPE: RNA
<213> ORGANISM: Homo sapiens

<400> SEQUENCE: 18
gccugcuugg gaaacauacu ucuuuauaug cccauaugga ccugcuaagc uauggaaugu     60
aaagaaguau guaucucagg ccggg                                           85

<210> SEQ ID NO 19
<211> LENGTH: 71
<212> TYPE: RNA
<213> ORGANISM: Homo sapiens

<400> SEQUENCE: 19
ugggaaacau acuucuuuau augcccauau ggaccugcua agcuauggaa uguaaagaag     60
uauguaucuc a                                                          71

<210> SEQ ID NO 20
<211> LENGTH: 85
<212> TYPE: RNA
<213> ORGANISM: Homo sapiens

<400> SEQUENCE: 20
```

```
accuacucag aguacauacu ucuuuaugua cccauaugaa cauacaaugc uauggaaugu    60
aaagaaguau guauuuuugg uaggc                                         85

<210> SEQ ID NO 21
<211> LENGTH: 108
<212> TYPE: RNA
<213> ORGANISM: Homo sapiens

<400> SEQUENCE: 21
uggauguugg ccuaguucug ugggaagac uagugauuuu guuguuuuua gauaacuaaa    60
ucgacaacaa aucacagucu gccauauggc acaggccaug ccucuaca               108

<210> SEQ ID NO 22
<211> LENGTH: 110
<212> TYPE: RNA
<213> ORGANISM: Homo sapiens

<400> SEQUENCE: 22
uuggauguug gccuaguucu gugggaaga cuagugauuu guuguuuuu agauaacuaa    60 aucgacaaca aaucacaguc ugccauaugg cacaggccau gccucuacag             110

<210> SEQ ID NO 23
<211> LENGTH: 110
<212> TYPE: RNA
<213> ORGANISM: Homo sapiens

<400> SEQUENCE: 23
cuggauacag aguggaccgg cuggccccau cuggaagacu agugauuuug uuguugucuu    60
acugcgcuca caacaaauc ccagucuacc uaauggugcc agccaucgca              110

<210> SEQ ID NO 24
<211> LENGTH: 110
<212> TYPE: RNA
<213> ORGANISM: Homo sapiens

<400> SEQUENCE: 24
agauuagagu ggcugugguc uagugcugug uggaagacua gugauuuugu uguucugaug    60
uacuacgaca caagucaca gccggccuca uagcgcagac ucccuucgac              110

<210> SEQ ID NO 25
<211> LENGTH: 89
<212> TYPE: RNA
<213> ORGANISM: Homo sapiens

<400> SEQUENCE: 25
cgggguuggu uguuaucuuu gguuaucuag cuguaugagu ggguggagu cuucauaaag    60 cuagauaacc gaaaguaaaa auaacccca                                     89

<210> SEQ ID NO 26
<211> LENGTH: 87
<212> TYPE: RNA
<213> ORGANISM: Homo sapiens

<400> SEQUENCE: 26
ggaagcgagu uguuaucuuu gguuaucuag cuguaugagu guauuggucu ucauaaagcu    60
agauaaccga aaguaaaaac uccuuca                                       87

<210> SEQ ID NO 27
```

```
<211> LENGTH: 90
<212> TYPE: RNA
<213> ORGANISM: Homo sapiens

<400> SEQUENCE: 27
ggaggcccgu uucucucuuu gguuaucuag cuguaugagu gccacagagc cgucauaaag    60
cuagauaacc gaaaguagaa augauucuca                                    90

<210> SEQ ID NO 28
<211> LENGTH: 110
<212> TYPE: RNA
<213> ORGANISM: Homo sapiens

<400> SEQUENCE: 28
gaucugucug ucuucuguau uacccuguau gauccgaauu uguguaagga auuuuguggu    60
cacaaauucg uaucuagggg aauauguagu ugacauaaac acuccgcucu             110

<210> SEQ ID NO 29
<211> LENGTH: 110
<212> TYPE: RNA
<213> ORGANISM: Homo sapiens

<400> SEQUENCE: 29
ccagagguug uaacguuguc uauauauacc cuguagaacc gaauugugu gguauccgua    60 uagucacaga uucgauucua ggggaauaua uggucgaugc aaaaacuuca             110

<210> SEQ ID NO 30
<211> LENGTH: 108
<212> TYPE: RNA
<213> ORGANISM: Homo sapiens

<400> SEQUENCE: 30
gcgcgaaugu guguuuaaaa aaauaaaac cuuggaguaa aguagcagca cauaauggu     60 uguggauuuu gaaaaggugc aggccauauu gugcugccuc aaaaauac              108

<210> SEQ ID NO 31
<211> LENGTH: 83
<212> TYPE: RNA
<213> ORGANISM: Homo sapiens

<400> SEQUENCE: 31
ccuuggagua aaguagcagc acauaauggu uuguggauuu ugaaaaggug caggccauau    60
ugugcugccu caaaaauaca agg                                           83

<210> SEQ ID NO 32
<211> LENGTH: 64
<212> TYPE: RNA
<213> ORGANISM: Homo sapiens

<400> SEQUENCE: 32
cuguagcagc acaucauggu uuacaugcua cagucaagau gcgaaucauu auuugcugcu    60
cuag                                                                64

<210> SEQ ID NO 33
<211> LENGTH: 98
<212> TYPE: RNA
<213> ORGANISM: Homo sapiens

<400> SEQUENCE: 33
uugaggccuu aaaguacugu agcagcacau cauggugguuuac augcuacagu caagaugcga    60
```
aucauuauuu gcugcucuag aaauuuaagg aaauucau           98

<210> SEQ ID NO 34
<211> LENGTH: 89
<212> TYPE: RNA
<213> ORGANISM: Homo sapiens

<400> SEQUENCE: 34
gucagcagug ccuuagcagc acguaaauau uggcguuaag auucuaaaau uaucuccagu      60
auuaacugug cugcugaagu aagguugac                                       89

<210> SEQ ID NO 35
<211> LENGTH: 81
<212> TYPE: RNA
<213> ORGANISM: Homo sapiens

<400> SEQUENCE: 35
guuccacucu agcagcacgu aaauauuggc guagugaaau auauauuaaa caccauauuu      60 acugucugc uuuaguguga c                                                81

<210> SEQ ID NO 36
<211> LENGTH: 81
<212> TYPE: RNA
<213> ORGANISM: Homo sapiens

<400> SEQUENCE: 36
gcagugccuu agcagcacgu aaauauuggc guuagauuc uaaaauuauc uccaguauua      60 acugucugc ugaaguaagg u                                                81

<210> SEQ ID NO 37
<211> LENGTH: 84
<212> TYPE: RNA
<213> ORGANISM: Homo sapiens

<400> SEQUENCE: 37
gucagaauaa ugucaaagug cuuacagugc agguagugau augugcaucu acugcaguga      60
aggcacuugu agcauuaugg ugac                                            84

<210> SEQ ID NO 38
<211> LENGTH: 71
<212> TYPE: RNA
<213> ORGANISM: Homo sapiens

<400> SEQUENCE: 38
uguucuaagg ugcaucuagu gcagauagug aaguagauua gcaucuacug cccuaagugc      60
uccuucuggc a                                                          71

<210> SEQ ID NO 39
<211> LENGTH: 81
<212> TYPE: RNA
<213> ORGANISM: Homo sapiens

<400> SEQUENCE: 39
uuuuuguucu aaggugcauc uagugcagau agugaaguag auuagcaucu acugcccuaa      60
gugcuccuuc uggcauaaga a                                               81

<210> SEQ ID NO 40
<211> LENGTH: 82
<212> TYPE: RNA

<213> ORGANISM: Homo sapiens

<400> SEQUENCE: 40
gcaguccucu guuaguuuug cauaguugca cuacaagaag aauguaguug ugcaaaucua    60
ugcaaaacug augguggccu gc    82

<210> SEQ ID NO 41
<211> LENGTH: 80
<212> TYPE: RNA
<213> ORGANISM: Homo sapiens

<400> SEQUENCE: 41
caguccucug uuaguuugc auaguugcac uacaagaaga auguaguugu gcaaaucuau    60
gcaaaacuga ugguggccug    80

<210> SEQ ID NO 42
<211> LENGTH: 87
<212> TYPE: RNA
<213> ORGANISM: Homo sapiens

<400> SEQUENCE: 42
cacuguucua ugguuaguuu ugcagguuug cauccagcug ugugauauuc ugcugugcaa    60
auccaugcaa aacugacugu gguagug    87

<210> SEQ ID NO 43
<211> LENGTH: 96
<212> TYPE: RNA
<213> ORGANISM: Homo sapiens

<400> SEQUENCE: 43
acauugcuac uuacaauuag uuuugcaggu uugcauuuca gcguauauau guauaugugg    60
cugugcaaau ccaugcaaaa cugauuguga uaaugu    96

<210> SEQ ID NO 44
<211> LENGTH: 80
<212> TYPE: RNA
<213> ORGANISM: Homo sapiens

<400> SEQUENCE: 44
uucuaugguu aguuugcag guuugcaucc agcuguguga uauucugcug ugcaaaucca    60
ugcaaaacug acuguggag    80

<210> SEQ ID NO 45
<211> LENGTH: 81
<212> TYPE: RNA
<213> ORGANISM: Homo sapiens

<400> SEQUENCE: 45
uuacaauuag uuuugcaggu uugcauuuca gcguauauau guauaugugg cugugcaaau    60
ccaugcaaaa cugauugaga u    81

<210> SEQ ID NO 46
<211> LENGTH: 71
<212> TYPE: RNA
<213> ORGANISM: Homo sapiens

<400> SEQUENCE: 46
guagcacuaa agugcuuaua gugcagguag uguuuaguua ucuacugcau uaugagcacu    60
uaaaguacug c    71

```
<210> SEQ ID NO 47
<211> LENGTH: 72
<212> TYPE: RNA
<213> ORGANISM: Homo sapiens

<400> SEQUENCE: 47
ugucggguag cuuaucagac ugauguugac uguugaaucu cauggcaaca ccagucgaug    60
ggcugucuga ca                                                       72

<210> SEQ ID NO 48
<211> LENGTH: 81
<212> TYPE: RNA
<213> ORGANISM: Homo sapiens

<400> SEQUENCE: 48
accuugucgg guagcuuauc agacugaugu ugacuguuga aucucauggc aacaccaguc    60
gaugggcugu cugacauuuu g                                             81

<210> SEQ ID NO 49
<211> LENGTH: 85
<212> TYPE: RNA
<213> ORGANISM: Homo sapiens

<400> SEQUENCE: 49
ggcugagccg caguaguucu ucagguggcaa gcuuuaugu c cugacccagc uaaagcugcc   60
aguugaagaa cguugcccu cugcc                                          85

<210> SEQ ID NO 50
<211> LENGTH: 73
<212> TYPE: RNA
<213> ORGANISM: Homo sapiens

<400> SEQUENCE: 50
ggccggcugg gguuccuggg gaugggauuu gcuuccuguc acaaaucaca uugccaggga    60
uuuccaaccg acc                                                      73

<210> SEQ ID NO 51
<211> LENGTH: 97
<212> TYPE: RNA
<213> ORGANISM: Homo sapiens

<400> SEQUENCE: 51
cucaggugcu cuggcugcuu ggguuccugg caugcugauu ugagacuuaa gauuaaaauc    60
acauugccag ggauuaccac gcaaccacga ccuuggc                            97

<210> SEQ ID NO 52
<211> LENGTH: 81
<212> TYPE: RNA
<213> ORGANISM: Homo sapiens

<400> SEQUENCE: 52
ccacggccgg cuggguucc uggggauggg auuugcuucc ugucacaaau cacauugcca    60
gggauuucca accgacccug a                                             81

<210> SEQ ID NO 53
<211> LENGTH: 68
<212> TYPE: RNA
<213> ORGANISM: Homo sapiens
```

<400> SEQUENCE: 53
cuccggugcc uacugagcug auaucaguuc ucauuuuaca cacuggcuca guucagcagg    60
aacaggag                                                              68

<210> SEQ ID NO 54
<211> LENGTH: 73
<212> TYPE: RNA
<213> ORGANISM: Homo sapiens

<400> SEQUENCE: 54
cucugccucc cgugccuacu gagcugaaac acaguugguu uguguacacu ggcucaguuc    60
agcaggaaca ggg                                                        73

<210> SEQ ID NO 55
<211> LENGTH: 81
<212> TYPE: RNA
<213> ORGANISM: Homo sapiens

<400> SEQUENCE: 55
cccugggcuc ugccucccgu gccuacugag cugaaacaca guugguuugu guacacuggc    60
ucaguucagc aggaacaggg g                                               81

<210> SEQ ID NO 56
<211> LENGTH: 71
<212> TYPE: RNA
<213> ORGANISM: Homo sapiens

<400> SEQUENCE: 56
cccuccggug ccuacugagc ugauaucagu ucucauuuua cacacuggcu caguucagca    60
ggaacagcau c                                                          71

<210> SEQ ID NO 57
<211> LENGTH: 84
<212> TYPE: RNA
<213> ORGANISM: Homo sapiens

<400> SEQUENCE: 57
ggccaguguu gagaggcgga gacuugggca auugcuggac gcugcccugg gcauugcacu    60
ugucucgguc ugacagugcc ggcc                                            84

<210> SEQ ID NO 58
<211> LENGTH: 86
<212> TYPE: RNA
<213> ORGANISM: Homo sapiens

<400> SEQUENCE: 58
aggccguggc cucguucaag uaauccagga uaggcugugc aggucccaau ggccuaucuu    60
gguuacuugc acgggacgc gggccu                                           86

<210> SEQ ID NO 59
<211> LENGTH: 77
<212> TYPE: RNA
<213> ORGANISM: Homo sapiens

<400> SEQUENCE: 59
guggccucgu ucaaguaauc caggauaggc ugugcagguc ccaaugggcc uauucuggu    60 uacuugcacg gggacgc                                                    77

-continued

```
<210> SEQ ID NO 60
<211> LENGTH: 84
<212> TYPE: RNA
<213> ORGANISM: Homo sapiens

<400> SEQUENCE: 60
ggcuguggcu ggauucaagu aauccaggau aggcuguuuc caucugugag gccuauucuu      60
gauuacuugu uucggaggc agcu                                             84

<210> SEQ ID NO 61
<211> LENGTH: 77
<212> TYPE: RNA
<213> ORGANISM: Homo sapiens

<400> SEQUENCE: 61
ccgggaccca guucaaguaa uucaggauag guugugugcu guccagccug uucuccauua     60
cuuggcucgg ggaccgg                                                    77

<210> SEQ ID NO 62
<211> LENGTH: 78
<212> TYPE: RNA
<213> ORGANISM: Homo sapiens

<400> SEQUENCE: 62
cugaggagca gggcuuagcu gcuugugagc aggguccaca ccaagucgug uucacagugg     60
cuaaguuccg cccccccag                                                  78

<210> SEQ ID NO 63
<211> LENGTH: 73
<212> TYPE: RNA
<213> ORGANISM: Homo sapiens

<400> SEQUENCE: 63
aggugcagag cuuagcugau uggugaacag ugauuggUUU ccgcuuuguu cacaguggcu     60
aaguucugca ccu                                                        73

<210> SEQ ID NO 64
<211> LENGTH: 97
<212> TYPE: RNA
<213> ORGANISM: Homo sapiens

<400> SEQUENCE: 64
accucucuaa caaggugcag agcuuagcug auuggugaac agugauuggu uccgcuuug      60 uucacagugg cuaaguucug caccugaaga gaaggug                              97

<210> SEQ ID NO 65
<211> LENGTH: 80
<212> TYPE: RNA
<213> ORGANISM: Homo sapiens

<400> SEQUENCE: 65
ccugaggagc agggcuuagc ugcuugugag cagguccac accaagucgu guucacagug      60
gcuaaguucc gccccccagg                                                 80

<210> SEQ ID NO 66
<211> LENGTH: 86
<212> TYPE: RNA
<213> ORGANISM: Homo sapiens

<400> SEQUENCE: 66
```

```
gguccuugcc cucaaggagc ucacagucua uugaguuacc uuucugacuu ucccacuaga    60
uugugagcuc cuggagggca ggcacu                                        86

<210> SEQ ID NO 67
<211> LENGTH: 108
<212> TYPE: RNA
<213> ORGANISM: Homo sapiens

<400> SEQUENCE: 67
ccuucuguga ccccuuagag gaugacugau uucuuuggu guucagaguc aauauaauuu    60
ucuagcacca ucugaaaucg guuauaauga uggggaaga gcaccaug                108

<210> SEQ ID NO 68
<211> LENGTH: 64
<212> TYPE: RNA
<213> ORGANISM: Homo sapiens

<400> SEQUENCE: 68
augacugauu ucuuuggug uucagaguca auauaauuuu cuagcaccau cugaaaucgg    60
uuau                                                               64

<210> SEQ ID NO 69
<211> LENGTH: 81
<212> TYPE: RNA
<213> ORGANISM: Homo sapiens

<400> SEQUENCE: 69
cuucaggaag cugguuucau auggugguu agauuuaaau agugauuguc uagcaccauu    60
ugaaaucagu guucuugggg g                                            81

<210> SEQ ID NO 70
<211> LENGTH: 81
<212> TYPE: RNA
<213> ORGANISM: Homo sapiens

<400> SEQUENCE: 70
cuucuggaag cugguuucac auggugggcuu agauuuuucc aucuuuguau cuagcaccau    60
uugaaaucag uguuuuagga g                                            81

<210> SEQ ID NO 71
<211> LENGTH: 110
<212> TYPE: RNA
<213> ORGANISM: Homo sapiens

<400> SEQUENCE: 71
accacuggcc caucucuuac acaggcugac cgauuucucc uggguucag agucuguuuu    60 ugucuagcac cauuugaaau cgguuaugau guagggggaa aagcagcagc              110

<210> SEQ ID NO 72
<211> LENGTH: 71
<212> TYPE: RNA
<213> ORGANISM: Homo sapiens

<400> SEQUENCE: 72
gcgacuguaa acauccucga cuggaagcug ugaagccaca gaugggcuuu cagucggaug    60
uuugcagcug c                                                       71

<210> SEQ ID NO 73
<211> LENGTH: 60
```

```
<212> TYPE: RNA
<213> ORGANISM: Homo sapiens

<400> SEQUENCE: 73
auguaaacau ccuacacuca gcuguaauac auggauuggc ugggaggugg auguuuacgu    60

<210> SEQ ID NO 74
<211> LENGTH: 88
<212> TYPE: RNA
<213> ORGANISM: Homo sapiens

<400> SEQUENCE: 74
accaaguuuc aguucaugua aacauccuac acucagcugu aauacaugga uuggcuggga    60 ggggauguu uacuucagcu gacuugga                                        88

<210> SEQ ID NO 75
<211> LENGTH: 72
<212> TYPE: RNA
<213> ORGANISM: Homo sapiens

<400> SEQUENCE: 75
agauacugua aacauccuac acucucagcu guggaaagua agaaagcugg gagaaggcug    60
uuuacucuuu cu                                                        72

<210> SEQ ID NO 76
<211> LENGTH: 70
<212> TYPE: RNA
<213> ORGANISM: Homo sapiens

<400> SEQUENCE: 76
guuguuguaa acauccccga cuggaagcug uaagacacag cuaagcuuuc agucagaugu    60
uugcugcuac                                                           70

<210> SEQ ID NO 77
<211> LENGTH: 64
<212> TYPE: RNA
<213> ORGANISM: Homo sapiens

<400> SEQUENCE: 77
cuguaaacau ccuugacugg aagcuguaag guguucagag gagcuuucag ucggauguuu    60
acag                                                                 64

<210> SEQ ID NO 78
<211> LENGTH: 71
<212> TYPE: RNA
<213> ORGANISM: Homo sapiens

<400> SEQUENCE: 78
ggagaggagg caagaugcug gcauagcugu ugaacuggga accugcuaug ccaacauauu    60
gccaucuuuc c                                                         71

<210> SEQ ID NO 79
<211> LENGTH: 70
<212> TYPE: RNA
<213> ORGANISM: Homo sapiens

<400> SEQUENCE: 79
ggagauauug cacauuacua aguugcaugu ugcacggcc ucaaugcaau uuagugugug    60
ugauauuuuc                                                           70
```

```
<210> SEQ ID NO 80
<211> LENGTH: 110
<212> TYPE: RNA
<213> ORGANISM: Homo sapiens

<400> SEQUENCE: 80
gggggccgag agaggcgggc ggccccgcgg ugcauugcug uugcauugca cgugugugag     60
gcgggugcag ugccucggca gugcagcccg agccggcccc cuggcaccac              110

<210> SEQ ID NO 81
<211> LENGTH: 88
<212> TYPE: RNA
<213> ORGANISM: Homo sapiens

<400> SEQUENCE: 81
accaaguuuc aguucaugua aacauccuac acucagcugu aauacaugga uuggcuggga     60
ggugaauguu uacuucagcu gacuugga                                       88

<210> SEQ ID NO 82
<211> LENGTH: 69
<212> TYPE: RNA
<213> ORGANISM: Homo sapiens

<400> SEQUENCE: 82
cuguggugca uguaguugc auugcauguu cuggugguac ccaugcaaug uuuccacagu      60
gcaucacag                                                            69

<210> SEQ ID NO 83
<211> LENGTH: 110
<212> TYPE: RNA
<213> ORGANISM: Homo sapiens

<400> SEQUENCE: 83
ggccagcugu gaguguuucu uuggcagugu cuuagcuggu uguugugagc aauaguaagg     60
aagcaaucag caaguauacu gcccuagaag ugcugcacgu uguggggccc              110

<210> SEQ ID NO 84
<211> LENGTH: 84
<212> TYPE: RNA
<213> ORGANISM: Homo sapiens

<400> SEQUENCE: 84
gugcucgguu uguaggcagu gucauuagcu gauuguacug uggugguuac aaucacuaac     60
uccacugcca ucaaaacaag gcac                                           84

<210> SEQ ID NO 85
<211> LENGTH: 77
<212> TYPE: RNA
<213> ORGANISM: Homo sapiens

<400> SEQUENCE: 85
agucuaguua cuaggcagug uaguuagcug auugcuaaua guaccaauca cuaaccacac     60
ggccagguaa aaagauu                                                   77

<210> SEQ ID NO 86
<211> LENGTH: 82
<212> TYPE: RNA
<213> ORGANISM: Homo sapiens

<400> SEQUENCE: 86
```

```
ucagaauaau gucaaagugc uuacagugca gguagugaua ugugcaucua cugcagugaa    60
ggcacuugua gcauuauggu ga                                            82

<210> SEQ ID NO 87
<211> LENGTH: 78
<212> TYPE: RNA
<213> ORGANISM: Homo sapiens

<400> SEQUENCE: 87
cuuucuacac agguugggau cgguugcaau gcuguguuuc uguaugguau ugcacuuguc    60
ccggccuguu gaguuugg                                                 78

<210> SEQ ID NO 88
<211> LENGTH: 75
<212> TYPE: RNA
<213> ORGANISM: Homo sapiens

<400> SEQUENCE: 88
ucaucccugg guggggauuu guugcauuac uuguguucua uauaaaguau ugcacuuguc    60
ccggccugug gaaga                                                    75

<210> SEQ ID NO 89
<211> LENGTH: 80
<212> TYPE: RNA
<213> ORGANISM: Homo sapiens

<400> SEQUENCE: 89 cuggggcuc caaagugcug uucgugcagg uagugugauu acccaaccua cugcugagcu     60
agcacuuccc gagccccgg                                                80

<210> SEQ ID NO 90
<211> LENGTH: 81
<212> TYPE: RNA
<213> ORGANISM: Homo sapiens

<400> SEQUENCE: 90
aacacagugg gcacucaaua aaugucuguu gaauugaaau gcguuacauu caacggguau    60
uuauugagca cccacucugu g                                             81

<210> SEQ ID NO 91
<211> LENGTH: 78
<212> TYPE: RNA
<213> ORGANISM: Homo sapiens

<400> SEQUENCE: 91
uggccgauuu uggcacuagc acauuuuugc uugugucucu ccgcucugag caaucaugug    60
cagugccaau augggaaa                                                 78

<210> SEQ ID NO 92
<211> LENGTH: 80
<212> TYPE: RNA
<213> ORGANISM: Homo sapiens

<400> SEQUENCE: 92
gugagcgacu guaaacaucc ucgacuggaa gcugugaagc cacagauggg cuuucagucg    60
gauguuugca gcugccuacu                                               80

<210> SEQ ID NO 93
```

```
<211> LENGTH: 80
<212> TYPE: RNA
<213> ORGANISM: Homo sapiens

<400> SEQUENCE: 93
gugagguagu aaguuguauu guugugggu agggauauua ggccccaauu agaagauaac      60
uauacaacuu acuacuuucc                                                80

<210> SEQ ID NO 94
<211> LENGTH: 70
<212> TYPE: RNA
<213> ORGANISM: Homo sapiens

<400> SEQUENCE: 94
ggcacccacc cguagaaccg accuugcggg gccuucgccg cacacaagcu cgucucugug      60
gguccguguc                                                            70

<210> SEQ ID NO 95
<211> LENGTH: 81
<212> TYPE: RNA
<213> ORGANISM: Homo sapiens

<400> SEQUENCE: 95
cccauuggca uaaacccgua gauccgaucu uguggugaag uggaccgcac aagcucgcuu      60
cuaugggucu gucucagugu g                                               81

<210> SEQ ID NO 96
<211> LENGTH: 108
<212> TYPE: RNA
<213> ORGANISM: Homo sapiens

<400> SEQUENCE: 96
aagagagaag auauugaggc cguugccac aaacccguag auccgaacuu gugguauuag      60
uccgcacaag cuuguaucua uagguaugug ucguuaggc aaucucac                  108

<210> SEQ ID NO 97
<211> LENGTH: 80
<212> TYPE: RNA
<213> ORGANISM: Homo sapiens

<400> SEQUENCE: 97
ccuguugcca caaacccgua gauccgaacu ugugguauua guccgcacaa gcuuguaucu      60
auagguaugu gucuguuagg                                                80

<210> SEQ ID NO 98
<211> LENGTH: 110
<212> TYPE: RNA
<213> ORGANISM: Homo sapiens

<400> SEQUENCE: 98
aggcugcccu ggcucaguua ucacagugcu gaugcugucu auucuaaagg uacaguacug      60
ugauaacuga aggauggcag ccaucuuacc uuccaucaga ggagccucac                110

<210> SEQ ID NO 99
<211> LENGTH: 57
<212> TYPE: RNA
<213> ORGANISM: Homo sapiens

<400> SEQUENCE: 99
ucaguuauca cagugcugau gcuguccauu cuaaagguac aguacuguga uaacuga         57
```

<210> SEQ ID NO 100
<211> LENGTH: 75
<212> TYPE: RNA
<213> ORGANISM: Homo sapiens

<400> SEQUENCE: 100
ugcccuggcu caguuaucac agugcugaug cugucuauuc uaaagguaca guacugugau    60
aacugaagga uggca    75

<210> SEQ ID NO 101
<211> LENGTH: 79
<212> TYPE: RNA
<213> ORGANISM: Homo sapiens

<400> SEQUENCE: 101
acuguccuuu uucgguuauc augguaccga ugcuguauau cugaaaggua caguacugug    60
auaacugaag aaugguggu    79

<210> SEQ ID NO 102
<211> LENGTH: 75
<212> TYPE: RNA
<213> ORGANISM: Homo sapiens

<400> SEQUENCE: 102
uguccuuuuu cgguuaucau gguaccgaug cuguauaucu gaaagguaca guacugugau    60
aacugaagaa uggug    75

<210> SEQ ID NO 103
<211> LENGTH: 81
<212> TYPE: RNA
<213> ORGANISM: Homo sapiens

<400> SEQUENCE: 103
cuucuggaag cugguuucac augguggcuu agauuuuucc aucuuuguau cuagcaccau    60
uugaaaucag uguuuuagga g    81

<210> SEQ ID NO 104
<211> LENGTH: 81
<212> TYPE: RNA
<213> ORGANISM: Homo sapiens

<400> SEQUENCE: 104
cuucaggaag cugguuucau auggugguuu agauuuaaau agugauuguc uagcaccauu    60
ugaaaucagu guucuugggg g    81

<210> SEQ ID NO 105
<211> LENGTH: 78
<212> TYPE: RNA
<213> ORGANISM: Homo sapiens

<400> SEQUENCE: 105
uugugcuuuc agcuucuuua cagugcugcc uuguagcauu caggucaagc aacauuguac    60
agggcuauga aagaacca    78

<210> SEQ ID NO 106
<211> LENGTH: 78
<212> TYPE: RNA
<213> ORGANISM: Homo sapiens

```
<400> SEQUENCE: 106
uacugcccuc ggcuucuuua cagugcugcc uuguugcaua uggaucaagc agcauuguac      60
agggcuauga aggcauug                                                    78

<210> SEQ ID NO 107
<211> LENGTH: 78
<212> TYPE: RNA
<213> ORGANISM: Homo sapiens

<400> SEQUENCE: 107
aaaugucaga cagcccaucg acuguguug ccaugagauu caacagucaa caucagucug       60
auaagcuacc cgacaagg                                                    78

<210> SEQ ID NO 108
<211> LENGTH: 81
<212> TYPE: RNA
<213> ORGANISM: Homo sapiens

<400> SEQUENCE: 108
ugugcaucgu ggucaaaugc ucagacuccu guggugcug cucaugcacc acggauguuu       60
gagcaugugc uacggugucu a                                                81

<210> SEQ ID NO 109
<211> LENGTH: 81
<212> TYPE: RNA
<213> ORGANISM: Homo sapiens

<400> SEQUENCE: 109
ugugcaucgu ggucaaaugc ucagacuccu guggugcug cuuaugcacc acggauguuu       60
gagcaugugc uauggugucu a                                                81

<210> SEQ ID NO 110
<211> LENGTH: 81
<212> TYPE: RNA
<213> ORGANISM: Homo sapiens

<400> SEQUENCE: 110
ccuuggccau guaaaagugc uuacagugca gguagcuuuu ugagaucuac ugcaauguaa      60
gcacuucuua cauuaccaug g                                                81

<210> SEQ ID NO 111
<211> LENGTH: 82
<212> TYPE: RNA
<213> ORGANISM: Homo sapiens

<400> SEQUENCE: 111
ccugccgggg cuaaagugcu gacagugcag auaguggucc ucuccgugcu accgcacugu      60
ggguacuugc ugcuccagca gg                                               82

<210> SEQ ID NO 112
<211> LENGTH: 81
<212> TYPE: RNA
<213> ORGANISM: Homo sapiens

<400> SEQUENCE: 112
cucucugcuu ucagcuucuu uacaguguug ccuugggca uggaguucaa gcagcauugu       60
acagggcuau caaagcacag a                                                81
```

```
<210> SEQ ID NO 113
<211> LENGTH: 90
<212> TYPE: RNA
<213> ORGANISM: Homo sapiens

<400> SEQUENCE: 113
acacugcaag aacaauaagg auuuuuaggg gcauuaugac ugagucagaa aacacagcug      60
ccccugaaag ucccucauuu uucuugcugu                                      90

<210> SEQ ID NO 114
<211> LENGTH: 80
<212> TYPE: RNA
<213> ORGANISM: Homo sapiens

<400> SEQUENCE: 114
acugcaagag caauaaggau uuuuaggggc auuaugauag uggaauggaa acacaucugc      60
ccccaaaagu ccccucauuuu                                                80

<210> SEQ ID NO 115
<211> LENGTH: 85
<212> TYPE: RNA
<213> ORGANISM: Homo sapiens

<400> SEQUENCE: 115
ccuuagcaga gcugggagu gugacaaugg uguuugguc uaaacuauca aacgccauua       60
ucacacuaaa uagcuacugc uaggc                                           85

<210> SEQ ID NO 116
<211> LENGTH: 66
<212> TYPE: RNA
<213> ORGANISM: Homo sapiens

<400> SEQUENCE: 116
agcuguggag ugugacaaug guguuugugu ccaaacuauc aaacgccauu aucacacuaa      60
auagcu                                                                66

<210> SEQ ID NO 117
<211> LENGTH: 61
<212> TYPE: RNA
<213> ORGANISM: Homo sapiens

<400> SEQUENCE: 117
acauuauuac uuuuggguacg cgcugugaca cuucaaacuc guaccgugag uaauaaugcg     60
c                                                                     61

<210> SEQ ID NO 118
<211> LENGTH: 85
<212> TYPE: RNA
<213> ORGANISM: Homo sapiens

<400> SEQUENCE: 118
aggccucucu cuccguguuc acagcggacc uugauuuaaa uguccauaca auuaaggcac      60
gcggugaaug ccaagaaugg ggcug                                           85

<210> SEQ ID NO 119
<211> LENGTH: 110
<212> TYPE: RNA
<213> ORGANISM: Homo sapiens

<400> SEQUENCE: 119
```

```
aucaagauua gaggcucugc ucuccgucuu cacagcggac cuugauuuaa ugucauacaa    60
uuaaggcacg cggugaaugc caagagcgga gccuacggcu gcacuugaag              110
```

<210> SEQ ID NO 120
<211> LENGTH: 87
<212> TYPE: RNA
<213> ORGANISM: Homo sapiens

<400> SEQUENCE: 120

```
ugagggcccc ucugcguguu cacagcggac cuugauuuaa ugucuauaca auuaaggcac    60
gcggugaaug ccaagagagg cgccucc                                        87
```

<210> SEQ ID NO 121
<211> LENGTH: 68
<212> TYPE: RNA
<213> ORGANISM: Homo sapiens

<400> SEQUENCE: 121

```
cucugcgugu ucacagcgga ccuugauuua augucuauac aauuaaggca cgcggugaau    60
gccaagag                                                             68
```

<210> SEQ ID NO 122
<211> LENGTH: 67
<212> TYPE: RNA
<213> ORGANISM: Homo sapiens

<400> SEQUENCE: 122

```
cucuccgugu ucacagcgga ccuugauuua augucauaca auuaaggcac gcggugaaug    60
ccaagag                                                              67
```

<210> SEQ ID NO 123
<211> LENGTH: 86
<212> TYPE: RNA
<213> ORGANISM: Homo sapiens

<400> SEQUENCE: 123

```
ugccagucuc uaggucccug agacccuuua accugugagg acauccaggg ucacaggugu    60
gguucuuggg agccuggcgu cuggcc                                         86
```

<210> SEQ ID NO 124
<211> LENGTH: 65
<212> TYPE: RNA
<213> ORGANISM: Homo sapiens

<400> SEQUENCE: 124

```
ggucccugag acccuuuaac cugugaggac auccagggu acaggugagg uucuugggag    60
ccugg                                                                65
```

<210> SEQ ID NO 125
<211> LENGTH: 88
<212> TYPE: RNA
<213> ORGANISM: Homo sapiens

<400> SEQUENCE: 125

```
ugcgcuccuc ucaguccccug agacccuaac uugugauguu uaccguuuaa auccacgggu    60
uaggcucuug ggagcugcga gucgugcu                                       88
```

<210> SEQ ID NO 126
<211> LENGTH: 89

```
<212> TYPE: RNA
<213> ORGANISM: Homo sapiens

<400> SEQUENCE: 126
accagacuuu uccuagcccc ugagacccua acuugugagg uauuuuagua acaucacaag    60
ucaggcucuu gggaccuagg cggagggga                                      89

<210> SEQ ID NO 127
<211> LENGTH: 85
<212> TYPE: RNA
<213> ORGANISM: Homo sapiens

<400> SEQUENCE: 127
cgcuggcgac gggacauuau uacuuuuggu acgcgcugug acacuucaaa cucguaccgu    60
gaguaauaau gcgccgucca cggca                                          85

<210> SEQ ID NO 128
<211> LENGTH: 61
<212> TYPE: RNA
<213> ORGANISM: Homo sapiens

<400> SEQUENCE: 128
acauuauuac uuuugguacg cgcugugaca cuucaaacuc guaccgugag uaauaaugcg    60
c                                                                    61

<210> SEQ ID NO 129
<211> LENGTH: 97
<212> TYPE: RNA
<213> ORGANISM: Homo sapiens

<400> SEQUENCE: 129
ugugaucacu gucuccagcc ugcugaagcu cagagggcuc ugauucagaa agaucaucgg    60
auccgucuga gcuuggcugg ucggaagucu caucauc                             97

<210> SEQ ID NO 130
<211> LENGTH: 70
<212> TYPE: RNA
<213> ORGANISM: Homo sapiens

<400> SEQUENCE: 130
ccagccugcu gaagcucaga gggcucugau ucagaaagau caucggaucc gucugagcuu    60
ggcuggucgg                                                           70

<210> SEQ ID NO 131
<211> LENGTH: 82
<212> TYPE: RNA
<213> ORGANISM: Homo sapiens

<400> SEQUENCE: 131
ugagcuguug gauucggggc cguagcacug ucgagaggu uuacauuucu cacagugaac     60
cggucucuuu uucagcugcu uc                                             82

<210> SEQ ID NO 132
<211> LENGTH: 110
<212> TYPE: RNA
<213> ORGANISM: Homo sapiens

<400> SEQUENCE: 132
gcccggcagc cacugugcag ugggaagggg ggccgauaca cuguacgaga gugaguagca    60
```
ggucucacag ugaaccgguc ucuuucccua cugugucaca cuccuaaugg    110

<210> SEQ ID NO 133
<211> LENGTH: 70
<212> TYPE: RNA
<213> ORGANISM: Homo sapiens

<400> SEQUENCE: 133
guuggauucg gggccguagc acugucugag agguuuacau uucucacagu gaaccggucu    60
cuuuuucagc    70

<210> SEQ ID NO 134
<211> LENGTH: 74
<212> TYPE: RNA
<213> ORGANISM: Homo sapiens

<400> SEQUENCE: 134
uggaucuuuu ugcggucugg gcuugcuguu ccucucaaca guagucagga agcccuuacc    60
ccaaaaagua ucua    74

<210> SEQ ID NO 135
<211> LENGTH: 90
<212> TYPE: RNA
<213> ORGANISM: Homo sapiens

<400> SEQUENCE: 135
ugcccuucgc gaaucuuuuu gcggucuggg cuugcuguac auaacucaau agccggaagc    60
ccuuacccca aaaagcauuu gcggagggcg    90

<210> SEQ ID NO 136
<211> LENGTH: 89
<212> TYPE: RNA
<213> ORGANISM: Homo sapiens

<400> SEQUENCE: 136
ugcugcuggc cagagcucuu uucacauugu gcuacugucu gcaccuguca cuagcagugc    60
aauguuaaaa gggcauuggc cguguagug    89

<210> SEQ ID NO 137
<211> LENGTH: 110
<212> TYPE: RNA
<213> ORGANISM: Homo sapiens

<400> SEQUENCE: 137
gccaggaggc ggguugguu guuaucuuug guuaucuagc uguaugagug guguggaguc    60
uucauaaagc uagauaaccg aaaguaaaaa uaaccccaua cacugcgcag    110

<210> SEQ ID NO 138
<211> LENGTH: 110
<212> TYPE: RNA
<213> ORGANISM: Homo sapiens

<400> SEQUENCE: 138
cacggcgcgg cagcggcacu ggcuaaggga ggcccguuuc ucucuuuggu uaucuagcug    60
uaugagugcc acagagccgu cauaaagcua gauaaccgaa aguagaaaug    110

<210> SEQ ID NO 139
<211> LENGTH: 72
<212> TYPE: RNA
<213> ORGANISM: Homo sapiens

<400> SEQUENCE: 139
guuguuaucu uugguuaucu agcuguauga guguauuggu cuucauaaag cuagauaacc    60
gaaaguaaaa ac    72

<210> SEQ ID NO 140
<211> LENGTH: 101
<212> TYPE: RNA
<213> ORGANISM: Homo sapiens

<400> SEQUENCE: 140
ccgcccccgc gucuccaggg caaccguggc uuucgauugu acgugggga acuggaggua    60 acagucuaca gccauggucg ccccgcagca cgcccacgcg c    101

<210> SEQ ID NO 141
<211> LENGTH: 66
<212> TYPE: RNA
<213> ORGANISM: Homo sapiens

<400> SEQUENCE: 141
gggcaaccgu ggcuuucgau uguuacugug ggaacuggag guaacagucu acagccaugg    60
ucgccc    66

<210> SEQ ID NO 142
<211> LENGTH: 88
<212> TYPE: RNA
<213> ORGANISM: Homo sapiens

<400> SEQUENCE: 142
acaaugcuuu gcuagagcug guaaaaugga accaaaucgc cucuucaaug gauuuggucc    60
ccuucaacca gcuguagcua ugcauuga    88

<210> SEQ ID NO 143
<211> LENGTH: 102
<212> TYPE: RNA
<213> ORGANISM: Homo sapiens

<400> SEQUENCE: 143
gggagccaaa ugcuuugcua gagcugguaa aauggaacca aaucgacugu ccaauggauu    60 uggucccuu caaccagcug uagcugugca uugauggcgc cg    102

<210> SEQ ID NO 144
<211> LENGTH: 68
<212> TYPE: RNA
<213> ORGANISM: Homo sapiens

<400> SEQUENCE: 144
gcuagagcug guaaaaugga accaaaucgc cucuucaaug gauuuggucc ccuucaacca    60
gcuguagc    68

<210> SEQ ID NO 145
<211> LENGTH: 119
<212> TYPE: RNA
<213> ORGANISM: Homo sapiens

<400> SEQUENCE: 145
ccucagaaga aagaugcccc cugcucuggc uggucaaacg gaaccaaguc cgucuuccug    60
agagguuugg uccccuucaa ccagcuacag cagggcuggc aaugcccagu ccuuggaga    119

```
<210> SEQ ID NO 146
<211> LENGTH: 80
<212> TYPE: RNA
<213> ORGANISM: Homo sapiens

<400> SEQUENCE: 146
gcccccugcu cuggcugguc aaacggaacc aaguccgucu uccugagagg uuuggucccc      60
uucaaccagc uacagcaggg                                                 80

<210> SEQ ID NO 147
<211> LENGTH: 73
<212> TYPE: RNA
<213> ORGANISM: Homo sapiens

<400> SEQUENCE: 147
cagggugugu gacugguuga ccagaggggc augcacugug uucacccugu gggccaccua      60
gucaccaacc cuc                                                        73

<210> SEQ ID NO 148
<211> LENGTH: 71
<212> TYPE: RNA
<213> ORGANISM: Homo sapiens

<400> SEQUENCE: 148
agggugugug acugguugac cagaggggca ugcacugugu cacccugugg ggccaccuag      60
ucaccaaccc u                                                          71

<210> SEQ ID NO 149
<211> LENGTH: 90
<212> TYPE: RNA
<213> ORGANISM: Homo sapiens

<400> SEQUENCE: 149
aggccucgcu guucucuaug gcuuuuuauu ccuaugugau ucuacugcuc acucauauag      60
ggauuggagc cguggcgcac ggcggggaca                                      90

<210> SEQ ID NO 150
<211> LENGTH: 100
<212> TYPE: RNA
<213> ORGANISM: Homo sapiens

<400> SEQUENCE: 150
agauaaauuc acucuagugc uuuauggcuu uuuauuccua ugugauagua auaaagcuc       60 auguagggau ggaagccaug aaauacauug ugaaaaauca                           100

<210> SEQ ID NO 151
<211> LENGTH: 60
<212> TYPE: RNA
<213> ORGANISM: Homo sapiens

<400> SEQUENCE: 151
cuauggcuuu uuauuccuau gugauucuac ugcucacuca auaugggauu ggagccgugg     60

<210> SEQ ID NO 152
<211> LENGTH: 97
<212> TYPE: RNA
<213> ORGANISM: Homo sapiens

<400> SEQUENCE: 152
cacucugcug uggccuaugg cuuuucauuc cuaugugauu gcugucccaa acucauguag     60
```

```
ggcuaaaagc caugggcuac agugaggggc gagcucc                                    97
```

<210> SEQ ID NO 153
<211> LENGTH: 82
<212> TYPE: RNA
<213> ORGANISM: Homo sapiens

<400> SEQUENCE: 153

```
ugagcccucg gaggacucca uuuguuuuga ugauggauuc uuaugcucca ucaucgucuc          60
aaaugagucu ucagagggu cu                                                    82
```

<210> SEQ ID NO 154
<211> LENGTH: 62
<212> TYPE: RNA
<213> ORGANISM: Homo sapiens

<400> SEQUENCE: 154

```
gaggacucca uuuguuuuga ugauggauuc uuaugcucca ucaucgucuc aaaugagucu          60
uc                                                                         62
```

<210> SEQ ID NO 155
<211> LENGTH: 73
<212> TYPE: RNA
<213> ORGANISM: Homo sapiens

<400> SEQUENCE: 155

```
cuucggugac ggguauucuu ggguggauaa uacggauuac guuguuauug cuuaagaaua          60
cgcguagucg agg                                                             73
```

<210> SEQ ID NO 156
<211> LENGTH: 99
<212> TYPE: RNA
<213> ORGANISM: Homo sapiens

<400> SEQUENCE: 156

```
cccuggcaug gugguggggg gcagcuggug uugugaauca ggccguugcc aaucagagaa          60
cggcuacuuc acaacaccag ggccacacca cacuacagg                                 99
```

<210> SEQ ID NO 157
<211> LENGTH: 84
<212> TYPE: RNA
<213> ORGANISM: Homo sapiens

<400> SEQUENCE: 157

```
cguugcugca gcuggguuug ugaaucaggc cgacgagcag cgcauccucu uacccggcua          60
uuucacgaca ccaggguugc auca                                                 84
```

<210> SEQ ID NO 158
<211> LENGTH: 71
<212> TYPE: RNA
<213> ORGANISM: Homo sapiens

<400> SEQUENCE: 158

```
cagcuggugu ugugaaucag gccgacgagc agcgcauccu cuuacccggc uauuucacga          60
caccaggguu g                                                               71
```

<210> SEQ ID NO 159
<211> LENGTH: 68
<212> TYPE: RNA

<213> ORGANISM: Homo sapiens

<400> SEQUENCE: 159
guguauucua cagugcacgu gucuccagug uggcucggag gcuggagacg cggcccuguu    60
ggaguaac                                                              68

<210> SEQ ID NO 160
<211> LENGTH: 100
<212> TYPE: RNA
<213> ORGANISM: Homo sapiens

<400> SEQUENCE: 160
ugugucucuc ucugugnccu gccagugguu uuacccuaug guagguuacg ucaugcuguu    60
cuaccacagg guagaaccac ggacaggaua ccggggcacc                          100

<210> SEQ ID NO 161
<211> LENGTH: 72
<212> TYPE: RNA
<213> ORGANISM: Homo sapiens

<400> SEQUENCE: 161
uccugccagu gguuuuaccc uaugguaggu uacgucaugc uguucuacca caggguagaa    60
ccacggacag ga                                                         72

<210> SEQ ID NO 162
<211> LENGTH: 70
<212> TYPE: RNA
<213> ORGANISM: Homo sapiens

<400> SEQUENCE: 162
ccugccagug guuuuacccu auggaugguu acgucaugcu guucuaccac aggguagaac    60
cacggacagg                                                            70

<210> SEQ ID NO 163
<211> LENGTH: 95
<212> TYPE: RNA
<213> ORGANISM: Homo sapiens

<400> SEQUENCE: 163
cggccggccc uggguccauc uuccaguaca guguuggaug gucuaauugu gaagcuccua    60
acacugucug guaaagaugg cucccgggug gguuc                               95

<210> SEQ ID NO 164
<211> LENGTH: 72
<212> TYPE: RNA
<213> ORGANISM: Homo sapiens

<400> SEQUENCE: 164
ggguccaucu uccaguacag guuggaugg ucuaauugug aagcuccuaa cacugucugg     60
uaaagauggc cc                                                         72

<210> SEQ ID NO 165
<211> LENGTH: 64
<212> TYPE: RNA
<213> ORGANISM: Homo sapiens

<400> SEQUENCE: 165
acccauaaag uagaaagcac uacuaacagc acuggagggu guaguguuuc cuacuuuaug    60
gaug                                                                  64

```
<210> SEQ ID NO 166
<211> LENGTH: 106
<212> TYPE: RNA
<213> ORGANISM: Homo sapiens

<400> SEQUENCE: 166
gcgcagcgcc cugucuccca gccugaggug cagugcugca ucucuggucca guugggaguc    60 ugagaugaag cacuguagcu caggaagaga gaaguuguuc ugcagc                   106

<210> SEQ ID NO 167
<211> LENGTH: 63
<212> TYPE: RNA
<213> ORGANISM: Homo sapiens

<400> SEQUENCE: 167
ccugaggugc agugcugcau cucggucag uuggagucu gagaugaagc acuguagcuc       60
agg                                                                   63

<210> SEQ ID NO 168
<211> LENGTH: 86
<212> TYPE: RNA
<213> ORGANISM: Homo sapiens

<400> SEQUENCE: 168
uggggcccug gcugggauau caucauauac uguaaguuug cgaugagaca cuacaguaua     60
gaugauguac uagccgggc accccc                                           86

<210> SEQ ID NO 169
<211> LENGTH: 66
<212> TYPE: RNA
<213> ORGANISM: Homo sapiens

<400> SEQUENCE: 169
ggcugggaua ucaucauaua cuguaaguuu gcgaugagac acuacaguau agaugaugua     60
cuaguc                                                                66

<210> SEQ ID NO 170
<211> LENGTH: 88
<212> TYPE: RNA
<213> ORGANISM: Homo sapiens

<400> SEQUENCE: 170
caccuugucc ucacggucca guuucccag gaaucccuua gaugcuaaga uggggauucc      60
uggaaauacu guucuugagg ucauggu                                         88

<210> SEQ ID NO 171
<211> LENGTH: 70
<212> TYPE: RNA
<213> ORGANISM: Homo sapiens

<400> SEQUENCE: 171
cucacggucc aguuuuccca ggaaucccuu agaugcuaag augggauuc cuggaaauac      60 uguucuugag                                                            70

<210> SEQ ID NO 172
<211> LENGTH: 99
<212> TYPE: RNA
<213> ORGANISM: Homo sapiens
```

<400> SEQUENCE: 172
ccgaugugua uccucagcuu ugagaacuga auuccauggg uugugucagu gucagaccuc    60
ugaaauucag uucuucagcu gggauaucuc ugucaucgu                          99

<210> SEQ ID NO 173
<211> LENGTH: 65
<212> TYPE: RNA
<213> ORGANISM: Homo sapiens

<400> SEQUENCE: 173
agcuuugaga acugaauucc auggguugug ucagugucag accugugaaa uucaguucuu    60
cagcu                                                               65

<210> SEQ ID NO 174
<211> LENGTH: 72
<212> TYPE: RNA
<213> ORGANISM: Homo sapiens

<400> SEQUENCE: 174
aaucuaaaga caacauuucu gcacacacac cagacuaugg aagccagugu guggaaaugc    60
uucugcuaga uu                                                       72

<210> SEQ ID NO 175
<211> LENGTH: 68
<212> TYPE: RNA
<213> ORGANISM: Homo sapiens

<400> SEQUENCE: 175
gaggcaaagu ucugagacac uccgacucug aguaugauag aagucagugc acuacagaac    60
uuugucuc                                                            68

<210> SEQ ID NO 176
<211> LENGTH: 99
<212> TYPE: RNA
<213> ORGANISM: Homo sapiens

<400> SEQUENCE: 176
caagcacgau uagcauuuga ggugaaguuc uguuauacac ucaggcugug gcucucugaa    60
agucagugca ucacagaacu uugucucgaa agcuuucua                          99

<210> SEQ ID NO 177
<211> LENGTH: 70
<212> TYPE: RNA
<213> ORGANISM: Homo sapiens

<400> SEQUENCE: 177
aagcacgauu agcauuugag gugaaguucu guuauacacu caggcugugg cucucugaaa    60
gucagugcau                                                          70

<210> SEQ ID NO 178
<211> LENGTH: 89
<212> TYPE: RNA
<213> ORGANISM: Homo sapiens

<400> SEQUENCE: 178
gccggcgccc gagcucuggc uccgugucuu cacucccgug cuugccgag gagggaggga    60 gggacggggg cugugcuggg gcagcugga                                     89

-continued

```
<210> SEQ ID NO 179
<211> LENGTH: 53
<212> TYPE: RNA
<213> ORGANISM: Homo sapiens

<400> SEQUENCE: 179
gcucuggcuc cgugucuuca cucccgugcu uguccgagga gggagggagg gac        53

<210> SEQ ID NO 180
<211> LENGTH: 84
<212> TYPE: RNA
<213> ORGANISM: Homo sapiens

<400> SEQUENCE: 180
cuccccaugg cccugucucc caacccuugu accagugcug ggcucagacc cugguacagg    60 ccuggggac agggaccugg ggac                                            84

<210> SEQ ID NO 181
<211> LENGTH: 64
<212> TYPE: RNA
<213> ORGANISM: Homo sapiens

<400> SEQUENCE: 181
cccugucucc caacccuugu accagugcug ggcucagacc cugguacagg ccuggggac    60 aggg                                                                 64

<210> SEQ ID NO 182
<211> LENGTH: 72
<212> TYPE: RNA
<213> ORGANISM: Homo sapiens

<400> SEQUENCE: 182
uuuccugccc ucgaggagcu cacagucuag uaugucucau ccccuacuag acugaagcuc    60
cuugaggaca gg                                                        72

<210> SEQ ID NO 183
<211> LENGTH: 69
<212> TYPE: RNA
<213> ORGANISM: Homo sapiens

<400> SEQUENCE: 183
ccuguccuca aggagcuuca gucuaguagg ggaugagaca uacuagacug ugagcuccuc    60
gagggcagg                                                            69

<210> SEQ ID NO 184
<211> LENGTH: 87
<212> TYPE: RNA
<213> ORGANISM: Homo sapiens

<400> SEQUENCE: 184 ugucccccc ggcccagguu cugugauaca cuccgacucg ggcucuggag cagucagugc    60
augacagaac uugggcccgg aaggacc                                        87

<210> SEQ ID NO 185
<211> LENGTH: 71
<212> TYPE: RNA
<213> ORGANISM: Homo sapiens

<400> SEQUENCE: 185
ggcccagguu cugugauaca cuccgacucg ggcucuggag cagucagugc augacagaac    60
```
uugggccccg g                                                          71

<210> SEQ ID NO 186
<211> LENGTH: 90
<212> TYPE: RNA
<213> ORGANISM: Homo sapiens

<400> SEQUENCE: 186
cucacagcug ccagugucau uuuugugauc ugcagcuagu auucucacuc caguugcaua     60
gucacaaaag ugaucauugg caggugugge                                     90

<210> SEQ ID NO 187
<211> LENGTH: 71
<212> TYPE: RNA
<213> ORGANISM: Homo sapiens

<400> SEQUENCE: 187
ucucucucuc ccucacagcu gccaguguca uugucacaaa agugaucauu ggcaggugug     60
gcugcugcau g                                                         71

<210> SEQ ID NO 188
<211> LENGTH: 87
<212> TYPE: RNA
<213> ORGANISM: Homo sapiens

<400> SEQUENCE: 188
agcgguggcc agugucauuu uugugauguu gcagcuagua auaugagccc aguugcauag     60
ucacaaaagu gaucauugga aacugug                                        87

<210> SEQ ID NO 189
<211> LENGTH: 69
<212> TYPE: RNA
<213> ORGANISM: Homo sapiens

<400> SEQUENCE: 189
cagugucauu uuugugaugu ugcagcuagu aauaugagcc caguugcaua gucacaaaag     60
ugaucauug                                                            69

<210> SEQ ID NO 190
<211> LENGTH: 84
<212> TYPE: RNA
<213> ORGANISM: Homo sapiens

<400> SEQUENCE: 190
gugguacuug aagauagguu auccguguug ccuucgcuuu auuugugacg aaucauacac     60
gguugaccua uuuuucagua ccaa                                           84

<210> SEQ ID NO 191
<211> LENGTH: 66
<212> TYPE: RNA
<213> ORGANISM: Homo sapiens

<400> SEQUENCE: 191
gaagauaggu uauccguguu gccuucgcuu uauuugugac gaaucauaca cgguugaccu     60
auuuuu                                                               66

<210> SEQ ID NO 192
<211> LENGTH: 65
<212> TYPE: RNA
<213> ORGANISM: Homo sapiens

<400> SEQUENCE: 192
cuguuaaugc uaaucgugau aggggguuuuu gccuccaacu gacuccuaca uauuagcauu    60
aacag                                                                65

<210> SEQ ID NO 193
<211> LENGTH: 82
<212> TYPE: RNA
<213> ORGANISM: Homo sapiens

<400> SEQUENCE: 193
ccuaacacug ucugguaaag auggcucccg ggugggwucu cucggcagua accuucaggg    60
agcccugaag accauggagg ac                                             82

<210> SEQ ID NO 194
<211> LENGTH: 110
<212> TYPE: RNA
<213> ORGANISM: Homo sapiens

<400> SEQUENCE: 194
gccgagaccg agugcacagg gcucugaccu augaauugac agccagugcu cucgucuccc    60
cucuggcugc caauuccaua ggucacaggu auguucgccu caaugccagc               110

<210> SEQ ID NO 195
<211> LENGTH: 80
<212> TYPE: RNA
<213> ORGANISM: Homo sapiens

<400> SEQUENCE: 195
ucccgccccc uguaacagca acuccaugug gaagugccca cugguuccag uggggcugcu    60
guuaucuggg gcgagggcca                                                80

<210> SEQ ID NO 196
<211> LENGTH: 70
<212> TYPE: RNA
<213> ORGANISM: Homo sapiens

<400> SEQUENCE: 196
aaagcugggu ugagagggcg aaaaaggaug aggugacugg ucugggcuac gcuaugcugc    60
ggcgcucggg                                                           70

<210> SEQ ID NO 197
<211> LENGTH: 64
<212> TYPE: RNA
<213> ORGANISM: Homo sapiens

<400> SEQUENCE: 197
cauuggccuc cuaagccagg gauugugggu ucgaguccca cccggggwuaa agaaaggccg    60 aauu                                                                 64

<210> SEQ ID NO 198
<211> LENGTH: 70
<212> TYPE: RNA
<213> ORGANISM: Homo sapiens

<400> SEQUENCE: 198
ccuaagccag ggauugugggg uucgaguccc accggggua gaggugaaag uuccuuuuac    60
ggaauuuuuu                                                           70

<210> SEQ ID NO 199
<211> LENGTH: 108
<212> TYPE: RNA
<213> ORGANISM: Homo sapiens

<400> SEQUENCE: 199
caaugucagc agugccuuag cagcacguaa auauuggcgu uaagauucua aaauuaucuc    60
caguauuaac ugugcugcug aaguaagguu gaccauacuc uacaguug                108

<210> SEQ ID NO 200
<211> LENGTH: 81
<212> TYPE: RNA
<213> ORGANISM: Homo sapiens

<400> SEQUENCE: 200
gggcuuucaa gucacuagug guuccguuua guagaugauu gugcauuguu ucaaaauggu    60
gcccuaguga cuacaaagcc c                                              81

<210> SEQ ID NO 201
<211> LENGTH: 70
<212> TYPE: RNA
<213> ORGANISM: Homo sapiens

<400> SEQUENCE: 201
acgcaagugu ccuaagguga gcucagggag cacagaaacc uccaguggaa cagaagggca    60
aaagcucauu                                                           70

<210> SEQ ID NO 202
<211> LENGTH: 70
<212> TYPE: RNA
<213> ORGANISM: Homo sapiens

<400> SEQUENCE: 202
caugugucac uuucaggugg aguuucaaga gucccuuccu gguucaccgu cuccuuugcu    60
cuuccacaac                                                           70

<210> SEQ ID NO 203
<211> LENGTH: 110
<212> TYPE: RNA
<213> ORGANISM: Homo sapiens

<400> SEQUENCE: 203
agaagggcua ucaggccagc cuucagagga cuccaaggaa cauucaacgc ugucggugag    60
uuugggauuu gaaaaaacca cugaccguug acuguaccuu ggggguccuua              110

<210> SEQ ID NO 204
<211> LENGTH: 110
<212> TYPE: RNA
<213> ORGANISM: Homo sapiens

<400> SEQUENCE: 204
ccugugcaga gauuauuuuu uaaaagguca caaucaacau ucauugcugu cgguggguug    60
aacugugugg acaagcucac ugaacaauga augcaacugu ggccccgcuu               110

<210> SEQ ID NO 205
<211> LENGTH: 89
<212> TYPE: RNA
<213> ORGANISM: Homo sapiens

<400> SEQUENCE: 205
cugauggcug cacucaacau ucauugcugu cgguggguuu gagucugaau caacucacug    60
aucaaugaau gcaaacugcg gaccaaaca                                      89

<210> SEQ ID NO 206
<211> LENGTH: 110
<212> TYPE: RNA
<213> ORGANISM: Homo sapiens

<400> SEQUENCE: 206
cggaaaauuu gccaaggguu uggggaaca uucaaccugu cggugaguuu gggcagcuca    60
ggcaaaccau cgaccguuga guggacccug aggccuggaa uugccauccu              110

<210> SEQ ID NO 207
<211> LENGTH: 110
<212> TYPE: RNA
<213> ORGANISM: Homo sapiens

<400> SEQUENCE: 207
gagcugcuug ccuccccccg uuuuuggcaa ugguagaacu cacacuggug agguaacagg    60
auccgguggu ucuagacuug ccaacuaugg ggcgaggacu cagccggcac              110

<210> SEQ ID NO 208
<211> LENGTH: 70
<212> TYPE: RNA
<213> ORGANISM: Homo sapiens

<400> SEQUENCE: 208
uuuuuggcaa ugguagaacu cacacuggug agguaacagg auccgguggu ucuagacuug    60
ccaacuaugg                                                           70

<210> SEQ ID NO 209
<211> LENGTH: 110
<212> TYPE: RNA
<213> ORGANISM: Homo sapiens

<400> SEQUENCE: 209
ccgcagagug ugacuccugu ucuguguaug gcacugguag aauucacugu gaacagucuc    60
agucagugaa uuaccgaagg gccauaaaca gagcagagac agauccacga              110

<210> SEQ ID NO 210
<211> LENGTH: 84
<212> TYPE: RNA
<213> ORGANISM: Homo sapiens

<400> SEQUENCE: 210
ccagucacgu ccccuuauca cuuuccagcc ccagcuuugu gacuguaagu guuggacgga    60
gaacugauaa ggguaggguga uuga                                          84

<210> SEQ ID NO 211
<211> LENGTH: 65
<212> TYPE: RNA
<213> ORGANISM: Homo sapiens

<400> SEQUENCE: 211
ccuuaucacu uuuccagccc agcuuuguga cuguaagugu uggacggaga acugauaagg    60
guagg                                                                65

<210> SEQ ID NO 212

```
<211> LENGTH: 82
<212> TYPE: RNA
<213> ORGANISM: Homo sapiens

<400> SEQUENCE: 212 aggggggcgag ggauuggaga gaaaggcagu uccugauggu ccccucccca ggggcuggcu      60
uuccucuggu ccuucccucc ca                                                82

<210> SEQ ID NO 213
<211> LENGTH: 66
<212> TYPE: RNA
<213> ORGANISM: Homo sapiens

<400> SEQUENCE: 213
agggauugga gagaaaggca guuccugaug gucccucccc aggggcuggc uuuccucug       60 guccuu                                                                 66

<210> SEQ ID NO 214
<211> LENGTH: 86
<212> TYPE: RNA
<213> ORGANISM: Homo sapiens

<400> SEQUENCE: 214
ugcuuguaac uuccaaaga auucuccuuu ugggcuuucu gguuuauuu uaagcccaaa        60 ggugaauuuu uugggaaguu ugagcu                                           86

<210> SEQ ID NO 215
<211> LENGTH: 71
<212> TYPE: RNA
<213> ORGANISM: Homo sapiens

<400> SEQUENCE: 215 acuuccaaa gaauucuccu uugggcuuu cugguuuuau uuuaagccca aaggugaauu        60
uuuugggaag u                                                           71

<210> SEQ ID NO 216
<211> LENGTH: 109
<212> TYPE: RNA
<213> ORGANISM: Homo sapiens

<400> SEQUENCE: 216
ggucgggcuc accaugacac agugugagac ucgggcuaca acacaggacc cggggcgcug      60
cucugacccc ucgugucuug uguugcagcc ggagggacgc agguccgca                 109

<210> SEQ ID NO 217
<211> LENGTH: 86
<212> TYPE: RNA
<213> ORGANISM: Homo sapiens

<400> SEQUENCE: 217
ugcucccucu cucacauccc uugcauggug gagggugagc uuucugaaaa ccccucccac      60 augcagggu ugcaggaugg cgagcc                                            86

<210> SEQ ID NO 218
<211> LENGTH: 68
<212> TYPE: RNA
<213> ORGANISM: Homo sapiens

<400> SEQUENCE: 218
ucucacaucc cuugcauggu ggagggugag cuuucugaaa accccuccca caugcagggu      60
``` uugcagga                                                                    68

<210> SEQ ID NO 219
<211> LENGTH: 102
<212> TYPE: RNA
<213> ORGANISM: Homo sapiens

<400> SEQUENCE: 219 cgucgauug acccgcccu ccggugccua cugagcugau aucaguucuc auuuuacaca    60
cuggcucagu ucagcaggaa caggagucga gcccuugagc aa                    102

<210> SEQ ID NO 220
<211> LENGTH: 68
<212> TYPE: RNA
<213> ORGANISM: Homo sapiens

<400> SEQUENCE: 220
cuccggugcc uacugagcug auaucaguuc ucauuuuaca cacuggcuca guucagcagg    60
aacaggag                                                            68

<210> SEQ ID NO 221
<211> LENGTH: 85
<212> TYPE: RNA
<213> ORGANISM: Homo sapiens

<400> SEQUENCE: 221
ugcaggccuc ugugugauau guuugauaua uuagguuguu auuuaaucca acuauauauc    60
aaacauauuc cuacaguguc uugcc                                         85

<210> SEQ ID NO 222
<211> LENGTH: 67
<212> TYPE: RNA
<213> ORGANISM: Homo sapiens

<400> SEQUENCE: 222
cugugugaua uguuugauau auuagguugu uauuuaaucc aacuauauau caaacauauu    60
ccuacag                                                             67

<210> SEQ ID NO 223
<211> LENGTH: 92
<212> TYPE: RNA
<213> ORGANISM: Homo sapiens

<400> SEQUENCE: 223
cggcuggaca gcgggcaacg gaaucccaaa agcagcuguu gucuccagag cauuccagcu    60
gcgcuuggau uucgucccu gcucuccugc cu                                  92

<210> SEQ ID NO 224
<211> LENGTH: 74
<212> TYPE: RNA
<213> ORGANISM: Homo sapiens

<400> SEQUENCE: 224
agcgggcaac ggaaucccaa aagcagcugu ugucuccaga gcauuccagc ugcgcuugga    60 uuucguccc ugcu                                                      74

<210> SEQ ID NO 225
<211> LENGTH: 108
<212> TYPE: RNA

<213> ORGANISM: Homo sapiens

<400> SEQUENCE: 225

```
ccgagaccga gugcacaggg cucugaccua ugaauugaca gccagugcuc ucgucuccc    60
ucuggcugcc aauuccauag gucacaggua uguucgccuc aaugccag                108
```

<210> SEQ ID NO 226
<211> LENGTH: 110
<212> TYPE: RNA
<213> ORGANISM: Homo sapiens

<400> SEQUENCE: 226

```
gccgagaccg agugcacagg gcucugaccu augaauugac agccagugcu cucgucccc    60
cucuggcugc caauuccaua ggucacaggu auguucgccu caaugccagc              110
```

<210> SEQ ID NO 227
<211> LENGTH: 88
<212> TYPE: RNA
<213> ORGANISM: Homo sapiens

<400> SEQUENCE: 227

```
cgaggauggg agcugagggc ugggucuuug cgggcgagau gagggugucg gaucaacugg    60
ccuacaaagu cccaguucuc ggcccccg                                       88
```

<210> SEQ ID NO 228
<211> LENGTH: 58
<212> TYPE: RNA
<213> ORGANISM: Homo sapiens

<400> SEQUENCE: 228

```
gcugggucuu ugcgggcgag augagggugu cggaucaacu ggccuacaaa gucccagu     58
```

<210> SEQ ID NO 229
<211> LENGTH: 85
<212> TYPE: RNA
<213> ORGANISM: Homo sapiens

<400> SEQUENCE: 229

```
augguguuau caaguguaac agcaacucca ugguggacugu guaccaauuu ccaguggaga    60
ugcuguuacu uuugaugguu accaa                                          85
```

<210> SEQ ID NO 230
<211> LENGTH: 63
<212> TYPE: RNA
<213> ORGANISM: Homo sapiens

<400> SEQUENCE: 230

```
guguaacagc aacuccaugu ggacugugua ccaauuccca guggagaugc uguuacuuuu    60
gau                                                                 63
```

<210> SEQ ID NO 231
<211> LENGTH: 87
<212> TYPE: RNA
<213> ORGANISM: Homo sapiens

<400> SEQUENCE: 231

```
agcuucccug gcucuagcag cacagaaaua uuggcacagg gaagcgaguc ugccaauauu    60
ggcugugcug cuccaggcag gguggug                                       87
```

```
<210> SEQ ID NO 232
<211> LENGTH: 58
<212> TYPE: RNA
<213> ORGANISM: Homo sapiens

<400> SEQUENCE: 232
uagcagcaca gaaauauugg cacagggaag cgagucugcc aauauuggcu gugcugcu          58

<210> SEQ ID NO 233
<211> LENGTH: 110
<212> TYPE: RNA
<213> ORGANISM: Homo sapiens

<400> SEQUENCE: 233
cuagagcuug aauuggaacu gcugagugaa uuagguaguu ucauguuguu gggccugggu        60
uucugaacac aacaacauua aaccacccga uucacggcag uuacugcucc                  110

<210> SEQ ID NO 234
<211> LENGTH: 70
<212> TYPE: RNA
<213> ORGANISM: Homo sapiens

<400> SEQUENCE: 234
gugaauuagg uaguuucaug uuguugggcc uggguuucug aacacaacaa cauuaaacca        60
cccgauucac                                                              70

<210> SEQ ID NO 235
<211> LENGTH: 110
<212> TYPE: RNA
<213> ORGANISM: Homo sapiens

<400> SEQUENCE: 235
ugcucgcuca gcugaucugu ggcuuaggua guuucauguu guugggauug aguuuugaac        60
ucggcaacaa gaaacugccu gaguuacauc agucgguuuu cgucgagggc                  110

<210> SEQ ID NO 236
<211> LENGTH: 70
<212> TYPE: RNA
<213> ORGANISM: Homo sapiens

<400> SEQUENCE: 236
gugaauuagg uaguuucaug uuguugggcc uggguuucug aacacaacaa cauuaaacca        60
cccgauucac                                                              70

<210> SEQ ID NO 237
<211> LENGTH: 84
<212> TYPE: RNA
<213> ORGANISM: Homo sapiens

<400> SEQUENCE: 237
acuggucggu gauuuaggua guuccuguu guugggaucc accuuucucu cgacagcacg         60
acacugccuu cauuacuuca guug                                              84

<210> SEQ ID NO 238
<211> LENGTH: 75
<212> TYPE: RNA
<213> ORGANISM: Homo sapiens

<400> SEQUENCE: 238
ggcugugccg gguagagagg gcagugggag guaagagcuc uucacccuuc accaccuucu        60
```

-continued ccacccagca uggcc                                              75

<210> SEQ ID NO 239
<211> LENGTH: 60
<212> TYPE: RNA
<213> ORGANISM: Homo sapiens

<400> SEQUENCE: 239
gugcaugugu auguaugugu gcaugugcau guguaugugu augagugcau gcgugugugc    60

<210> SEQ ID NO 240
<211> LENGTH: 62
<212> TYPE: RNA
<213> ORGANISM: Homo sapiens

<400> SEQUENCE: 240
ucauuggucc agaggggaga uagguuccug ugauuuuccc uucuucucua uagaauaaau    60
ga                                                                   62

<210> SEQ ID NO 241
<211> LENGTH: 71
<212> TYPE: RNA
<213> ORGANISM: Homo sapiens

<400> SEQUENCE: 241
gccaacccag uguucagacu accuguucag gaggcucuca auguuacag uagucugcac     60 auugguuagg c                                                         71

<210> SEQ ID NO 242
<211> LENGTH: 110
<212> TYPE: RNA
<213> ORGANISM: Homo sapiens

<400> SEQUENCE: 242
aggaagcuuc uggagauccu gcuccgucgc cccaguguuc agacuaccug uucaggacaa    60
ugccguugua caguagucug cacauugguu agacugggca agggagagca              110

<210> SEQ ID NO 243
<211> LENGTH: 110
<212> TYPE: RNA
<213> ORGANISM: Homo sapiens

<400> SEQUENCE: 243
ccagaggaca ccuccacucc gucuaccag uguuuagacu aucuguucag gacucccaaa     60
uuguacagua gucugcacau ugguuaggcu gggcugggu agacccucgg              110

<210> SEQ ID NO 244
<211> LENGTH: 71
<212> TYPE: RNA
<213> ORGANISM: Homo sapiens

<400> SEQUENCE: 244
gccaacccag uguucagacu accuguucag gaggcucuca auguuacag uagucugcac     60 auugguuagg c                                                         71

<210> SEQ ID NO 245
<211> LENGTH: 70
<212> TYPE: RNA
<213> ORGANISM: Homo sapiens

<400> SEQUENCE: 245

```
gccguggcca ucuuacuggg cagcauugga uggagucagg ucucuaauac ugccugguaa    60
ugaugacggc                                                           70

<210> SEQ ID NO 246
<211> LENGTH: 95
<212> TYPE: RNA
<213> ORGANISM: Homo sapiens

<400> SEQUENCE: 246
ccagcucggg cagccguggc caucuuacug ggcagcauug gauggaguca ggucucuaau    60
acugccuggu aaugaugacg gcggagcccu gcacg                               95

<210> SEQ ID NO 247
<211> LENGTH: 68
<212> TYPE: RNA
<213> ORGANISM: Homo sapiens

<400> SEQUENCE: 247
cccucgucuu acccagcagu guuggguggc gguugggagu cucuaauacu gccggguaau    60
gauggagg                                                             68

<210> SEQ ID NO 248
<211> LENGTH: 72
<212> TYPE: RNA
<213> ORGANISM: Homo sapiens

<400> SEQUENCE: 248
guuccuuuuu ccuaugcaua uacuucuuug aggaucuggc cuaaagaggu auagggcaug    60
ggaagaugga gc                                                        72

<210> SEQ ID NO 249
<211> LENGTH: 110
<212> TYPE: RNA
<213> ORGANISM: Homo sapiens

<400> SEQUENCE: 249 guguuggga cucgcgcgcu gggucagug guucuuaaca guucaacagu ucuguagcgc      60
aauugugaaa uguuuaggac cacuagaccc ggcgggcgcg gcgacagcga              110

<210> SEQ ID NO 250
<211> LENGTH: 110
<212> TYPE: RNA
<213> ORGANISM: Homo sapiens

<400> SEQUENCE: 250
ggcuacaguc uuucuucaug ugacucgugg acuuccccuuu gucauccuau gccugagaau   60
auaugaagga ggcugggaag gcaaagggac guucaauugu caucacuggc              110

<210> SEQ ID NO 251
<211> LENGTH: 110
<212> TYPE: RNA
<213> ORGANISM: Homo sapiens

<400> SEQUENCE: 251
aaagauccuc agacaaucca ugugcuucuc uugccuuca uuccaccgga gucugucuca    60
uacccaacca gauuucagug gagugaaguu caggaggcau ggagcugaca              110

<210> SEQ ID NO 252
```

```
<211> LENGTH: 86
<212> TYPE: RNA
<213> ORGANISM: Homo sapiens

<400> SEQUENCE: 252
ugcuucccga ggccacaugc uucuuuauau ccccauaugg auuacuuugc uauggaaugu    60
aaggaagugu gugguuucgg caagug                                        86

<210> SEQ ID NO 253
<211> LENGTH: 69
<212> TYPE: RNA
<213> ORGANISM: Homo sapiens

<400> SEQUENCE: 253
aggccacaug cuucuuuaua uccccauaug gauuacuuug cuauggaaug uaaggaagug    60
ugugguuuu                                                           69

<210> SEQ ID NO 254
<211> LENGTH: 71
<212> TYPE: RNA
<213> ORGANISM: Homo sapiens

<400> SEQUENCE: 254
ugacgggcga gcuuuggcc cggguuauac cugaugcuca cguauaagac gagcaaaaag     60
cuuguugguc a                                                        71

<210> SEQ ID NO 255
<211> LENGTH: 110
<212> TYPE: RNA
<213> ORGANISM: Homo sapiens

<400> SEQUENCE: 255
acccggcagu gccuccaggc cagggcagc cccugcccac cgcacacugc gcugcccag      60 acccacugug cgugugacag cggcugaucu gugccugggc agcgcgaccc              110

<210> SEQ ID NO 256
<211> LENGTH: 110
<212> TYPE: RNA
<213> ORGANISM: Homo sapiens

<400> SEQUENCE: 256
ucaccuggcc augugacuug ugggcuuccc uuugucaucc uucgccuagg gcucugagca    60
gggcagggac agcaaagggg ugcucaguug ucacuuccca cagcacggag              110

<210> SEQ ID NO 257
<211> LENGTH: 110
<212> TYPE: RNA
<213> ORGANISM: Homo sapiens

<400> SEQUENCE: 257
cggggcaccc cgcccggaca gcgcgccggc accuuggcuc uagacugcuu acugcccggg    60
ccgcccucag uaacagucuc cagucacggc caccgacgcc uggccccgcc              110

<210> SEQ ID NO 258
<211> LENGTH: 110
<212> TYPE: RNA
<213> ORGANISM: Homo sapiens

<400> SEQUENCE: 258
ccugugcaga gauuauuuuu uaaaagguca caaucaacau ucauugcugu cgguggguug    60
```
aacugugugg acaagcucac ugaacaauga augcaacugu ggccccgcuu      110

<210> SEQ ID NO 259
<211> LENGTH: 108
<212> TYPE: RNA
<213> ORGANISM: Homo sapiens

<400> SEQUENCE: 259 gaguuugag guugcuucag ugaacauuca acgcugucgg ugaguuugga auuaaaauca     60
aaaccaucga ccguugauug uacccuaugg cuaaccauca ucuacucc              108

<210> SEQ ID NO 260
<211> LENGTH: 110
<212> TYPE: RNA
<213> ORGANISM: Homo sapiens

<400> SEQUENCE: 260
ggccuggcug gacagaguug ucaugugucu gccugucuac acuugcugug cagaacaucc    60
gcucaccugu acagcaggca cagacaggca gucacaugac aacccagccu             110

<210> SEQ ID NO 261
<211> LENGTH: 110
<212> TYPE: RNA
<213> ORGANISM: Homo sapiens

<400> SEQUENCE: 261
aucauucaga aauggauauac aggaaaauga ccuaugaauu gacagacaau auagcugagu   60
uugucuguca uuucuuuagg ccaauauucu guaugacugu gcuacuucaa             110

<210> SEQ ID NO 262
<211> LENGTH: 110
<212> TYPE: RNA
<213> ORGANISM: Homo sapiens

<400> SEQUENCE: 262
gauggcugug aguuggcuua aucucagcug gcaacuguga gauguucaua caaucccuca    60
caguggucuc ugggauuaug cuaaacagag caauuuccua gcccucacga             110

<210> SEQ ID NO 263
<211> LENGTH: 110
<212> TYPE: RNA
<213> ORGANISM: Homo sapiens

<400> SEQUENCE: 263
aguauaauua uuacauaguu uuugaugucg cagauacugc aucaggaacu gauuggauaa    60
gaaucaguca ccaucaguuc cuaaugcauu gccuucagca ucuaaacaag             110

<210> SEQ ID NO 264
<211> LENGTH: 110
<212> TYPE: RNA
<213> ORGANISM: Homo sapiens

<400> SEQUENCE: 264
gugauaaugu agcgagauuu ucuguugugc uugaucuaac cauguggung cgagguauga    60
guaaaacaug guuccgucaa gcaccaugga acgucacgca gcuuucuaca             110

<210> SEQ ID NO 265
<211> LENGTH: 110
<212> TYPE: RNA

<213> ORGANISM: Homo sapiens

<400> SEQUENCE: 265
gaccagucgc ugcggggcuu uccuuugugc uugaucuaac caugugguggaacgauggaa   60 acggaacaug guucugucaa gcaccgcgga aagcaccgug cucuccugca             110

<210> SEQ ID NO 266
<211> LENGTH: 110
<212> TYPE: RNA
<213> ORGANISM: Homo sapiens

<400> SEQUENCE: 266
ccgccccggg ccgcggcucc ugauugucca aacgcaauuc ucgagucuau ggcuccggcc   60
gagaguugag ucggacguc ccgagccgcc gccccaaac cucgagcggg              110

<210> SEQ ID NO 267
<211> LENGTH: 110
<212> TYPE: RNA
<213> ORGANISM: Homo sapiens

<400> SEQUENCE: 267
ccgccccggg ccgcggcucc ugauugucca aacgcaauuc ucgagucuau ggcuccggcc   60
gagaguugag ucggacguc ccgagccgcc gccccaaac cucgagcggg              110

<210> SEQ ID NO 268
<211> LENGTH: 97
<212> TYPE: RNA
<213> ORGANISM: Homo sapiens

<400> SEQUENCE: 268
acucaggggc uucgccacug auuguccaaa cgcaauucuu guacgagucu gcggccaacc   60
gagaauugug gcuggacauc uguggcugag cuccggg                          97

<210> SEQ ID NO 269
<211> LENGTH: 110
<212> TYPE: RNA
<213> ORGANISM: Homo sapiens

<400> SEQUENCE: 269
gacagugugg cauuguaggg cuccacaccg uaucugacac uuugggcgag ggcaccaugc   60 ugaaggguguu caugaugcgg ucuggaacu ccucacggau cuuacugaug            110

<210> SEQ ID NO 270
<211> LENGTH: 110
<212> TYPE: RNA
<213> ORGANISM: Homo sapiens

<400> SEQUENCE: 270
ugaacaucca ggucugggc augaaccugg cauacaaugu agauuucugu guucguuagg   60
caacagcuac auugucugcu ggguuucagg cuaccuggaa acauguucuc             110

<210> SEQ ID NO 271
<211> LENGTH: 110
<212> TYPE: RNA
<213> ORGANISM: Homo sapiens

<400> SEQUENCE: 271
gcugcuggaa gguguaggua cccucaaugg cucaguagcc aguguagauc cgucuuucg   60 uaaucagcag cuacaucugg cuacuggguc ucugauggca ucuucuagcu             110

<210> SEQ ID NO 272
<211> LENGTH: 110
<212> TYPE: RNA
<213> ORGANISM: Homo sapiens

<400> SEQUENCE: 272
ccuggccucc ugcagugcca cgcuccgugu auuugacaag cugaguugga cacuccaugu    60
gguagagugu caguuuguca aauacccaa gugcggcaca ugcuuaccag              110

<210> SEQ ID NO 273
<211> LENGTH: 81
<212> TYPE: RNA
<213> ORGANISM: Homo sapiens

<400> SEQUENCE: 273
gggcuuucaa gucacuagug guuccguuua guagaugauu gugcauuguu ucaaaauggu    60
gcccuaguga cuacaaagcc c                                              81

<210> SEQ ID NO 274
<211> LENGTH: 60
<212> TYPE: RNA
<213> ORGANISM: Homo sapiens

<400> SEQUENCE: 274
caaucuuccu uuaucauggu auugauuuuu cagugcuucc cuuugugug agagaagaua    60

<210> SEQ ID NO 275
<211> LENGTH: 80
<212> TYPE: RNA
<213> ORGANISM: Homo sapiens

<400> SEQUENCE: 275
aggacccuuc cagagggccc ccccucaauc cuguguguucc uaauucagag gguugggugg    60
aggcucuccu gaagggcucu                                                80

<210> SEQ ID NO 276
<211> LENGTH: 63
<212> TYPE: RNA
<213> ORGANISM: Homo sapiens

<400> SEQUENCE: 276
aagaaauggu uuaccguccc acauacauuu ugaauaugua gugggaugg uaaaccgcuu     60 cuu                                                                  63

<210> SEQ ID NO 277
<211> LENGTH: 86
<212> TYPE: RNA
<213> ORGANISM: Homo sapiens

<400> SEQUENCE: 277
acugcuaacg aaugcucuga cuuuauugca cuacuguacu uuacagcuag cagugcaaua   60
guauugucaa agcaucugaa agcagg                                        86

<210> SEQ ID NO 278
<211> LENGTH: 69
<212> TYPE: RNA
<213> ORGANISM: Homo sapiens

<400> SEQUENCE: 278

```
ccaccacuua aacguggaug uacuugcuuu gaaacuaaag aaguaagugc uuccauguuu    60
uggugaugg                                                            69

<210> SEQ ID NO 279
<211> LENGTH: 73
<212> TYPE: RNA
<213> ORGANISM: Homo sapiens

<400> SEQUENCE: 279
gcucccuuca acuuuaacau ggaagugcuu ucgugacuu uaaaaguaag ugcuuccaug     60
uuuuaguagg agu                                                       73

<210> SEQ ID NO 280
<211> LENGTH: 68
<212> TYPE: RNA
<213> ORGANISM: Homo sapiens

<400> SEQUENCE: 280
ccuuugcuuu aacauggggg uaccugcugu gugaaacaaa aguaagugcu uccauguuuc    60
aguggagg                                                             68

<210> SEQ ID NO 281
<211> LENGTH: 68
<212> TYPE: RNA
<213> ORGANISM: Homo sapiens

<400> SEQUENCE: 281
ccucuacuuu aacauggagg cacuugcugu gacaugacaa aaauaagugc uuccauguuu    60
gagugugg                                                             68

<210> SEQ ID NO 282
<211> LENGTH: 82
<212> TYPE: RNA
<213> ORGANISM: Homo sapiens

<400> SEQUENCE: 282
gcuucgcucc ccuccgccuu cucuucccgg uucuucccgg agucgggaaa agcuggguug    60
agagggcgaa aaaggaugag gu                                             82

<210> SEQ ID NO 283
<211> LENGTH: 59
<212> TYPE: RNA
<213> ORGANISM: Homo sapiens

<400> SEQUENCE: 283
uuggccuccu aagccaggga uuguggguuc gagucccacc cgggguaaag aaaggccga    59

<210> SEQ ID NO 284
<211> LENGTH: 86
<212> TYPE: RNA
<213> ORGANISM: Homo sapiens

<400> SEQUENCE: 284
uugguacuug gagagaggug guccguggcg cguucgcuuu auuuauggcg cacauuacac    60
ggucgaccuc uuugcaguau cuaauc                                         86

<210> SEQ ID NO 285
<211> LENGTH: 83
<212> TYPE: RNA
<213> ORGANISM: Homo sapiens
```

```
<400> SEQUENCE: 285
cugacuaugc cuccccgcau ccccuagggc auugguguaa agcuggagac ccacugcccc      60
aggugcugcu gggggguugua guc                                            83

<210> SEQ ID NO 286
<211> LENGTH: 98
<212> TYPE: RNA
<213> ORGANISM: Homo sapiens

<400> SEQUENCE: 286
auacagugcu ugguuccuag uagguguccca guaaguguuu ugacauaau uuguuuauug      60 aggaccuccu aucaaucaag cacugugcua ggcucugg                             98

<210> SEQ ID NO 287
<211> LENGTH: 95
<212> TYPE: RNA
<213> ORGANISM: Homo sapiens

<400> SEQUENCE: 287
cucaucuguc uguuggggcug gaggcagggc cuuugugaag gcgggugug cucagaucgc      60 cucugggccc uuccuccagc cccgaggcgg auuca                                95

<210> SEQ ID NO 288
<211> LENGTH: 75
<212> TYPE: RNA
<213> ORGANISM: Homo sapiens

<400> SEQUENCE: 288 uggaguggggg gggcaggagg ggcucaggga gaaagugcau acagcccug gcccucucug      60 cccuuccguc cccug                                                      75

<210> SEQ ID NO 289
<211> LENGTH: 94
<212> TYPE: RNA
<213> ORGANISM: Homo sapiens

<400> SEQUENCE: 289
cuuuggcgau cacugccucu cugggccugu gucuuaggcu cugcaagauc aaccgagcaa      60
agcacacggc cugcagagag gcagcgcucu gccc                                 94

<210> SEQ ID NO 290
<211> LENGTH: 94
<212> TYPE: RNA
<213> ORGANISM: Homo sapiens

<400> SEQUENCE: 290
gaguuugguu uuguuugggu uuguucuagg uaugguccca gggaucccag aucaaaccag      60
gccccugggc cuauccuaga accaaccuaa gcuc                                 94

<210> SEQ ID NO 291
<211> LENGTH: 94
<212> TYPE: RNA
<213> ORGANISM: Homo sapiens

<400> SEQUENCE: 291
uguuuugagc ggggggucaag agcaauaacg aaaaauguuu gucauaaacc guuuucauu      60 auugcuccug accuccucuc auuugcuaua uuca                                 94
```

<210> SEQ ID NO 292
<211> LENGTH: 93
<212> TYPE: RNA
<213> ORGANISM: Homo sapiens

<400> SEQUENCE: 292
guagucagua guuggggggu gggaacggcu ucauacagga guugaugcac aguuauccag    60
cuccuauaug augccuuucu ucaucccuu caa                                  93

<210> SEQ ID NO 293
<211> LENGTH: 67
<212> TYPE: RNA
<213> ORGANISM: Homo sapiens

<400> SEQUENCE: 293
ucuccaacaa uauccuggug cugagugaug acucaggcga cuccagcauc agugauuuug    60
uugaaga                                                              67

<210> SEQ ID NO 294
<211> LENGTH: 94
<212> TYPE: RNA
<213> ORGANISM: Homo sapiens

<400> SEQUENCE: 294
cggggcggcc gcucucccug uccuccagga gcucacgugu gccugccugu gagcgccucg    60
acgacagagc cggcgccugc cccagugucu gcgc                                94

<210> SEQ ID NO 295
<211> LENGTH: 95
<212> TYPE: RNA
<213> ORGANISM: Homo sapiens

<400> SEQUENCE: 295
uuguaccugg ugugauuaua aagcaaugag acugauuguc auaugucguu uguggaucc    60 gucucaguua cuuuauagcc auaccuggua ucuua                               95

<210> SEQ ID NO 296
<211> LENGTH: 99
<212> TYPE: RNA
<213> ORGANISM: Homo sapiens

<400> SEQUENCE: 296
gaaacugggc ucaaggugag gggugcuauc ugugauugag ggacaugguu aauggaauug    60
ucucacacag aaaucgcacc cgucaccuug gccuacuua                           99

<210> SEQ ID NO 297
<211> LENGTH: 98
<212> TYPE: RNA
<213> ORGANISM: Homo sapiens

<400> SEQUENCE: 297
acccaaaccc uagucugcu gacuccuagu ccagggcucg ugauggcugg ugggcccuga    60 acgaggggguc uggaggccug gguuugaaua ucgacagc                           98

<210> SEQ ID NO 298
<211> LENGTH: 86
<212> TYPE: RNA
<213> ORGANISM: Homo sapiens

<400> SEQUENCE: 298

```
gucugucugc ccgcaugccu gccucucugu ugcucugaag gaggcagggg cugggccugc    60
agcugccugg gcagagcggc uccugc                                        86

<210> SEQ ID NO 299
<211> LENGTH: 68
<212> TYPE: RNA
<213> ORGANISM: Homo sapiens

<400> SEQUENCE: 299
ccauuacugu ugcuaauaug caacucuguu gaauauaaau uggaauugca cuuuagcaau    60
ggugaugg                                                            68

<210> SEQ ID NO 300
<211> LENGTH: 66
<212> TYPE: RNA
<213> ORGANISM: Homo sapiens

<400> SEQUENCE: 300
aaaaggugga uauccuucu auguuuaugu uauuuauggu uaaacauaga ggaaauucca    60
cguuuu                                                              66

<210> SEQ ID NO 301
<211> LENGTH: 70
<212> TYPE: RNA
<213> ORGANISM: Homo sapiens

<400> SEQUENCE: 301
uugaagggag aucgaccgug uuauauucgc uuuauugacu ucgaauaaua cagguugau    60 cuuuucucag                                                          70

<210> SEQ ID NO 302
<211> LENGTH: 75
<212> TYPE: RNA
<213> ORGANISM: Homo sapiens

<400> SEQUENCE: 302
agacagagaa gccaggucac gucucugcag uuacacagcu cacgagugcc ugcuggggug    60
gaaccugguc ugucu                                                    75

<210> SEQ ID NO 303
<211> LENGTH: 67
<212> TYPE: RNA
<213> ORGANISM: Homo sapiens

<400> SEQUENCE: 303
guggcacuca aacugugggg gcacuuucug cucucuggug aaagugccgc caucuuuga    60 guguuac                                                             67

<210> SEQ ID NO 304
<211> LENGTH: 67
<212> TYPE: RNA
<213> ORGANISM: Homo sapiens

<400> SEQUENCE: 304
gugggccuca aaugugagc acuauucuga ugucaagug gaaagugcug cgacauuuga    60
gcgucac                                                             67

<210> SEQ ID NO 305
```

```
<211> LENGTH: 69
<212> TYPE: RNA
<213> ORGANISM: Homo sapiens

<400> SEQUENCE: 305
gggauacuca aaauggggc gcuuccuuu uugucuguac ugggaagugc uucgauuuug      60
ggugucccc                                                           69

<210> SEQ ID NO 306
<211> LENGTH: 72
<212> TYPE: RNA
<213> ORGANISM: Homo sapiens

<400> SEQUENCE: 306
uacaucggcc auuauaauac aaccugauaa guguuauagc acuuaucaga uuguauugua   60
auugucugug ua                                                       72

<210> SEQ ID NO 307
<211> LENGTH: 102
<212> TYPE: RNA
<213> ORGANISM: Homo sapiens

<400> SEQUENCE: 307
auggagcugc ucacccugug ggccucaaau guggaggaac uauucugaug uccaagugga   60
aagugcugcg acauuugagc gucaccggug acgcccauau ca                      102

<210> SEQ ID NO 308
<211> LENGTH: 101
<212> TYPE: RNA
<213> ORGANISM: Homo sapiens

<400> SEQUENCE: 308
gcauccccuc agccugugge acucaaacug uggggcacu uucugcucuc uggugaaagu   60
gccgccaucu uuugaguguu accgcuugag aagacucaac c                       101

<210> SEQ ID NO 309
<211> LENGTH: 102
<212> TYPE: RNA
<213> ORGANISM: Homo sapiens

<400> SEQUENCE: 309
cgaggagcuc auacugggau acucaaaaug ggggcgcuuu ccuuuugucc uguuacuggg   60
aagugcuucg auuuuggggu gucccuguuu gaguagggca uc                      102

<210> SEQ ID NO 310
<211> LENGTH: 22
<212> TYPE: RNA
<213> ORGANISM: Homo sapiens

<400> SEQUENCE: 310
ugagguagua gguuguauag uu                                            22

<210> SEQ ID NO 311
<211> LENGTH: 22
<212> TYPE: RNA
<213> ORGANISM: Homo sapiens

<400> SEQUENCE: 311
ugagguagua gguugugugg uu                                            22
```

-continued

```
<210> SEQ ID NO 312
<211> LENGTH: 22
<212> TYPE: RNA
<213> ORGANISM: Homo sapiens

<400> SEQUENCE: 312
ugagguagua gguuguaugg uu                                              22

<210> SEQ ID NO 313
<211> LENGTH: 21
<212> TYPE: RNA
<213> ORGANISM: Homo sapiens

<400> SEQUENCE: 313
agagguagua gguugcauag u                                               21

<210> SEQ ID NO 314
<211> LENGTH: 21
<212> TYPE: RNA
<213> ORGANISM: Homo sapiens

<400> SEQUENCE: 314
ugagguagga gguuguauag u                                               21

<210> SEQ ID NO 315
<211> LENGTH: 22
<212> TYPE: RNA
<213> ORGANISM: Homo sapiens

<400> SEQUENCE: 315
ugagguagua gauuguauag uu                                              22

<210> SEQ ID NO 316
<211> LENGTH: 21
<212> TYPE: RNA
<213> ORGANISM: Homo sapiens

<400> SEQUENCE: 316
ugagguagua guuuguacag u                                               21

<210> SEQ ID NO 317
<211> LENGTH: 19
<212> TYPE: RNA
<213> ORGANISM: Homo sapiens

<400> SEQUENCE: 317
ugagguagua guuugugcu                                                  19

<210> SEQ ID NO 318
<211> LENGTH: 21
<212> TYPE: RNA
<213> ORGANISM: Homo sapiens

<400> SEQUENCE: 318
uggaauguaa agaaguaugu a                                               21

<210> SEQ ID NO 319
<211> LENGTH: 21
<212> TYPE: RNA
<213> ORGANISM: Homo sapiens

<400> SEQUENCE: 319
uggaagacua gugauuuugu u                                               21
```

```
<210> SEQ ID NO 320
<211> LENGTH: 23
<212> TYPE: RNA
<213> ORGANISM: Homo sapiens

<400> SEQUENCE: 320
ucuuugguua ucuagcugua uga                                              23

<210> SEQ ID NO 321
<211> LENGTH: 21
<212> TYPE: RNA
<213> ORGANISM: Homo sapiens

<400> SEQUENCE: 321
uaaagcuaga uaaccgaaag u                                                21

<210> SEQ ID NO 322
<211> LENGTH: 23
<212> TYPE: RNA
<213> ORGANISM: Homo sapiens

<400> SEQUENCE: 322
uacccuguag auccgaauuu gug                                              23

<210> SEQ ID NO 323
<211> LENGTH: 22
<212> TYPE: RNA
<213> ORGANISM: Homo sapiens

<400> SEQUENCE: 323
uacccuguag aaccgaauuu gu                                               22

<210> SEQ ID NO 324
<211> LENGTH: 22
<212> TYPE: RNA
<213> ORGANISM: Homo sapiens

<400> SEQUENCE: 324
uagcagcaca uaaugguuug ug                                               22

<210> SEQ ID NO 325
<211> LENGTH: 22
<212> TYPE: RNA
<213> ORGANISM: Homo sapiens

<400> SEQUENCE: 325
uagcagcaca ucaugguuua ca                                               22

<210> SEQ ID NO 326
<211> LENGTH: 22
<212> TYPE: RNA
<213> ORGANISM: Homo sapiens

<400> SEQUENCE: 326
uagcagcacg uaaauauugg cg                                               22

<210> SEQ ID NO 327
<211> LENGTH: 24
<212> TYPE: RNA
<213> ORGANISM: Homo sapiens

<400> SEQUENCE: 327
caaagugcuu acagugcagg uagu                                             24
```

```
<210> SEQ ID NO 328
<211> LENGTH: 20
<212> TYPE: RNA
<213> ORGANISM: Homo sapiens

<400> SEQUENCE: 328
acugcaguga aggcacuugu                                              20

<210> SEQ ID NO 329
<211> LENGTH: 22
<212> TYPE: RNA
<213> ORGANISM: Homo sapiens

<400> SEQUENCE: 329
uaaggugcau cuagugcaga ua                                           22

<210> SEQ ID NO 330
<211> LENGTH: 23
<212> TYPE: RNA
<213> ORGANISM: Homo sapiens

<400> SEQUENCE: 330
ugugcaaauc uaugcaaaac uga                                          23

<210> SEQ ID NO 331
<211> LENGTH: 23
<212> TYPE: RNA
<213> ORGANISM: Homo sapiens

<400> SEQUENCE: 331
ugugcaaauc caugcaaaac uga                                          23

<210> SEQ ID NO 332
<211> LENGTH: 22
<212> TYPE: RNA
<213> ORGANISM: Homo sapiens

<400> SEQUENCE: 332
uaaagugcuu auagugcagg ua                                           22

<210> SEQ ID NO 333
<211> LENGTH: 22
<212> TYPE: RNA
<213> ORGANISM: Homo sapiens

<400> SEQUENCE: 333
uagcuuauca gacugauguu ga                                           22

<210> SEQ ID NO 334
<211> LENGTH: 22
<212> TYPE: RNA
<213> ORGANISM: Homo sapiens

<400> SEQUENCE: 334
aagcugccag uugaagaacu gu                                           22

<210> SEQ ID NO 335
<211> LENGTH: 21
<212> TYPE: RNA
<213> ORGANISM: Homo sapiens

<400> SEQUENCE: 335
```
aucacauugc cagggauuuc c                                         21

<210> SEQ ID NO 336
<211> LENGTH: 23
<212> TYPE: RNA
<213> ORGANISM: Homo sapiens

<400> SEQUENCE: 336
aucacauugc cagggauuac cac                                       23

<210> SEQ ID NO 337
<211> LENGTH: 22
<212> TYPE: RNA
<213> ORGANISM: Homo sapiens

<400> SEQUENCE: 337
uggcucaguu cagcaggaac ag                                        22

<210> SEQ ID NO 338
<211> LENGTH: 22
<212> TYPE: RNA
<213> ORGANISM: Homo sapiens

<400> SEQUENCE: 338
cauugcacuu gucucggucu ga                                        22

<210> SEQ ID NO 339
<211> LENGTH: 22
<212> TYPE: RNA
<213> ORGANISM: Homo sapiens

<400> SEQUENCE: 339
uucaaguaau ccaggauagg cu                                        22

<210> SEQ ID NO 340
<211> LENGTH: 21
<212> TYPE: RNA
<213> ORGANISM: Homo sapiens

<400> SEQUENCE: 340
uucaaguaau ucaggauagg u                                         21

<210> SEQ ID NO 341
<211> LENGTH: 22
<212> TYPE: RNA
<213> ORGANISM: Homo sapiens

<400> SEQUENCE: 341
uucacagugg cuaaguuccg cc                                        22

<210> SEQ ID NO 342
<211> LENGTH: 20
<212> TYPE: RNA
<213> ORGANISM: Homo sapiens

<400> SEQUENCE: 342
uucacagugg cuaaguucug                                           20

<210> SEQ ID NO 343
<211> LENGTH: 22
<212> TYPE: RNA
<213> ORGANISM: Homo sapiens

<400> SEQUENCE: 343

-continued aaggagcuca cagucuauug ag                    22

<210> SEQ ID NO 344
<211> LENGTH: 22
<212> TYPE: RNA
<213> ORGANISM: Homo sapiens

<400> SEQUENCE: 344
cuagcaccau cugaaaucgg uu                    22

<210> SEQ ID NO 345
<211> LENGTH: 20
<212> TYPE: RNA
<213> ORGANISM: Homo sapiens

<400> SEQUENCE: 345
uagcaccauu ugaaaucagu                       20

<210> SEQ ID NO 346
<211> LENGTH: 22
<212> TYPE: RNA
<213> ORGANISM: Homo sapiens

<400> SEQUENCE: 346
uagcaccauu ugaaaucggu ua                    22

<210> SEQ ID NO 347
<211> LENGTH: 23
<212> TYPE: RNA
<213> ORGANISM: Homo sapiens

<400> SEQUENCE: 347
uguaaacauc cucgacugga agc                   23

<210> SEQ ID NO 348
<211> LENGTH: 22
<212> TYPE: RNA
<213> ORGANISM: Homo sapiens

<400> SEQUENCE: 348
cuuucagucg gauguuugca gc                    22

<210> SEQ ID NO 349
<211> LENGTH: 21
<212> TYPE: RNA
<213> ORGANISM: Homo sapiens

<400> SEQUENCE: 349
uguaaacauc cuacacucag c                     21

<210> SEQ ID NO 350
<211> LENGTH: 23
<212> TYPE: RNA
<213> ORGANISM: Homo sapiens

<400> SEQUENCE: 350
uguaaacauc cuacacucuc agc                   23

<210> SEQ ID NO 351
<211> LENGTH: 22
<212> TYPE: RNA
<213> ORGANISM: Homo sapiens

```
<400> SEQUENCE: 351
uguaaacauc cccgacugga ag                                      22

<210> SEQ ID NO 352
<211> LENGTH: 20
<212> TYPE: RNA
<213> ORGANISM: Homo sapiens

<400> SEQUENCE: 352
uguaaacauc cuugacugga                                         20

<210> SEQ ID NO 353
<211> LENGTH: 21
<212> TYPE: RNA
<213> ORGANISM: Homo sapiens

<400> SEQUENCE: 353
ggcaagaugc uggcauagcu g                                       21

<210> SEQ ID NO 354
<211> LENGTH: 21
<212> TYPE: RNA
<213> ORGANISM: Homo sapiens

<400> SEQUENCE: 354
uauugcacau uacuaaguug c                                       21

<210> SEQ ID NO 355
<211> LENGTH: 19
<212> TYPE: RNA
<213> ORGANISM: Homo sapiens

<400> SEQUENCE: 355
gugcauugua guugcauug                                          19

<210> SEQ ID NO 356
<211> LENGTH: 22
<212> TYPE: RNA
<213> ORGANISM: Homo sapiens

<400> SEQUENCE: 356
uggcaguguc uuagcugguu gu                                      22

<210> SEQ ID NO 357
<211> LENGTH: 22
<212> TYPE: RNA
<213> ORGANISM: Homo sapiens

<400> SEQUENCE: 357
aggcaguguc auuagcugau ug                                      22

<210> SEQ ID NO 358
<211> LENGTH: 22
<212> TYPE: RNA
<213> ORGANISM: Homo sapiens

<400> SEQUENCE: 358
aggcagugua guuagcugau ug                                      22

<210> SEQ ID NO 359
<211> LENGTH: 22
<212> TYPE: RNA
<213> ORGANISM: Homo sapiens
```

```
<400> SEQUENCE: 359
uauugcacuu gucccggccu gu                                              22

<210> SEQ ID NO 360
<211> LENGTH: 22
<212> TYPE: RNA
<213> ORGANISM: Homo sapiens

<400> SEQUENCE: 360
aaagugcugu ucgugcaggu ag                                              22

<210> SEQ ID NO 361
<211> LENGTH: 22
<212> TYPE: RNA
<213> ORGANISM: Homo sapiens

<400> SEQUENCE: 361
uucaacgggu auuuauugag ca                                              22

<210> SEQ ID NO 362
<211> LENGTH: 22
<212> TYPE: RNA
<213> ORGANISM: Homo sapiens

<400> SEQUENCE: 362
uuuggcacua gcacauuuuu gc                                              22

<210> SEQ ID NO 363
<211> LENGTH: 22
<212> TYPE: RNA
<213> ORGANISM: Homo sapiens

<400> SEQUENCE: 363
ugagguagua aguuguauug uu                                              22

<210> SEQ ID NO 364
<211> LENGTH: 22
<212> TYPE: RNA
<213> ORGANISM: Homo sapiens

<400> SEQUENCE: 364
aacccguaga uccgaucuug ug                                              22

<210> SEQ ID NO 365
<211> LENGTH: 22
<212> TYPE: RNA
<213> ORGANISM: Homo sapiens

<400> SEQUENCE: 365
cacccguaga accgaccuug cg                                              22

<210> SEQ ID NO 366
<211> LENGTH: 22
<212> TYPE: RNA
<213> ORGANISM: Homo sapiens

<400> SEQUENCE: 366
uacaguacug ugauaacuga ag                                              22

<210> SEQ ID NO 367
<211> LENGTH: 22
<212> TYPE: RNA
```

```
<213> ORGANISM: Homo sapiens

<400> SEQUENCE: 367
uacaguacug ugauaacuga ag                                          22

<210> SEQ ID NO 368
<211> LENGTH: 23
<212> TYPE: RNA
<213> ORGANISM: Homo sapiens

<400> SEQUENCE: 368
agcagcauug uacagggcua uga                                         23

<210> SEQ ID NO 369
<211> LENGTH: 20
<212> TYPE: RNA
<213> ORGANISM: Homo sapiens

<400> SEQUENCE: 369
ucaaaugcuc agacuccugu                                             20

<210> SEQ ID NO 370
<211> LENGTH: 24
<212> TYPE: RNA
<213> ORGANISM: Homo sapiens

<400> SEQUENCE: 370
aaaagugcuu acagugcagg uagc                                        24

<210> SEQ ID NO 371
<211> LENGTH: 21
<212> TYPE: RNA
<213> ORGANISM: Homo sapiens

<400> SEQUENCE: 371
uaaagugcug acagugcaga u                                           21

<210> SEQ ID NO 372
<211> LENGTH: 23
<212> TYPE: RNA
<213> ORGANISM: Homo sapiens

<400> SEQUENCE: 372
agcagcauug uacagggcua uca                                         23

<210> SEQ ID NO 373
<211> LENGTH: 23
<212> TYPE: RNA
<213> ORGANISM: Homo sapiens

<400> SEQUENCE: 373
uggaguguga caaugguguu ugu                                         23

<210> SEQ ID NO 374
<211> LENGTH: 22
<212> TYPE: RNA
<213> ORGANISM: Homo sapiens

<400> SEQUENCE: 374
uuaaggcacg cggugaaugc ca                                          22

<210> SEQ ID NO 375
<211> LENGTH: 23
```

```
<212> TYPE: RNA
<213> ORGANISM: Homo sapiens

<400> SEQUENCE: 375
ucccugagac ccuuuaaccu gug                                          23

<210> SEQ ID NO 376
<211> LENGTH: 22
<212> TYPE: RNA
<213> ORGANISM: Homo sapiens

<400> SEQUENCE: 376
ucccugagac ccuaacuugu ga                                           22

<210> SEQ ID NO 377
<211> LENGTH: 21
<212> TYPE: RNA
<213> ORGANISM: Homo sapiens

<400> SEQUENCE: 377
cauuauuacu uuugguacgc g                                            21

<210> SEQ ID NO 378
<211> LENGTH: 21
<212> TYPE: RNA
<213> ORGANISM: Homo sapiens

<400> SEQUENCE: 378
ucguaccgug aguaauaaug c                                            21

<210> SEQ ID NO 379
<211> LENGTH: 22
<212> TYPE: RNA
<213> ORGANISM: Homo sapiens

<400> SEQUENCE: 379
ucggauccgu cugagcuugg cu                                           22

<210> SEQ ID NO 380
<211> LENGTH: 22
<212> TYPE: RNA
<213> ORGANISM: Homo sapiens

<400> SEQUENCE: 380
ucacagugaa ccggucucuu uu                                           22

<210> SEQ ID NO 381
<211> LENGTH: 22
<212> TYPE: RNA
<213> ORGANISM: Homo sapiens

<400> SEQUENCE: 381
ucacagugaa ccggucucuu uc                                           22

<210> SEQ ID NO 382
<211> LENGTH: 21
<212> TYPE: RNA
<213> ORGANISM: Homo sapiens

<400> SEQUENCE: 382
cuuuuugcgg ucugggcuug c                                            21

<210> SEQ ID NO 383
```

```
<211> LENGTH: 20
<212> TYPE: RNA
<213> ORGANISM: Homo sapiens

<400> SEQUENCE: 383
cagugcaaug uuaaaagggc                                                   20

<210> SEQ ID NO 384
<211> LENGTH: 22
<212> TYPE: RNA
<213> ORGANISM: Homo sapiens

<400> SEQUENCE: 384
cagugcaaug augaaagggc au                                                22

<210> SEQ ID NO 385
<211> LENGTH: 22
<212> TYPE: RNA
<213> ORGANISM: Homo sapiens

<400> SEQUENCE: 385
uaacagucua cagccauggu cg                                                22

<210> SEQ ID NO 386
<211> LENGTH: 22
<212> TYPE: RNA
<213> ORGANISM: Homo sapiens

<400> SEQUENCE: 386
uugguccccu ucaaccagcu gu                                                22

<210> SEQ ID NO 387
<211> LENGTH: 21
<212> TYPE: RNA
<213> ORGANISM: Homo sapiens

<400> SEQUENCE: 387
uugguccccu ucaaccagcu a                                                 21

<210> SEQ ID NO 388
<211> LENGTH: 21
<212> TYPE: RNA
<213> ORGANISM: Homo sapiens

<400> SEQUENCE: 388
ugugacuggu ugaccagagg g                                                 21

<210> SEQ ID NO 389
<211> LENGTH: 23
<212> TYPE: RNA
<213> ORGANISM: Homo sapiens

<400> SEQUENCE: 389
uauggcuuuu uauuccuaug uga                                               23

<210> SEQ ID NO 390
<211> LENGTH: 22
<212> TYPE: RNA
<213> ORGANISM: Homo sapiens

<400> SEQUENCE: 390
uauggcuuuu cauuccuaug ug                                                22
```

```
<210> SEQ ID NO 391
<211> LENGTH: 23
<212> TYPE: RNA
<213> ORGANISM: Homo sapiens

<400> SEQUENCE: 391
acuccauuug uuuugaugau gga                                              23

<210> SEQ ID NO 392
<211> LENGTH: 22
<212> TYPE: RNA
<213> ORGANISM: Homo sapiens

<400> SEQUENCE: 392
uauugcuuaa gaauacgcgu ag                                               22

<210> SEQ ID NO 393
<211> LENGTH: 17
<212> TYPE: RNA
<213> ORGANISM: Homo sapiens

<400> SEQUENCE: 393
agcuggucuu gugaauc                                                     17

<210> SEQ ID NO 394
<211> LENGTH: 18
<212> TYPE: RNA
<213> ORGANISM: Homo sapiens

<400> SEQUENCE: 394
ucuacagugc acgugucu                                                    18

<210> SEQ ID NO 395
<211> LENGTH: 21
<212> TYPE: RNA
<213> ORGANISM: Homo sapiens

<400> SEQUENCE: 395
agugguuuua cccuauggua g                                                21

<210> SEQ ID NO 396
<211> LENGTH: 21
<212> TYPE: RNA
<213> ORGANISM: Homo sapiens

<400> SEQUENCE: 396
aacacugucu gguaaagaug g                                                21

<210> SEQ ID NO 397
<211> LENGTH: 23
<212> TYPE: RNA
<213> ORGANISM: Homo sapiens

<400> SEQUENCE: 397
uguaguguuu ccuacuuuau gga                                              23

<210> SEQ ID NO 398
<211> LENGTH: 20
<212> TYPE: RNA
<213> ORGANISM: Homo sapiens

<400> SEQUENCE: 398
cauaaaguag aaagcacuac                                                  20
```

```
<210> SEQ ID NO 399
<211> LENGTH: 22
<212> TYPE: RNA
<213> ORGANISM: Homo sapiens

<400> SEQUENCE: 399
ugagaugaag cacuguagcu ca                                              22

<210> SEQ ID NO 400
<211> LENGTH: 22
<212> TYPE: RNA
<213> ORGANISM: Homo sapiens

<400> SEQUENCE: 400
uacaguauag augauguacu ag                                              22

<210> SEQ ID NO 401
<211> LENGTH: 24
<212> TYPE: RNA
<213> ORGANISM: Homo sapiens

<400> SEQUENCE: 401
guccaguuuu cccaggaauc ccuu                                            24

<210> SEQ ID NO 402
<211> LENGTH: 22
<212> TYPE: RNA
<213> ORGANISM: Homo sapiens

<400> SEQUENCE: 402
ugagaacuga auuccauggg uu                                              22

<210> SEQ ID NO 403
<211> LENGTH: 20
<212> TYPE: RNA
<213> ORGANISM: Homo sapiens

<400> SEQUENCE: 403
guguguggaa augcuucugc                                                 20

<210> SEQ ID NO 404
<211> LENGTH: 22
<212> TYPE: RNA
<213> ORGANISM: Homo sapiens

<400> SEQUENCE: 404
ucagugcacu acagaacuuu gu                                              22

<210> SEQ ID NO 405
<211> LENGTH: 22
<212> TYPE: RNA
<213> ORGANISM: Homo sapiens

<400> SEQUENCE: 405
ucagugcauc acagaacuuu gu                                              22

<210> SEQ ID NO 406
<211> LENGTH: 22
<212> TYPE: RNA
<213> ORGANISM: Homo sapiens

<400> SEQUENCE: 406
ucuggcuccg ugucuucacu cc                                              22
```

```
<210> SEQ ID NO 407
<211> LENGTH: 22
<212> TYPE: RNA
<213> ORGANISM: Homo sapiens

<400> SEQUENCE: 407
ucucccaacc cuuguaccag ug                                               22

<210> SEQ ID NO 408
<211> LENGTH: 22
<212> TYPE: RNA
<213> ORGANISM: Homo sapiens

<400> SEQUENCE: 408
acuagacuga agcuccuuga gg                                               22

<210> SEQ ID NO 409
<211> LENGTH: 21
<212> TYPE: RNA
<213> ORGANISM: Homo sapiens

<400> SEQUENCE: 409
ucagugcaug acagaacuug g                                                21

<210> SEQ ID NO 410
<211> LENGTH: 20
<212> TYPE: RNA
<213> ORGANISM: Homo sapiens

<400> SEQUENCE: 410
uugcauaguc acaaaaguga                                                  20

<210> SEQ ID NO 411
<211> LENGTH: 22
<212> TYPE: RNA
<213> ORGANISM: Homo sapiens

<400> SEQUENCE: 411
uagguuaucc guguugccuu cg                                               22

<210> SEQ ID NO 412
<211> LENGTH: 22
<212> TYPE: RNA
<213> ORGANISM: Homo sapiens

<400> SEQUENCE: 412
aaucauacac gguugaccua uu                                               22

<210> SEQ ID NO 413
<211> LENGTH: 22
<212> TYPE: RNA
<213> ORGANISM: Homo sapiens

<400> SEQUENCE: 413
uuaaugcuaa ucgugauagg gg                                               22

<210> SEQ ID NO 414
<211> LENGTH: 23
<212> TYPE: RNA
<213> ORGANISM: Homo sapiens

<400> SEQUENCE: 414
```

```
aacauucaac gcugucggug agu                                              23

<210> SEQ ID NO 415
<211> LENGTH: 24
<212> TYPE: RNA
<213> ORGANISM: Homo sapiens

<400> SEQUENCE: 415
aacauucauu gcugucggug gguu                                             24

<210> SEQ ID NO 416
<211> LENGTH: 22
<212> TYPE: RNA
<213> ORGANISM: Homo sapiens

<400> SEQUENCE: 416
aacauucaac cugucgguga gu                                               22

<210> SEQ ID NO 417
<211> LENGTH: 22
<212> TYPE: RNA
<213> ORGANISM: Homo sapiens

<400> SEQUENCE: 417
uuuggcaaug guagaacuca ca                                               22

<210> SEQ ID NO 418
<211> LENGTH: 21
<212> TYPE: RNA
<213> ORGANISM: Homo sapiens

<400> SEQUENCE: 418
ugguucuaga cuugccaacu a                                                21

<210> SEQ ID NO 419
<211> LENGTH: 23
<212> TYPE: RNA
<213> ORGANISM: Homo sapiens

<400> SEQUENCE: 419
uauggcacug guagaauuca cug                                              23

<210> SEQ ID NO 420
<211> LENGTH: 22
<212> TYPE: RNA
<213> ORGANISM: Homo sapiens

<400> SEQUENCE: 420
uggacggaga acugauaagg gu                                               22

<210> SEQ ID NO 421
<211> LENGTH: 18
<212> TYPE: RNA
<213> ORGANISM: Homo sapiens

<400> SEQUENCE: 421
uggagagaaa ggcaguuc                                                    18

<210> SEQ ID NO 422
<211> LENGTH: 23
<212> TYPE: RNA
<213> ORGANISM: Homo sapiens

<400> SEQUENCE: 422
```

```
caaagaauuc uccuuuuggg cuu                                              23

<210> SEQ ID NO 423
<211> LENGTH: 21
<212> TYPE: RNA
<213> ORGANISM: Homo sapiens

<400> SEQUENCE: 423
ucgugucuug uguugcagcc g                                                21

<210> SEQ ID NO 424
<211> LENGTH: 22
<212> TYPE: RNA
<213> ORGANISM: Homo sapiens

<400> SEQUENCE: 424
caucccuugc augguggagg gu                                               22

<210> SEQ ID NO 425
<211> LENGTH: 23
<212> TYPE: RNA
<213> ORGANISM: Homo sapiens

<400> SEQUENCE: 425
gugccuacug agcugauauc agu                                              23

<210> SEQ ID NO 426
<211> LENGTH: 22
<212> TYPE: RNA
<213> ORGANISM: Homo sapiens

<400> SEQUENCE: 426
ugauauguuu gauauauuag gu                                               22

<210> SEQ ID NO 427
<211> LENGTH: 22
<212> TYPE: RNA
<213> ORGANISM: Homo sapiens

<400> SEQUENCE: 427
caacggaauc ccaaaagcag cu                                               22

<210> SEQ ID NO 428
<211> LENGTH: 21
<212> TYPE: RNA
<213> ORGANISM: Homo sapiens

<400> SEQUENCE: 428
cugaccuaug aauugacagc c                                                21

<210> SEQ ID NO 429
<211> LENGTH: 21
<212> TYPE: RNA
<213> ORGANISM: Homo sapiens

<400> SEQUENCE: 429
aacuggccua caaaguccca g                                                21

<210> SEQ ID NO 430
<211> LENGTH: 22
<212> TYPE: RNA
<213> ORGANISM: Homo sapiens
```

```
<400> SEQUENCE: 430
uguaacagca acuccaugug ga                                            22

<210> SEQ ID NO 431
<211> LENGTH: 21
<212> TYPE: RNA
<213> ORGANISM: Homo sapiens

<400> SEQUENCE: 431
uagcagcaca gaaauauugg c                                             21

<210> SEQ ID NO 432
<211> LENGTH: 21
<212> TYPE: RNA
<213> ORGANISM: Homo sapiens

<400> SEQUENCE: 432
uagguaguuu cauguuguug g                                             21

<210> SEQ ID NO 433
<211> LENGTH: 21
<212> TYPE: RNA
<213> ORGANISM: Homo sapiens

<400> SEQUENCE: 433
uagguaguuu ccuguuguug g                                             21

<210> SEQ ID NO 434
<211> LENGTH: 22
<212> TYPE: RNA
<213> ORGANISM: Homo sapiens

<400> SEQUENCE: 434
uucaccaccu ucuccaccca gc                                            22

<210> SEQ ID NO 435
<211> LENGTH: 19
<212> TYPE: RNA
<213> ORGANISM: Homo sapiens

<400> SEQUENCE: 435
gguccagagg ggagauagg                                                19

<210> SEQ ID NO 436
<211> LENGTH: 23
<212> TYPE: RNA
<213> ORGANISM: Homo sapiens

<400> SEQUENCE: 436
cccaguguuc agacuaccug uuc                                           23

<210> SEQ ID NO 437
<211> LENGTH: 22
<212> TYPE: RNA
<213> ORGANISM: Homo sapiens

<400> SEQUENCE: 437
uacaguaguc ugcacauugg uu                                            22

<210> SEQ ID NO 438
<211> LENGTH: 23
<212> TYPE: RNA
<213> ORGANISM: Homo sapiens
```

```
<400> SEQUENCE: 438
cccaguguuu agacuaucug uuc                                            23

<210> SEQ ID NO 439
<211> LENGTH: 22
<212> TYPE: RNA
<213> ORGANISM: Homo sapiens

<400> SEQUENCE: 439
uaacacuguc ugguaacgau gu                                             22

<210> SEQ ID NO 440
<211> LENGTH: 24
<212> TYPE: RNA
<213> ORGANISM: Homo sapiens

<400> SEQUENCE: 440
cucuaauacu gccugguaau gaug                                           24

<210> SEQ ID NO 441
<211> LENGTH: 22
<212> TYPE: RNA
<213> ORGANISM: Homo sapiens

<400> SEQUENCE: 441
aauacugccg gguaaugaug ga                                             22

<210> SEQ ID NO 442
<211> LENGTH: 22
<212> TYPE: RNA
<213> ORGANISM: Homo sapiens

<400> SEQUENCE: 442
agagguauag ggcaugggaa ga                                             22

<210> SEQ ID NO 443
<211> LENGTH: 22
<212> TYPE: RNA
<213> ORGANISM: Homo sapiens

<400> SEQUENCE: 443
gugaaauguu uaggaccacu ag                                             22

<210> SEQ ID NO 444
<211> LENGTH: 22
<212> TYPE: RNA
<213> ORGANISM: Homo sapiens

<400> SEQUENCE: 444
uucccuuugu cauccuaugc cu                                             22

<210> SEQ ID NO 445
<211> LENGTH: 22
<212> TYPE: RNA
<213> ORGANISM: Homo sapiens

<400> SEQUENCE: 445
uccuucauuc caccggaguc ug                                             22

<210> SEQ ID NO 446
<211> LENGTH: 22
<212> TYPE: RNA
```

```
<213> ORGANISM: Homo sapiens

<400> SEQUENCE: 446
uggaauguaa ggaagugugu gg                                              22

<210> SEQ ID NO 447
<211> LENGTH: 22
<212> TYPE: RNA
<213> ORGANISM: Homo sapiens

<400> SEQUENCE: 447
auaagacgag caaaaagcuu gu                                              22

<210> SEQ ID NO 448
<211> LENGTH: 21
<212> TYPE: RNA
<213> ORGANISM: Homo sapiens

<400> SEQUENCE: 448
cugugcgugu gacagcggcu g                                               21

<210> SEQ ID NO 449
<211> LENGTH: 22
<212> TYPE: RNA
<213> ORGANISM: Homo sapiens

<400> SEQUENCE: 449
uucccuuugu cauccuucgc cu                                              22

<210> SEQ ID NO 450
<211> LENGTH: 21
<212> TYPE: RNA
<213> ORGANISM: Homo sapiens

<400> SEQUENCE: 450
uaacagucuc cagucacggc c                                               21

<210> SEQ ID NO 451
<211> LENGTH: 22
<212> TYPE: RNA
<213> ORGANISM: Homo sapiens

<400> SEQUENCE: 451
accaucgacc guugauugua cc                                              22

<210> SEQ ID NO 452
<211> LENGTH: 21
<212> TYPE: RNA
<213> ORGANISM: Homo sapiens

<400> SEQUENCE: 452
acagcaggca cagacaggca g                                               21

<210> SEQ ID NO 453
<211> LENGTH: 21
<212> TYPE: RNA
<213> ORGANISM: Homo sapiens

<400> SEQUENCE: 453
augaccuaug aauugacaga c                                               21

<210> SEQ ID NO 454
<211> LENGTH: 21
```

```
<212> TYPE: RNA
<213> ORGANISM: Homo sapiens

<400> SEQUENCE: 454
uaaucucagc uggcaacugu g                                          21

<210> SEQ ID NO 455
<211> LENGTH: 24
<212> TYPE: RNA
<213> ORGANISM: Homo sapiens

<400> SEQUENCE: 455
uacugcauca ggaacugauu ggau                                       24

<210> SEQ ID NO 456
<211> LENGTH: 21
<212> TYPE: RNA
<213> ORGANISM: Homo sapiens

<400> SEQUENCE: 456
uugugcuuga ucuaaccaug u                                          21

<210> SEQ ID NO 457
<211> LENGTH: 21
<212> TYPE: RNA
<213> ORGANISM: Homo sapiens

<400> SEQUENCE: 457
ugauugucca aacgcaauuc u                                          21

<210> SEQ ID NO 458
<211> LENGTH: 21
<212> TYPE: RNA
<213> ORGANISM: Homo sapiens

<400> SEQUENCE: 458
ccacaccgua ucugacacuu u                                          21

<210> SEQ ID NO 459
<211> LENGTH: 23
<212> TYPE: RNA
<213> ORGANISM: Homo sapiens

<400> SEQUENCE: 459
agcuacauug ucugcugggu uuc                                        23

<210> SEQ ID NO 460
<211> LENGTH: 24
<212> TYPE: RNA
<213> ORGANISM: Homo sapiens

<400> SEQUENCE: 460
agcuacaucu ggcuacuggg ucuc                                       24

<210> SEQ ID NO 461
<211> LENGTH: 21
<212> TYPE: RNA
<213> ORGANISM: Homo sapiens

<400> SEQUENCE: 461
ugucaguuug ucaaauaccc c                                          21

<210> SEQ ID NO 462
```

```
<211> LENGTH: 23
<212> TYPE: RNA
<213> ORGANISM: Homo sapiens

<400> SEQUENCE: 462
caagucacua gugguuccgu uua                                             23

<210> SEQ ID NO 463
<211> LENGTH: 21
<212> TYPE: RNA
<213> ORGANISM: Homo sapiens

<400> SEQUENCE: 463 agggccccccc cucaauccug u                                              21

<210> SEQ ID NO 464
<211> LENGTH: 22
<212> TYPE: RNA
<213> ORGANISM: Homo sapiens

<400> SEQUENCE: 464
ugguuuaccg ucccacauac au                                              22

<210> SEQ ID NO 465
<211> LENGTH: 23
<212> TYPE: RNA
<213> ORGANISM: Homo sapiens

<400> SEQUENCE: 465
cagugcaaua guauugucaa agc                                             23

<210> SEQ ID NO 466
<211> LENGTH: 23
<212> TYPE: RNA
<213> ORGANISM: Homo sapiens

<400> SEQUENCE: 466
uaagugcuuc cauguuuugg uga                                             23

<210> SEQ ID NO 467
<211> LENGTH: 23
<212> TYPE: RNA
<213> ORGANISM: Homo sapiens

<400> SEQUENCE: 467
acuuuaacau ggaagugcuu ucu                                             23

<210> SEQ ID NO 468
<211> LENGTH: 23
<212> TYPE: RNA
<213> ORGANISM: Homo sapiens

<400> SEQUENCE: 468
uaagugcuuc cauguuuuag uag                                             23

<210> SEQ ID NO 469
<211> LENGTH: 22
<212> TYPE: RNA
<213> ORGANISM: Homo sapiens

<400> SEQUENCE: 469
uuuaacaugg ggguaccugc ug                                              22
```

```
<210> SEQ ID NO 470
<211> LENGTH: 23
<212> TYPE: RNA
<213> ORGANISM: Homo sapiens

<400> SEQUENCE: 470
uaagugcuuc cauguuucag ugg                                              23

<210> SEQ ID NO 471
<211> LENGTH: 23
<212> TYPE: RNA
<213> ORGANISM: Homo sapiens

<400> SEQUENCE: 471
uaagugcuuc cauguugag ugu                                               23

<210> SEQ ID NO 472
<211> LENGTH: 23
<212> TYPE: RNA
<213> ORGANISM: Homo sapiens

<400> SEQUENCE: 472
aaaagcuggg uugagagggc gaa                                              23

<210> SEQ ID NO 473
<211> LENGTH: 21
<212> TYPE: RNA
<213> ORGANISM: Homo sapiens

<400> SEQUENCE: 473
uaagccaggg auugugggu c                                                 21

<210> SEQ ID NO 474
<211> LENGTH: 22
<212> TYPE: RNA
<213> ORGANISM: Homo sapiens

<400> SEQUENCE: 474
gcacauuaca cggucgaccu cu                                               22

<210> SEQ ID NO 475
<211> LENGTH: 23
<212> TYPE: RNA
<213> ORGANISM: Homo sapiens

<400> SEQUENCE: 475
cgcauccccu agggcauugg ugu                                              23

<210> SEQ ID NO 476
<211> LENGTH: 22
<212> TYPE: RNA
<213> ORGANISM: Homo sapiens

<400> SEQUENCE: 476
ccacugcccc aggugcugcu gg                                               22

<210> SEQ ID NO 477
<211> LENGTH: 21
<212> TYPE: RNA
<213> ORGANISM: Homo sapiens

<400> SEQUENCE: 477
ccuaguaggu guccaguaag u                                                21
```

<210> SEQ ID NO 478
<211> LENGTH: 20
<212> TYPE: RNA
<213> ORGANISM: Homo sapiens

<400> SEQUENCE: 478
ccucugggcc cuuccuccag								20

<210> SEQ ID NO 479
<211> LENGTH: 22
<212> TYPE: RNA
<213> ORGANISM: Homo sapiens

<400> SEQUENCE: 479
cuggcccucu cugcccuucc gu							22

<210> SEQ ID NO 480
<211> LENGTH: 23
<212> TYPE: RNA
<213> ORGANISM: Homo sapiens

<400> SEQUENCE: 480
gcaaagcaca cggccugcag aga							23

<210> SEQ ID NO 481
<211> LENGTH: 21
<212> TYPE: RNA
<213> ORGANISM: Homo sapiens

<400> SEQUENCE: 481
gccccugggc cuauccuaga a								21

<210> SEQ ID NO 482
<211> LENGTH: 23
<212> TYPE: RNA
<213> ORGANISM: Homo sapiens

<400> SEQUENCE: 482
ucaagagcaa uaacgaaaaa ugu							23

<210> SEQ ID NO 483
<211> LENGTH: 23
<212> TYPE: RNA
<213> ORGANISM: Homo sapiens

<400> SEQUENCE: 483
uccagcuccu auaugaugcc uuu							23

<210> SEQ ID NO 484
<211> LENGTH: 23
<212> TYPE: RNA
<213> ORGANISM: Homo sapiens

<400> SEQUENCE: 484
uccagcauca gugauuuugu uga							23

<210> SEQ ID NO 485
<211> LENGTH: 21
<212> TYPE: RNA
<213> ORGANISM: Homo sapiens

<400> SEQUENCE: 485
ucccuguccu ccaggagcuc a								21

```
<210> SEQ ID NO 486
<211> LENGTH: 23
<212> TYPE: RNA
<213> ORGANISM: Homo sapiens

<400> SEQUENCE: 486
uccgucucag uuacuuuaua gcc                                            23

<210> SEQ ID NO 487
<211> LENGTH: 24
<212> TYPE: RNA
<213> ORGANISM: Homo sapiens

<400> SEQUENCE: 487
ucucacacag aaaucgcacc cguc                                           24

<210> SEQ ID NO 488
<211> LENGTH: 21
<212> TYPE: RNA
<213> ORGANISM: Homo sapiens

<400> SEQUENCE: 488
ugcugacucc uaguccaggg c                                              21

<210> SEQ ID NO 489
<211> LENGTH: 23
<212> TYPE: RNA
<213> ORGANISM: Homo sapiens

<400> SEQUENCE: 489
ugucugcccg caugccugcc ucu                                            23

<210> SEQ ID NO 490
<211> LENGTH: 22
<212> TYPE: RNA
<213> ORGANISM: Homo sapiens

<400> SEQUENCE: 490
aauugcacuu uagcaauggu ga                                             22

<210> SEQ ID NO 491
<211> LENGTH: 22
<212> TYPE: RNA
<213> ORGANISM: Homo sapiens

<400> SEQUENCE: 491
acauagagga aauuccacgu uu                                             22

<210> SEQ ID NO 492
<211> LENGTH: 21
<212> TYPE: RNA
<213> ORGANISM: Homo sapiens

<400> SEQUENCE: 492
aauaauacau gguugaucuu u                                              21

<210> SEQ ID NO 493
<211> LENGTH: 21
<212> TYPE: RNA
<213> ORGANISM: Homo sapiens

<400> SEQUENCE: 493
gccugcuggg guggaaccug g                                              21
```

```
<210> SEQ ID NO 494
<211> LENGTH: 21
<212> TYPE: RNA
<213> ORGANISM: Homo sapiens

<400> SEQUENCE: 494
gugccgccau cuuuugagug u                                            21

<210> SEQ ID NO 495
<211> LENGTH: 23
<212> TYPE: RNA
<213> ORGANISM: Homo sapiens

<400> SEQUENCE: 495
aaagugcugc gacauuugag cgu                                          23

<210> SEQ ID NO 496
<211> LENGTH: 22
<212> TYPE: RNA
<213> ORGANISM: Homo sapiens

<400> SEQUENCE: 496
acucaaaaug ggggcgcuuu cc                                           22

<210> SEQ ID NO 497
<211> LENGTH: 23
<212> TYPE: RNA
<213> ORGANISM: Homo sapiens

<400> SEQUENCE: 497
gaagugcuuc gauuuugggg ugu                                          23

<210> SEQ ID NO 498
<211> LENGTH: 22
<212> TYPE: RNA
<213> ORGANISM: Homo sapiens

<400> SEQUENCE: 498
uuauaauaca accugauaag ug                                           22
```

METHODS FOR DIAGNOSING LUNG CANCER USING MICRORNA SIGNATURES

CROSS-REFERENCE TO RELATED APPLICATIONS

This application is filed under 35 U.S.C. §111(a) as a divisional application which claims priority under 35 U.S.C. §119, 35 U.S.C. §120 and the Patent Cooperation Treaty to: parent application U.S. Ser. No. 12/160,061 filed under 35 U.S.C. §371 on Jul. 3, 2008, now allowed; which claims priority to PCT/US2007/000159 filed under the authority of the Patent Cooperation Treaty on Jan. 3, 2007, published; which claims priority to U.S. Provisional Application Ser. No. 60/756,585 filed under 35 U.S.C. §111(b) on Jan. 5, 2006; the disclosures of all priority applications are incorporated herein by reference.

GOVERNMENT SUPPORT

This invention was supported, in whole or in part, by Program Project Grant Nos. P01CA76259, P01CA81534 and P30CA56036 from the National Cancer Institute. The Government has certain rights in this invention.

BACKGROUND OF THE INVENTION

Cancer, the uncontrolled growth of malignant cells, is a major health problem of the modern medical era and is one of the leading causes of death in developed countries. In the United States, one in four deaths is caused by cancer (Jemal, A. et al., *CA Cancer J. Clin.* 52:23-47 (2002)). Among cancers, those that arise from organs and solid tissues, known as solid cancers (e.g., colon cancer, lung cancer, breast cancer, stomach cancer, prostate cancer, pancreatic cancer) are among the most-commonly identified human cancers.

For example, prostate cancer is the most frequently diagnosed noncutaneous malignancy among men in industrialized countries, and, in the United States, 1 in 8 men will develop prostate cancer during his life (Simard, J. et al., *Endocrinology* 143(6):2029-40 (2002)). The incidence of prostate cancer has dramatically increased over the last decades and prostate cancer is now a leading cause of death in the United States and Western Europe (Peschel, R. E. and J. W. Colberg, *Lancet* 4:233-41 (2003); Nelson, W. G. et al., *N. Engl. J. Med.* 349(4):366-81 (2003)). An average 40% reduction in life expectancy affects males with prostate cancer. If detected early, prior to metastasis and local spread beyond the capsule, prostate cancer can often times be cured (e.g., using surgery). However, if diagnosed after spread and metastasis from the prostate, prostate cancer is typically a fatal disease with low cure rates. While prostate-specific antigen (PSA)-based screening has aided early diagnosis of prostate cancer, it is neither highly sensitive nor specific (Punglia et al., *N. Engl. J. Med.* 349(4):335-42 (2003)). This means that a high percentage of false negative and false positive diagnoses are associated with the test. The consequences are both many instances of missed cancers and unnecessary follow-up biopsies for those without cancer.

Breast cancer remains the second leading cause of cancer-related deaths in women, affecting more than 180,000 women in the United States each year. For women in North America, the life-time odds of getting breast cancer are now one in eight. Although the discovery of BRCA1 and BRCA2 were important steps in identifying key genetic factors involved in breast cancer, it has become clear that mutations in BRCA1 and BRCA2 account for only a fraction of inherited susceptibility to breast cancer (Nathanson, K. L., et al., *Human Mol. Gen.* 10(7):715-720 (2001); Anglican Breast Cancer Study Group. *Br. J. Cancer* 83(10):1301-08 (2000); and Syrjakoski, K., et al., *J. Natl. Cancer Inst.* 92:1529-31 (2000)). Despite considerable research into therapies for breast cancer, breast cancer remains difficult to diagnose and treat effectively, and the high mortality observed in breast cancer patients indicates that improvements are needed in the diagnosis, treatment and prevention of the disease.

Excluding skin cancer, colorectal cancer is the third most frequently diagnosed cancer in the United States and Canada (after lung and breast in women, and lung and prostate in men). The American Cancer Society estimates that there will be approximately 145,000 new cases of colorectal cancer diagnosed in the U.S. in 2005. Colorectal cancer is the second leading cause of cancer death among men and women in the United States and Canada (after lung cancer).

The annual incidence of pancreas cancer is nearly equivalent to the annual mortality, estimated to be 31,860 and 31,270, respectively, in the U.S. in 2004. Patients with locally advanced and metastatic pancreas cancer have poor prognosis, and diagnosis generally occurs too late for surgery or radiotherapy to be curative (Burr, H. A., et al., *The Oncologist* 10(3): 183-190, (2005)). Chemotherapy can provide relief of symptoms for some patients with advanced pancreas cancer, but its impact on survival has been modest to date.

In the United States, more than 20,000 individuals are diagnosed with stomach (gastric) cancer each year. The American Cancer Society estimates that there will be 22,710 new cases of colorectal cancer diagnosed in the U.S. in 2004. Because stomach cancer may occur without symptoms, it may be in advanced stages by the time the diagnosis is made. Treatment is then directed at making the patient more comfortable and improving the quality of life.

Lung cancer causes more deaths worldwide than any other form of cancer (Goodman, G. E., *Thorax* 57:994-999 (2002)). In the United States, lung cancer is the primary cause of cancer death among both men and women. In 2002, the death rate from lung cancer was an estimated 134,900 deaths, exceeding the combined total for breast, prostate and colon cancer. Id. Lung cancer is also the leading cause of cancer death in all European countries, and numbers of lung cancer-related deaths are rapidly increasing in developing countries as well.

The five-year survival rate among all lung cancer patients, regardless of the stage of disease at diagnosis, is only about 13%. This contrasts with a five-year survival rate of 46% among cases detected while the disease is still localized. However, only 16% of lung cancers are discovered before the disease has spread. Early detection is difficult as clinical symptoms are often not observed until the disease has reached an advanced stage. Despite research into therapies for this and other cancers, lung cancer remains difficult to diagnose and treat effectively.

Clearly, the identification of markers and genes that are responsible for susceptibility to particular forms of solid cancer (e.g., prostate cancer, breast cancer, lung cancer, stomach cancer, colon cancer, pancreatic cancer) is one of the major challenges facing oncology today. There is a need to identify means for the early detection of individuals that have a genetic susceptibility to cancer so that more aggressive screening and intervention regimens may be instituted for the early detection and treatment of cancer. Cancer genes may also reveal key molecular pathways that may be manipulated (e.g., using small or large molecule weight drugs) and may lead to more effective treatments regardless of the cancer stage when a particular cancer is first diagnosed.

MicroRNAs are a class of small, non-coding RNAs that control gene expression by hybridizing to and triggering either translational repression or, less frequently, degradation of a messenger RNA (mRNA) target. The discovery and study of miRNAs has revealed miRNA-mediated gene regulatory mechanisms that play important roles in organismal development and various cellular processes, such as cell differentiation, cell growth and cell death (Cheng, A. M., et al., *Nucleic Acids Res.* 33:1290-1297 (2005)). Recent studies suggest that aberrant expression of particular miRNAs may be involved in human diseases, such as neurological disorders (Ishizuka, A., et al., *Genes Dev.* 16:2497-2508 (2002)) and cancer. In particular, misexpression of miR-16-1 and/or miR-15a has been found in human chronic lymphocytic leukemias (Calin, G. A., et al., *Proc. Natl. Acad. Sci. U.S.A.* 99:15524-15529 (2002)).

Clearly, there is a great need in the art for improved methods for detecting and treating solid cancers (e.g., prostate cancer, breast cancer, lung cancer, stomach cancer, colon cancer, pancreatic cancer). The present invention provides novel methods and compositions for the diagnosis and treatment of solid cancers.

SUMMARY OF THE INVENTION

The present invention is based, in part, on the identification of specific miRNAs that have altered expression levels in particular solid cancers.

Accordingly, the invention encompasses methods of diagnosing whether a subject has, or is at risk for developing, a solid cancer. According to the methods of the invention, the level of at least one miR gene product in a test sample from the subject is compared to the level of a corresponding miR gene product in a control sample. An alteration (e.g., an increase, a decrease) in the level of the miR gene product in the test sample, relative to the level of a corresponding miR gene product in a control sample, is indicative of the subject either having, or being at risk for developing, a solid cancer. The solid cancer can be any cancer that arises from organs and solid tissues. In certain embodiments, the solid cancer is stomach cancer, breast cancer, pancreatic cancer, colon cancer, lung cancer or prostate cancer. In particular embodiments, the solid cancer is not breast cancer, lung cancer, prostate cancer, pancreatic cancer or gastrointestinal cancer.

In one embodiment, the at least one miR gene product measured in the test sample is selected from the group consisting of miR-21, miR-191, miR-17-5p and combinations thereof. In another embodiment, the at least one miR gene product measured in the test sample is selected from the group consisting of miR-21, miR-17-5p, miR-191, miR-29b-2, miR-223, miR-128b, miR-199a-1, miR-24-1, miR-24-2, miR-146, miR-155, miR-181b-1, miR-20a, miR-107, miR-32, miR-92-2, miR-214, miR-30c, miR-25, miR-221, miR-106a and combinations thereof.

In one embodiment, the solid cancer is breast cancer or lung cancer and the at least one miR gene product measured in the test sample is selected from the group consisting of miR-210, miR-213 and a combination thereof.

In another embodiment, the solid cancer is colon cancer, stomach cancer, prostate cancer or pancreas cancer and the at least one miR gene product measured in the test sample is miR-218-2.

In a certain embodiment, the solid cancer is breast cancer and the at least one miR gene product measured in the test sample is selected from the group consisting of miR-125b-1, miR-125b-2, miR-145, miR-21 and combinations thereof. In a related embodiment, the solid cancer is breast cancer and the at least one miR gene product in the test sample is selected from the group consisting of miR-21, miR-29b-2, miR-146, miR-125b-2, miR-125b-1, miR-10b, miR-145, miR-181a, miR-140, miR-213, miR-29a prec, miR-181b-1, miR-199b, miR-29b-1, miR-130a, miR-155, let-7a-2, miR-205, miR-29c, miR-224, miR-100, miR-31, miR-30c, miR-17-5p, miR-210, miR-122a, miR-16-2 and combinations thereof.

In another embodiment, the solid cancer is colon cancer and the at least one miR gene product in the test sample is selected from the group consisting of miR-24-1, miR-29b-2, miR-20a, miR-10a, miR-32, miR-203, miR-106a, miR-17-5p, miR-30c, miR-223, miR-126*, miR-128b, miR-21, miR-24-2, miR-99b prec, miR-155, miR-213, miR-150, miR-107, miR-191, miR-221, miR-9-3 and combinations thereof.

In yet another embodiment, the solid cancer is lung cancer and the miR gene product in the test sample is selected from the group consisting of miR-21, miR-205, miR-200b, miR-9-1, miR-210, miR-148, miR-141, miR-132, miR-215, miR-128b, let-7g, miR-16-2, miR-129-1/2 prec, miR-126*, miR-142-as, miR-30d, miR-30a-5p, miR-7-2, miR-199a-1, miR-127, miR-34a prec, miR-34a, miR-136, miR-202, miR-196-2, miR-199a-2, let-7a-2, miR-124a-1, miR-149, miR-17-5p, miR-196-1 prec, miR-10a, miR-99b prec, miR-196-1, miR-199b, miR-191, miR-195, miR-155 and combinations thereof.

In an additional embodiment, the solid cancer is pancreatic cancer and the at least one miR gene product measured in the test sample is selected from the group consisting of miR-103-1, miR-103-2, miR-155, miR-204 and combinations thereof. In a related embodiment, the solid cancer is pancreatic cancer and the miR gene product in the test sample is selected from the group consisting of miR-103-2, miR-103-1, miR-24-2, miR-107, miR-100, miR-125b-2, miR-125b-1, miR-24-1, miR-191, miR-23a, miR-26a-1, miR-125a, miR-130a, miR-26b, miR-145, miR-221, miR-126*, miR-16-2, miR-146, miR-214, miR-99b, miR-128b, miR-155, miR-29b-2, miR-29a, miR-25, miR-16-1, miR-99a, miR-224, miR-30d, miR-92-2, miR-199a-1, miR-223, miR-29c, miR-30b, miR-129-1/2, miR-197, miR-17-5p, miR-30c, miR-7-1, miR-93-1, miR-140, miR-30a-5p, miR-132, miR-181b-1, miR-152 prec, miR-23b, miR-20a, miR-222, miR-27a, miR-92-1, miR-21, miR-129-1/2 prec, miR-150, miR-32, miR-106a, miR-29b-1 and combinations thereof.

In another embodiment, the solid cancer is prostate cancer and the miR gene product in the test sample is selected from the group consisting of let-7d, miR-128a prec, miR-195, miR-203, let-7a-2 prec, miR-34a, miR-20a, miR-218-2, miR-29a, miR-25, miR-95, miR-197, miR-135-2, miR-187, miR-196-1, miR-148, miR-191, miR-21, let-71, miR-198, miR-199a-2, miR-30c, miR-17-5p, miR-92-2, miR-146, miR-181b-1 prec, miR-32, miR-206, miR-184 prec, miR-29a prec, miR-29b-2, miR-149, miR-181b-1, miR-196-1 prec, miR-93-1, miR-223, miR-16-1, miR-101-1, miR-124a-1, miR-26a-1, miR-214, miR-27a, miR-24-1, miR-106a, miR-199a-1 and combinations thereof.

In yet another embodiment, the solid cancer is stomach cancer and the miR gene product in the test sample is selected from the group consisting of miR-223, miR-21, miR-218-2, miR-103-2, miR-92-2, miR-25, miR-136, miR-191, miR-221, miR-125b-2, miR-103-1, miR-214, miR-222, miR-212 prec, miR-125b-1, miR-100, miR-107, miR-92-1, miR-96, miR-192, miR-23a, miR-215, miR-7-2, miR-138-2, miR-24-1, miR-99b, miR-33b, miR-24-2 and combinations thereof.

The level of the at least one miR gene product can be measured using a variety of techniques that are well known to those of skill in the art (e.g., quantitative or semi-quantitative RT-PCR, Northern blot analysis, solution hybridization detection). In a particular embodiment, the level of at least one miR gene product is measured by reverse transcribing RNA from a test sample obtained from the subject to provide a set of target oligodeoxynucleotides, hybridizing the target oligodeoxynucleotides to one or more miRNA-specific probe oligonucleotides (e.g., hybridzing to a microarray that comprises several miRNA-specific probe oligonucleotides) to provide a hybridization profile for the test sample, and comparing the test sample hybridization profile to a hybridization profile from a control sample. An alteration in the signal of at least one miRNA in the test sample relative to the control sample is indicative of the subject either having, or being at risk for developing, a solid cancer. In a particular embodiment, target oligonucleotides are hybridized to a microarray comprising miRNA-specific probe oligonucleotides for one or more miRNAs selected from the group consisting of miR-21, miR-17-5p, miR-191, miR-29b-2, miR-223, miR-128b, miR-199a-1, miR-24-1, miR-24-2, miR-146, miR-155, miR-181b-1, miR-20a, miR-107, miR-32, miR-92-2, miR-214, miR-30c, miR-25, miR-221, miR-106a and combinations thereof.

The invention also encompasses methods of inhibiting tumorigenesis in a subject who has, or is suspected of having, a solid cancer (e.g., prostate cancer, stomach cancer, pancreatic cancer, lung cancer, breast cancer, colon cancer), wherein at least one miR gene product is deregulated (e.g., down-regulated, up-regulated) in the cancer cells of the subject. When the at least one isolated miR gene product is down-regulated in the cancer cells, the method comprises administering an effective amount of an isolated miR gene product, an isolated variant or a biologically-active fragment of the miR gene product or variant, such that proliferation of cancer cells in the subject is inhibited. In a further embodiment, the at least one isolated miR gene product is selected from the group consisting of miR-145, miR-155, miR-218-2 and combinations thereof. In a particular embodiment, the miR gene product is not miR-15a or miR-16-1. When the at least one isolated miR gene product is up-regulated in the cancer cells, the method comprises administering to the subject an effective amount of at least one compound for inhibiting expression of the at least one miR gene product (referred to herein as a "miR expression-inhibition compound"), such that proliferation of cancer cells in the subject is inhibited. In a particular embodiment, the at least one miR expression-inhibition compound is specific for a miR gene product selected from the group consisting of miR-21, miR-17-5p, miR-191, miR-29b-2, miR-223, miR-128b, miR-199a-1, miR-24-1, miR-24-2, miR-146, miR-155, miR-181b-1, miR-20a, miR-107, miR-32, miR-92-2, miR-214, miR-30c, miR-25, miR-221, miR-106a and combinations thereof.

In a related embodiment, the methods of inhibiting tumorigenesis in a subject additionally comprise the step of determining the amount of at least one miR gene product in cancer cells from the subject, and comparing that level of the miR gene product in the cells to the level of a corresponding miR gene product in control cells. If expression of the miR gene product is deregulated (e.g., down-regulated, up-regulated) in cancer cells, the methods further comprise altering the amount of the at least one miR gene product expressed in the cancer cells. In one embodiment, the amount of the miR gene product expressed in the cancer cells is less than the amount of the miR gene product expressed in a control cell (e.g., control cells), and an effective amount of the down-regulated miR gene product, isolated variant or biologically-active fragment of the miR gene product or variant, is administered to the subject. Suitable miR gene products for this embodiment include miR-145, miR-155, miR-218-2 and combinations thereof, among others. In a particular embodiment, the miR gene product is not miR-15a or miR-16-1. In another embodiment, the amount of the miR gene product expressed in the cancer cells is greater than the amount of the miR gene product expressed in the control cell (e.g., control cells), and an effective amount of at least one compound for inhibiting expression of the at least one up-regulated miR gene product is administered to the subject. Suitable compounds for inhibiting expression of the at least one miR gene product include, but are not limited to, compounds that inhibit the expression of miR-21, miR-17-5p, miR-191, miR-29b-2, miR-223, miR-128b, miR-199a-1, miR-24-1, miR-24-2, miR-146, miR-155, miR-181b-1, miR-20a, miR-107, miR-32, miR-92-2, miR-214, miR-30c, miR-25, miR-221, miR-106a and combinations thereof.

The invention further provides pharmaceutical compositions for treating solid cancers (e.g., prostate cancer, stomach cancer, pancreatic cancer, lung cancer, breast cancer, colon cancer). In one embodiment, the pharmaceutical compositions comprise at least one isolated miR gene product and a pharmaceutically-acceptable carrier. In a particular embodiment, the at least one miR gene product corresponds to a miR gene product that has a decreased level of expression in cancer cells relative to control cells. In certain embodiments the isolated miR gene product is selected from the group consisting of miR-145, miR-155, miR-218-2 and combinations thereof.

In another embodiment, the pharmaceutical compositions of the invention comprise at least one miR expression-inhibition compound and a pharmaceutically-acceptable carrier. In a particular embodiment, the at least one miR expression-inhibition compound is specific for a miR gene product whose expression is greater in cancer cells than in control cells. In certain embodiments, the miR expression-inhibition compound is specific for one or more miR gene products selected from the group consisting of miR-21, miR-17-5p, miR-191, miR-29b-2, miR-223, miR-128b, miR-199a-1, miR-24-1, miR-24-2, miR-146, miR-155, miR-181b-1, miR-20a, miR-107, miR-32, miR-92-2, miR-214, miR-30c, miR-25, miR-221, miR-106a and combinations thereof.

The invention also encompasses methods of identifying an inhibitor of tumorigenesis, comprising providing a test agent to a cell and measuring the level of at least one miR gene product in the cell. In one embodiment, the method comprises providing a test agent to a cell and measuring the level of at least one miR gene product associated with decreased expression levels in solid cancers (e.g., prostate cancer, stomach cancer, pancreatic cancer, lung cancer, breast cancer, colon cancer). An increase in the level of the miR gene product in the cell, relative to a suitable control cell, is indicative of the test agent being an inhibitor of tumorigenesis. In a particular embodiment, the at least one miR gene product associated with decreased expression levels in solid cancer cells is selected from the group consisting of miR-145, miR-155, miR-218-2 and combinations thereof.

In other embodiments, the method comprises providing a test agent to a cell and measuring the level of at least one miR gene product associated with increased expression levels in solid cancers. A decrease in the level of the miR gene product in the cell, relative to a suitable control cell, is indicative of the test agent being an inhibitor of tumorigenesis. In a particular embodiment, the at least one miR gene product associated with increased expression levels in solid cancer cells is selected from the group consisting of miR-21, miR-17-5p, miR-191, miR-29b-2, miR-223, miR-128b, miR-199a-1, miR-24-1, miR-24-2, miR-146, miR-155, miR-181b-1, miR-20a, miR-107, miR-32, miR-214, miR-30c, miR-25, miR-221, miR-106a and combinations thereof.

BRIEF DESCRIPTION OF THE DRAWINGS

The patent or application file contains at least one drawing executed in color. Copies of this patent or patent application publication with color drawings will be provided by the Office upon request and payment of the necessary fee.

DETAILED DESCRIPTION OF THE INVENTION

Figure 1:
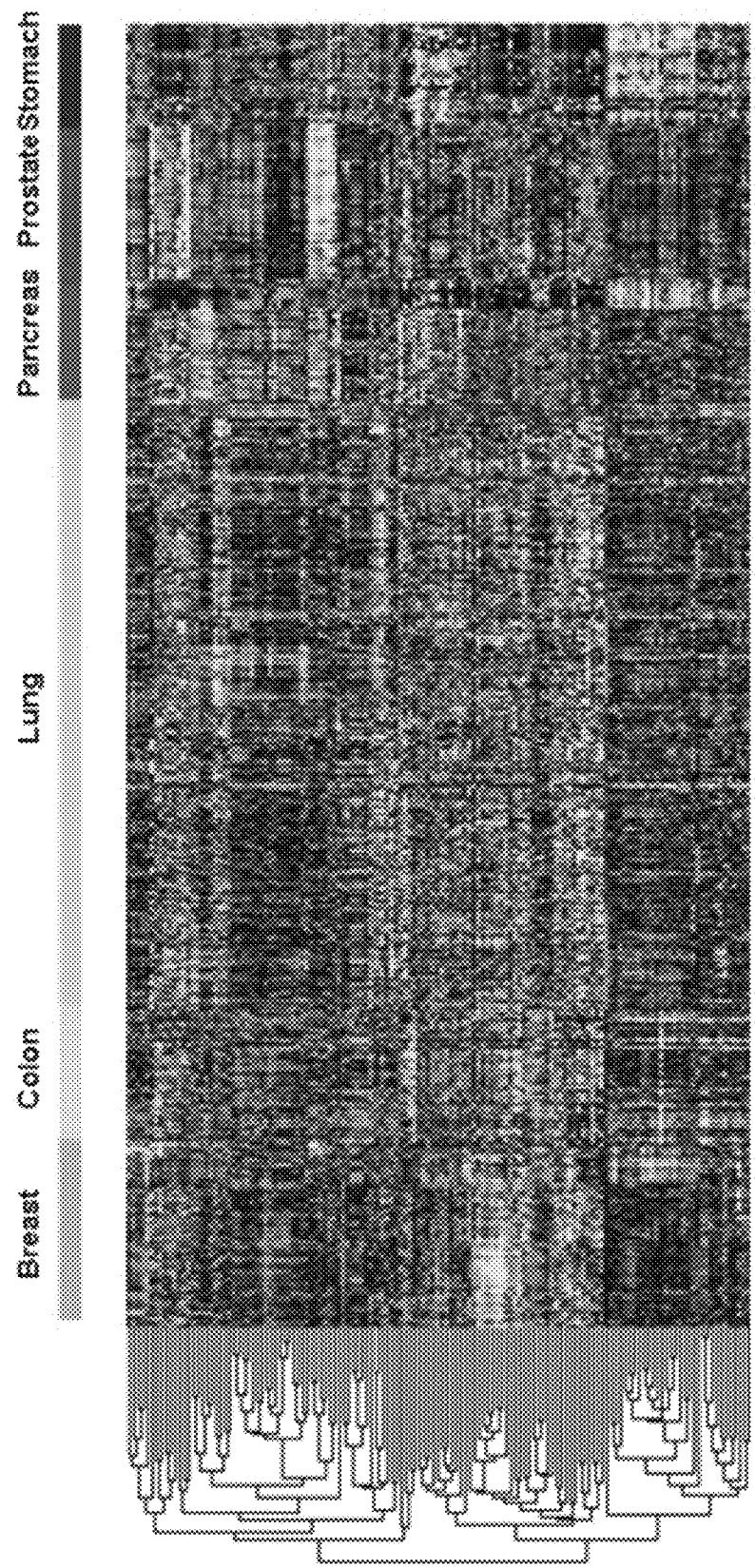
FIG. 1 depicts a clustering analysis of 540 samples, representing 6 solid cancers (top) and the respective normal tissues. miRNAs included in the tree (n=137) represent those whose expression level (background-subtracted intensity) was higher than the threshold value (256) in at least 50% of the samples analyzed. Arrays were median-centered and normalized using Gene Cluster 2.0. Average linkage clustering was performed by using uncentered correlation metric. The colors indicate the difference in expression level from the median for the microRNAs in each sample.

The present invention is based, in part, on the identification of particular microRNAs whose expression is altered in cancer cells associated with different solid cancers, such as colon, stomach, pancreatic, lung, breast and prostate cancer, relative to normal control cells.

As used herein interchangeably, a "miR gene product," "microRNA," "miR," or "miRNA" refers to the unprocessed (e.g., precursor) or processed (e.g., mature) RNA transcript from a miR gene. As the miR gene products are not translated into protein, the term "miR gene products" does not include proteins. The unprocessed miR gene transcript is also called a "miR precursor" or "miR prec" and typically comprises an RNA transcript of about 70-100 nucleotides in length. The miR precursor can be processed by digestion with an RNAse (for example, Dicer, Argonaut, or RNAse III (e.g., *E. coli* RNAse III)) into an active 19-25 nucleotide RNA molecule. This active 19-25 nucleotide RNA molecule is also called the "processed" miR gene transcript or "mature" miRNA.

The active 19-25 nucleotide RNA molecule can be obtained from the miR precursor through natural processing routes (e.g., using intact cells or cell lysates) or by synthetic processing routes (e.g., using isolated processing enzymes, such as isolated Dicer, Argonaut, or RNAse III). It is understood that the active 19-25 nucleotide RNA molecule can also be produced directly by biological or chemical synthesis, without having been processed from the miR precursor. When a microRNA is referred to herein by name, the name corresponds to both the precursor and mature forms, unless otherwise indicated.

Tables 1a and 1b depict the nucleotide sequences of particular precursor and mature human microRNAs.

TABLE 1a

Human microRNA Precursor Sequences

| Precursor Name | Sequence (5' To 3')* | SEQ ID NO. |
|---|---|---|
| let-7a-1 | CACUGUGGGAUGAGGUAGUAGGUUGUAUAGUUUUAGGGUCACACCCACCACUGGGAGAUAACUAUACAAUCUACUGUCUUUCCUAACGUG | 1 |
| let-7a-2 | AGGUUGAGGUAGUAGGUUGUAUAGUUUAGAAUUACAUCAAGGGAGAUAACUGUACAGCCUCCUAGCUUUCCU | 2 |
| let-7a-3 | GGGUGAGGUAGUAGGUUGUAUAGUUUGGGGCUCUGCCCUGCUAUGGGAUAACUAUACAAUCUACUGUCUUUCCU | 3 |
| let-7a-4 | GUGACUGCAUGCUCCCAGGUUGAGGUAGUAGGUUGUAUAGUUUAGAAUUACACAAGGGAGAUAACUGUACAGCCUCCUAGCUUUCCUUGGGUCUUGCACUAAACAAC | 4 |
| let-7b | GGCGGGGUGAGGUAGUAGGUUGUGUGGUUUCAGGGCAGUGAUGUUGCCCCUCGGAAGAUAACUAUACAACCUACUGCCUUCCCUG | 5 |
| let-7c | GCAUCCGGGUUGAGGUAGUAGGUUGUAUGGUUUAGAGUUACACCCUGGGAGUUAACUGUACAACCUUCUAGCUUUCCUUGGAGC | 6 |
| let-7d | CCUAGGAAGAGGUAGUAGGUUGCAUAGUUUUAGGGCAGGGAUUUUGCCCACAAGGAGGUAACUAUACGACCUGCUGCCUUUCUUAGG | 7 |
| let-7d-v1 | CUAGGAAGAGGUAGUAGUUUGCAUAGUUUUAGGGCAAAGAUUUUGCCCACAAGUAGUUAGCUAUACGACCUGCAGCUUUUGUAG | 8 |
| let-7d-v2 | CUGGCUGAGGUAGUAGUUUGUGCUGUUGGUCGGGUUGUGACAUUGCCCGCUGUGGAGAUAACUGCGCAAGCUACUGCCUUGCUAG | 9 |
| let-7e | CCCGGGCUGAGGUAGGAGGUUGUAUAGUUGAGGAGGACACCCAAGGAGAUCACUAUACGGCCUCCUAGCUUUCCCCAGG | 10 |
| let-7f-1 | UCAGAGUGAGGUAGUAGAUUGUAUAGUUGUGGGGUAGUGAUUUUACCCUGUUCAGGAGAUAACUAUACAAUCUAUUGCCUUCCCUGA | 11 |
| let-7f-2-1 | CUGUGGGAUGAGGUAGUAGAUUGUAUAGUUGUGGGGUAGUGAUUUUACCCUGUUCAGGAGAUAACUAUACAAUCUAUUGCCUUCCCUGA | 12 |
| let-7f-2-2 | CUGUGGGAUGAGGUAGUAGAUUGUAUAGUUUAGGGUCAUACCCCAUCUUGGAGAUAACUAUACAGUCUACUGUCUUUCCACGG | 13 |
| let-7g | UUGCCUGAUUCCAGGCUGAGGUAGUAGUUUGUACAGUUUGAGGGUCUAUGAUACCACCCGGUACAGGAGAUAACUGUACAGGCCACUGCCUUGCCAGGAACAGCGCGC | 14 |
| let-7i | CUGGCUGAGGUAGUAGUUUGUGCUGUUGGUCGGGUUGUGACAUUGCCCGCUGUGGAGAUAACUGCGCAAGCUACUGCCUUGCUAG | 15 |
| miR-1b-1-1 | ACCUACUCAGAGUACAUACUUCUUUAUGUACCCAUAUGAACAUACAAUGCUAUGGAAUGUAAAGAAGUAUGUAUUUUGGUAGGC | 16 |
| miR-1b-1-2 | CAGCUAACAACUUAGUAAUACCUACUCAGAGUACAUACUUCUUUAUGUACCCAUAUGAACAUACAAUGCUAUGGAAUGUAAAGAAGUAUGUAUUUUGGUAGGCAAUA | 17 |
| miR-1b-2 | GCCUGCUUGGGAAACAUACUUCUUUAUAUGCCCAUAUGGACCUGCUAAGCUAUGGAAUGUAAAGAAGUAUGUAUCUCAGGCCGGG | 18 |
| miR-1b | UGGGAAACAUACUUCUUUAUAUGCCCAUAUGGACCUGCUAAGCUAUGGAAUGUAAAGAAGUAUGUAUCUCA | 19 |
| miR-1d | ACCUACUCAGAGUACAUACUUCUUUAUGUACCCAUAUGAACAUACAAUGCUAUGGAAUGUAAAGAAGUAUGUAUUUUGGUAGGC | 20 |
| miR-7-1a | UGGAUGUUGGCCUAGUUCUGUGUGGAAGACUAGUGAUUUUGUUGUUUUAGAUAACUAAAUCGACAACAAAUCACAGUCUGCCAUAUGGCACAGGCCAUGCCUCUACA | 21 |
| miR-7-1b | UUGGAUGUUGGCCUAGUUCUGUGUGGAAGACUAGUGAUUUUGUUGUUUUAGAUAACUAAAUCGACAACAAAUCACAGUCUGCCAUAUGGCACAGGCCAUGCCUCUACAG | 22 |
| miR-7-2 | CUGGAUACAGAGUGGACCGGCUGGCCCCAUCUGGAAGACUAGUGAUUUUGUUGUUGUCUUACUGCGCUCAACAACAAAUCCCAGUCUACCUAAUGGUGCCAGCCAUCGCA | 23 |
| miR-7-3 | AGAUUAGAGUGGCUGUGGUCUAGUGCUGUGUGGAAGACUAGUGAUUUUGUUGUUCUGAUGUACUACGACAACAAGUCACAGCCGGCCUCAUAGCGCAGACUCCCUUCGAC | 24 |
| miR-9-1 | CGGGGUUGGUUGUUAUCUUUGGUUAUCUAGCUGUAUGAGUGGUGUGGAGUCUUCAUAAAGCUAGAUAACCGAAAGUAAAAAUAACCCCA | 25 |
| miR-9-2 | GGAAGCGAGUUGUUAUCUUUGGUUAUCUAGCUGUAUGAGUGUAUUGGUCUUCAUAAAGCUAGAUAACCGAAAGUAAAAACUCCUUCA | 26 |
| miR-9-3 | GGAGGCCCGUUUCUCUCUUUGGUUAUCUAGCUGUAUGAGUGCCACAGAGCCGUCAUAAAGCUAGAUAACCGAAAGUAGAAAUGAUUCUCA | 27 |
| miR-10a | GAUCUGUCUGUCUUCUGUAUAUACCCUGUAGAUCCGAAUUUGUGUAAGGAAUUUUGUGGUCACAAAUUCGUAUCUAGGGGAAUAUGUAGUUGACAUAAACACUCCGCUCU | 28 |
| miR-10b | CCAGAGGUUGUAACGUUGUCUAUAUAUACCCUGUAGAACCGAAUUUGUGUGGUAUCCGUAUAGUCACAGAUUCGAUUCUAGGGGAAUAUAUGGUCGAUGCAAAAACUUCA | 29 |
| miR-15a-2 | GCGCGAAUGUGUGUUUAAAAAAAUAAAACCUUGGAGUAAAGUAGCAGCACAUAAUGGUUUGUGGAUUUUGAAAAGGUGCAGGCCAUAUUGUGCUGCCUCAAAAAUAC | 30 |
| miR-15a | CCUUGGAGUAAAGUAGCAGCACAUAAUGGUUUGUGGAUUUUGAAAAGGUGCAGGCCAUAUUGUGCUGCCUCAAAAAUACAAGG | 31 |
| miR-15b-1 | CUGUAGCAGCACAUCAUGGUUUACAUGCUACAGUCAAGAUGCGAAUCAUUAUUUGCUGCUCUAG | 32 |
| miR-15b-2 | UUGAGGCCUUAAAGUACUGUAGCAGCACAUCAUGGUUUACAUGCUACAGUCAAGAUGCGAAUCAUUAUUUGCUGCUCUAGAAAUUUAAGGAAAUUCAU | 33 |
| miR-16-1 | GUCAGCAGUGCCUUAGCAGCACGUAAAUAUUGGCGUUAAGAUUCUAAAAUUAUCUCCAGUAUACUGUGCUGCUGAAGUAAGGUUGAC | 34 |
| miR-16-2 | GUUCCACUCUAGCAGCACGUAAAUAUUGGCGUAGUGAAAUAUAUAUUAAACACCAAUAUUACUGUGCUGCUUUAGUGUGAC | 35 |

TABLE 1a-continued

Human microRNA Precursor Sequences

| Precursor Name | Sequence (5' To 3')* | SEQ ID NO. |
|---|---|---|
| miR-16-13 | GCAGUGCCUU<u>AGCAGCACGUAAAUAUUGGCG</u>UU AAGAUUCUAAAAUUAUCUCCAGUAUUAACUGUG CUGCUGAAGUAAGGU | 36 |
| miR-17 | GUCAGAAUAAUGU<u>CAAAGUGCUUACAGUGCAGG</u> UAGUGAUAUGUGCAUCU<u>ACUGCAGUGAAGGCAC UUGU</u>AGCAUUAUGGUGAC | 37 |
| miR-18 | UGUUC<u>UAAGGUGCAUCUAGUGCAGAUAG</u>UGAAG UAGAUUAGCAUCUACUGCCCUAAGUGCUCCUUC UGGCA | 38 |
| miR-18-13 | UUUUUGUUC<u>UAAGGUGCAUCUAGUGCAGAUAG</u>U GAAGUAGAUUAGCAUCUACUGCCCUAAGUGCUC CUUCUGGCAUAAGAA | 39 |
| miR-19a | GCAGUCCUCUGUUAGUUUUGCAUAGUUGCACUA CAAGAAGAAUGUAGU<u>UGUGCAAAUCUAUGCAAA ACUGA</u>UGGUGGCCUGC | 40 |
| miR-19a-13 | CAGUCCUCUGUUAGUUUUGCAUAGUUGCACUAC AAGAAGAAUGUAGUU<u>UGUGCAAAUCUAUGCAAAA CUGA</u>UGGUGGCCUG | 41 |
| miR-19b-1 | CACUGUUCUAUGGUUAGUUUUGCAGGUUUGCAU CCAGCUGUGUGAUAUUCUGC<u>UGUGCAAAUCCAU GCAAAACUGA</u>CUGUGGUAGUG | 42 |
| miR-19b-2 | ACAUUGCUACUUACAAUUAGUUUUGCAGGUUUG CAUUUCAGCGUAUAUAUGUAUAUGUGGC<u>UGUGC AAAUCCAUGCAAAACUGA</u>UUGUGAUAAUGU | 43 |
| miR-19b-13 | UUCUAUGGUUAGUUUUGCAGGUUUGCAUCCAGC UGUGUGAUAUUC<u>UGCUGUGCAAAUCCAUGCAAA ACUGA</u>CUGUGGUAG | 44 |
| miR-19b-X | UUACAAUUAGUUUUGCAGGUUUGCAUUUCAGCG UAUAUAUGUAUAUG<u>UGGCUGUGCAAAUCCAUGC AAAACUGA</u>UUGUGAU | 45 |
| miR-20 (miR-20a) | GUAGCACU<u>AAAGUGCUUAUAGUGCAGGUAG</u>UGU UUAGUUAUCUACUGCAUUAUGAGCACUUAAAGU ACUGC | 46 |
| miR-21 | UGUCGGG<u>UAGCUUAUCAGACUGAUGUUGA</u>CUGU UGAAUCUCAUGGCAACACCAGUCGAUGGGCUGU CUGACA | 47 |
| miR-21-17 | ACCUUGUCGGG<u>UAGCUUAUCAGACUGAUGUUGA</u> CUGUUGAAUCUCAUGGCAACACCAGUCGAUGGG CUGUCUGACAUUUUG | 48 |
| miR-22 | GGCUGAGCCGCAGUAGUUCUUCAGUGGCAAGCU UUAUGUCCUGACCCAGCUA<u>AAGCUGCCAGUUGA AGAACUGU</u>UGCCCUCUGCC | 49 |
| miR-23a | GGCCGGCUGGGGUUCCUGGGGAUGGGAUUUGCU UCCUGUCACA<u>AAUCACAUUGCCAGGGAUUUCCA</u> ACCGACC | 50 |
| miR-23b | CUCAGGUGCUCUGGCUGCUUGGGUUCCUGGCAU GCUGAUUUGUGACUUAAGAUUAAAA<u>AUCACAUUG CCAGGGAUUAC</u>CACGCAACCACGACCUUGGC | 51 |
| miR-23-19 | CCACGGCCGGCUGGGGUUCCUGGGGAUGGGAUU UGCUUCCUGUCACAA<u>AUCACAUUGCCAGGGAUU UC</u>CAACCGACCCUGA | 52 |
| miR-24-1 | CUCCGGUGCCUACUGAGCUGAUAUCAGUUCUCA UUUUACACAC<u>UGGCUCAGUUCAGCAGGAACAGG</u> AG | 53 |
| miR-24-2 | CUCUGCCUCCCGUGCCUACUGAGCUGAAACACAG UUGGUUUGUGUACAC<u>UGGCUCAGUUCAGCAGGA ACAGGG</u> | 54 |
| miR-24-19 | CCCUGGGCUCUGCCUCCCGUGCCUACUGAGCUGA AACACAGUUGGUUUGUGUACAC<u>UGGCUCAGUUC AGCAGGAACAGGGG</u> | 55 |
| miR-24-9 | CCCUCCGGUGCCUACUGAGCUGAUAUCAGUUCU CAUUUUACACAC<u>UGGCUCAGUUCAGCAGGAACA GCAUC</u> | 56 |
| miR-25 | GGCCAGUGUUGAGAGGCGGAGACUUGGGCAAUU GCUGGACGCUGCCCUGGG<u>CAUUGCACUUGUCUC GGUCUGA</u>CAGUGCCGGCC | 57 |
| miR-26a | AGGCCGUGGCCUCGUUCAAGUAAUCCAGGAUAG GCUGUGCAGGUCCCAAUGGGCCUAUCUUGGUUAC UUGCACGGGACGCGGGCCU | 58 |
| miR-26a-1 | GUGGCCUCGUUCAAGUAAUCCAGGAUAGGCUGU GCAGGUCCCAAUGGGCCUAUUCUUGGUUACUUG CACGGGGACGC | 59 |
| miR-26a-2 | GGCUGUGGCUGGAUUCAAGUAAUCCAGGAUAGG <u>CU</u>GUUUCCAUCUGUGAGGCCUAUUCUUGAUUAC UUGUUUCGGAGGCAGCU | 60 |
| miR-26b | CCGGGACCCAGUUCAAGUAAUUCAGGAUAGGUU GUGUGCUGUCCAGCCUGUUCUCCAUUACUUGGC UCGGGGACCGG | 61 |
| miR-27a | CUGAGGAGCAGGGCUUAGCUGCUUGUGAGCAGG GUCCACACCAAGUCGUG<u>UUCACAGUGGCUAAGU UCCGCCCCCAG</u> | 62 |
| miR-27b-1 | AGGUGCAGAGCUUAGCUGAUUGGUGAACAGUGA UUGGUUUCCGCUUUG<u>UUCACAGUGGCUAAGUUC UGCACCU</u> | 63 |
| miR-27b-2 | ACCUCUCUAACAAGGUGCAGAGCUUAGCUGAUU GGUGAACAGUGAUUGGUUUCCGCUUUG<u>UUCACA GUGGCUAAGUUCUG</u>CACCUGAAGAGAAGGUG | 64 |
| miR-27-19 | CCUGAGGAGCAGGGCUUAGCUGCUUGUGAGCAG GGUCCACACCAAGUCGUG<u>UUCACAGUGGCUAAG UUCCGCCCCCAGG</u> | 65 |
| miR-28 | GGUCCUUGCCCUC<u>AAGGAGCUCACAGUCUAUUG</u> AGUUACUUUCUGACUUUCCCACUAGAUUGUGA GCUCCUGGAGGGCAGGCACU | 66 |
| miR-29a-2 | CCUUCUGUGACCCCUUAGAGGAUGACUGAUUUC UUUUGGUGUUCAGAGUCAAUAUAAUUUU<u>CUAGC ACCAUCUGAAAUCGGUUAUAAUGAUUGGGGAAG AGCACCAUG</u> | 67 |
| miR-29a | AUGACUGAUUUCUUUUGGUGUUCAGAGUCAAUA UAAUUUU<u>CUAGCACCAUCUGAAAUCGGUUAU</u> | 68 |
| miR-29b-1 | CUUCAGGAAGCUGGUUUCAUAUGGUGGUUUAGA UUUAAAUAGUGAUUGUC<u>UAGCACCAUUUGAAAU CAGUGUUCUUGGGGG</u> | 69 |
| miR-29b-2 | CUUCUGGAAGCUGGUUUCACAUGGUGGCUUAGA UUUUUCCAUCUUUGUAUC<u>UAGCACCAUUUGAAA UCAGUGUUUUAGGAG</u> | 70 |
| miR-29c | ACCACUGGCCCAUCUCUUACACAGGCUGACCGAU UUCUCCUGGUGUUCAGAGUCUGUUUUUGU<u>CUAG CACCAUUUGAAAUCGGUUAUGAUGUAGGGGAA AAGCAGCAGC</u> | 71 |

TABLE 1a-continued

Human microRNA Precursor Sequences

| Precursor Name | Sequence (5' To 3')* | SEQ ID NO. |
|---|---|---|
| miR-30a | GCGACUGUAAACAUCCUCGACUGGAAGCUGUGA AGCCACAGAUGGGCUUUCAGUCGGAUGUUUGCA GCUGC | 72 |
| miR-30b-1 | AUGUAAACAUCCUACACUCAGCUGUAAUACAUG GAUUGGCUGGGAGGUGGAUGUUUACGU | 73 |
| miR-30b-2 | ACCAAGUUUCAGUUCAUGUAAACAUCCUACACU CAGCUGUAAUACAUGGAUUGGCUGGGAGGUGGA UGUUUACUUCAGCUGACUUGGA | 74 |
| miR-30c | AGAUACUGUAAACAUCCUACACUCUCAGCUGUG GAAAGUAAGAAAGCUGGGAGAAGGCUGUUUACU CUUUCU | 75 |
| miR-30d | GUUGUUGUAAACAUCCCCGACUGGAAGCUGUAA GACACAGCUAAGCUUUCAGUCAGAUGUUUGCUG CUAC | 76 |
| miR-30e | CUGUAAACAUCCUUGACUGGAAGCUGUAAGGUG UUCAGAGGAGCUUUCAGUCGGAUGUUUACAG | 77 |
| miR-31 | GGAGAGGAGGCAAGAUGCUGGCAUAGCUGUUGA ACUGGGAACCUGCUAUGCCAACAUAUUGCCAUC UUUCC | 78 |
| miR-32 | GGAGAUAUUGCACAUUACUAAGUUGCAUGUUGU CACGGCCUCAAUGCAAUUUAGUGUGUGUGAUAU UUUC | 79 |
| miR-33b | GGGGGCCGAGAGAGGCGGGCGGCCCCGCGGUGC AUUGCUGUUGCAUUGCACGUGUGUGAGGCGGGU GCAGUGCCUCGGCAGUGCAGCCCGGAGCCGGCCC CUGGCACCAC | 80 |
| miR-33b-2 | ACCAAGUUUCAGUUCAUGUAAACAUCCUACACU CAGCUGUAAUACAUGGAUUGGCUGGGAGGUGGA UGUUUACUUCAGCUGACUUGGA | 81 |
| miR-33 | CUGUGGUGCAUUGUAGUUGCAUUGCAUGUUCUG GUGGUACCCAUGCAAUGUUUCCACAGUGCAUCA CAG | 82 |
| miR-34-a | GGCCAGCUGUGAGUGUUUCUUUGGCAGUGUCUU AGCUGGUUGUUGUGAGCAAUAGUAAGGAAGCAA UCAGCAAGUAUACUGCCCUAGAAGUGCUGCACG UUGUGGGGCCC | 83 |
| miR-34-b | GUGCUCGGUUUGUAGGCAGUGUCAUUAGCUGAU UGUACUGUGGUGGUUACAACACUAACUCCACU GCCAUCAAAACAAGGCAC | 84 |
| miR-34-c | AGUCUAGUUACUAGGCAGUGUAGUUAGCUGAUU GCUAAUAGUACCAAUCACUAACCACACGGCCAG GUAAAAGAUU | 85 |
| miR-91-13 | UCAGAAUAAUGUCAAAGUGCUUACAGUGCAGGU AGUGAUAUGUGCAUCUACUGCAGUGAAGGCACU UGUAGCAUUAUGGUGA | 86 |
| miR-92-1 | CUUUCUACACAGGUUGGGAUCGGUUGCAAUGCU GUGUUUCUGUAUGGUAUUGCACUUGUCCCGGCC UGUUGAGUUUGG | 87 |
| miR-92-2 | UCAUCCCUGGGUGGGGAUUUGUUGCAUUACUUG UGUUCUAUAUAAAGUAUUGCACUUGUCCCGGCC UGUGGAAGA | 88 |
| miR-93-1 (miR-93-2) | CUGGGGGCUCCAAAGUGCUGUUCGUGCAGGUAG UGUGAUUACCCAACCUACUGCUGAGCUAGCACU UCCCGAGCCCCCGG | 89 |
| miR-95-4 | AACACAGUGGGCACUCAAUAAAUGUCUGUUGAA UUGAAAUGCGUUACAUUCAACGGGUAUUUAUUG AGCACCCACUCUGUG | 90 |
| miR-96-7 | UGGCCGAUUUUGGCACUAGCACAUUUUUGCUUG UGUCUCUCCGCUCUGAGCAAUCAUGUGCAGUGC CAAUAUGGGAAA | 91 |
| miR-97-6 (miR-30*) | GUGAGCGACUGUAAACAUCCUCGACUGGAAGCU GUGAAGCCACAGAUGGGCUUUCAGUCGGAUGUU UGCAGCUGCCUACU | 92 |
| miR-98 | GUGAGGUAGUAAGUUGUAUUGUUGUGGGGUAGG GAUAUUAGGCCCCAAUUAGAAGAUAACUAUACA ACUUACUACUUUCC | 93 |
| miR-99b | GGCACCCACCCCGUAGAACCGACCUUGCGGGGCCU UCGCCGCACACAAGCUCGUGUCUGUGGGGUCCGU GUC | 94 |
| miR-99a | CCCAUUGGCAUAAACCCGUAGAUCCGAUCUUGU GGUGAAGUGGACCGCACAAGCUCGCUUCUAUGG GUCUGUGUCAGUGUG | 95 |
| miR-100-1/2 | AAGAGAGAAGAUAUUGAGGCCUGUUGCCACAAA CCCGUAGAUCCGAACUUGUGGUAUUAGUCCGCA CAAGCUUGUAUCUAUAGGUAUGUGUCUGUUAGG CAAUCUCAC | 96 |
| miR-100-11 | CCUGUUGCCACAAACCCGUAGAUCCGAACUUGU GGUAUUAGUCCGCACAAGCUUGUAUCUAUAGGU AUGUGUCUGUUAGG | 97 |
| miR-101-1/2 | AGGCUGCCCUGGCUCAGUUAUCACAGUGCUGAU GCUGUCUAUUCUAAAGGUACAGUACUGUGAUAA CUGAAGGAUGGCAGCCAUCUUACCUUCCAUCAG AGGAGCCUCAC | 98 |
| miR-101 | UCAGUUAUCACAGUGCUGAUGCUGUCCAUUCUA AAGGUACAGUACUGUGAUAACUGA | 99 |
| miR-101-1 | UGCCCUGGCUCAGUUAUCACAGUGCUGAUGCUG UCUAUUCUAAAGGUACAGUACUGUGAUAACUGA AGGAUGGCA | 100 |
| miR-101-2 | ACUGUCCUUUUUCGGUUAUCAUGGUACCGAUGC UGUAUAUCUGAAAGGUACAGUACUGUGAUAACU GAAGAAUGGUGGU | 101 |
| miR-101-9 | UGUCCUUUUUCGGUUAUCAUGGUACCGAUGCUG UAUAUCUGAAAGGUACAGUACUGUGAUAACUGA AGAAUGGUG | 102 |
| miR-102-1 | CUUCUGGAAGCUGGUUUCACAUGGUGGCUUAGA UUUUUCCAUCUUUGUAUCUAGCACCAUUUGAAA UCAGUGUUUAGGAG | 103 |
| miR-102-7.1 (miR-102-7.2) | CUUCAGGAAGCUGGUUUCAUAUGGUGGUUUAGA UUUAAAUAGUGAUUGUCUAGCACCAUUUGAAAU CAGUGUUCUGGGGG | 104 |
| miR-103-2 | UUGUGCUUUCAGCUUCUUUACAGUGCUGCCUUG UAGCAUUCAGGUCAAGCAACAUUGUACAGGGCU AUGAAGAACCA | 105 |
| miR-103-1 | UACUGCCCUCGGCUUCUUUACAGUGCUGCCUUG UUGCAUAUGGAUCAAGCAGCAUUGUACAGGGCU AUGAAGGCAUUG | 106 |
| miR-104-17 | AAAUGUCAGACAGCCCAUCGACUGGUGUUGCCA UGAGAUUCAACGUCAACAUCAGUCUGAUAAGCU ACCCGACAAGG | 107 |

TABLE 1a-continued

Human microRNA Precursor Sequences

| Precursor Name | Sequence (5' To 3')* | SEQ ID NO. |
|---|---|---|
| miR-105-1 | UGUGCAUCGUGGUCAAAUGCUCAGACUCCUGUGGUGGCUGCUCAUGCACCACGGAUGUUUGAGCAUGUGCUACGGUGUCUA | 108 |
| miR-105-2 | UGUGCAUCGUGGUCAAAUGCUCAGACUCCUGUGGUGGCUGCUUAUGCACCACGGAUGUUUGAGCAUGUGCUAUGGUGUCUA | 109 |
| miR-106-a | CCUUGGCCAUGUAAAAGUGCUUACAGUGCAGGUAGCUUUUUGAGAUCUACUGCAAUGUAAGCACUUCUUACAUUACCAUGG | 110 |
| miR-106-b | CCUGCCGGGGCUAAAGUGCUGACAGUGCAGAUAGUGGUCCUCUCCGUGCUACCGCACUGUGGGUACUUGCUGCUCCAGCAGG | 111 |
| miR-107 | CUCUCUGCUUUCAGCUUCUUUACAGUGUUGCCUUGUGGCAUGGAGUUCAAGCAGCAUUGUACAGGGCUAUCAAAGCACAGA | 112 |
| miR-108-1-small | ACACUGCAAGAACAAUAAGGAUUUUUAGGGGCAUUUAUGACUGAGUCAGAAAACACAGCUGCCCCUGAAAGUCCCUCAUUUUUCUUGCUGU | 113 |
| miR-108-2-small | ACUGCAAGAGCAAUAAGGAUUUUUAGGGGCAUUAUGAUAGUGGAAUGGAAACAUCUGCCCCCAAAAGUCCCUCAUUUU | 114 |
| miR-122a-1 | CCUUAGCAGAGCUGUGGAGUGUGACAAUGGUGUUUGUGUCUAAACUAUCAAACGCCAUUAUCACACUAAAUAGCUACUGCUAGGC | 115 |
| miR-122a-2 | AGCUGUGGAGUGUGACAAUGGUGUUUGUGUCCAAACUAUCAAACGCCAUUAUCACACUAAAUAGCU | 116 |
| miR-123 | ACAUUAUUACUUUUGGUACGCGCUGUGACACUUCAAACUCGUACCGUGAGUAAUAAUGCGC | 117 |
| miR-124a-1 | AGGCCUCUCUCUCCGUGUUCACAGCGGACCUUGAUUUAAAUGUCCAUACAAUUAAGGCACGCGGUGAAUGCCAAGAAUGGGCUG | 118 |
| miR-124a-2 | AUCAAGAUUAGAGGCUCUGCUCUCCGUGUUCACAGCGGACCUUGAUUUAAUGUCAUACAAUUAAGGCACGCGGUGAAUGCCAAGAGCGGAGCCUACGGCUGCACUUGAAG | 119 |
| miR-124a-3 | UGAGGGCCCCUCUGCGUGUUCACAGCGGACCUUGAUUUAAUGUCUAUACAAUUAAGGCACGCGGUGAAUGCCAAGAGAGGCGCCUCC | 120 |
| miR-124a | CUCUGCGUGUUCACAGCGGACCUUGAUUUAAUGUCUAUACAAUUAAGGCACGCGGUGAAUGCCAAGAG | 121 |
| miR-124b | CUCUCCGUGUUCACAGCGGACCUUGAUUUAAUGUCAUACAAUUAAGGCACGCGGUGAAUGCCAAGAG | 122 |
| miR-125a-1 | UGCCAGUCUCUAGGUCCCUGAGACCCUUUAACCUGUGAGGACAUCCAGGGUCACAGGUGAGGUUCUUGGGAGCCUGGCGUCUGGCC | 123 |
| miR-125a-2 | GGUCCCUGAGACCCUUUAACCUGUGAGGACAUCCAGGGUCACAGGUGAGGUUCUUGGGAGCCUGG | 124 |
| miR-125b-1 | UGCGCUCCUCUCAGUCCCUGAGACCCUAACUUGUGAUGUUUACCGUUUAAAUCCACGGGUUAGGCUCUUGGGAGCUGCGAGUCGUGCU | 125 |
| miR-125b-2 | ACCAGACUUUUCCUAGUCCCUGAGACCCUAACUUGUGAGGUAUUUUAGUAACAUCACAAGUCAGGCUCUUGGGACCUAGGCGGAGGGGA | 126 |
| miR-126-1 | CGCUGGCGACGGGACAUUAUUACUUUUGGUACGCGCUGUGACACUUCAAACUCGUACCGUGAGUAAUAAUGCGCCGUCCACGGCA | 127 |
| miR-126-2 | ACAUUAUUACUUUUGGUACGCGCUGUGACACUUCAAACUCGUACCGUGAGUAAUAAUGCGC | 128 |
| miR-127-1 | UGUGAUCACUGUCUCCAGCCUGCUGAAGCUCAGAGGGCUCUGAUUCAGAAAGAUCAUCGGAUCCGUCUGAGCUUGGCUGGUCGGAAGUCUCAUCAUC | 129 |
| miR-127-2 | CCAGCCUGCUGAAGCUCAGAGGGCUCUGAUUCAGAAAGAUCAUCGGAUCCGUCUGAGCUUGGCUGGUCGG | 130 |
| miR-128a | UGAGCUGUUGGAUUCGGGGCCGUAGCACUGUCUGAGAGGUUUACAUUUCUCACAGUGAACCGGUCUCUUUUUCAGCUGCUUC | 131 |
| miR-128b | GCCCGGCAGCCACUGUGCAGUGGGAAGGGGGCCGAUACACUGUACGAGAGUGAGUAGCAGGUCUCACAGUGAACCGGUCUCUUUCCCUACUGUGUCACACUCCUAAUGG | 132 |
| miR-128 | GUUGGAUUCGGGGCCGUAGCACUGUCUGAGAGGUUUACAUUUCUCACAGUGAACCGGUCUCUUUUCAGC | 133 |
| miR-129-1 | UGGAUCUUUUUGCGGUCUGGGCUUGCUGUUCCUCUCAACAGUAGUCAGGAAGCCCUUACCCCAAAAGUAUCUA | 134 |
| miR-129-2 | UGCCCUUCGCGAAUCUUUUUGCGGUCUGGGCUUGCUGUACAUAACUCAAUAGCCGGAAGCCCUUACCCCAAAAAGCAUUUGCGGAGGGCG | 135 |
| miR-130a | UGCUGCUGGCCAGAGCUCUUUUCACAUUGUGCUACUGUCUGCACCUGUCACUAGCAGUGCAAUGUUAAAAGGGCAUUGGCCGUGUAGUG | 136 |
| miR-131-1 | GCCAGGAGGCGGGGUUGGUUGUUAUCUUUGGUUAUCUAGCUGUAUGAGUGGUGUGGAGUCUUCAUAAAGCUAGAUAACCGAAAGUAAAAAUAACCCCAUACACUGCGCAG | 137 |
| miR-131-3 | CACGGCGCGGCAGCGGCACUGGCUAAGGGAGGCCGUUUCUCUCUUUGGUUAUCUAGCUGUAUGAGUGCCACAGAGCCGUCAUAAAGCUAGAUAACCGAAAGUAGAAAUG | 138 |
| miR-131 | GUUGUUAUCUUUGGUUAUCUAGCUGUAUGAGUAUUGGUCUUCAUAAAGCUAGAUAACCGAAAGUAAAAAC | 139 |
| miR-132-1 | CCGCCCCCGCGUCUCCAGGGCAACCGUGGCUUUCGAUUGUUACUGUGGGAACUGGAGGUAACAGUCUACAGCCAUGGUCGCCCCGCAGCACGCCCACGCGC | 140 |
| miR-132-2 | GGGCAACCGUGGCUUUCGAUUGUUACUGUGGGAACUGGAGGUAACAGUCUACAGCCAUGGUCGCCC | 141 |
| miR-133a-1 | ACAAUGCUUUGCUAGAGCUGGUAAAAUGGAACCAAAUCGCCUCUUCAAUGGAUUUGGUCCCCUUCAACCAGCUGUAGCUAUGCAUUGA | 142 |
| miR-133a-2 | GGGAGCCAAAUGCUUUGCUAGAGCUGGUAAAAUGGAACCAAAUCGACUGUCCAAUGGAUUUGGUCCCUUCAACCAGCUGUAGCUGUGCAUUGAUGGCGCCG | 143 |
| miR-133 | GCUAGAGCUGGUAAAAUGGAACCAAAUCGCCUCUUCAAUGGAUUUGGUCCCCUUCAACCAGCUGUAGC | 144 |

TABLE 1a-continued

Human microRNA Precursor Sequences

| Precursor Name | Sequence (5' To 3')* | SEQ ID NO. |
|---|---|---|
| miR-133b | CCUCAGAAGAAAGAUGCCCCCUGCUCUGGCUGG UCAAACGGAACCAAGUCCGUCUUCCUGAGAGGU UUGGUCCCCUUCAACCAGCUACAGCAGGGCUGG CAAUGCCCAGUCCUUGGAGA | 145 |
| miR-133b-small | GCCCCCUGCUCUGGCUGGUCAAACGGAACCAAG UCCGUCUUCCUGAGAGGUUUGGUCCCCUUCAAC CAGCUACAGCAGGG | 146 |
| miR-134-1 | CAGGGUGUGUGACUGGUUGACCAGAGGGGCAUG CACUGUGUUCACCCUGUGGGCCACCUAGUCACCA ACCCUC | 147 |
| miR-134-2 | AGGGUGUGUGACUGGUUGACCAGAGGGGCAUGC ACUGUGUUCACCCUGUGGGCCACCUAGUCACCA ACCCU | 148 |
| miR-135a-1 | AGGCCUCGCUGUUCUCUAUGGCUUUUUAUUCCU AUGUGAUUCUACUGCUCACUCAUAUAGGGAUUG GAGCCGUGGCGCACGGCGGGGACA | 149 |
| miR-135a-2 (miR-135-2) | AGAUAAAUUCACUCUAGUGCUUUUAUGGCUUUUU AUUCCUAUGUGAUAGUAAUAAAGUCUCAUGUAG GGAUGGAAGCCAUGAAAUACAUUGUGAAAAAUCA | 150 |
| miR-135 | CUAUGGCUUUUUAUUCCUAUGUGAUUCUACUGC UCACUCAUAUAGGGAUUGGAGCCGUGG | 151 |
| miR-135b | CACUCUGCUGUGGCCUAUGGCUUUUCAUUCCUA UGUGAUUGCUGUCCCAAACUCAUGUAGGGCUAA AAGCCAUGGGCUACAGUGAGGGGCGAGCUCC | 152 |
| miR-136-1 | UGAGCCCUCGGAGGACUCCAUUUGUUUUGAUGA UGGAUUCUUAUGCUCCAUCAUCGUCUCAAAUGA GUCUUCAGAGGGUUCU | 153 |
| miR-136-2 | GAGGACUCCAUUUGUUUUGAUGAUGGAUUCUUA UGCUCCAUCAUCGUCUCAAAUGAGUCUUC | 154 |
| miR-137 | CUUCGGUGACGGGUAUUCUUGGGUGGAUAAUAC GGAUUACGUUGUUAUUGCUUAAGAAUACGCGUA GUCGAGG | 155 |
| miR-138-1 | CCCUGGCAUGGUGUGGUGGGGCAGCUGGUGUUG UGAAUCAGGCCGUUGCCAAUCAGAGAACGGCUA CUUCACAACACCAGGGCCACACCACACUACAGG | 156 |
| miR-138-2 | CGUUGCUGCAGCUGGUGUUGUGAAUCAGGCCGA CGAGCAGCGCAUCCUCUUACCCGGCUAUUUCACG ACACCAGGGUUGCAUCA | 157 |
| miR-138 | CAGCUGGUGUUGUGAAUCAGGCCGACGAGCAGC GCAUCCUCUUACCCGGCUAUUUCACGACACCAGG GUUG | 158 |
| miR-139 | GUGUAUCUACAGUGCACGUGUCUCCAGUGUGG CUCGGAGGCUGGAGACGCGGCCCUGUUGGAGUA AC | 159 |
| miR-140 | UGUGUCUCUCUCUGUGUCCUGCCAGUGGUUUUA CCCUAUGGUAGUUACGUCAUGCUGUUUCUACCA CAGGGUAGAACCACGGACAGGAUACCGGGGCACC | 160 |
| miR-140as | UCCUGCCAGUGGUUUUUACCCUAUGGUAGUUAC GUCAUGCUGUUCUACCACAGGGUAGAACCACGG ACAGGA | 161 |
| miR-140s | CCUGCCAGUGGUUUUUACCCUAUGGUAGUUACG UCAUGCUGUUCUACCACAGGGUAGAACCACGGA CAGG | 162 |
| miR-141-1 | CGGCCGGCCCUGGGUCCAUCUUCCAGUACAGUG UUGGAUGGUCUAAUUGUGAAGCUCCUAACACUG UCUGGUAAAGAUGGCUCCCGGGUGGGUUC | 163 |
| miR-141-2 | GGGUCCAUCUUCCAGUACAGUGUUGGAUGGUCU AAUUGUGAAGCUCCUAACACUGUCUGGUAAAGA UGGCCC | 164 |
| miR-142 | ACCCAUAAAGUAGAAAGCACUACUAACAGCACU GGAGGGUGUAGUGUUUCCUACUUUAUGGAUG | 165 |
| miR-143-1 | GCGCAGCGCCCUGUCUCCCAGCCUGAGGUGCAGU GCUGCAUCUCUGGUCAGUUGGGAGUCUGAGAUG AAGCACUGUAGCUCAGGAAGAGAGAAGUUGUUC UGCAGC | 166 |
| miR-143-2 | CCUGAGGUGCAGUGCUGCAUCUCUGGUCAGUUG GGAGUCUGAGAUGAAGCACUGUAGCUCAGG | 167 |
| miR-144-1 | UGGGGCCCUGGCUGGGAUAUCAUCAUAUACUGU AAGUUUGCGAUGAGACACUACAGUAUAGAUGAU GUACUAGUCCGGGCACCCCC | 168 |
| miR-144-2 | GGCUGGGAUAUCAUCAUAUACUGUAAGUUUGCG AUGAGACACUACAGUAUAGAUGAUGUACUAGUC | 169 |
| miR-145-1 | CACCUUGUCCUCACGGUCCAGUUUUCCCAGGAA UCCCUUAGAUGCUAAGAUGGGGAUUCCUGGAAA UACUGUUCUUGAGGUCAUGGUU | 170 |
| miR-145-2 | CUCACGGUCCAGUUUUCCCAGGAAUCCCUUAGA UGCUAAGAUGGGGAUUCCUGGAAAUACUGUUCU UGAG | 171 |
| miR-146-1 | CCGAUGUGUAUCCUCAGCUUUGAGAACUGAAUU CCAUGGGUUGUGUCAGUGUCAGACCUCUGAAAU UCAGUUCUUCAGCUGGGAUAUCUCUGUCAUCGU | 172 |
| miR-146-2 | AGCUUUGAGAACUGAAUUCCAUGGGUUGUGUCA GUGUCAGACCUGUGAAAUUCAGUUCUUCAGCU | 173 |
| miR-147 | AAUCUAAAGACAACAUUUCUGCACACACACCAG ACUAUGGAAGCCAGUGUGUGGAAAUGCUUCUGC UAGAUU | 174 |
| miR-148a (miR-148) | GAGGCAAAGUUCUGAGACACUCCGACUCUGAGU AUGAUAGAAGUCAGUGCACUACAGAACUUUGUC UC | 175 |
| miR-148b | CAAGCACGAUUAGCAUUUGAGGUGAAGUUCUGU UAUACACUCAGGCUGUGGCUCUCUGAAAGUCAG UGCAUCACAGAACUUUGUCUCGAAAGCUUUCUA | 176 |
| miR-148b-small | AAGCACGAUUAGCAUUUGAGGUGAAGUUCUGUU AUACACUCAGGCUGUGGCUCUCUGAAAGUCAGU GCAU | 177 |
| miR-149-1 | GCCGGCGCCCGAGCUCUGGCUCCGUGUCUUCACU CCCGUGCUUGUCCGAGGAGGGAGGGAGGGACGG GGGCUGUGCUGGGGCAGCUGGA | 178 |
| miR-149-2 | GCUCUGGCUCCGUGUCUUCACUCCCGUGCUUGUC CGAGGAGGGAGGGAGGGAC | 179 |
| miR-150-1 | CUCCCCAUGGCCCUGUCUCCCAACCCUUGUACCA GUGCUGGGCUCAGACCCUGGUACAGGCCUGGGG GACAGGGACCUGGGGAC | 180 |
| miR-150-2 | CCCUGUCUCCCAACCCUUGUACCAGUGCUGGGCU CAGACCCUGGUACAGGCCUGGGGGACAGGG | 181 |
| miR-151 | UUUCCUGCCCUCGAGGAGCUCACAGUCUAGUAU GUCUCAUCCCCUACUAGACUGAAGCUCCUUGAG GACAGG | 182 |
| miR-151-2 | CCUGUCCUCAAGGAGCUUCAGUCUAGUAGGGGA UGAGACAUACUAGACUGUGAGCUCCUCGAGGGC AGG | 183 |

TABLE 1a-continued

Human microRNA Precursor Sequences

| Precursor Name | Sequence (5' To 3')* | SEQ ID NO. |
|---|---|---|
| miR-152-1 | UGUCCCCCCGGCCCAGGUUCUGUGAUACACUCC GACUCGGGCUCUGGAGCAGUCAGUGCAUGACAG AACUUGGGCCCGGAAGGACC | 184 |
| miR-152-2 | GGCCCAGGUUCUGUGAUACACUCCGACUCGGGC UCUGGAGCAGUCAGUGCAUGACAGAACUUGGGC CCCGG | 185 |
| miR-153-1-1 | CUCACAGCUGCCAGUGUCAUUUUUGUGAUCUGC AGCUAGUAUUCUCACUCCAGUUGCAUAGUCACA AAAGUGAUCAUUGGCAGGUGUGGC | 186 |
| miR-153-1-2 | UCUCUCUCUCCCUCACAGCUGCCAGUGUCAUUGU CACAAAAGUGAUCAUUGGCAGGUGUGGCUGCUG CAUG | 187 |
| miR-153-2-1 | AGCGGUGGCCAGUGUCAUUUUUGUGAUGUUGCA GCUAGUAAUAUGAGCCCAGUUGCAUAGUCACAA AAGUGAUCAUUGGAAACUGUG | 188 |
| miR-153-2-2 | CAGUGUCAUUUUUGUGAUGUUGCAGCUAGUAAU AUGAGCCCAGUUGCAUAGUCACAAAAGUGAUCA UUG | 189 |
| miR-154-1 | GUGGUACUUGAAGAUAGGUUAUCCGUGUUGCCU UCGCUUUAUUGUGACGAAUCAUACACGGUUGA CCUAUUUUUCAGUACCAA | 190 |
| miR-154-2 | GAAGAUAGGUUAUCCGUGUUGCCUUCGCUUUAU UGUGACGAAUCAUACACGGUUGACCUAUUUUU | 191 |
| miR-155 | CUGUUAAUGCUAAUCGUGAUAGGGGUUUUUGCC UCCAACUGACUCCUACAUAUUAGCAUUAACAG | 192 |
| miR-156 = miR-157 = overlap miR-141 | CCUAACACUGUCUGGUAAAGAUGGCUCCCGGGU GGGUUCCUCGGCAGUAACCUUCAGGGAGCCCU GAAGACCAUGGAGGAC | 193 |
| miR-158-small = miR-192 | GCCGAGACCGAGUGCACAGGGCUCUGACCUAUG AAUUGACAGCCAGUGCUCUCGUCUCCCCUCUGGC UGCCAAUUCCAUAGGUCACAGGUAUGUUCGCCU CAAUGCCAGC | 194 |
| miR-159-1-small | UCCCGCCCCCUGUAACAGCAACUCCAUGUGGAAG UGCCCACUGGUUCCAGUGGGGCUGCUGUUAUCU GGGGCGAGGGCCA | 195 |
| miR-161-small | AAAGCUGGGUUGAGAGGGCGAAAAAGGAUGAGG UGACUGGUCUGGGCUACGCUAUGCUGCGGCGCU CGGG | 196 |
| miR-163-1b-small | CAUUGGCCUCCUAAGCCAGGGAUUGUGGGUUCG AGUCCCACCCGGGUAAAGAAAGGCCGAAUU | 197 |
| miR-163-3-small | CCUAAGCCAGGGAUUGUGGGUUCGAGUCCCACC UGGGGUAGAGGUGAAAGUUCCUUUUACGGAAUU UUUU | 198 |
| miR-162 | CAAUGUCAGCAGUGCCUUAGCAGCACGUAAAUA UUGGCGUUAAGAUUCUAAAAUUAUCUCCAGUAU UAACUGUGCUGCUGAAGUAAGGUUGACCAUACU CUACAGUUG | 199 |
| miR-175-small = miR-224 | GGGCUUUCAAGUCACUAGUGGUUCCGUUUAGUA GAUGAUUGUGCAUUGUUUCAAAAUGGUGCCCUA GUGACUACAAAGCCC | 200 |
| miR-177-small | ACGCAAGUGUCCUAAGGUGAGCUCAGGGAGCAC AGAAACCUCCAGUGGAACAGAAGGGCAAAAGCU CAUU | 201 |
| miR-180-small | CAUGUGUCACUUUCAGGUGGAGUUUCAAGAGUC CCUUCCUGGUUCACCGUCUCCUUUGCUCUUCCAC AAC | 202 |
| miR-181a | AGAAGGGCUAUCAGGCCAGCCUUCAGAGGACUC CAAGGAACAUUCAACGCUGUCGGUGAGUUUGGG AUUUGAAAAAACCACUGACCGUUGACUGUACCU UGGGGUCCUUA | 203 |
| miR-181b-1 | CCUGUGCAGAGAUUAUUUUUAAAAGGUCACAA UCAACAUUCAUUGCUGUCGGUGGGUUGAACUGU GUGGACAAGCUCACUGAACAAUGAAUGCAACUG UGGCCCCGCUU | 204 |
| miR-181b-2 | CUGAUGGCUGCACUCAACAUUCAUUGCUGUCGG UGGGUUUGAGUCUGAAUCAACUCACUGAUCAAU GAAUGCAAACUGCGGACCAAACA | 205 |
| miR-181c | CGGAAAAUUUGCCAAGGGUUUGGGGGAACAUUC AACCUGUCGGUGAGUUUGGGCAGCUCAGGCAAA CCAUCGACCGUUGAGUGGACCCUGAGGCCUGGA AUUGCCAUCCU | 206 |
| miR-182-as | GAGCUGCUUGCCUCCCCCCGUUUUGGCAAUGG UAGAACUCACACUGGUGAGGUAACAGGAUCCGG UGGUUCUAGACUUGCCAACUAUGGGGCGAGGAC UCAGCCGGCAC | 207 |
| miR-182 | UUUUUGGCAAUGGUAGAACUCACACUGGUGAGG UAACAGGAUCCGGUGGUUCUAGACUUGCCAACU AUGG | 208 |
| miR-183 | CCGCAGAGUGUGACUCCUGUUCUGUGUAUGGCA CUGGUAGAAUUCACUGUGAACAGUCUCAGUCAG UGAAUUACCGAAGGGCCAUAAACAGAGCAGAGA CAGAUCCACGA | 209 |
| miR-184-1 | CCAGUCACGUCCCCUUAUCACUUUUCCAGCCCAG CUUUGUGACUGUAAGUGUUGGACGGAGAACUGA UAAGGGUAGGUGAUUGA | 210 |
| miR-184-2 | CCUUAUCACUUUUCCAGCCCAGCUUUGUGACUG UAAGUGUUGGACGGAGAACUGAUAAGGGUAGG | 211 |
| miR-185-1 | AGGGGGCGAGGGAUUGGAGAGAAAGGCAGUUCC UGAUGGUCCCCUCCCCAGGGGCUGGCUUUCCUCU GGUCCUUCCCUCCCA | 212 |
| miR-185-2 | AGGGAUUGGAGAGAAAGGCAGUUCCUGAUGGUC CCCUCCCCAGGGGCUGGCUUUCCUCUGGUCCUU | 213 |
| miR-186-1 | UGCUUGUAACUUUCCAAAGAAUUCUCCUUUUGG GCUUUCUGGUUUUAUUUUAAGCCCAAAGGUGAA UUUUUUGGGAAGUUUGAGCU | 214 |
| miR-186-2 | ACUUUCCAAAGAAUUCUCCUUUUGGGCUUUCUG GUUUUAUUUUAAGCCCAAAGGUGAAUUUUUUGG GAAGU | 215 |
| miR-187 | GGUCGGGCUCACCAUGACACAGUGUGAGACUCG GGCUACAACACAGGACCCGGGGCGCUGCUCUGA CCCCUCGUGUCUUGUGUUGCAGCCGGAGGGACG CAGGUCCGCA | 216 |
| miR-188-1 | UGCUCCCUCUCUCACAUCCCUUGCAUGGUGGAG GGUGAGCUUUCUGAAAACCCCUCCCCACAUGCAG GGUUUGCAGGAUGGCGAGCC | 217 |
| miR-188-2 | UCUCACAUCCCUUGCAUGGUGGAGGGUGAGCUU UCUGAAAACCCCUCCCCACAUGCAGGGUUUGCAG GA | 218 |

TABLE 1a-continued

Human microRNA Precursor Sequences

| Precursor Name | Sequence (5' To 3')* | SEQ ID NO. |
|---|---|---|
| miR-189-1 | CUGUCGAUUGGACCCGCCCUCCGGUGCCUACUGA GCUGAUAUCAGUUCUCAUUUUACACACUGGCUC AGUUCAGCAGGAACAGGAGUCGAGCCCUUGAGC AA | 219 |
| miR-189-2 | CUCCGGUGCCUACUGAGCUGAUAUCAGUUCUCA UUUUACACACUGGCUCAGUUCAGCAGGAACAGG AG | 220 |
| miR-190-1 | UGCAGGCCUCUGUGUGAUAUGUUUGAUAUAUUA GGUUGUUAUUUAAUCCAACUAUAUAUCAAACAU AUUCCUACAGUGUCUUGCC | 221 |
| miR-190-2 | CUGUGUGAUAUGUUUGAUAUAUUAGGUUGUUAU UUAAUCCAACUAUAUAUCAAACAUAUUCCUACAG | 222 |
| miR-191-1 | CGGCUGGACAGCGGGCAACGGAAUCCCAAAAGC AGCUGUUGUCUCCAGAGCAUUCCAGCUGCGCUU GGAUUUCGUCCCCUGCUCUCCUGCCU | 223 |
| miR-191-2 | AGCGGGCAACGGAAUCCCAAAAGCAGCUGUUGU CUCCAGAGCAUUCCAGCUGCGCUUGGAUUUCGU CCCCUGCU | 224 |
| miR-192-2/3 | CCGAGACCGAGUGCACAGGGCUCUGACCUAUGA AUUGACAGCCAGUGCUCUCGUCUCCCCUCUGGCU GCCAAUUCCAUAGGUCACAGGUAUGUUCGCCUC AAUGCCAG | 225 |
| miR-192 | GCCGAGACCGAGUGCACAGGGCUCUGACCUAUG AAUUGACAGCCAGUGCUCUCGUCUCCCCUCUGGC UGCCAAUUCCAUAGGUCACAGGUAUGUUCGCCU CAAUGCCAGC | 226 |
| miR-193-1 | CGAGGAUGGGAGCUGAGGGCUGGGUCUUUGCGG GCGAGAUGAGGGUGUCGGAUCAACUGGCCUACA AAGUCCCAGUUCUCGGCCCCCG | 227 |
| miR-193-2 | GCUGGGUCUUUGCGGGCGAGAUGAGGGUGUCGG AUCAACUGGCCUACAAAGUCCCAGU | 228 |
| miR-194-1 | AUGGUGUUAUCAAGUGUAACAGCAACUCCAUGU GGACUGUGUACCAAUUUCCAGUGGAGAUGCUGU UACUUUUGAUGGUUACCAA | 229 |
| miR-194-2 | GUGUAACAGCAACUCCAUGUGGACUGUGUACCA AUUUCCAGUGGAGAUGCUGUUACUUUUGAU | 230 |
| miR-195-1 | AGCUUCCCUGGCUCUAGCAGCACAGAAAUAUUG GCACAGGGAAGCGAGUCUGCCAAUAUUGGCUGU GCUGCUCCAGGCAGGGUGGUG | 231 |
| miR-195-2 | UAGCAGCACAGAAAUAUUGGCACAGGGAAGCGA GUCUGCCAAUAUUGGCUGUGCUGCU | 232 |
| miR-196-1 | CUAGAGCUUGAAUUGGAACUGCUGAGUGAAUUA GGUAGUUUCAUGUUGUUGGGCCUGGGUUUCUGA ACACAACAACAUUAAACCACCCGAUUCACGGCA GUUACUGCUCC | 233 |
| miR-196a-1 | GUGAAUUAGGUAGUUUCAUGUUGUUGGGCCUGG GUUUCUGAACACAACAACAUUAAACCACCCGAU UCAC | 234 |
| miR-196a-2 (miR-196-2) | UGCUCGCUCAGCUGAUCUGUGGCUUAGGUAGUU UCAUGUUGUUGGGAUUGAGUUUUGAACUCGGCA ACAAGAAACUGCCUGAGUUACAUCAGUCGGUUU UCGUCGAGGGC | 235 |
| miR-196 | GUGAAUUAGGUAGUUUCAUGUUGUUGGGCCUGG GUUUCUGAACACAACAACAUUAAACCACCCGAU UCAC | 236 |
| miR-196b | ACUGGUCGGUGAUUUAGGUAGUUUCCUGUUGUU GGGAUCCACCUUUCUCUCGACAGCACGACACUGC CUUCAUUACUUCAGUUG | 237 |
| miR-197 | GGCUGUGCCGGGUAGAGAGGGCAGUGGGAGGUA AGAGCUCUUCACCCUUCACCACCUUCUCCACCCA GCAUGGCC | 238 |
| miR-197-2 | GUGCAUGUGUAUGUAUGUGUGCAUGUGCAUGUG UAUGUGUAUGAGUGCAUGCGUGUGUGC | 239 |
| miR-198 | UCAUUGGUCCAGAGGGGAGAUAGGUUCCUGUGA UUUUUCCUUCUUCUCUAUAGAAUAAAUGA | 240 |
| miR-199a-1 | GCCAACCCAGUGUUCAGACUACCUGUUCAGGAG GCUCUCAAUGUGUACAGUAGUCUGCACAUUGGU UAGGC | 241 |
| miR-199a-2 | AGGAAGCUUCUGGAGAUCCUGCUCCGUCGCCCC AGUGUUCAGACUACCUGUUCAGGACAAUGCCGU UGUACAGUAGUCUGCACAUUGGUUAGACUGGGC AAGGGAGAGCA | 242 |
| miR-199b | CCAGAGGACACCUCCACUCCGCUCUACCCAGUGUU UAGACUAUCUGUUCAGGACUCCCAAAUUGUACA GUAGUCUGCACAUUGGUUAGGCUGGGCUGGGUU AGACCCUCGG | 243 |
| miR-199s | GCCAACCCAGUGUUCAGACUACCUGUUCAGGAG GCUCUCAAUGUGUACAGUAGUCUGCACAUUGGU UAGGC | 244 |
| miR-200a | GCCGUGGCCAUCUUACUGGGCAGCAUUGGAUGG AGUCAGGUCUCUAAUACUGCCUGGUAAUGAUGA CGGC | 245 |
| miR-200b | CCAGCUCGGGCAGCCGUGGCCAUCUUACUGGGC AGCAUUGGAUGGAGUCAGGUCUCUAAUACUGCC UGGUAAUGAUGACGGCGGAGCCCUGCACG | 246 |
| miR-200c | CCCUCGUCUUACCCAGCAGUGUUUGGGUGCGGU UGGGAGUCUCUAAUACUGCCGGGUAAUGAUGGA GG | 247 |
| miR-202 | GUUCCUUUUUCCUAUGCAUAUACUUCUUUGAGG AUCUGGCCUAAAGAGGUAUAGGGCAUGGGAAGA UGGAGC | 248 |
| miR-203 | GUGUUGGGACUCGCGCGCUGGGUCCAGUGGUU CUUAACAGUUCAACAGUUCUGUAGCGCAAUUGU GAAAUGUUUAGGACCACUAGACCCGGCGGGCGC GGCGACAGCGA | 249 |
| miR-204 | GGCUACAGUCUUUCUUCAUGUGACUCGUGGACU UCCCUUUGUCAUCCUAUGCCUGAGAAUAUAUGA AGGAGGCUGGGAAGGCAAAGGGACGUUCAAUUG UCAUCACUGGC | 250 |
| miR-205 | AAAGAUCCUCAGACAAUCCAUGUGCUUUCUCUUU UCCUUCAUUCCACCGGAGUCUGUCUCAUACCCAA CCAGAUUUCACUGUGGAGUGAAGUUCAGGAGGCAU GGAGCUGACA | 251 |
| miR-206-1 | UGCUUCCCGAGGCCACAUGCUUCUUUAUAUCCCC AUAUGGAUUACUUUGCUAUGGAAUGUAAGGAAG UGUGUGGUUUCGGCAAGUG | 252 |
| miR-206-2 | AGGCCACAUGCUUCUUUAUAUCCCCAUAUGGAU UACUUUGCUAUGGAAUGUAAGGAAGUGUGUGGU UUU | 253 |
| miR-208 | UGACGGGCGAGCUUUUGGCCCGGGUUAUACCUG AUGCUCACGUAUAAGACGAGCAAAAAGCUUGUU GGUCA | 254 |

TABLE 1a-continued

Human microRNA Precursor Sequences

| Precursor Name | Sequence (5' To 3')* | SEQ ID NO. |
|---|---|---|
| miR-210 | ACCCGGCAGUGCCUCCAGGCGCAGGGCAGCCCCU GCCCACCGCACACUGCGCUGCCCCAGACCCACUG UGCGUGUGACAGCGGCUGAUCUGUGCCUGGGCA GCGCGACCC | 255 |
| miR-211 | UCACCUGGCCAUGUGACUUGUGGGCUUCCCUUU GUCAUCCUUCGCCUAGGGCUCUGAGCAGGGCAG GGACAGCAAAGGGGUGCUCAGUUGUCACUUCCC ACAGCACGGAG | 256 |
| miR-212 | CGGGGCACCCCGCCCGGACAGCGCGCCGGCACCU UGGCUCUAGACUGCUUACUGCCCGGGCCGCCCUC AGUAACAGUCUCCAGUCACGGCCACCGACGCCUG GCCCCGCC | 257 |
| miR-213-2 | CCUGUGCAGAGAUUAUUUUUUAAAAGGUCACAA UCAACAUUCAUUGCUGUCGGUGGGUUGAACUGU GUGGACAAGCUCACUGAACAAUGAAUGCAACUG UGGCCCCGCUU | 258 |
| miR-213 | GAGUUUUGAGGUUGCUUCAGUGAACAUUCAACG CUGUCGGUGAGUUUGGAAUUAAAAUCAAAACCA UCGACCGUUGAUUGUACCCUAUGGCUAACCAUC AUCUACUCC | 259 |
| miR-214 | GGCCUGGCUGGACAGAGUUGUCAUGUGUCUGCC UGUCUACACUUGCUGUGCAGAACAUCCGCUCAC CUGUACAGCAGGCACAGACAGGCAGUCACAUGA CAACCCAGCCU | 260 |
| miR-215 | AUCAUUCAGAAAUGGUAUACAGGAAAAUGACCU AUGAAUUGACAGACAAUAUAGCUGAGUUUGUCU GUCAUUUCUUUAGGCCAAUAUUCUGUAUGACUG UGCUACUUCAA | 261 |
| miR-216 | GAUGGCUGUGAGUUGGCUUAAUCUCAGCUGGCA ACUGUGAGAUGUUCAUACAAUCCCUCACAGUGG UCUCUGGGAUUAUGCUAAACAGAGCAAUUUCCU AGCCCUCACGA | 262 |
| miR-217 | AGUAUAAUUAUUACAUAGUUUUUGAUGUCGCAG AUACUGCAUCAGGAACUGAUUGGAUAAGAAUCA GUCACCAUCAGUUCCUAAUGCAUUGCCUUCAGC AUCUAAACAAG | 263 |
| miR-218-1 | GUGAUAAUGUAGCGAGAUUUUCUGUUGUGCUUG AUCUAACCAUGUGGUUGCGAGGUAUGAGUAAAA CAUGGUUCCGUCAAGCACCAUGGAACGUCACGC AGCUUUCUACA | 264 |
| miR-218-2 | GACCAGUCGCUGCGGGGCUUUCCUUUGUGCUUG AUCUAACCAUGUGGUGGAACGAUGGAAACGGAA CAUGGUUCUGUCAAGCACCGCGGAAAGCACCGU GCUCUCCUGCA | 265 |
| miR-219 | CCGCCCCGGGCCGCGGCUCCUGAUUGUCCAAACG CAAUUCUCGAGUCUAUGGCUCCGGCCGAGAGUU GAGUCUGGACGUCCCGAGCCGCCGCCCCCAAACC UCGAGCGGG | 266 |
| miR-219-1 | CCGCCCCGGGCCGCGGCUCCUGAUUGUCCAAACG CAAUUCUCGAGUCUAUGGCUCCGGCCGAGAGUU GAGUCUGGACGUCCCGAGCCGCCGCCCCCAAACC UCGAGCGGG | 267 |
| miR-219-2 | ACUCAGGGCUUCGCCACUGAUUGUCCAAACGC AAUUCUUGUACGAGUCUGCGGCCAACCGAGAAU UGUGGCUGGACAUCUGUGGCUGAGCUCCGGG | 268 |
| miR-220 | GACAGUGUGGGCAUUGUAGGGCUCCACACCGUAU CUGACACUUUGGGCGAGGGCACCAUGCUGAAGG UGUUCAUGAUGCGGUCUGGGAACUCCUCACGGA UCUUACUGAUG | 269 |
| miR-221 | UGAACAUCCAGGUCUGGGGCAUGAACCUGGCAU ACAAUGUAGAUUUCUGUGUUCGUUAGGCAACAG CUACAUUGUCUGCUGGGUUUCAGGCUACCUGGA AACAUGUUCUC | 270 |
| miR-222 | GCUGCUGGAAGGUGUAGGUACCCUCAAUGGCUC AGUAGCCAGUGUAGAUCCUGUCUUUCGUAAUCA GCAGCUACAUCUGGCUACUGGGUCUCUGAUGGC AUCUUCUAGCU | 271 |
| miR-223 | CCUGGCCUCCUGCAGUGCCACGCUCCGUGUAUUU GACAAGCUGAGUUGGACACUCCAUGUGGUAGAG UGUCAGUUUGUCAAAUACCCCAAGUGCGGCACA UGCUUACCAG | 272 |
| miR-224 | GGGCUUUCAAGUCACUAGUGGUUCCGUUUAGUA GAUGAUUGUGCAUUGUUUCAAAAUGGUGCCCUA GUGACUACAAAGCCC | 273 |
| miR-294-1 (chr16) | CAAUCUCCUUUAUCAUGGUAUUGAUUUUUCAG UGCUUCCCUUUUGUGUGAGAGAAGAUA | 274 |
| miR-296 | AGGACCCUUCCAGAGGGCCCCCCCUCAAUCCUGU UGUGCCUAAUUCAGAGGGUUGGGUGGAGGCUCU CCUGAAGGGCUCU | 275 |
| miR-299 | AAGAAAUGGUUUACCGUCCCACAUACAUUUUGA AUAUGUAUGUGGGAUGGUAAACCGCUUCUU | 276 |
| miR-301 | ACUGCUAACGAAUGCUCUGACUUUAUUGCACUA CUGUACUUUACAGCUAGCAGUGCAAUAGUAUUG UCAAAGCAUCUGAAAGCAGG | 277 |
| miR-302a | CCACCACUUAAACGUGGAUGUACUUGCUUUGAA ACUAAAGAAGUAAGUGCUUCCAUGUUUUGGUGA UGG | 278 |
| miR-302b | GCUCCCUUCAACUUUAACAUGGAAGUGCUUUCU GUGACUUUAAAAGUAAGUGCUUCCAUGUUUUAG UAGGAGU | 279 |
| miR-302c | CCUUUGCUUUAACAUGGGGGUACCUGCUGUGUG AAACAAAAGUAAGUGCUUCCAUGUUUCAGUGGA GG | 280 |
| miR-302d | CCUCUACUUUAACAUGGAGGCACUUGCUGUGAC AUGACAAAAAUAAGUGCUUCCAUGUUUGAGUGU GG | 281 |
| miR-320 | GCUUCGCUCCCCUCCGCCUUCUCUUCCCGGUUCU UCCCGGAGUCGGGAAAAGCUGGGUUGAGAGGGC GAAAAAGGAUGAGGU | 282 |
| miR-321 | UUGGCCUCCUAAGCCAGGGAUUGUGGGUUCGAG UCCCACCCGGGGUAAAGAAAGGCCGA | 283 |
| miR-323 | UUGGUACUUGGAGAGAGGUGGUCCGUGGCGCGU UCGCUUUAUUUAUGGCGCACAUUACACGGUCGA CCUCUUUGCAGUAUCUAAUC | 284 |
| miR-324 | CUGACUAUGCCUCCCCGCAUCCCCUAGGGCAUUG GUGUAAAGCUGGAGACCCACUGCCCCAGGUGCU GCUGGGGGUUGUAGUC | 285 |
| miR-325 | AUACAGUGCUUUGGUUCCUAGUAGGUGUCCAGUA AGUGUUUGUGACAUAAUUUGUUUAUUGAGGACC UCCUAUCAAUCAAGCACUGUGCUAGGCUCUGG | 286 |
| miR-326 | CUCAUCUGUCUGUUGGGCUGGAGGCAGGGCCUU UGUGAAGGCGGGUGGUGCUCAGAUCGCUCCUGG GCCUUCCUCCAGCCCCGAGGCGGAUUCA | 287 |

TABLE 1a-continued

Human microRNA Precursor Sequences

| Precursor Name | Sequence (5' To 3')* | SEQ ID NO. |
|---|---|---|
| miR-328 | UGGAGUGGGGGGCAGGAGGGGCUCAGGGAGAA AGUGCAUACAGCCCCUGGCCCUCUCUGCCCUUCC GUCCCCUG | 288 |
| miR-330 | CUUUGGCGAUCACUGCCUCUCUGGGCCUGUGUC UUAGGCUCUGCAAGAUCAACCGAGCAAAGCACA CGGCCUGCAGAGAGGCAGCGCUCUGCCC | 289 |
| miR-331 | GAGUUUGGUUUUGUUUGGGUUUGUUCUAGGUAU GGUCCCAGGGAUCCCAGAUCAAACCAGGCCCCUG GGCCUAUCCUAGAACCAACCUAAGCUC | 290 |
| miR-335 | UGUUUUGAGCGGGGGUCAAGAGCAAUAACGAAA AAUGUUUGUCAUAAACCGUUUUUCAUUAUUGCU CCUGACCUCCUCAUUUGCUAUAUUCA | 291 |
| miR-337 | GUAGUCAGUAGUUGGGGGUGGGAACGGCUUCA UACAGGAGUUGAUGCACAGUUAUCCAGCUCCUA UAUGAUGCCUUUCUUCAUCCCCUUCAA | 292 |
| miR-338 | UCUCCAACAAUAUCCUGGUGCUGAGUGAUGACU CAGGCGACUCCAGCAUCAGUGAUUUUGUUGAAGA | 293 |
| miR-339 | CGGGGCGGCCGCUCUCCCUGUCCUCCAGGAGCUC ACGUGUGCCUGCCUGUGAGCGCCUCGACGACAG AGCCGGCGCCUGCCCCAGUGUCUGCGC | 294 |
| miR-340 | UUGUACCUGGUGUGAUUAUAAAGCAAUGAGACU GAUUGUCAUAUGUCGUUUGUGGGAUCCGUCUCA GUUACUUUAUAGCCAUACCUGGUAUCUUA | 295 |
| miR-342 | GAAACUGGGCUCAAGGUGAGGGGUGCUAUCUGU GAUUGAGGGACAUGGUUAAUGGAAUUGUCUCAC ACAGAAAUCGCACCCGUCACCUUGGCCUACUUA | 296 |
| miR-345 | ACCCAAACCCUAGGUCUGCUGACUCCUAGUCCAG GGCUCGUGAUGGCUGGUGGGCCCUGAACGAGGG GUCUGGAGGCCUGGGUUUGAAUAUCGACAGC | 297 |
| miR-346 | GUCUGUCUGCCCGCAUGCCUGCCUCUCUGUUGCU CUGAAGGAGGCAGGGGCUGGGCCUGCAGCUGCC UGGGCAGAGCGGCUCCGC | 298 |
| miR-367 | CCAUUACUGUUGCUAAUAUGCAACUCUGUUGAA UAUAAAUUGGAAUUGCACUUUAGCAAUGGUGAU GG | 299 |
| miR-368 | AAAAGGUGGAUAUUCCUUCUAUGUUUAUGUUAU UUAUGGUUAAACAUAGAGGAAAUUCCACGUUUU | 300 |
| miR-369 | UUGAAGGGAGAUCGACCGUGUUAUAUUCGCUUU AUUGACUUCGAAUAAUACAUGGUUGAUCUUUUC UCAG | 301 |
| miR-370 | AGACAGAGAAGCCAGGUCACGUCUCUGCAGUUA CACAGCUCACGAGUGCCUGCUGGGGUGGAACCU GGUCUGUCU | 302 |
| miR-371 | GUGGCACUCAAACUGUGGGGGCACUUUCUGCUC UCUGGGUGAAAGUGCCGCCAUCUUUUGAGUGUUAC | 303 |
| miR-372 | GUGGGCCUCAAAUGUGGAGCACUAUUCUGAUGU CCAAGUGGAAAGUGCUGCGACAUUUGAGCGUCAC | 304 |
| miR-373 | GGGAUACUCAAAAUGGGGGCGCUUUCCUUUUUG UCUGUACUGGGAAGUGCUUCGAUUUUGGGGUGU CCC | 305 |
| miR-374 | UACAUCGGCCAUUAUAAUACAACCUGAUAAGUG UUAUAGCACUUAUCAGAUUGUAUUGUAAUUGUC UGUGUA | 306 |
| miR-hes1 | AUGGAGCUGCUCACCCUGUGGGCCUCAAAUGUG GAGGAACUAUUCUGAUGUCCAAGUGGAAAGUGC UGCGACAUUUGAGCGUCACCGGUGACGCCCAUA UCA | 307 |
| miR-hes2 | GCAUCCCCUCAGCCUGUGGCACUCAAACUGUGG GGGCACUUUCUGCUCUCUGGUGAAAGUGCCGCC AUCUUUUGAGUGUUACCGCUUGAGAAGACUCAA CC | 308 |
| miR-hes3 | CGAGGAGCUCAUACUGGGAUACUCAAAAUGGGG GCGCUUUCCUUUUUGUCUGUUACUGGGAAGUGC UUCGAUUUUGGGGUGUCCCUGUUUGAGUAGGGC AUC | 309 |

*An underlined sequence within a precursor sequence corresponds to a mature processed miR transcript (see Table 1b). Some precursor sequences have two underlined sequences denoting two different mature miRs that are derived from the same precursor. All sequences are human.

TABLE 1b

Human Mature microRNA Sequences.

| Mature miRNA Name | Mature miRNA Sequence (5' to 3') | SEQ ID NO. | Corresponding precursor microRNA(s); see Table 1a |
|---|---|---|---|
| let-7a | ugagguaguagguuguauaguu | 310 | let-7a-1; let-7a-2; let-7a-3; let-7a-4 |
| let-7b | ugagguaguagguugugugguu | 311 | let-7b |
| let-7c | ugagguaguagguuguaugguu | 312 | let-7c |
| let-7d | agagguaguagguugcauagu | 313 | let-7d; let-7d-v1 |
| let-7e | ugagguaggagguuguauagu | 314 | let-7e |
| let-7f | ugagguaguagauuguauaguu | 315 | let-7f-1; let-7f-2-1; let-7f-2-2 |
| let-7g | ugagguaguaguuuguacagu | 316 | let-7g |
| let-7i | ugagguaguaguuugugcu | 317 | let-7i |

TABLE 1b-continued

Human Mature microRNA Sequences.

| Mature miRNA Name | Mature miRNA Sequence (5' to 3') | SEQ ID NO. | Corresponding precursor microRNA(s); see Table 1a |
|---|---|---|---|
| miR-1 | uggaauguaaagaaguaugua | 318 | miR-1b; miR-1b-1; miR-1b-2 |
| miR-7 | uggaagacuagugauuuuguu | 319 | miR-7-1; miR-7-1a; miR-7-2; miR-7-3 |
| miR-9 | ucuuugguuaucuagcuguauga | 320 | miR-9-1; miR-9-2; miR-9-3 |
| miR-9* | uaaagcuagauaaccgaaagu | 321 | miR-9-1; miR-9-2; miR-9-3 |
| miR-10a | uacccuguagauccgaauuugug | 322 | miR-10a |
| miR-10b | uacccuguagaaccgaauuugu | 323 | miR-10b |
| miR-15a | uagcagcacauaaugguuugug | 324 | miR-15a; miR-15a-2 |
| miR-15b | uagcagcacaucaugguuuaca | 325 | miR-15b |
| miR-16 | uagcagcacguaaauauuggcg | 326 | miR-16-1; miR-16-2; miR-16-13 |
| miR-17-5p | caaagugcuuacagugcagguagu | 327 | miR-17 |
| miR-17-3p | acugcagugaaggcacuugu | 328 | miR-17 |
| miR-18 | uaaggugcaucuagugcagaua | 329 | miR-18; miR-18-13 |
| miR-19a | ugugcaaaucuaugcaaaacuga | 330 | miR-19a; miR-19a-13 |
| miR-19b | ugugcaaauccaugcaaaacuga | 331 | miR-19b-1; miR-19b-2 |
| miR-20 | uaaagugcuuauagugcaggua | 332 | miR-20 (miR-20a) |
| miR-21 | uagcuuaucagacugauguuga | 333 | miR-21; miR-21-17 |
| miR-22 | aagcugccaguugaagaacugu | 334 | miR-22 |
| miR-23a | aucacauugccagggauuucc | 335 | miR-23a |
| miR-23b | aucacauugccagggauuaccac | 336 | miR-23b |
| miR-24 | uggcucaguucagcaggaacag | 337 | miR-24-1; miR-24-2; miR-24-19; miR-24-9 |
| miR-25 | cauugcacuugucucggucuga | 338 | miR-25 |
| miR-26a | uucaaguaauccaggauaggcu | 339 | miR-26a; miR-26a-1; miR-26a-2 |
| miR-26b | uucaaguaauucaggauaggu | 340 | miR-26b |
| miR-27a | uucacaguggcuaaguuccgcc | 341 | miR-27a |
| miR-27b | uucacaguggcuaaguucug | 342 | miR-27b-1; miR-27b-2 |
| miR-28 | aaggagcucacagucuauugag | 343 | miR-28 |
| miR-29a | cuagcaccaucugaaaucgguu | 344 | miR-29a-2; miR-29a |
| miR-29b | uagcaccauuugaaaucagu | 345 | miR-29b-1; miR-29b-2 |
| miR-29c | uagcaccauuugaaaucgguua | 346 | miR-29c |
| miR-30a-5p | uguaaacauccucgacuggaagc | 347 | miR-30a |
| miR-30a-3p | cuuucagucggauguuugcagc | 348 | miR-30a |
| miR-30b | uguaaacauccuacacucagc | 349 | miR-30b-1; miR-30b-2 |

TABLE 1b-continued

Human Mature microRNA Sequences.

| Mature miRNA Name | Mature miRNA Sequence (5' to 3') | SEQ ID NO. | Corresponding precursor microRNA(s); see Table 1a |
|---|---|---|---|
| miR-30c | uguaaacauccuacacucucagc | 350 | miR-30c |
| miR-30d | uguaaacaucccccgacuggaag | 351 | miR-30d |
| miR-30e | uguaaacauccuugacugga | 352 | miR-30e |
| miR-31 | ggcaagaugcuggcauagcug | 353 | miR-31 |
| miR-32 | uauugcacauuacuaaguugc | 354 | miR-32 |
| miR-33 | gugcauuguaguugcauug | 355 | miR-33; miR-33b |
| miR-34a | uggcagugucuuagcugguugu | 356 | miR-34a |
| miR-34b | aggcagugucauuagcugauug | 357 | miR-34b |
| miR-34c | aggcaguguaguuagcugauug | 358 | miR-34c |
| miR-92 | uauugcacuugucccggccugu | 359 | miR-92-2; miR-92-1 |
| miR-93 | aaagugcuguucgugcagguag | 360 | miR-93-1; miR-93-2 |
| miR-95 | uucaacggguauuuauugagca | 361 | miR-95 |
| miR-96 | uuuggcacuagcacauuuuugc | 362 | miR-96 |
| miR-98 | ugagguaguaaguuguauuguu | 363 | miR-98 |
| miR-99a | aacccguagauccgaucuugug | 364 | miR-99a |
| miR-99b | cacccguagaaccgaccuugcg | 365 | miR-99b |
| miR-100 | uacaguacugugauaacugaag | 366 | miR-100 |
| miR-101 | uacaguacugugauaacugaag | 367 | miR-101-1; miR-101-2 |
| miR-103 | agcagcauuguacagggcuauga | 368 | miR-103-1 |
| miR-105 | ucaaaugcucagacuccugu | 369 | miR-105 |
| miR-106-a | aaaagugcuuacagugcagguagc | 370 | miR-106-a |
| miR-106-b | uaaagugcugacagugcagau | 371 | miR-106-b |
| miR-107 | agcagcauuguacagggcuauca | 372 | miR-107 |
| miR-122a | uggagugugacaauggguguuugu | 373 | miR-122a-1; miR-122a-2 |
| miR-124a | uuaaggcacgcggugaaugcca | 374 | miR-124a-1; miR-124a-2; miR-124a-3 |
| miR-125a | ucccugagacccuuuaaccugug | 375 | miR-125a-1; miR-125a-2 |
| miR-125b | ucccugagacccuaacuuguga | 376 | miR-125b-1; miR-125b-2 |
| miR-126* | cauuauuacuuuugguacgcg | 377 | miR-126-1; miR-126-2 |
| miR-126 | ucguaccgugaguaauaaugc | 378 | miR-126-1; miR-126-2 |
| miR-127 | ucggauccgucugagcuuggcu | 379 | miR-127-1; miR-127-2 |
| miR-128a | ucacagugaaccggucucuuuu | 380 | miR-128; miR-128a |
| miR-128b | ucacagugaaccggucucuuuc | 381 | miR-128b |
| miR-129 | cuuuuugcggucugggcuugc | 382 | miR-129-1; miR-129-2 |
| miR-130a | cagugcaauguuaaaagggc | 383 | miR-130a |
| miR-130b | cagugcaaugaugaaagggcau | 384 | miR-130b |
| miR-132 | uaacagucuacagccauggucg | 385 | miR-132-1 |
| miR-133a | uugguccccuucaaccagcugu | 386 | miR-133a-1; miR-133a-2 |

TABLE 1b-continued

Human Mature microRNA Sequences.

| Mature miRNA Name | Mature miRNA Sequence (5' to 3') | SEQ ID NO. | Corresponding precursor microRNA(s); see Table 1a |
|---|---|---|---|
| miR-133b | uugguccccuucaaccagcua | 387 | miR-133b |
| miR-134 | ugugacugguugaccagaggg | 388 | miR-134-1; miR-134-2 |
| miR-135a | uauggcuuuuauuccuauguga | 389 | miR-135a; miR-135a-2 (miR-135-2) |
| miR-135b | uauggcuuucauuccuaugug | 390 | miR-135b |
| miR-136 | acuccauuguuuugaugaugga | 391 | miR-136-1; miR-136-2 |
| miR-137 | uauugcuuaagaauacgcguag | 392 | miR-137 |
| miR-138 | agcuggguugugugaauc | 393 | miR-138-1; miR-138-2 |
| miR-139 | ucuacagugcacgugucu | 394 | miR-139 |
| miR-140 | agugguuuuacccuaugguag | 395 | miR-140; miR-140as; miR-140s |
| miR-141 | aacacugucugguaaagaugg | 396 | miR-141-1; miR-141-2 |
| miR-142-3p | uguaguguuuccuacuuuaugga | 397 | miR-142 |
| miR-142-5p | cauaaaguagaaagcacuac | 398 | miR-142 |
| miR-143 | ugagaugaagcacuguagcuca | 399 | miR-143-1 |
| miR-144 | uacaguauagaugauguacuag | 400 | miR-144-1; miR-144-2 |
| miR-145 | guccaguuuucccaggaaucccuu | 401 | miR-145-1; miR-145-2 |
| miR-146 | ugagaacugaauuccauggguu | 402 | miR-146-1; miR-146-2 |
| miR-147 | guguguggaaaugcuucugc | 403 | miR-147 |
| miR-148a | ucagugcacuacagaacuuugu | 404 | miR-148a (miR-148) |
| miR-148b | ucagugcaucacagaacuuugu | 405 | miR-148b |
| miR-149 | ucuggcuccgugucuucacucc | 406 | miR-149 |
| miR-150 | ucucccaacccuuguaccagug | 407 | miR-150-1; miR-150-2 |
| miR-151 | acuagacugaagcuccuugagg | 408 | miR-151 |
| miR-152 | ucagugcaugacagaacuugg | 409 | miR-152-1; miR-152-2 |
| miR-153 | uugcauagucacaaaaguga | 410 | miR-153-1-1; miR-153-1-2; miR-153-2-1; miR-153-2-2 |
| miR-154 | uagguuauccguguugccuucg | 411 | miR-154-1; miR-154-2 |
| miR-154* | aaucauacacgguugaccuauu | 412 | miR-154-1; miR-154-2 |
| miR-155 | uuaaugcuaaucgugauagggg | 413 | miR-155 |
| miR-181a | aacauucaacgcugucggugagu | 414 | miR-181a |
| miR-181b | aacauucauugcugucgguggguu | 415 | miR-181b-1; miR-181b-2 |
| miR-181c | aacauucaaccugucgugagu | 416 | miR-181c |
| miR-182 | uuuggcaaugguagaacucaca | 417 | miR-182; miR-182as |
| miR-182* | ugguucuagacuugccaacua | 418 | miR-182; miR-182as |
| miR-183 | uauggcacugguagaauucacug | 419 | miR-183 |
| miR-184 | uggacggagaacugauaagggu | 420 | miR-184-1; miR-184-2 |

TABLE 1b-continued

Human Mature microRNA Sequences.

| Mature miRNA Name | Mature miRNA Sequence (5' to 3') | SEQ ID NO. | Corresponding precursor microRNA(s); see Table 1a |
|---|---|---|---|
| miR-185 | uggagagaaaggcaguuc | 421 | miR-185-1; miR-185-2 |
| miR-186 | caaagaauucuccuuuugggcuu | 422 | miR-186-1; miR-186-2 |
| miR-187 | ucgugucuuguguugcagccg | 423 | miR-187 |
| miR-188 | caucccuugcaugguggagggu | 424 | miR-188 |
| miR-189 | gugccuacugagcugauaucagu | 425 | miR-189-1; miR-189-2 |
| miR-190 | ugauauguuugauauauuaggu | 426 | miR-190-1; miR-190-2 |
| miR-191 | caacggaaucccaaaagcagcu | 427 | miR-191-1; miR-191-2 |
| miR-192 | cugaccuaugaauugacagcc | 428 | miR-192 |
| miR-193 | aacuggccuacaaaguccag | 429 | miR-193-1; miR-193-2 |
| miR-194 | uguaacagcaacuccaugugga | 430 | miR-194-1; miR-194-2 |
| miR-195 | uagcagcacagaaauauuggc | 431 | miR-195-1; miR-195-2 |
| miR-196a | uagguaguuucauguuguugg | 432 | miR-196a; miR-196a-2 (miR196-2) |
| miR-196b | uagguaguuuccuguuguugg | 433 | miR-196b |
| miR-197 | uucaccaccuucuccacccagc | 434 | miR-197 |
| miR-198 | ggucccagaggggagauagg | 435 | miR-198 |
| miR-199a | cccaguguucagacuaccuguuc | 436 | miR-199a-1; miR-199a-2 |
| miR-199a* | uacaguagucugcacauugguu | 437 | miR-199a-1; miR-199a-2; miR-199s; miR-199b |
| miR-199b | cccaguguuuagacuaucuguuc | 438 | miR-199b |
| miR-200a | uaacacugucucgguaacgaugu | 439 | miR-200a |
| miR-200b | cucuaauacugccugguaaugaug | 440 | miR-200b |
| miR-200c | aauacugccggguaaugaugga | 441 | miR-200c |
| miR-202 | agagguauagggcaugggaaga | 442 | miR-202 |
| miR-203 | gugaaauguuuaggaccacuag | 443 | miR-203 |
| miR-204 | uucccuuugucauccuaugccu | 444 | miR-204 |
| miR-205 | uccuucauuccaccggagucug | 445 | miR-205 |
| miR-206 | uggaauguaaggaagugugugg | 446 | miR-206-1; miR-206-2 |
| miR-208 | auaagacgagcaaaaagcuugu | 447 | miR-208 |
| miR-210 | cugugcgugugacagcggcug | 448 | miR-210 |
| miR-211 | uucccuuugucauccuucgccu | 449 | miR-211 |
| miR-212 | uaacagucuccagucacggcc | 450 | miR-212 |
| miR-213 | accaucgaccguugauuguacc | 451 | miR-213 |
| miR-214 | acagcaggcacagacaggcag | 452 | miR-214 |
| miR-215 | augaccuaugaauugacagac | 453 | miR-215 |
| miR-216 | uaaucucagcuggcaacugug | 454 | miR-216 |
| miR-217 | uacugcaucaggaacugauuggau | 455 | miR-217 |
| miR-218 | uugugcuugaucuaaccaugu | 456 | miR-218-1; miR-218-2 |

TABLE 1b-continued

Human Mature microRNA Sequences.

| Mature miRNA Name | Mature miRNA Sequence (5' to 3') | SEQ ID NO. | Corresponding precursor microRNA(s); see Table 1a |
|---|---|---|---|
| miR-219 | ugauuguccaaacgcaauucu | 457 | miR-219; miR-219-1; miR-219-2 |
| miR-220 | ccacaccguaucugacacuuu | 458 | miR-220 |
| miR-221 | agcuacauugucugcuggguuuc | 459 | miR-221 |
| miR-222 | agcuacaucuggcuacugggucuc | 460 | miR-222 |
| miR-223 | ugucaguuugucaaauacccc | 461 | miR-223 |
| miR-224 | caagucacuagugguuccguuua | 462 | miR-224 |
| miR-296 | agggccccccucaauccugu | 463 | miR-296 |
| miR-299 | ugguuuaccgucccacauacau | 464 | miR-299 |
| miR-301 | cagugcaauaguauugucaaagc | 465 | miR-301 |
| miR-302a | uaagugcuuccauguuuugguga | 466 | miR-302a |
| miR-302b* | acuuuaacauggaagugcuuucu | 467 | miR-302b |
| miR-302b | uaagugcuuccauguuuuaguag | 468 | miR-302b |
| miR-302c* | uuuaacauggggguaccugcug | 469 | miR-302c |
| miR-302c | uaagugcuuccauguuucaguqg | 470 | miR-302c |
| miR-302d | uaagugcuuccauguuugagugu | 471 | miR-302d |
| miR-320 | aaaagcuggguugagagggcgaa | 472 | miR-320 |
| miR-321 | uaagccagggauuguggguuc | 473 | miR-321 |
| miR-323 | gcacauuacacggucgaccucu | 474 | miR-323 |
| miR-324-5p | cgcauccccuagggcauuggugu | 475 | miR-324 |
| miR-324-3p | ccacugccccaggugcugcugg | 476 | miR-324 |
| miR-325 | ccuaguagguguccaguaagu | 477 | miR-325 |
| miR-326 | ccucugggcccuuccuccag | 478 | miR-326 |
| miR-328 | cuggcccucucugcccuuccgu | 479 | miR-328 |
| miR-330 | gcaaagcacacggccugcagaga | 480 | miR-330 |
| miR-331 | gccccugggccuauccuagaa | 481 | miR-331 |
| miR-335 | ucaagagcaauaacgaaaaaugu | 482 | miR-335 |
| miR-337 | uccagcuccuauaugaugccuuu | 483 | miR-337 |
| miR-338 | uccagcaucagugauuuuguuga | 484 | miR-338 |
| miR-339 | ucccuguccuccaggagcuca | 485 | miR-339 |
| miR-340 | uccgucucaguuacuuuauagcc | 486 | miR-340 |
| miR-342 | ucucacacagaaaucgcacccguc | 487 | miR-342 |
| miR-345 | ugcugacuccuaguccagggc | 488 | miR-345 |
| miR-346 | ugucugcccgcaugccugccucu | 489 | miR-346 |
| miR-367 | aauugcacuuuagcaaugguga | 490 | miR-367 |
| miR-368 | acauagaggaaauuccacguuu | 491 | miR-368 |

TABLE 1b-continued

Human Mature microRNA Sequences.

| Mature miRNA Name | Mature miRNA Sequence (5' to 3') | SEQ ID NO. | Corresponding precursor microRNA(s); see Table 1a |
|---|---|---|---|
| miR-369 | aauaauacaugguugaucuuu | 492 | miR-369 |
| miR-370 | gccugcuggggguggaaccugg | 493 | miR-370 |
| miR-371 | gugccgccaucuuuugagugu | 494 | miR-371 |
| miR-372 | aaagugcugcgacauuugagcgu | 495 | miR-372 |
| miR-373* | acucaaaauggggcgcuuucc | 496 | miR-373 |
| miR-373 | gaagugcuucgauuuuggguguu | 497 | miR-373 |
| miR-374 | uuauaauacaaccugauaagug | 498 | miR-374 |

The present invention encompasses methods of diagnosing whether a subject has, or is at risk for developing, a solid cancer, comprising measuring the level of at least one miR gene product in a test sample from the subject and comparing the level of the miR gene product in the test sample to the level of a corresponding miR gene product in a control sample. As used herein, a "subject" can be any mammal that has, or is suspected of having, a solid cancer. In a preferred embodiment, the subject is a human who has, or is suspected of having, a solid cancer.

In one embodiment, the at least one miR gene product measured in the test sample is selected from the group consisting of miR-21, miR-17-5p, miR-191, miR-29b-2, miR-223, miR-128b, miR-199a-1, miR-24-1, miR-24-2, miR-146, miR-155, miR-181b-1, miR-20a, miR-107, miR-32, miR-92-2, miR-214, miR-30c, miR-25, miR-221, miR-106a and combinations thereof. In a particular embodiment, the miR gene product is miR-21, miR-191 or miR-17-5p. In another embodiment, the miR gene product is not miR-15a or miR-16-1. In an additional embodiment, the miR gene product is not miR 159-1 or miR-192. In an additional embodiment, the miR gene product is not miR-186, miR-101-1, miR-194, miR-215, miR-106b, miR-25, miR-93, miR-29b, miR-29a, miR-96, miR-182s, miR-182 as, miR-183, miR-129-1, let-7a-1, let-7d, let-7f-1, miR-23b, miR-24-1, miR-27b, miR-32, miR-159-1, miR-192, miR-125b-1, let-7a-2, miR-100, miR-196-2, miR-148b, miR-190, miR-21, miR-301, miR-142s, miR-142 as, miR-105-1, or miR-175. In a further embodiment, the miR gene product is not miR-21, miR-301, miR-142 as, miR-142s, miR-194, miR-215, or miR-32. In another embodiment, the miR gene product is not miR-148, miR-10a, miR-196-1, miR-152, miR-196-2, miR-148b, miR-10b, miR-129-1, miR-153-2, miR-202, miR-139, let-7a, let-7f, or let-7d. In yet another embodiment, the miR gene product is not miR-15a, miR-16-1, miR-182, miR-181, miR-30, miR-15a, miR-16-1, miR-15b, miR-16-2, miR-195, miR-34, miR-153, miR-21, miR-217, miR-205, miR-204, miR-211, miR-143, miR-96, miR-103, miR-107, miR-129, miR-9, miR-137, miR-217, miR-186.

The solid cancer can be any cancer that arises from organs and solid tissues. Such cancers are typically associated with the formation and/or presence of tumor masses and can be carcinomas, sarcomas and lymphomas. Specific examples of solid cancers to be diagnosed by the methods of the invention include, but are not limited to, colon cancer, rectal cancer, stomach (gastric) cancer, pancreatic cancer, breast cancer, lung cancer, prostate cancer, bronchial cancer, testicular cancer, ovarian cancer, uterine cancer, penile cancer, melanoma and other skin cancers, liver cancer, esophageal cancer, cancers of the oral cavity and pharynx (e.g., tongue cancer, mouth cancer), cancers of the digestive system (e.g., intestinal cancer, gall bladder cancer), bone and joint cancers, cancers of the endocrine system (e.g., thyroid cancer), brain cancer, eye cancer, cancers of the urinary system (e.g., kidney cancer, urinary bladder cancer), Hodgkin disease and non-Hodgkin lymphoma. In particular embodiments, the solid cancer is not one or more of breast cancer, lung cancer, prostate cancer, pancreatic cancer or gastrointestinal cancer.

In one embodiment, the solid cancer is breast cancer or lung cancer and the at least one miR gene product measured in the test sample is selected from the group consisting of miR-210, miR-213 and a combination thereof.

In a further embodiment, the solid cancer is colon cancer, stomach cancer, prostate cancer or pancreas cancer and the at least one miR gene product measured in the test sample is miR-218-2.

In a certain embodiment of the invention, the solid cancer is breast cancer and the at least one miR gene product measured in the test sample is selected from the group consisting of miR-125b-1, miR-125b-2, miR-145, miR-21 and combinations thereof. In a related embodiment, the solid cancer is breast cancer and the at least one miR gene product in the test sample is selected from the group consisting of miR-21, miR-29b-2, miR-146, miR-125b-2, miR-125b-1, miR-10b, miR-145, miR-181a, miR-140, miR-213, miR-29a prec, miR-181b-1, miR-199b, miR-29b-1, miR-130a, miR-155, let-7a-2, miR-205, miR-29c, miR-224, miR-100, miR-31, miR-30c, miR-17-5p, miR-210, miR-122a, miR-16-2 and combinations thereof. In a related embodiment, the solid cancer is breast cancer and the at least one miR gene product is not miR-15a or miR-16-1. In a further embodiment, the solid cancer is breast cancer and the at least one miR gene product is not miR-145, miR-21, miR-155, miR-10b, miR-125b-1, miR-125b-2, let7a-2, let7a-3, let-7d, miR-122a, miR-191, miR-206, miR-210, let-71, miR-009-1 (miR 131-1), miR-34 (miR-170), miR-102 (miR-29b), miR-123 (miR-126), miR-140-as, miR-125a, miR-194, miR-204, miR-213, let-7f-2, miR-101, miR-128b, miR-136, miR-143, miR-149, miR-191, miR-196-1, miR-196-2, miR-202, miR-103-1, or miR-30c. In another embodiment, the solid cancer is breast cancer and the miR gene product is not miR-21, miR-125b-1, let-7a-2, let-71, miR-100, let-7g, miR-31, miR-32a-1, miR-33b, miR-34a-2, miR-101-1, miR-135-1, miR-142 as, miR-142s, miR-144, miR-301, miR-29c, miR-30c, miR-106a, or miR-29b-1. In yet another embodiment, the solid cancer is breast cancer and the miR gene product is not miR-159-1 or miR-192. In an additional embodiment, the solid cancer is breast cancer and the miR gene product is not miR-186, miR-101-1, miR-194, miR-215, miR-106b, miR-25, miR-93, miR-29b, miR-29a, miR-96, miR-182s, miR-182 as, miR-183, miR-129-1, let-7a-1, let-7d, let-7f-1, miR-23b, miR-24-1, miR-27b, miR-32, miR-159-1, miR-192, miR-125b-1, let-7a-2, miR-100, miR-196-2, miR-148b, miR-190, miR-21, miR-301, miR-142s, miR-142 as, miR-105-1, or miR-175. In a further embodiment, the solid cancer is breast cancer and the miR gene product is not miR-21, miR-301, miR-142 as, miR-142s, miR-194, miR-215, or miR-32. In another embodiment, the solid cancer is breast cancer and the miR gene product is not miR-148, miR-10a, miR-196-1, miR-152, miR-196-2, miR-148b, miR-10b, miR-129-1, miR-153-2, miR-202, miR-139, let-7a, let-7f, or let-7d. In yet another embodiment, the solid cancer is breast cancer and the miR gene product is not miR-181b, miR-181c, miR-181d, miR-30, miR-15b, miR-16-2, miR-153-1, miR-217, miR-205, miR-204, miR-103, miR-107, miR-129-2, miR-9 or miR-137.

In another embodiment, the solid cancer is colon cancer and the at least one miR gene product in the test sample is selected from the group consisting of miR-24-1, miR-29b-2, miR-20a, miR-10a, miR-32, miR-203, miR-106a, miR-17-5p, miR-30c, miR-223, miR-126*, miR-128b, miR-21, miR-24-2, miR-99b prec, miR-155, miR-213, miR-150, miR-107, miR-191, miR-221, miR-9-3 and combinations thereof. In another embodiment, the solid cancer is colon cancer and the miR gene product is not miR 159-1 or miR-192. In an additional embodiment, the solid cancer is colon cancer and the miR gene product is not miR-186, miR-101-1, miR-194, miR-215, miR-106b, miR-25, miR-93, miR-29b, miR-29a, miR-96, miR-182s, miR-182 as, miR-183, miR-129-1, let-7a-1, let-7d, let-7f-1, miR-23b, miR-24-1, miR-27b, miR-32, miR-159-1, miR-192, miR-125b-1, let-7a-2, miR-100, miR-196-2, miR-148b, miR-190, miR-21, miR-301, miR-142s, miR-142 as, miR-105-1, or miR-175. In a further embodiment, the solid cancer is colon cancer and the miR gene product is not miR-21, miR-301, miR-142 as, miR-142s, miR-194, miR-215, or miR-32. In another embodiment, the solid cancer is colon cancer and the miR gene product is not miR-148, miR-10a, miR-196-1, miR-152, miR-196-2, miR-148b, miR-10b, miR-129-1, miR-153-2, miR-202, miR-139, let-7a, let-7f, or let-7d. In yet another embodiment, the solid cancer is colon cancer and the miR gene product is not miR-181b, miR-181c, miR-181d, miR-30, miR-15b, miR-16-2, miR-153-1, miR-217, miR-205, miR-204, miR-103, miR-107, miR-129-2, miR-9 or miR-137.

In yet another embodiment, the solid cancer is lung cancer and the miR gene product in the test sample is selected from the group consisting of miR-21, miR-205, miR-200b, miR-9-1, miR-210, miR-148, miR-141, miR-132, miR-215, miR-128b, let-7g, miR-16-2, miR-129-1/2 prec, miR-126*, miR-142-as, miR-30d, miR-30a-5p, miR-7-2, miR-199a-1, miR-127, miR-34a prec, miR-34a, miR-136, miR-202, miR-196-2, miR-199a-2, let-7a-2, miR-124a-1, miR-149, miR-17-5p, miR-196-1 prec, miR-10a, miR-99b prec, miR-196-1, miR-199b, miR-191, miR-195, miR-155 and combinations thereof. In a related embodiment, the solid cancer is lung cancer and the at least one miR gene product is not miR-15a or miR-16-1. In a further embodiment, the solid cancer is lung cancer and the at least one miR gene product is not miR-21, miR-191, miR-126*, miR-210, miR-155, miR-143, miR-205, miR-126, miR-30a-5p, miR-140, miR-214, miR-218-2, miR-145, miR-106a, miR-192, miR-203, miR-150, miR-220, miR-192, miR-224, miR-24-2, miR-212, miR-9, miR-17, miR-124a-1, miR-95, miR-198, miR-216, miR-219-1, miR-197, miR-125a, miR-26a-1, miR-146, miR-199b, let7a-2, miR-27b, miR-32, miR-29b-2, miR-33, miR-181c, miR-101-1, miR-124a-3, miR-125b-1 or let7f-1. In another embodiment, the solid cancer is lung cancer and the at least one miR gene product is not miR-21, miR-182, miR-181, miR-30, miR-15a, miR-143, miR-205, miR-96, miR-103, miR-107, miR-129, miR-137, miR-186, miR-15b, miR-16-2, miR-195, miR-34, miR-153, miR-217, miR-204, miR-211, miR-9, miR-217, let-7a-2 or miR-32. In a further embodiment, the solid cancer is lung cancer and the miR gene product is not let-7c, let-7g, miR-7-3, miR-210, miR-31, miR-34a-1, miR-a-2, miR-99a, miR-100, miR-125b-2, miR-132, miR-135-1, miR-195, miR-34, miR-123, miR-203. In another embodiment, the solid cancer is lung cancer and the miR gene product is not miR 159-1 or miR-192. In an additional embodiment, the solid cancer is lung cancer and the miR gene product is not miR-186, miR-101-1, miR-194, miR-215, miR-106b, miR-25, miR-93, miR-29b, miR-29a, miR-96, miR-182s, miR-182 as, miR-183, miR-129-1, let-7a-1, let-7d, let-7f-1, miR-23b, miR-24-1, miR-27b, miR-32, miR-159-1, miR-192, miR-125b-1, let-7a-2, miR-100, miR-196-2, miR-148b, miR-190, miR-21, miR-301, miR-142s, miR-142 as, miR-105-1, or miR-175. In a further embodiment, the solid cancer is lung cancer and the miR gene product is not miR-21, miR-301, miR-142 as, miR-142s, miR-194, miR-215, or miR-32. In another embodiment, the solid cancer is lung cancer and the miR gene product is not miR-148, miR-10a, miR-196-1, miR-152, miR-196-2, miR-148b, miR-10b, miR-129-1, miR-153-2, miR-202, miR-139, let-7a, let-7f, or let-7d. In yet another embodiment, the solid cancer is lung cancer and the miR gene product is not miR-181b, miR-181c, miR-181d, miR-30, miR-15b, miR-16-2, miR-153-1, miR-217, miR-205, miR-204, miR-103, miR-107, miR-129-2, miR-9 or miR-137.

In a further embodiment, the solid cancer is pancreatic cancer and the at least one miR gene product measured in the test sample is selected from the group consisting of miR-103-1, miR-103-2, miR-155, miR-204 and combinations thereof. In a related embodiment, the solid cancer is pancreatic cancer and the miR gene product in the test sample is selected from the group consisting of miR-103-2, miR-103-1, miR-24-2, miR-107, miR-100, miR-125b-2, miR-125b-1, miR-24-1, miR-191, miR-23a, miR-26a-1, miR-125a, miR-130a, miR-26b, miR-145, miR-221, miR-126*, miR-16-2, miR-146, miR-214, miR-99b, miR-128b, miR-155, miR-29b-2, miR-29a, miR-25, miR-16-1, miR-99a, miR-224, miR-30d, miR-92-2, miR-199a-1, miR-223, miR-29c, miR-30b, miR-129-1/2, miR-197, miR-17-5p, miR-30c, miR-7-1, miR-93-1, miR-140, miR-30a-5p, miR-132, miR-181b-1, miR-152 prec, miR-23b, miR-20a, miR-222, miR-27a, miR-92-1, miR-21, miR-129-1/2 prec, miR-150, miR-32, miR-106a, miR-29b-1 and combinations thereof. In one embodiment, the solid cancer is pancreatic cancer and the miR gene product is not miR-15a or miR-16-1. In another embodiment, the solid cancer is pancreatic cancer and the miR gene product is not miR 159-1 or miR-192. In an additional embodiment, the solid cancer is pancreatic cancer and the miR gene product is not miR-186, miR-101-1, miR-194, miR-215, miR-106b, miR-25, miR-93, miR-29b, miR-29a, miR-96, miR-182s, miR-182 as, miR-183, miR-129-1, let-7a-1, let-7d, let-7f-1, miR-23b, miR-24-1, miR-27b, miR-32, miR-159-1, miR-192, miR-125b-1, let-7a-2, miR-100, miR-196-2, miR-148b, miR-190, miR-21, miR-301, miR-142s, miR-142 as, miR-105-1, or miR-175. In a further embodiment, the solid cancer is pancreatic cancer and the miR gene product is not miR-21, miR-301, miR-142 as, miR-142s, miR-194, miR-215, or miR-32. In another embodiment, the solid cancer is pancreatic cancer and the miR gene product is not miR-148, miR-10a, miR-196-1, miR-152, miR-196-2, miR-148b, miR-10b, miR-129-1, miR-153-2, miR-202, miR-139, let-7a, let-7f, or let-7d. In yet another embodiment, the solid cancer is pancreatic cancer and the miR gene product is not miR-181b, miR-181c, miR-181d, miR-30, miR-15b, miR-16-2, miR-153-1, miR-217, miR-205, miR-204, miR-103, miR-107, miR-129-2, miR-9 or miR-137.

In another embodiment, the solid cancer is prostate cancer and the miR gene product in the test sample is selected from the group consisting of let-7d, miR-128a prec, miR-195, miR-203, let-7a-2 prec, miR-34a, miR-20a, miR-218-2, miR-29a, miR-25, miR-95, miR-197, miR-135-2, miR-187, miR-196-1, miR-148, miR-191, miR-21, let-71, miR-198, miR-199a-2, miR-30c, miR-17-5p, miR-92-2, miR-146, miR-181b-1 prec, miR-32, miR-206, miR-184 prec, miR-29a prec, miR-29b-2, miR-149, miR-181b-1, miR-196-1 prec, miR-93-1, miR-223, miR-16-1, miR-101-1, miR-124a-1, miR-26a-1, miR-214, miR-27a, miR-24-1, miR-106a, miR-199a-1 and combinations thereof. In a related embodiment, the solid cancer is prostate cancer and the miR gene product is not miR-15a or miR-16-1. In another embodiment, the solid cancer is prostate cancer and the miR gene product is not miR 159-1 or miR-192. In an additional embodiment, the solid cancer is prostate cancer and the miR gene product is not miR-186, miR-101-1, miR-194, miR-215, miR-106b, miR-25, miR-93, miR-29b, miR-29a, miR-96, miR-182s, miR-182 as, miR-183, miR-129-1, let-7a-1, let-7d, let-7f-1, miR-23b, miR-24-1, miR-27b, miR-32, miR-159-1, miR-192, miR-125b-1, let-7a-2, miR-100, miR-196-2, miR-148b, miR-190, miR-21, miR-301, miR-142s, miR-142 as, miR-105-1, or miR-175. In a further embodiment, the solid cancer is prostate cancer and the miR gene product is not miR-21, miR-301, miR-142 as, miR-142s, miR-194, miR-215, or miR-32. In another embodiment, the solid cancer is prostate cancer and the miR gene product is not miR-148, miR-10a, miR-196-1, miR-152, miR-196-2, miR-148b, miR-10b, miR-129-1, miR-153-2, miR-202, miR-139, let-7a, let-7f, or let-7d. In yet another embodiment, the solid cancer is prostate cancer and the miR gene product is not miR-181b, miR-181c, miR-181d, miR-30, miR-15b, miR-16-2, miR-153-1, miR-217, miR-205, miR-204, miR-103, miR-107, miR-129-2, miR-9 or miR-137.

In yet another embodiment, the solid cancer is stomach cancer and the miR gene product in the test sample is selected from the group consisting of miR-223, miR-21, miR-218-2, miR-103-2, miR-92-2, miR-25, miR-136, miR-191, miR-221, miR-125b-2, miR-103-1, miR-214, miR-222, miR-212 prec, miR-125b-1, miR-100, miR-107, miR-92-1, miR-96, miR-192, miR-23a, miR-215, miR-7-2, miR-138-2, miR-24-1, miR-99b, miR-33b, miR-24-2 and combinations thereof. In a related embodiment, the solid cancer is stomach cancer and the miR gene product is not miR-15a or miR-16-1. In another embodiment, the solid cancer is stomach cancer and the miR gene product is not miR 159-1 or miR-192. In an additional embodiment, the solid cancer is stomach cancer and the miR gene product is not miR-186, miR-101-1, miR-194, miR-215, miR-106b, miR-25, miR-93, miR-29b, miR-29a, miR-96, miR-182s, miR-182 as, miR-183, miR-129-1, let-7a-1, let-7d, let-7f-1, miR-23b, miR-24-1, miR-27b, miR-32, miR-159-1, miR-192, miR-125b-1, let-7a-2, miR-100, miR-196-2, miR-148b, miR-190, miR-21, miR-301, miR-142s, miR-142 as, miR-105-1, or miR-175. In a further embodiment, the solid cancer is stomach cancer and the miR gene product is not miR-21, miR-301, miR-142a5, miR-142s, miR-194, miR-215, or miR-32. In another embodiment, the solid cancer is stomach cancer and the miR gene product is not miR-148, miR-10a, miR-196-1, miR-152, miR-196-2, miR-148b, miR-10b, miR-129-1, miR-153-2, miR-202, miR-139, let-7a, let-7f, or let-7d. In yet another embodiment, the solid cancer is stomach cancer and the miR gene product is not miR-181b, miR-181c, miR-181d, miR-30, miR-15b, miR-16-2, miR-153-1, miR-217, miR-205, miR-204, miR-103, miR-107, miR-129-2, miR-9 or miR-137.

The level of at least one miR gene product can be measured in a biological sample (e.g., cells, tissues) obtained from the subject. For example, a tissue sample (e.g., from a tumor) can be removed from a subject suspected of having a solid cancer by conventional biopsy techniques. In another embodiment, a blood sample can be removed from the subject, and blood cells (e.g., white blood cells) can be isolated for DNA extraction by standard techniques. The blood or tissue sample is preferably obtained from the subject prior to initiation of radiotherapy, chemotherapy or other therapeutic treatment. A corresponding control tissue or blood sample can be obtained from unaffected tissues of the subject, from a normal human individual or population of normal individuals, or from cultured cells corresponding to the majority of cells in the subject's sample. The control tissue or blood sample is then processed along with the sample from the subject, so that the levels of miR gene product produced from a given miR gene in cells from the subject's sample can be compared to the corresponding miR gene product levels from cells of the control sample. A reference miR expression standard for the biological sample can also be used as a control.

An alteration (e.g., an increase or decrease) in the level of a miR gene product in the sample obtained from the subject, relative to the level of a corresponding miR gene product in a control sample, is indicative of the presence of a solid cancer in the subject. In one embodiment, the level of the at least one miR gene product in the test sample is greater than the level of the corresponding miR gene product in the control sample (i.e., expression of the miR gene product is "up-regulated"). As used herein, expression of a miR gene product is "up-regulated" when the amount of miR gene product in a cell or tissue sample from a subject is greater than the amount of the same gene product in a control cell or tissue sample. In another embodiment, the level of the at least one miR gene product in the test sample is less than the level of the corresponding miR gene product in the control sample (i.e., expression of the miR gene product is "down-regulated"). As used herein, expression of a miR gene is "down-regulated" when the amount of miR gene product produced from that gene in a cell or tissue sample from a subject is less than the amount produced from the same gene in a control cell or tissue sample. The relative miR gene expression in the control and normal samples can be determined with respect to one or more RNA expression standards. The standards can comprise, for example, a zero miR gene expression level, the miR gene expression level in a standard cell line, the miR gene expression level in unaffected tissues of the subject, or the average level of miR gene expression previously obtained for a population of normal human controls.

The level of a miR gene product in a sample can be measured using any technique that is suitable for detecting RNA expression levels in a biological sample. Suitable techniques (e.g., Northern blot analysis, RT-PCR, in situ hybridization) for determining RNA expression levels in a biological sample (e.g., cells, tissues) are well known to those of skill in the art. In a particular embodiment, the level of at least one miR gene product is detected using Northern blot analysis. For example, total cellular RNA can be purified from cells by homogenization in the presence of nucleic acid extraction buffer, followed by centrifugation. Nucleic acids are precipitated, and DNA is removed by treatment with DNase and precipitation. The RNA molecules are then separated by gel electrophoresis on agarose gels according to standard techniques, and transferred to nitrocellulose filters. The RNA is then immobilized on the filters by heating. Detection and quantification of specific RNA is accomplished using appropriately labeled DNA or RNA probes complementary to the RNA in question. See, for example, Molecular Cloning: A Laboratory Manual, J. Sambrook et al., eds., 2nd edition, Cold Spring Harbor Laboratory Press, 1989, Chapter 7, the entire disclosure of which is incorporated by reference.

Suitable probes for Northern blot hybridization of a given miR gene product can be produced from the nucleic acid sequences provided in Table 1a and Table 1b and include, but are not limited to, probes having at least about 70%, 75%, 80%, 85%, 90%, 95%, 98%, 99% or complete complementarity to a miR gene product of interest. Methods for preparation of labeled DNA and RNA probes, and the conditions for hybridization thereof to target nucleotide sequences, are described in Molecular Cloning: A Laboratory Manual, J. Sambrook et al., eds., 2nd edition, Cold Spring Harbor Laboratory Press, 1989, Chapters 10 and 11, the disclosures of which are incorporated herein by reference.

For example, the nucleic acid probe can be labeled with, e.g., a radionuclide, such as 3H, $^{32}P$, $^{33}P$, $^{14}C$, or $^{35}S$; a heavy metal; a ligand capable of functioning as a specific binding pair member for a labeled ligand (e.g., biotin, avidin or an antibody); a fluorescent molecule; a chemiluminescent molecule; an enzyme or the like.

Probes can be labeled to high specific activity by either the nick translation method of Rigby et al. (1977), *J. Mol. Biol.* 113:237-251 or by the random priming method of Fienberg et al. (1983), *Anal. Biochem.* 132:6-13, the entire disclosures of which are incorporated herein by reference. The latter is the method of choice for synthesizing $^{32}P$-labeled probes of high specific activity from single-stranded DNA or from RNA templates. For example, by replacing preexisting nucleotides with highly radioactive nucleotides according to the nick translation method, it is possible to prepare $^{32}P$-labeled nucleic acid probes with a specific activity well in excess of $10^8$ cpm/microgram. Autoradiographic detection of hybridization can then be performed by exposing hybridized filters to photographic film. Densitometric scanning of the photographic films exposed by the hybridized filters provides an accurate measurement of miR gene transcript levels. Using another approach, miR gene transcript levels can be quantified by computerized imaging systems, such as the Molecular Dynamics 400-B 2D Phosphorimager available from Amersham Biosciences, Piscataway, N.J.

Where radionuclide labeling of DNA or RNA probes is not practical, the random-primer method can be used to incorporate an analogue, for example, the dTTP analogue 5-(N—(N-biotinyl-epsilon-aminocaproyl)-3-aminoallyl)deoxyuridine triphosphate, into the probe molecule. The biotinylated probe oligonucleotide can be detected by reaction with biotin-binding proteins, such as avidin, streptavidin, and antibodies (e.g., anti-biotin antibodies) coupled to fluorescent dyes or enzymes that produce color reactions.

In addition to Northern and other RNA hybridization techniques, determining the levels of RNA transcripts can be accomplished using the technique of in situ hybridization. This technique requires fewer cells than the Northern blotting technique, and involves depositing whole cells onto a microscope cover slip and probing the nucleic acid content of the cell with a solution containing radioactive or otherwise labeled nucleic acid (e.g., cDNA or RNA) probes. This technique is particularly well-suited for analyzing tissue biopsy samples from subjects. The practice of the in situ hybridization technique is described in more detail in U.S. Pat. No. 5,427,916, the entire disclosure of which is incorporated herein by reference. Suitable probes for in situ hybridization of a given miR gene product can be produced from the nucleic acid sequences provided in Table 1a and Table 1b, and include, but are not limited to, probes having at least about 70%, 75%, 80%, 85%, 90%, 95%, 98%, 99% or complete complementarity to a miR gene product of interest, as described above.

The relative number of miR gene transcripts in cells can also be determined by reverse transcription of miR gene transcripts, followed by amplification of the reverse-transcribed transcripts by polymerase chain reaction (RT-PCR). The levels of miR gene transcripts can be quantified in comparison with an internal standard, for example, the level of mRNA from a "housekeeping" gene present in the same sample. A suitable "housekeeping" gene for use as an internal standard includes, e.g., myosin or glyceraldehyde-3-phosphate dehydrogenase (G3PDH). Methods for performing quantitative and semi-quantitative RT-PCR, and variations thereof, are well known to those of skill in the art.

In some instances, it may be desirable to simultaneously determine the expression level of a plurality of different miR gene products in a sample. In other instances, it may be desirable to determine the expression level of the transcripts of all known miR genes correlated with a cancer. Assessing cancer-specific expression levels for hundreds of miR genes or gene products is time consuming and requires a large amount of total RNA (e.g., at least 20 µg for each Northern blot) and autoradiographic techniques that require radioactive isotopes.

To overcome these limitations, an oligolibrary, in microchip format (i.e., a microarray), may be constructed containing a set of oligonucleotide (e.g., oligodeoxynucleotides) probes that are specific for a set of miR genes. Using such a microarray, the expression level of multiple microRNAs in a biological sample can be determined by reverse transcribing the RNAs to generate a set of target oligodeoxynucleotides, and hybridizing them to probe the oligonucleotides on the microarray to generate a hybridization, or expression, profile. The hybridization profile of the test sample can then be compared to that of a control sample to determine which microRNAs have an altered expression level in solid cancer cells. As used herein, "probe oligonucleotide" or "probe oligodeoxynucleotide" refers to an oligonucleotide that is capable of hybridizing to a target oligonucleotide. "Target oligonucleotide" or "target oligodeoxynucleotide" refers to a molecule to be detected (e.g., via hybridization). By "miR-specific probe oligonucleotide" or "probe oligonucleotide specific for a miR" is meant a probe oligonucleotide that has a sequence selected to hybridize to a specific miR gene product, or to a reverse transcript of the specific miR gene product.

An "expression profile" or "hybridization profile" of a particular sample is essentially a fingerprint of the state of the sample; while two states may have any particular gene similarly expressed, the evaluation of a number of genes simultaneously allows the generation of a gene expression profile that is unique to the state of the cell. That is, normal tissue may be distinguished from cancerous (e.g., tumor) tissue, and within cancerous tissue, different prognosis states (for example, good or poor long term survival prospects) may be determined. By comparing expression profiles of solid cancer tissue in different states, information regarding which genes are important (including both up- and down-regulation of genes) in each of these states is obtained. The identification of sequences that are differentially expressed in solid cancer tissue, as well as differential expression resulting in different prognostic outcomes, allows the use of this information in a number of ways. For example, a particular treatment regime may be evaluated (e.g., to determine whether a chemotherapeutic drug acts to improve the long-term prognosis in a particular patient). Similarly, diagnosis may be done or confirmed by comparing patient samples with known expression profiles. Furthermore, these gene expression profiles (or individual genes) allow screening of drug candidates that suppress the solid cancer expression profile or convert a poor prognosis profile to a better prognosis profile.

Accordingly, the invention provides methods of diagnosing whether a subject has, or is at risk for developing, a solid cancer, comprising reverse transcribing RNA from a test sample obtained from the subject to provide a set of target oligodeoxynucleotides, hybridizing the target oligodeoxynucleotides to a microarray comprising miRNA-specific probe oligonucleotides to provide a hybridization profile for the test sample, and comparing the test sample hybridization profile to a hybridization profile generated from a control sample or reference standard, wherein an alteration in the signal of at least one miRNA is indicative of the subject either having, or being at risk for developing, a solid cancer. In one embodiment, the microarray comprises miRNA-specific probe oligonucleotides for a substantial portion of all known human miRNAs. In a particular embodiment, the microarray comprises miRNA-specific probe oligonucleotides for one or more miRNAs selected from the group consisting of miR-21, miR-17-5p, miR-191, miR-29b-2, miR-223, miR-128b, miR-199a-1, miR-24-1, miR-24-2, miR-146, miR-155, miR-181b-1, miR-20a, miR-107, miR-32, miR-92-2, miR-214, miR-30c, miR-25, miR-221, miR-106a and combinations thereof.

The microarray can be prepared from gene-specific oligonucleotide probes generated from known miRNA sequences. The array may contain two different oligonucleotide probes for each miRNA, one containing the active, mature sequence and the other being specific for the precursor of the miRNA. The array may also contain controls, such as one or more mouse sequences differing from human orthologs by only a few bases, which can serve as controls for hybridization stringency conditions. tRNAs or other RNAs (e.g., rRNAs, mRNAs) from both species may also be printed on the microchip, providing an internal, relatively stable, positive control for specific hybridization. One or more appropriate controls for non-specific hybridization may also be included on the microchip. For this purpose, sequences are selected based upon the absence of any homology with any known miRNAs.

The microarray may be fabricated using techniques known in the art. For example, probe oligonucleotides of an appropriate length, e.g., 40 nucleotides, are 5'-amine modified at position C6 and printed using commercially available microarray systems, e.g., the GeneMachine OmniGrid™ 100 Microarrayer and Amersham CodeLink™ activated slides. Labeled cDNA oligomer corresponding to the target RNAs is prepared by reverse transcribing the target RNA with labeled primer. Following first strand synthesis, the RNA/DNA hybrids are denatured to degrade the RNA templates. The labeled target cDNAs thus prepared are then hybridized to the microarray chip under hybridizing conditions, e.g., 6×SSPE/30% formamide at 25° C. for 18 hours, followed by washing in 0.75×TNT (Tris HCl/NaCl/Tween 20) at 37° C. for 40 minutes. At positions on the array where the immobilized probe DNA recognizes a complementary target cDNA in the sample, hybridization occurs. The labeled target cDNA marks the exact position on the array where binding occurs, allowing automatic detection and quantification. The output consists of a list of hybridization events, indicating the relative abundance of specific cDNA sequences, and therefore the relative abundance of the corresponding complementary miRs, in the patient sample. According to one embodiment, the labeled cDNA oligomer is a biotin-labeled cDNA, prepared from a biotin-labeled primer. The microarray is then processed by direct detection of the biotin-containing transcripts using, e.g., Streptavidin-Alexa647 conjugate, and scanned utilizing conventional scanning methods. Image intensities of each spot on the array are proportional to the abundance of the corresponding miR in the patient sample.

The use of the array has several advantages for miRNA expression detection. First, the global expression of several hundred genes can be identified in the same sample at one time point. Second, through careful design of the oligonucleotide probes, expression of both mature and precursor molecules can be identified. Third, in comparison with Northern blot analysis, the chip requires a small amount of RNA, and provides reproducible results using 2.5 µg of total RNA. The relatively limited number of miRNAs (a few hundred per species) allows the construction of a common microarray for several species, with distinct oligonucleotide probes for each. Such a tool would allow for analysis of trans-species expression for each known miR under various conditions.

In addition to use for quantitative expression level assays of specific miRs, a microchip containing miRNA-specific probe oligonucleotides corresponding to a substantial portion of the miRNome, preferably the entire miRNome, may be employed to carry out miR gene expression profiling, for analysis of miR expression patterns. Distinct miR signatures can be associated with established disease markers, or directly with a disease state.

According to the expression profiling methods described herein, total RNA from a sample from a subject suspected of having a cancer (e.g., a solid cancer) is quantitatively reverse transcribed to provide a set of labeled target oligodeoxynucleotides complementary to the RNA in the sample. The target oligodeoxynucleotides are then hybridized to a microarray comprising miRNA-specific probe oligonucleotides to provide a hybridization profile for the sample. The result is a hybridization profile for the sample representing the expression pattern of miRNA in the sample. The hybridization profile comprises the signal from the binding of the target oligodeoxynucleotides from the sample to the miRNA-specific probe oligonucleotides in the microarray. The profile may be recorded as the presence or absence of binding (signal vs. zero signal). More preferably, the profile recorded includes the intensity of the signal from each hybridization. The profile is compared to the hybridization profile generated from a normal, i.e., noncancerous, control sample. An alteration in the signal is indicative of the presence of, or propensity to develop, cancer in the subject.

Other techniques for measuring miR gene expression are also within the skill in the art, and include various techniques for measuring rates of RNA transcription and degradation.

The invention also provides methods of determining the prognosis of a subject with a solid cancer, comprising measuring the level of at least one miR gene product, which is associated with a particular prognosis in a solid cancer (e.g., a good or positive prognosis, a poor or adverse prognosis), in a test sample from the subject. According to these methods, an alteration in the level of a miR gene product that is associated with a particular prognosis in the test sample, as compared to the level of a corresponding miR gene product in a control sample, is indicative of the subject having a solid cancer with a particular prognosis. In one embodiment, the miR gene product is associated with an adverse (i.e., poor) prognosis. Examples of an adverse prognosis include, but are not limited to, low survival rate and rapid disease progression. In certain embodiments, the level of the at least one miR gene product is measured by reverse transcribing RNA from a test sample obtained from the subject to provide a set of target oligodeoxynucleotides, hybridizing the target oligodeoxynucleotides to a microarray that comprises miRNA-specific probe oligonucleotides to provide a hybridization profile for the test sample, and comparing the test sample hybridization profile to a hybridization profile generated from a control sample.

Without wishing to be bound by any one theory, it is believed that alterations in the level of one or more miR gene products in cells can result in the deregulation of one or more intended targets for these miRs, which can lead to the formation of solid cancers. Therefore, altering the level of the miR gene product (e.g., by decreasing the level of a miR gene product that is up-regulated in solid cancer cells, by increasing the level of a miR gene product that is down-regulated in solid cancer cells) may successfully treat the solid cancer.

Accordingly, the present invention encompasses methods of inhibiting tumorigenesis in a subject who has, or is suspected of having, a solid cancer wherein at least one miR gene product is deregulated (e.g., down-regulated, up-regulated) in the cancer cells of the subject. When the at least one isolated miR gene product is down-regulated in the cancer cells (e.g., miR-145, miR-155, miR-218-2), the method comprises administering an effective amount of the at least one isolated miR gene product, or an isolated variant or biologically-active fragment thereof, such that proliferation of cancer cells in the subject is inhibited. In one embodiment, the isolated miR gene product that is administered is not miR-15a or miR-16-1. In another embodiment, the miR gene product is not miR 159-1 or miR-192. In an additional embodiment, the miR gene product is not miR-186, miR-101-1, miR-194, miR-215, miR-106b, miR-25, miR-93, miR-29b, miR-29a, miR-96, miR-182s, miR-182 as, miR-183, miR-129-1, let-7a-1, let-7d, let-7f-1, miR-23b, miR-24-1, miR-27b, miR-32, miR-159-1, miR-192, miR-125b-1, let-7a-2, miR-100, miR-196-2, miR-148b, miR-190, miR-21, miR-301, miR-142s, miR-142 as, miR-105-1, or miR-175. In a further embodiment, the miR gene product is not miR-21, miR-301, miR-142 as, miR-142s, miR-194, miR-215, or miR-32. In another embodiment, the miR gene product is not miR-148, miR-10a, miR-196-1, miR-152, miR-196-2, miR-148b, miR-10b, miR-129-1, miR-153-2, miR-202, miR-139, let-7a, let-7f, or let-7d. In yet another embodiment, the miR gene product is not miR-30, miR-15b, miR-16-2, miR-217, miR-205, miR-204, miR-103, miR-107, miR-9, and miR-137. In a further embodiment, the miR gene product is not miR-145, miR-21, miR-155, miR-10b, miR-125b-1, miR-125b-2, let7a-2, let7a-3, let-7d, miR-122a, miR-191, miR-206, miR-210, let-71, miR-009-1 (miR 131-1), miR-34 (miR-170), miR-102 (miR-29b), miR-123 (miR-126), miR-140-as, miR-125a, miR-194, miR-204, miR-213, let-7f-2, miR-101, miR-128b, miR-136, miR-143, miR-149, miR-191, miR-196-1, miR-196-2, miR-202, miR-103-1, or miR-30c. In another embodiment, the miR gene product is not miR-21, miR-125b-1, let-7a-2, let-71, miR-100, let-7g, miR-31, miR-32a-1, miR-33b, miR-34a-2, miR-101-1, miR-135-1, miR-142 as, miR-142s, miR-144, miR-301, miR-29c, miR-30c, miR-106a, or miR-29b-1.

For example, when a miR gene product is down-regulated in a cancer cell in a subject, administering an effective amount of an isolated miR gene product to the subject can inhibit proliferation of the cancer cell. The isolated miR gene product that is administered to the subject can be identical to the endogenous wild-type miR gene product (e.g., a miR gene product shown in Table 1a or Table 1b) that is down-regulated in the cancer cell or it can be a variant or biologically-active fragment thereof. As defined herein, a "variant" of a miR gene product refers to a miRNA that has less than 100% identity to a corresponding wild-type miR gene product and possesses one or more biological activities of the corresponding wild-type miR gene product. Examples of such biological activities include, but are not limited to, inhibition of expression of a target RNA molecule (e.g., inhibiting translation of a target RNA molecule, modulating the stability of a target RNA molecule, inhibiting processing of a target RNA molecule) and inhibition of a cellular process associated with solid cancer (e.g., cell differentiation, cell growth, cell death). These variants include species variants and variants that are the consequence of one or more mutations (e.g., a substitution, a deletion, an insertion) in a miR gene. In certain embodiments, the variant is at least about 70%, 75%, 80%, 85%, 90%, 95%, 98%, or 99% identical to a corresponding wild-type miR gene product.

As defined herein, a "biologically-active fragment" of a miR gene product refers to an RNA fragment of a miR gene product that possesses one or more biological activities of a corresponding wild-type miR gene product. As described above, examples of such biological activities include, but are not limited to, inhibition of expression of a target RNA molecule and inhibition of a cellular process associated with solid cancer. In certain embodiments, the biologically-active fragment is at least about 5, 7, 10, 12, 15, or 17 nucleotides in length. In a particular embodiment, an isolated miR gene product can be administered to a subject in combination with one or more additional anti-cancer treatments. Suitable anti-cancer treatments include, but are not limited to, chemotherapy, radiation therapy and combinations thereof (e.g., chemoradiation).

When the at least one isolated miR gene product is up-regulated in the cancer cells, the method comprises administering to the subject an effective amount of at least one compound for inhibiting expression of the at least one miR gene product, referred to herein as miR gene expression-inhibition compounds, such that proliferation of solid cancer cells is inhibited. In a particular embodiment, the at least one miR expression-inhibition compound is specific for a miR gene product selected from the group consisting of miR-21, miR-17-5p, miR-191, miR-29b-2, miR-223, miR-128b, miR-199a-1, miR-24-1, miR-24-2, miR-146, miR-155, miR-181b-1, miR-20a, miR-107, miR-32, miR-92-2, miR-214, miR-30c, miR-25, miR-221, miR-106a and combinations thereof. A miR gene expression-inhibiting compound can be administered to a subject in combination with one or more additional anti-cancer treatments. Suitable anti-cancer treatments include, but are not limited to, chemotherapy, radiation therapy and combinations thereof (e.g., chemoradiation).

The terms "treat", "treating" and "treatment", as used herein, refer to ameliorating symptoms associated with a disease or condition, for example, a solid cancer, including preventing or delaying the onset of the disease symptoms, and/or lessening the severity or frequency of symptoms of the disease or condition. The terms "subject", "patient" and "individual" are defined herein to include animals, such as mammals, including, but not limited to, primates, cows, sheep, goats, horses, dogs, cats, rabbits, guinea pigs, rats, mice or other bovine, ovine, equine, canine, feline, rodent, or murine species. In a preferred embodiment, the animal is a human.

As used herein, an "effective amount" of an isolated miR gene product is an amount sufficient to inhibit proliferation of a cancer cell in a subject suffering from a solid cancer. One skilled in the art can readily determine an effective amount of a miR gene product to be administered to a given subject, by taking into account factors, such as the size and weight of the subject; the extent of disease penetration; the age, health and sex of the subject; the route of administration; and whether the administration is regional or systemic.

For example, an effective amount of an isolated miR gene product can be based on the approximate weight of a tumor mass to be treated. The approximate weight of a tumor mass can be determined by calculating the approximate volume of the mass, wherein one cubic centimeter of volume is roughly equivalent to one gram. An effective amount of the isolated miR gene product based on the weight of a tumor mass can be in the range of about 10-500 micrograms/gram of tumor mass. In certain embodiments, the tumor mass can be at least about 10 micrograms/gram of tumor mass, at least about 60 micrograms/gram of tumor mass or at least about 100 micrograms/gram of tumor mass.

An effective amount of an isolated miR gene product can also be based on the approximate or estimated body weight of a subject to be treated. Preferably, such effective amounts are administered parenterally or enterally, as described herein. For example, an effective amount of the isolated miR gene product is administered to a subject can range from about 5 3000 micrograms/kg of body weight, from about 700-1000 micrograms/kg of body weight, or greater than about 1000 micrograms/kg of body weight.

One skilled in the art can also readily determine an appropriate dosage regimen for the administration of an isolated miR gene product to a given subject. For example, a miR gene product can be administered to the subject once (e.g., as a single injection or deposition). Alternatively, a miR gene product can be administered once or twice daily to a subject for a period of from about three to about twenty-eight days, more particularly from about seven to about ten days. In a particular dosage regimen, a miR gene product is administered once a day for seven days. Where a dosage regimen comprises multiple administrations, it is understood that the effective amount of the miR gene product administered to the subject can comprise the total amount of gene product administered over the entire dosage regimen.

As used herein, an "isolated" miR gene product is one that is synthesized, or altered or removed from the natural state through human intervention. For example, a synthetic miR gene product, or a miR gene product partially or completely separated from the coexisting materials of its natural state, is considered to be "isolated." An isolated miR gene product can exist in substantially-purified form, or can exist in a cell into which the miR gene product has been delivered. Thus, a miR gene product that is deliberately delivered to, or expressed in, a cell is considered an "isolated" miR gene product. A miR gene product produced inside a cell from a miR precursor molecule is also considered to be an "isolated" molecule. According to the invention, the isolated miR gene products described herein can be used for the manufacture of a medicament for treating a solid cancer in a subject (e.g., a human).

Isolated miR gene products can be obtained using a number of standard techniques. For example, the miR gene products can be chemically synthesized or recombinantly produced using methods known in the art. In one embodiment, miR gene products are chemically synthesized using appropriately protected ribonucleoside phosphoramidites and a conventional DNA/RNA synthesizer. Commercial suppliers of synthetic RNA molecules or synthesis reagents include, e.g., Proligo (Hamburg, Germany), Dharmacon Research (Lafayette, Colo., U.S.A.), Pierce Chemical (part of Perbio Science, Rockford, Ill., U.S.A.), Glen Research (Sterling, Va., U.S.A.), ChemGenes (Ashland, Mass., U.S.A.) and Cruachem (Glasgow, UK).

Alternatively, the miR gene products can be expressed from recombinant circular or linear DNA plasmids using any suitable promoter. Suitable promoters for expressing RNA from a plasmid include, e.g., the U6 or H1 RNA pol III promoter sequences, or the cytomegalovirus promoters. Selection of other suitable promoters is within the skill in the art. The recombinant plasmids of the invention can also comprise inducible or regulatable promoters for expression of the miR gene products in cancer cells.

The miR gene products that are expressed from recombinant plasmids can be isolated from cultured cell expression systems by standard techniques. The miR gene products that are expressed from recombinant plasmids can also be delivered to, and expressed directly in, the cancer cells. The use of recombinant plasmids to deliver the miR gene products to cancer cells is discussed in more detail below.

The miR gene products can be expressed from a separate recombinant plasmid, or they can be expressed from the same recombinant plasmid. In one embodiment, the miR gene products are expressed as RNA precursor molecules from a single plasmid, and the precursor molecules are processed into the functional miR gene product by a suitable processing system, including, but not limited to, processing systems extant within a cancer cell. Other suitable processing systems include, e.g., the in vitro *Drosophila* cell lysate system (e.g., as described in U.S. Published Patent Application No. 2002/0086356 to Tuschl et al., the entire disclosure of which is incorporated herein by reference) and the *E. coli* RNAse III system (e.g., as described in U.S. Published Patent Application No. 2004/0014113 to Yang et al., the entire disclosure of which is incorporated herein by reference).

Selection of plasmids suitable for expressing the miR gene products, methods for inserting nucleic acid sequences into the plasmid to express the gene products, and methods of delivering the recombinant plasmid to the cells of interest are within the skill in the art. See, for example, Zeng et al. (2002), *Molecular Cell* 9:1327-1333; Tuschl (2002), *Nat. Biotechnol,* 20:446-448; Brummelkamp et al. (2002), *Science* 296:550-553; Miyagishi et al. (2002), *Nat. Biotechnol.* 20:497-500; Paddison et al. (2002), *Genes Dev.* 16:948-958; Lee et al. (2002), *Nat. Biotechnol.* 20:500-505; and Paul et al. (2002), *Nat. Biotechnol.* 20:505-508, the entire disclosures of which are incorporated herein by reference.

In one embodiment, a plasmid expressing the miR gene products comprises a sequence encoding a miR precursor RNA under the control of the CMV intermediate-early promoter. As used herein, "under the control" of a promoter means that the nucleic acid sequences encoding the miR gene product are located 3' of the promoter, so that the promoter can initiate transcription of the miR gene product coding sequences.

The miR gene products can also be expressed from recombinant viral vectors. It is contemplated that the miR gene products can be expressed from two separate recombinant viral vectors, or from the same viral vector. The RNA expressed from the recombinant viral vectors can either be isolated from cultured cell expression systems by standard techniques, or can be expressed directly in cancer cells. The use of recombinant viral vectors to deliver the miR gene products to cancer cells is discussed in more detail below.

The recombinant viral vectors of the invention comprise sequences encoding the miR gene products and any suitable promoter for expressing the RNA sequences. Suitable promoters include, but are not limited to, the U6 or H1 RNA pol III promoter sequences, or the cytomegalovirus promoters. Selection of other suitable promoters is within the skill in the art. The recombinant viral vectors of the invention can also comprise inducible or regulatable promoters for expression of the miR gene products in a cancer cell.

Any viral vector capable of accepting the coding sequences for the miR gene products can be used; for example, vectors derived from adenovirus (AV); adeno-associated virus (AAV); retroviruses (e.g., lentiviruses (LV), Rhabdoviruses, murine leukemia virus); herpes virus, and the like. The tropism of the viral vectors can be modified by pseudotyping the vectors with envelope proteins or other surface antigens from other viruses, or by substituting different viral capsid proteins, as appropriate.

For example, lentiviral vectors of the invention can be pseudotyped with surface proteins from vesicular stomatitis virus (VSV), rabies, Ebola, Mokola, and the like. AAV vectors of the invention can be made to target different cells by engineering the vectors to express different capsid protein serotypes. For example, an AAV vector expressing a serotype 2 capsid on a serotype 2 genome is called AAV 2/2. This serotype 2 capsid gene in the AAV 2/2 vector can be replaced by a serotype 5 capsid gene to produce an AAV 2/5 vector. Techniques for constructing AAV vectors that express different capsid protein serotypes are within the skill in the art; see, e.g., Rabinowitz, J. E., et al. (2002), *J. Virol.* 76:791-801, the entire disclosure of which is incorporated herein by reference.

Selection of recombinant viral vectors suitable for use in the invention, methods for inserting nucleic acid sequences for expressing RNA into the vector, methods of delivering the viral vector to the cells of interest, and recovery of the expressed RNA products are within the skill in the art. See, for example, Dornburg (1995), *Gene Therapy* 2:301-310; Eglitis (1988), *Biotechniques* 6:608-614; Miller (1990), *Hum. Gene Therapy* 1:5-14; and Anderson (1998), *Nature* 392:25-30, the entire disclosures of which are incorporated herein by reference.

Particularly suitable viral vectors are those derived from AV and AAV. A suitable AV vector for expressing the miR gene products, a method for constructing the recombinant AV vector, and a method for delivering the vector into target cells, are described in Xia et al. (2002), *Nat. Biotech.* 20:1006-1010, the entire disclosure of which is incorporated herein by reference. Suitable AAV vectors for expressing the miR gene products, methods for constructing the recombinant AAV vector, and methods for delivering the vectors into target cells are described in Samulski et al. (1987), *J. Virol.* 61:3096-3101; Fisher et al. (1996), *J. Virol.*, 70:520-532; Samulski et al. (1989), *J. Virol.* 63:3822-3826; U.S. Pat. No. 5,252,479; U.S. Pat. No. 5,139,941; International Patent Application No. WO 94/13788; and International Patent Application No. WO 93/24641, the entire disclosures of which are incorporated herein by reference. In one embodiment, the miR gene products are expressed from a single recombinant AAV vector comprising the CMV intermediate early promoter.

In a certain embodiment, a recombinant AAV viral vector of the invention comprises a nucleic acid sequence encoding a miR precursor RNA in operable connection with a polyT termination sequence under the control of a human U6 RNA promoter. As used herein, "in operable connection with a polyT termination sequence" means that the nucleic acid sequences encoding the sense or antisense strands are immediately adjacent to the polyT termination signal in the 5' direction. During transcription of the miR sequences from the vector, the polyT termination signals act to terminate transcription.

In other embodiments of the treatment methods of the invention, an effective amount of at least one compound that inhibits miR expression can be administered to the subject. As used herein, "inhibiting miR expression" means that the production of the precursor and/or active, mature form of miR gene product after treatment is less than the amount produced prior to treatment. One skilled in the art can readily determine whether miR expression has been inhibited in a cancer cell, using, for example, the techniques for determining miR transcript level discussed above for the diagnostic method. Inhibition can occur at the level of gene expression (i.e., by inhibiting transcription of a miR gene encoding the miR gene product) or at the level of processing (e.g., by inhibiting processing of a miR precursor into a mature, active miR).

As used herein, an "effective amount" of a compound that inhibits miR expression is an amount sufficient to inhibit proliferation of a cancer cell in a subject suffering from a cancer (e.g., a solid cancer). One skilled in the art can readily determine an effective amount of a miR expression-inhibition compound to be administered to a given subject, by taking into account factors, such as the size and weight of the subject; the extent of disease penetration; the age, health and sex of the subject; the route of administration; and whether the administration is regional or systemic.

For example, an effective amount of the expression-inhibition compound can be based on the approximate weight of a tumor mass to be treated, as described herein. An effective amount of a compound that inhibits miR expression can also be based on the approximate or estimated body weight of a subject to be treated, as described herein.

One skilled in the art can also readily determine an appropriate dosage regimen for administering a compound that inhibits miR expression to a given subject.

Suitable compounds for inhibiting miR gene expression include double-stranded RNA (such as short- or small-interfering RNA or "siRNA"), antisense nucleic acids, and enzymatic RNA molecules, such as ribozymes. Each of these compounds can be targeted to a given miR gene product and interfere with the expression of (e.g., inhibit translation of, induce cleavage or destruction of) the target miR gene product.

For example, expression of a given miR gene can be inhibited by inducing RNA interference of the miR gene with an isolated double-stranded RNA ("dsRNA") molecule which has at least 90%, for example at least 95%, at least 98%, at least 99%, or 100%, sequence homology with at least a portion of the miR gene product. In a particular embodiment, the dsRNA molecule is a "short or small interfering RNA" or "siRNA."

siRNA useful in the present methods comprise short double-stranded RNA from about 17 nucleotides to about 29 nucleotides in length, preferably from about 19 to about 25 nucleotides in length. The siRNA comprise a sense RNA strand and a complementary antisense RNA strand annealed together by standard Watson-Crick base-pairing interactions (hereinafter "base-paired"). The sense strand comprises a nucleic acid sequence that is substantially identical to a nucleic acid sequence contained within the target miR gene product.

As used herein, a nucleic acid sequence in an siRNA which is "substantially identical" to a target sequence contained within the target mRNA is a nucleic acid sequence that is identical to the target sequence, or that differs from the target sequence by one or two nucleotides. The sense and antisense strands of the siRNA can comprise two complementary, single-stranded RNA molecules, or can comprise a single molecule in which two complementary portions are base-paired and are covalently linked by a single-stranded "hairpin" area.

The siRNA can also be altered RNA that differs from naturally-occurring RNA by the addition, deletion, substitution and/or alteration of one or more nucleotides. Such alterations can include addition of non-nucleotide material, such as to the end(s) of the siRNA or to one or more internal nucleotides of the siRNA, or modifications that make the siRNA resistant to nuclease digestion, or the substitution of one or more nucleotides in the siRNA with deoxyribonucleotides.

One or both strands of the siRNA can also comprise a 3' overhang. As used herein, a "3' overhang" refers to at least one unpaired nucleotide extending from the 3'-end of a duplexed RNA strand. Thus, in certain embodiments, the siRNA comprises at least one 3' overhang of from 1 to about 6 nucleotides (which includes ribonucleotides or deoxyribonucleotides) in length, from 1 to about 5 nucleotides in length, from 1 to about 4 nucleotides in length, or from about 2 to about 4 nucleotides in length. In a particular embodiment, the 3' overhang is present on both strands of the siRNA, and is 2 nucleotides in length. For example, each strand of the siRNA can comprise 3' overhangs of dithymidylic acid ("TT") or diuridylic acid ("uu").

The siRNA can be produced chemically or biologically, or can be expressed from a recombinant plasmid or viral vector, as described above for the isolated miR gene products. Exemplary methods for producing and testing dsRNA or siRNA molecules are described in U.S. Published Patent Application No. 2002/0173478 to Gewirtz and in U.S. Published Patent Application No. 2004/0018176 to Reich et al., the entire disclosures of both of which are incorporated herein by reference.

Expression of a given miR gene can also be inhibited by an antisense nucleic acid. As used herein, an "antisense nucleic acid" refers to a nucleic acid molecule that binds to target RNA by means of RNA-RNA, RNA-DNA or RNA-peptide nucleic acid interactions, which alters the activity of the target RNA. Antisense nucleic acids suitable for use in the present methods are single-stranded nucleic acids (e.g., RNA, DNA, RNA-DNA chimeras, peptide nucleic acid (PNA)) that generally comprise a nucleic acid sequence complementary to a contiguous nucleic acid sequence in a miR gene product. The antisense nucleic acid can comprise a nucleic acid sequence that is 50-100% complementary, 75-100% complementary, or 95-100% complementary to a contiguous nucleic acid sequence in a miR gene product. Nucleic acid sequences for the miR gene products are provided in Tables 1a and 1b. Without wishing to be bound by any theory, it is believed that the antisense nucleic acids activate RNase H or another cellular nuclease that digests the miR gene product/antisense nucleic acid duplex.

Antisense nucleic acids can also contain modifications to the nucleic acid backbone or to the sugar and base moieties (or their equivalent) to enhance target specificity, nuclease resistance, delivery or other properties related to efficacy of the molecule. Such modifications include cholesterol moieties, duplex intercalators, such as acridine, or one or more nuclease-resistant groups.

Antisense nucleic acids can be produced chemically or biologically, or can be expressed from a recombinant plasmid or viral vector, as described above for the isolated miR gene products. Exemplary methods for producing and testing are within the skill in the art; see, e.g., Stein and Cheng (1993), *Science* 261:1004 and U.S. Pat. No. 5,849,902 to Woolf et al., the entire disclosures of which are incorporated herein by reference.

Expression of a given miR gene can also be inhibited by an enzymatic nucleic acid. As used herein, an "enzymatic nucleic acid" refers to a nucleic acid comprising a substrate binding region that has complementarity to a contiguous nucleic acid sequence of a miR gene product, and which is able to specifically cleave the miR gene product. The enzymatic nucleic acid substrate binding region can be, for example, 50-100% complementary, 75-100% complementary, or 95-100% complementary to a contiguous nucleic acid sequence in a miR gene product. The enzymatic nucleic acids can also comprise modifications at the base, sugar, and/or phosphate groups. An exemplary enzymatic nucleic acid for use in the present methods is a ribozyme.

The enzymatic nucleic acids can be produced chemically or biologically, or can be expressed from a recombinant plasmid or viral vector, as described above for the isolated miR gene products. Exemplary methods for producing and testing dsRNA or siRNA molecules are described in Werner and Uhlenbeck (1995), *Nucl. Acids Res.* 23:2092-96; Hammann et al. (1999), *Antisense and Nucleic Acid Drug Dev.* 9:25-31; and U.S. Pat. No. 4,987,071 to Cech et al, the entire disclosures of which are incorporated herein by reference.

Administration of at least one miR gene product, or at least one compound for inhibiting miR expression, will inhibit the proliferation of cancer cells in a subject who has a solid cancer. As used herein, to "inhibit the proliferation of a cancer cell" means to kill the cell, or permanently or temporarily arrest or slow the growth of the cell. Inhibition of cancer cell proliferation can be inferred if the number of such cells in the subject remains constant or decreases after administration of the miR gene products or miR gene expression-inhibition compounds. An inhibition of cancer cell proliferation can also be inferred if the absolute number of such cells increases, but the rate of tumor growth decreases.

The number of cancer cells in the body of a subject can be determined by direct measurement, or by estimation from the size of primary or metastatic tumor masses. For example, the number of cancer cells in a subject can be measured by immunohistological methods, flow cytometry, or other techniques designed to detect characteristic surface markers of cancer cells.

The size of a tumor mass can be ascertained by direct visual observation, or by diagnostic imaging methods, such as X-ray, magnetic resonance imaging, ultrasound, and scintigraphy. Diagnostic imaging methods used to ascertain size of the tumor mass can be employed with or without contrast agents, as is known in the art. The size of a tumor mass can also be ascertained by physical means, such as palpation of the tissue mass or measurement of the tissue mass with a measuring instrument, such as a caliper.

The miR gene products or miR gene expression-inhibition compounds can be administered to a subject by any means suitable for delivering these compounds to cancer cells of the subject. For example, the miR gene products or miR expression-inhibition compounds can be administered by methods suitable to transfect cells of the subject with these compounds, or with nucleic acids comprising sequences encoding these compounds. In one embodiment, the cells are transfected with a plasmid or viral vector comprising sequences encoding at least one miR gene product or miR gene expression-inhibition compound.

Transfection methods for eukaryotic cells are well known in the art, and include, e.g., direct injection of the nucleic acid into the nucleus or pronucleus of a cell; electroporation; liposome transfer or transfer mediated by lipophilic materials; receptor-mediated nucleic acid delivery, bioballistic or particle acceleration; calcium phosphate precipitation, and transfection mediated by viral vectors.

For example, cells can be transfected with a liposomal transfer compound, e.g., DOTAP (N-[1-(2,3-dioleoyloxy) propyl]-N,N,N-trimethyl-ammonium methylsulfate, Boehringer-Mannheim) or an equivalent, such as LIPOFECTIN. The amount of nucleic acid used is not critical to the practice of the invention; acceptable results may be achieved with 0.1-100 micrograms of nucleic acid/$10^5$ cells. For example, a ratio of about 0.5 micrograms of plasmid vector in 3 micrograms of DOTAP per $10^5$ cells can be used.

A miR gene product or miR gene expression-inhibition compound can also be administered to a subject by any suitable enteral or parenteral administration route. Suitable enteral administration routes for the present methods include, e.g., oral, rectal, or intranasal delivery. Suitable parenteral administration routes include, e.g., intravascular administration (e.g., intravenous bolus injection, intravenous infusion, intra-arterial bolus injection, intra-arterial infusion and catheter instillation into the vasculature); peri- and intra-tissue injection (e.g., peri-tumoral and intra-tumoral injection, intra-retinal injection, or subretinal injection); subcutaneous injection or deposition, including subcutaneous infusion (such as by osmotic pumps); direct application to the tissue of interest, for example by a catheter or other placement device (e.g., a retinal pellet or a suppository or an implant comprising a porous, non-porous, or gelatinous material); and inhalation. Particularly suitable administration routes are injection, infusion and direct injection into the tumor.

In the present methods, a miR gene product or miR gene product expression-inhibition compound can be administered to the subject either as naked RNA, in combination with a delivery reagent, or as a nucleic acid (e.g., a recombinant plasmid or viral vector) comprising sequences that express the miR gene product or miR gene product expression-inhibition compound. Suitable delivery reagents include, e.g., the Mirus Transit TKO lipophilic reagent; lipofectin; lipofectamine; cellfectin; polycations (e.g., polylysine), and liposomes.

Recombinant plasmids and viral vectors comprising sequences that express the miR gene products or miR gene expression-inhibition compounds, and techniques for delivering such plasmids and vectors to cancer cells, are discussed herein and/or are well known in the art.

In a particular embodiment, liposomes are used to deliver a miR gene product or miR gene expression-inhibition compound (or nucleic acids comprising sequences encoding them) to a subject. Liposomes can also increase the blood half-life of the gene products or nucleic acids. Suitable liposomes for use in the invention can be formed from standard vesicle-forming lipids, which generally include neutral or negatively charged phospholipids and a sterol, such as cholesterol. The selection of lipids is generally guided by consideration of factors, such as the desired liposome size and half-life of the liposomes in the blood stream. A variety of methods are known for preparing liposomes, for example, as described in Szoka et al. (1980), *Ann. Rev. Biophys. Bioeng.* 9:467; and U.S. Pat. Nos. 4,235,871, 4,501,728, 4,837,028, and 5,019,369, the entire disclosures of which are incorporated herein by reference.

The liposomes for use in the present methods can comprise a ligand molecule that targets the liposome to cancer cells. Ligands that bind to receptors prevalent in cancer cells, such as monoclonal antibodies that bind to tumor cell antigens, are preferred.

The liposomes for use in the present methods can also be modified so as to avoid clearance by the mononuclear macrophage system ("MMS") and reticuloendothelial system ("RES"). Such modified liposomes have opsonization-inhibition moieties on the surface or incorporated into the liposome structure. In a particularly preferred embodiment, a liposome of the invention can comprise both an opsonization-inhibition moiety and a ligand.

Opsonization-inhibiting moieties for use in preparing the liposomes of the invention are typically large hydrophilic polymers that are bound to the liposome membrane. As used herein, an opsonization-inhibiting moiety is "bound" to a liposome membrane when it is chemically or physically attached to the membrane, e.g., by the intercalation of a lipid-soluble anchor into the membrane itself, or by binding directly to active groups of membrane lipids. These opsonization-inhibiting hydrophilic polymers form a protective surface layer that significantly decreases the uptake of the liposomes by the MMS and RES; e.g., as described in U.S. Pat. No. 4,920,016, the entire disclosure of which is incorporated herein by reference.

Opsonization-inhibiting moieties suitable for modifying liposomes are preferably water-soluble polymers with a number-average molecular weight from about 500 to about 40,000 daltons, and more preferably from about 2,000 to about 20,000 daltons. Such polymers include polyethylene glycol (PEG) or polypropylene glycol (PPG) derivatives; e.g., methoxy PEG or PPG, and PEG or PPG stearate; synthetic polymers, such as polyacrylamide or poly N-vinyl pyrrolidone; linear, branched, or dendrimeric polyamidoamines; polyacrylic acids; polyalcohols, e.g., polyvinylalcohol and polyxylitol to which carboxylic or amino groups are chemically linked, as well as gangliosides, such as ganglioside GM1. Copolymers of PEG, methoxy PEG, or methoxy PPG, or derivatives thereof, are also suitable. In addition, the opsonization-inhibiting polymer can be a block copolymer of PEG and either a polyamino acid, polysaccharide, polyamidoamine, polyethyleneamine, or polynucleotide. The opsonization-inhibiting polymers can also be natural polysaccharides containing amino acids or carboxylic acids, e.g., galacturonic acid, glucuronic acid, mannuronic acid, hyaluronic acid, pectic acid, neuraminic acid, alginic acid, carrageenan; aminated polysaccharides or oligosaccharides (linear or branched); or carboxylated polysaccharides or oligosaccharides, e.g., reacted with derivatives of carbonic acids with resultant linking of carboxylic groups. Preferably, the opsonization-inhibiting moiety is a PEG, PPG, or a derivative thereof. Liposomes modified with PEG or PEG-derivatives are sometimes called "PEGylated liposomes."

The opsonization-inhibiting moiety can be bound to the liposome membrane by any one of numerous well-known techniques. For example, an N-hydroxysuccinimide ester of PEG can be bound to a phosphatidyl-ethanolamine lipid-soluble anchor, and then bound to a membrane. Similarly, a dextran polymer can be derivatized with a stearylamine lipid-soluble anchor via reductive amination using Na(CN)BH$_3$ and a solvent mixture, such as tetrahydrofuran and water in a 30:12 ratio at 60° C.

Liposomes modified with opsonization-inhibition moieties remain in the circulation much longer than unmodified liposomes. For this reason, such liposomes are sometimes called "stealth" liposomes. Stealth liposomes are known to accumulate in tissues fed by porous or "leaky" microvasculature. Thus, tissue characterized by such microvasculature defects, for example, solid tumors, will efficiently accumulate these liposomes; see Gabizon, et al. (1988), Proc. Natl. Acad. Sci., U.S.A., 18:6949-53. In addition, the reduced uptake by the RES lowers the toxicity of stealth liposomes by preventing significant accumulation of the liposomes in the liver and spleen. Thus, liposomes that are modified with opsonization-inhibition moieties are particularly suited to deliver the miR gene products or miR gene expression-inhibition compounds (or nucleic acids comprising sequences encoding them) to tumor cells.

The miR gene products or miR gene expression-inhibition compounds can be formulated as pharmaceutical compositions, sometimes called "medicaments," prior to administering them to a subject, according to techniques known in the art. Accordingly, the invention encompasses pharmaceutical compositions for treating a solid cancer. In one embodiment, the pharmaceutical composition comprises at least one isolated miR gene product, or an isolated variant or biologically-active fragment thereof, and a pharmaceutically-acceptable carrier. In a particular embodiment, the at least one miR gene product corresponds to a miR gene product that has a decreased level of expression in solid cancer cells relative to suitable control cells. In certain embodiments the isolated miR gene product is selected from the group consisting of miR-145, miR-155, miR-218-2 combinations thereof.

In other embodiments, the pharmaceutical compositions of the invention comprise at least one miR expression-inhibition compound. In a particular embodiment, the at least one miR gene expression-inhibition compound is specific for a miR gene whose expression is greater in solid cancer cells than control cells. In certain embodiments, the miR gene expression-inhibition compound is specific for one or more miR gene products selected from the group consisting of miR-21, miR-17-5p, miR-191, miR-29b-2, miR-223, miR-128b, miR-199a-1, miR-24-1, miR-24-2, miR-146, miR-155, miR-181b-1, miR-20a, miR-107, miR-32, miR-92-2, miR-214, miR-30c, miR-25, miR-221, miR-106a and combinations thereof.

Pharmaceutical compositions of the present invention are characterized as being at least sterile and pyrogen-free. As used herein, "pharmaceutical compositions" include formulations for human and veterinary use. Methods for preparing pharmaceutical compositions of the invention are within the skill in the art, for example as described in Remington's Pharmaceutical Science, 17th ed., Mack Publishing Company, Easton, Pa. (1985), the entire disclosure of which is incorporated herein by reference.

The present pharmaceutical compositions comprise at least one miR gene product or miR gene expression-inhibition compound (or at least one nucleic acid comprising sequences encoding them) (e.g., 0.1 to 90% by weight), or a physiologically-acceptable salt thereof, mixed with a pharmaceutically-acceptable carrier. In certain embodiments, the pharmaceutical compositions of the invention additionally comprise one or more anti-cancer agents (e.g., chemotherapeutic agents). The pharmaceutical formulations of the invention can also comprise at least one miR gene product or miR gene expression-inhibition compound (or at least one nucleic acid comprising sequences encoding them), which are encapsulated by liposomes and a pharmaceutically-acceptable carrier. In one embodiment, the pharmaceutical composition comprises a miR gene or gene product that is not miR-15 and/or miR-16.

Especially suitable pharmaceutically-acceptable carriers are water, buffered water, normal saline, 0.4% saline, 0.3% glycine, hyaluronic acid and the like.

In a particular embodiment, the pharmaceutical compositions of the invention comprise at least one miR gene product or miR gene expression-inhibition compound (or at least one nucleic acid comprising sequences encoding them) that is resistant to degradation by nucleases. One skilled in the art can readily synthesize nucleic acids that are nuclease resistant, for example, by incorporating one or more ribonucleotides that is modified at the 2'-position into the miR gene product. Suitable 2'-modified ribonucleotides include those modified at the 2'-position with fluoro, amino, alkyl, alkoxy, and O-allyl.

Pharmaceutical compositions of the invention can also comprise conventional pharmaceutical excipients and/or additives. Suitable pharmaceutical excipients include stabilizers, antioxidants, osmolality adjusting agents, buffers, and pH adjusting agents. Suitable additives include, e.g., physiologically biocompatible buffers (e.g., tromethamine hydrochloride), additions of chelants (such as, for example, DTPA or DTPA-bisamide) or calcium chelate complexes (such as, for example, calcium DTPA, CaNaDTPA-bisamide), or, optionally, additions of calcium or sodium salts (for example, calcium chloride, calcium ascorbate, calcium gluconate or calcium lactate). Pharmaceutical compositions of the invention can be packaged for use in liquid form, or can be lyophilized.

For solid pharmaceutical compositions of the invention, conventional nontoxic solid pharmaceutically-acceptable carriers can be used; for example, pharmaceutical grades of mannitol, lactose, starch, magnesium stearate, sodium saccharin, talcum, cellulose, glucose, sucrose, magnesium carbonate, and the like.

For example, a solid pharmaceutical composition for oral administration can comprise any of the carriers and excipients listed above and 10-95%, preferably 25%-75%, of the at least one miR gene product or miR gene expression-inhibition compound (or at least one nucleic acid comprising sequences encoding them). A pharmaceutical composition for aerosol (inhalational) administration can comprise 0.01-20% by weight, preferably 1%-10% by weight, of the at least one miR gene product or miR gene expression-inhibition compound (or at least one nucleic acid comprising sequences encoding them) encapsulated in a liposome as described above, and a propellant. A carrier can also be included as desired; e.g., lecithin for intranasal delivery.

The pharmaceutical compositions of the invention can further comprise one or more anti-cancer agents. In a particular embodiment, the compositions comprise at least one miR gene product or miR gene expression-inhibition compound (or at least one nucleic acid comprising sequences encoding them) and at least one chemotherapeutic agent. Chemotherapeutic agents that are suitable for the methods of the invention include, but are not limited to, DNA-alkylating agents, antitumor antibiotic agents, anti-metabolic agents, tubulin stabilizing agents, tubulin destabilizing agents, hormone antagonist agents, topoisomerase inhibitors, protein kinase inhibitors, HMG-CoA inhibitors, CDK inhibitors, cyclin inhibitors, caspase inhibitors, metalloproteinase inhibitors, antisense nucleic acids, triple-helix DNAs, nucleic acids aptamers, and molecularly-modified viral, bacterial and exotoxic agents. Examples of suitable agents for the compositions of the present invention include, but are not limited to, cytidine arabinoside, methotrexate, vincristine, etoposide (VP-16), doxorubicin (adriamycin), cisplatin (CDDP), dexamethasone, arglabin, cyclophosphamide, sarcolysin, methylnitrosourea, fluorouracil, 5-fluorouracil (5FU), vinblastine, camptothecin, actinomycin-D, mitomycin C, hydrogen peroxide, oxaliplatin, irinotecan, topotecan, leucovorin, carmustine, streptozocin, CPT-11, taxol, tamoxifen, dacarbazine, rituximab, daunorubicin, 1-β-D-arabinofuranosylcytosine, imatinib, fludarabine, docetaxel, FOLFOX4.

The invention also encompasses methods of identifying an inhibitor of tumorigenesis, comprising providing a test agent to a cell and measuring the level of at least one miR gene product in the cell. In one embodiment, the method comprises providing a test agent to a cell and measuring the level of at least one miR gene product associated with decreased expression levels in cancer cells. An increase in the level of the miR gene product in the cell after the agent is provided, relative to a suitable control cell (e.g., agent is not provided), is indicative of the test agent being an inhibitor of tumorigenesis. In a particular embodiment, at least one miR gene product associated with decreased expression levels in cancer cells is selected from the group consisting of miR-145, miR-155, miR-218-2 and combinations thereof.

In other embodiments the method comprises providing a test agent to a cell and measuring the level of at least one miR gene product associated with increased expression levels in cancer cells. A decrease in the level of the miR gene product in the cell after the agent is provided, relative to a suitable control cell (e.g., agent is not provided), is indicative of the test agent being an inhibitor of tumorigenesis. In a particular embodiment, at least one miR gene product associated with increased expression levels in cancer cells is selected from the group consisting of miR-21, miR-17-5p, miR-191, miR-29b-2, miR-223, miR-128b, miR-199a-1, miR-24-1, miR-24-2, miR-146, miR-155, miR-181b-1, miR-20a, miR-107, miR-32, miR-92-2, miR-214, miR-30c, miR-25, miR-221, miR-106a.

Suitable agents include, but are not limited to drugs (e.g., small molecules, peptides), and biological macromolecules (e.g., proteins, nucleic acids). The agent can be produced recombinantly, synthetically, or it may be isolated (i.e., purified) from a natural source. Various methods for providing such agents to a cell (e.g., transfection) are well known in the art, and several of such methods are described hereinabove. Methods for detecting the expression of at least one miR gene product (e.g., Northern blotting, in situ hybridization, RT-PCR, expression profiling) are also well known in the art. Several of these methods are also described hereinabove.

The invention will now be illustrated by the following non-limiting examples.

EXEMPLIFICATION

The following Materials and Methods were used in the Examples:
Samples

A total of 540 samples, including 363 primary tumor samples and 177 normal tissues, were used in this study (Table 2). The following solid cancers were represented: lung carcinoma, breast carcinoma, prostate carcinoma, stomach carcinoma, colon carcinoma and pancreatic endocrine tumors. All samples were obtained with informed consent from each patient and were confirmed histologically. Normal samples were paired with samples from individuals affected with lung and stomach carcinoma, and from normal individuals for the remaining tissues. All normal breast samples were obtained by pooling 5 unrelated normal tissues. Total RNA was isolated from tissues using TRIzol™ reagent (Invitrogen), according to manufacturer's instructions. MicroRNA microarrays.

Microarray analysis was performed as previously described (Liu, C.-G., et al., *Proc. Natl. Acad. Sci. USA* 101: 11755-11760 (2004)). Briefly, 5 µg of total RNA was used for hybridization on miRNA microarray chips. These chips contain gene-specific 40-mer oligonucleotide probes, spotted by contacting technologies and covalently attached to a polymeric matrix. The microarrays were hybridized in 6×SSPE (0.9 M NaCl/60 mM $NaH_2PO_4.H_2O$/8 mM EDTA, pH 7.4)/ 30% formamide at 25° C. for 18 hr, washed in 0.75×TNT (Tris-HCl/NaCl/Tween 20) at 37° C. for 40 min, and processed using direct detection of the biotin-labeled transcripts by streptavidin-Alexa647 (Molecular Probes) conjugate. Processed slides were scanned using a microarray scanner (GenePix Pro, Axon), with the laser set to 635 nm, at fixed PMT setting and a scan resolution of 10 mm. The data were confirmed by Northern blotting as described (Calin, G. A., et al., *Proc. Natl. Acad. Sci. USA* 101:11755-11760 (2004); Iorio, M. V., et al., *Cancer Res.* 65: 7065-7070 (2005)).

TABLE 2

Samples used in the study (tumors and corresponding normals).

| Tumour type | Cancer Samples | Normal Samples |
|---|---|---|
| Lung carcinoma | 123 | 123 |
| Breast carcinoma | 79 | 6* |
| Colon carcinoma | 46 | 8 |
| Gastric carcinoma | 20 | 21 |
| Endocrine pancreatic tumours | 39 | 12 |
| Prostate cancer | 56 | 7 |
| All tissues (527) | 363 | 177 |

*Pools of 5 unrelated normal breast tissues per sample (for a total of 30 unrelated individuals).

Computational Analysis.

Microarray images were analyzed using GenePix Pro (Axon). Average values of the replicate spots of each miRNA were background-subtracted, normalized, and subjected to further analysis. Normalization was performed by using a per chip median normalization method, using the median array as a reference. Finally, miRNAs measured as present in at least the smallest of the two classes in a dataset were selected. Absent calls were thresholded to 4.5 prior to statistical analysis. This level is the average minimum intensity level detected in the experiments. MicroRNA nomenclature was according to the Genome Browser and the microRNA database at Sanger Center (Griffiths-Jones, S., *Nucleic Acids Res* 32: D109-11(2004)); in case of discrepancies we followed the microRNA database. Differentially-expressed microRNA were identified by using the t test procedure within significance analysis of microarrays (SAM) (Tusher, V. G., et al., *Proc Natl Acad Sci USA* 98: 5116-21 (2001). SAM calculates a score for each gene on the basis of the change in expression relative to the standard deviation of all measurements. Within SAM, t test was used. The microRNA signatures were determined by applying nearest shrunken centroids method. This method identifies a subgroup of genes that best characterizes each solid cancer from its respective normal counterpart. The prediction error was calculated by means of 10-fold cross validation, and for each cancer, we obtained the miR signature that resulted in the minimal prediction error. A resampling test was performed by random permutation analysis to compute the p-value of the shared signature.

Example 1

Identification of a microRNA Expression Signature in Human Solid Cancers Statistics The combined cancers/normal tissue comparison was conducted using a reduced number of lung samples (80 cancer and 40 normal samples), in order to balance the different tissues numerically, yielding a total of 404 samples. For statistical analysis, 137 miRs, whose expression values were above 256 (threshold value) in at least 50% of the samples, were retained from the 228 that were measured. A T test was used to identify differentially-expressed microRNAs (Table 3). The p-values of the T test were corrected for multiple testing procedures and to control Type I error rates. Adjusted p-values were obtained by performing resampling with 500,000 permutations (Jung, S. H., et al. *Biostatistics* 6: 157-69 (2005)). This analysis was performed in order to evaluate the results by using the same method as Lu and co-workers (Lu, J., et al., *Nature* 435: 834-8 (2005)).

As an alternative to T test, significance analysis of microarrays (SAM) was used to identify differentially-expressed microRNAs. This procedure allows for the control of false detection rate (FDR). The delta was chosen to result in an FDR less than or equal to 0.01. microRNA subsets which result in the best tumor classification, i.e., which best predict the two classes (cancer and normal), were then identified using the method of the nearest shrunken centroids, as implemented in PAM (prediction analysis of microarray). The prediction error was calculated by means of 10-fold cross validation. The microRNAs were selected yielding the minimum misclassification error after cross-validation.

Results

By T-test, 43 differentially-expressed miRs with an adjusted p-value below 0.05 were obtained (Table 3). Twenty six miRs were overexpressed and 17 were under-expressed relative to corresponding normal tissues when the six solid cancers are grouped together (breast, colon, lung, pancreas, prostate, stomach). These results indicated that the spectrum of expressed miRNAs in solid cancers is very different from that of normal cells (43 out of 137 miRNAs, 31%). Using SAM, 49 miRNAs were identified as differentially-expressed, of which 34 were up-regulated (Table 4). Using PAM, 36 over-expressed miRNAs in cancer (indicated by positive cancer scores) and 21 down-regulated miRs (indicated by negative cancer scores) were identified as differentially-expressed (Table 5). However, these analyses are not tailored to identify alterations in miR expression that consistently result in transformation, because miR expression is heavily tissue-specific (He, L., et al. *Nature* 435: 828-833 (2005); also see FIG. 1 and FIG. 2).

Figure 2:
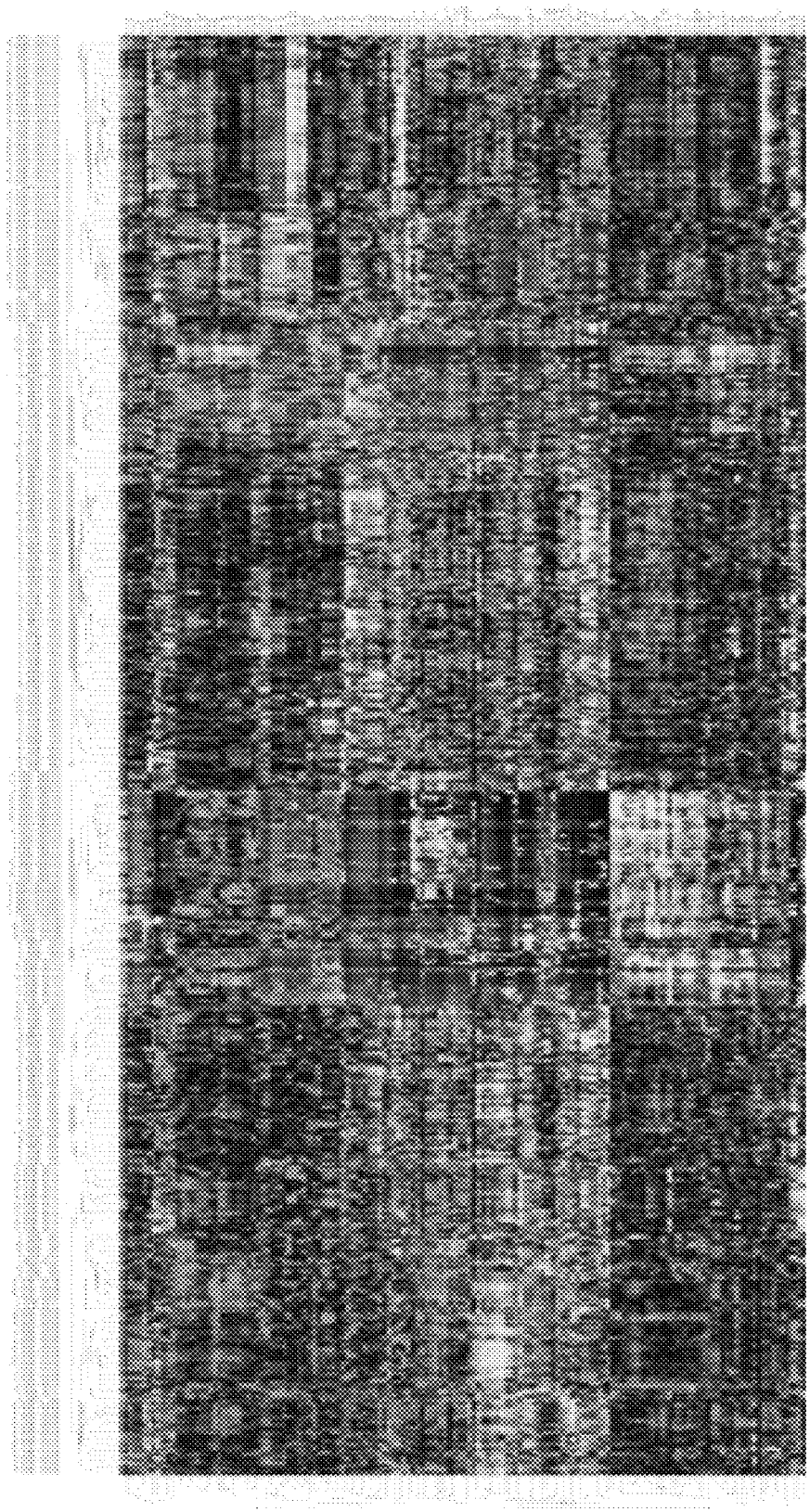
FIG. 2 depicts unsupervised analysis of microRNA expression data. MicroRNA profiling of 540 samples (indicated at top of panel) covering breast, colon, lung, pancreas, prostate and stomach (normal tissues and tumors) were filtered, centered and normalized for each feature. The data were subject to hierarchical clustering on both the samples (horizontally-oriented) and the features (vertically-oriented with average linkage and Pearson correlation as a similarity measure. Sample names are indicated at the top of the figure and miRNA names on the left. The probe ID is indicated in parentheses, as the same microRNA can be measured by different oligonucleotides. The colors indicate the difference in expression level from the median for the microRNAs in each sample.

The clustering of miRs based on expression profiles derived from 363 solid cancer and 177 normal samples using 228 miRs is shown in FIG. 1. The tree, which shows a very good separation between the different tissues, was constructed using 137 different miRNAs that were expressed in at least 50% of the samples used in the study.

TABLE 3

Differentially regulated miRs in 6 solid cancer types vs. normal tissues (T test stats.) *.

| miR | ID | Cancer Mean | Normal Mean | Test stat | Raw p | Adj p |
|---|---|---|---|---|---|---|
| miR-21 | #47 | 11.538663 | 9.648338 | 7.861136 | 2.00E−06 | 2.00E−06 |
| miR-141 | #137 | 9.024091 | 7.905398 | 6.238014 | 2.00E−06 | 2.00E−06 |
| miR-212 | #208 | 13.540651 | 14.33617 | −6.57942 | 2.00E−06 | 2.00E−06 |
| miR-128a prec | #113 | 12.32588 | 13.522675 | −6.76388 | 2.00E−06 | 2.00E−06 |
| miR-138-2 | #133 | 11.739557 | 13.144746 | −7.01204 | 2.00E−06 | 2.00E−06 |
| miR-218-2 | #221 | 11.279787 | 12.539366 | −7.40557 | 2.00E−06 | 2.00E−06 |
| miR-23b | #51 | 14.169748 | 15.949736 | −8.37744 | 2.00E−06 | 2.00E−06 |
| miR-195 | #184 | 10.343991 | 9.172985 | 5.763262 | 2.00E−06 | 1.00E−05 |
| miR-212 prec | #209 | 12.686966 | 13.661763 | −5.83132 | 4.00E−06 | 1.00E−05 |
| miR-29b-2 | #95 | 11.27556 | 9.940731 | 5.660854 | 2.00E−06 | 1.40E−05 |
| miR-199a-1 | #191 | 10.032008 | 8.920183 | 5.528849 | 2.00E−06 | 3.00E−05 |
| miR-9-3 | #28 | 11.461922 | 12.570412 | −5.43006 | 2.00E−06 | 4.60E−05 |
| miR-128a | #114 | 13.024235 | 13.856624 | −5.35102 | 6.00E−06 | 7.20E−05 |
| let-7a-1 | #1 | 12.616569 | 13.455246 | −5.35346 | 2.00E−06 | 7.20E−05 |
| let-7b | #5 | 13.42636 | 14.068521 | −5.17701 | 1.00E−05 | 0.000146 |
| miR-16-2 | #39 | 10.460707 | 9.305895 | 5.048375 | 4.00E−06 | 0.000224 |
| miR-199a-2 | #192 | 9.714225 | 8.759237 | 4.862553 | 1.00E−05 | 0.000494 |
| miR-152 prec | #151 | 11.388676 | 12.357529 | −4.83716 | 2.00E−06 | 0.00053 |
| miR-16-1 | #38 | 10.443169 | 9.338182 | 4.755258 | 1.00E−05 | 0.00071 |
| miR-30d | #72 | 13.982017 | 14.775206 | −4.5707 | 1.20E−05 | 0.001476 |
| miR-34a | #78 | 10.675566 | 9.63769 | 4.467301 | 2.60E−05 | 0.00217 |
| miR-17-5p | #41 | 11.567244 | 10.281468 | 4.341834 | 3.80E−05 | 0.0034 |
| miR-128b | #115 | 10.930395 | 9.947746 | 4.304764 | 3.80E−05 | 0.003912 |
| miR-20a | #46 | 11.409852 | 10.19284 | 4.304678 | 3.20E−05 | 0.003912 |
| miR-181b-1 prec | #211 | 9.577504 | 8.804294 | 4.285968 | 4.80E−05 | 0.004126 |
| miR-132 | #121 | 9.599947 | 8.775966 | 4.284737 | 5.60E−05 | 0.004126 |
| miR-200b | #195 | 9.475221 | 8.527243 | 4.221511 | 4.00E−05 | 0.0052 |
| let-7a-3 | #4 | 10.436089 | 9.511546 | 4.08952 | 0.000104 | 0.008242 |
| miR-138-1 | #132 | 8.299613 | 9.200253 | −4.05204 | 5.60E−05 | 0.00931 |
| miR-29c | #65 | 11.291005 | 10.326912 | 4.019385 | 0.000144 | 0.010312 |
| miR-29a | #62 | 11.381359 | 10.461075 | 4.013697 | 0.00015 | 0.010398 |
| miR-96 | #86 | 11.37218 | 12.136636 | −3.94825 | 0.000138 | 0.012962 |
| miR-191 | #177 | 13.498207 | 12.729872 | 3.817228 | 0.000158 | 0.02015 |
| miR-27a | #59 | 10.399338 | 9.548582 | 3.715048 | 0.000344 | 0.028096 |
| let-7g | #15 | 10.819688 | 10.01157 | 3.653239 | 0.000426 | 0.033874 |
| miR-9-1 | #24 | 10.102819 | 9.212988 | 3.651886 | 0.000388 | 0.033874 |
| miR-125a | #107 | 10.960998 | 10.005312 | 3.651356 | 0.000452 | 0.033874 |
| miR-95 | #84 | 9.435733 | 8.751331 | 3.59406 | 0.000478 | 0.039594 |
| miR-155 | #157 | 12.505359 | 13.231221 | −3.58369 | 0.000614 | 0.040394 |
| miR-199b | #194 | 9.755066 | 9.082751 | 3.55934 | 0.000588 | 0.04314 |
| miR-24-2 | #54 | 12.611696 | 11.612557 | 3.518774 | 0.00087 | 0.048278 |
| let-7e | #11 | 12.497795 | 13.055093 | −3.51589 | 0.00054 | 0.048354 |
| miR-92-1 | #81 | 16.081074 | 16.592426 | −3.50446 | 0.000928 | 0.049828 |

* Forty-three miRs have an adjusted p-value lower than 0.05. Twenty-six miRs are overexpressed and 17 down-regulated in breast, colon, lung, pancreas, prostate, stomach carcinomas.

TABLE 4

Differentially regulated miRs in 6 solid cancer types vs. normal tissues (SAM, significance analysis of microarrays) *.

| miR | ID | d. value | stdev | p. value | q. value | R. fold |
|---|---|---|---|---|---|---|
| miR-21 | #47 | 3.156 | 0.24 | 0 | 0 | 2.593 |
| miR-23b | #51 | −3.117 | 0.212 | 0 | 0 | 0.443 |
| miR-138-2 | #133 | −2.514 | 0.2 | 0 | 0 | 0.402 |
| miR-218-2 | #221 | −2.383 | 0.17 | 0 | 0 | 0.384 |
| miR-29b-2 | #95 | 2.246 | 0.236 | 0 | 0 | 1.868 |
| miR-128a prec | #113 | −2.235 | 0.177 | 0 | 0 | 0.368 |
| miR-195 | #184 | 2.085 | 0.203 | 0 | 0 | 1.695 |
| miR-141 | #137 | 2.08 | 0.179 | 0 | 0 | 2.459 |
| miR-199a-1 | #191 | 1.987 | 0.201 | 0 | 0 | 1.945 |
| miR-9-3 | #28 | −1.97 | 0.204 | 0 | 0 | 0.433 |
| miR-16-2 | #39 | 1.966 | 0.229 | 0 | 0 | 1.788 |
| miR-17-5p | #41 | 1.964 | 0.296 | 0 | 0 | 0.725 |
| miR-20a | #46 | 1.898 | 0.283 | 0 | 0 | 0.969 |
| miR-16-1 | #38 | 1.87 | 0.232 | 0 | 0 | 1.447 |
| miR-212 prec | #209 | −1.854 | 0.167 | 0 | 0 | 0.509 |
| miR-34a | #78 | 1.756 | 0.232 | 0 | 0 | 1.219 |
| miR-152 prec | #151 | −1.734 | 0.2 | 0 | 0 | 0.46 |
| miR-199a-2 | #192 | 1.721 | 0.196 | 0 | 0 | 1.838 |
| miR-128b | #115 | 1.674 | 0.228 | 0 | 0 | 1.266 |
| miR-212 | #208 | −1.659 | 0.121 | 0 | 0 | 0.627 |
| let-7a-1 | #1 | −1.628 | 0.157 | 0 | 0 | 0.461 |
| miR-200b | #195 | 1.626 | 0.225 | 0 | 0 | 1.432 |
| miR-128a | #114 | −1.619 | 0.156 | 0 | 0 | 0.511 |
| miR-29c | #65 | 1.611 | 0.24 | 0 | 0 | 1.225 |
| let-7a-3 | #4 | 1.581 | 0.226 | 0 | 0 | 1.109 |
| miR-29a | #62 | 1.565 | 0.229 | 0 | 0 | 1.706 |
| miR-24-2 | #54 | 1.555 | 0.284 | 0 | 0 | 0.831 |
| miR-138-1 | #132 | −1.551 | 0.222 | 0 | 0 | 0.432 |
| miR-125a | #107 | 1.541 | 0.262 | 0 | 0 | 1.164 |
| miR-106a | #99 | 1.514 | 0.275 | 0 | 0 | 0.952 |
| miR-132 | #121 | 1.496 | 0.192 | 0 | 0 | 2.158 |
| miR-30d | #72 | −1.491 | 0.174 | 0 | 0 | 0.424 |
| miR-9-1 | #24 | 1.478 | 0.244 | 0 | 0 | 0.763 |
| miR-27a | #59 | 1.448 | 0.229 | 0 | 0 | 1.174 |
| miR-181b-1 prec | #211 | 1.435 | 0.18 | 0 | 0 | 1.525 |
| let-7g | #15 | 1.394 | 0.221 | 0 | 0 | 1.072 |
| miR-96 | #86 | −1.384 | 0.194 | 0 | 0 | 0.519 |
| miR-191 | #177 | 1.372 | 0.201 | 0 | 0 | 1.165 |
| miR-93-1 | #83 | 1.363 | 0.266 | 0 | 0 | 0.775 |
| miR-136 | #130 | −1.355 | 0.267 | 0 | 0 | 0.364 |
| miR-205 | #201 | 1.343 | 0.309 | 0 | 0 | 1.281 |
| miR-185 | #170 | 1.287 | 0.222 | 0.001 | 0.001 | 0.609 |
| miR-125b-1 | #109 | 1.262 | 0.283 | 0.001 | 0.001 | 1.215 |
| miR-10a | #30 | 1.252 | 0.227 | 0.001 | 0.001 | 1.643 |
| miR-95 | #84 | 1.247 | 0.19 | 0.001 | 0.001 | 1.509 |
| miR-199b | #194 | 1.228 | 0.189 | 0.001 | 0.001 | 1.246 |
| miR-10b | #32 | 1.219 | 0.232 | 0.002 | 0.001 | 1.342 |
| let-7i | #10 | 1.216 | 0.203 | 0.002 | 0.001 | 1.026 |
| miR-210 | #205 | 1.213 | 0.237 | 0.002 | 0.001 | 1.088 |

* Thirty five miRs are over-expressed and 14 are down-regulated in breast, colon, lung, pancreas, prostate, stomach carcinomas (Delta = 0.9, FDR = 0.001).

TABLE 5

MicroRNAs selected by PAM (prediction analysis of microarray) in 6 solid cancer types vs. normal tissues

| miR | ID | Solid cancer score | Normal tissues score |
|---|---|---|---|
| miR-21 | #47 | 0.0801 | −0.2643 |
| miR-138-2 | #133 | −0.055 | 0.1815 |
| miR-218-2 | #221 | −0.0535 | 0.1765 |
| miR-23b | #51 | −0.0516 | 0.17 |
| miR-128a prec | #113 | −0.0498 | 0.1642 |
| miR-29b-2 | #95 | 0.0457 | −0.1508 |
| miR-195 | #184 | 0.0404 | −0.1333 |
| miR-17-5p | #41 | 0.0383 | −0.1263 |
| miR-9-3 | #28 | −0.0357 | 0.1176 |
| miR-212 prec | #209 | −0.0342 | 0.1129 |
| miR-20a | #46 | 0.0322 | −0.1061 |
| miR-141 | #137 | 0.0322 | −0.1061 |
| miR-199a-1 | #191 | 0.0319 | −0.1053 |

TABLE 5-continued

MicroRNAs selected by PAM (prediction analysis of microarray) in 6 solid cancer types vs. normal tissues

| miR | ID | Solid cancer score | Normal tissues score |
|---|---|---|---|
| miR-16-2 | #39 | 0.0315 | −0.1037 |
| miR-152 prec | #151 | −0.0283 | 0.0933 |
| miR-16-1 | #38 | 0.0277 | −0.0913 |
| miR-34a | #78 | 0.0269 | −0.0886 |
| miR-212 | #208 | −0.0265 | 0.0875 |
| let-7a-1 | #1 | −0.0264 | 0.0872 |
| miR-128a | #114 | −0.0259 | 0.0855 |
| miR-128b | #115 | 0.0254 | −0.0839 |
| miR-24-2 | #54 | 0.0244 | −0.0803 |
| miR-29c | #65 | 0.0224 | −0.0738 |
| miR-199a-2 | #192 | 0.0223 | −0.0736 |
| let-7a-3 | #4 | 0.0221 | −0.073 |
| miR-191 | #177 | 0.0188 | −0.062 |
| miR-125a | #107 | 0.0186 | −0.0613 |
| miR-30d | #72 | −0.0185 | 0.061 |
| miR-29a | #62 | 0.0184 | −0.0608 |
| miR-106a | #99 | 0.0177 | −0.0584 |
| miR-93-1 | #83 | 0.0163 | −0.0537 |
| miR-200b | #195 | 0.0159 | −0.0524 |
| let-7g | #15 | 0.0158 | −0.0521 |
| miR-27a | #59 | 0.0157 | −0.0518 |
| miR-96 | #86 | −0.0156 | 0.0514 |
| let-7b | #5 | −0.0152 | 0.0501 |
| miR-138-1 | #132 | −0.0151 | 0.0499 |
| miR-9-1 | #24 | 0.0136 | −0.0448 |
| miR-181b-1 prec | #211 | 0.0134 | −0.0442 |
| miR-155 | #157 | −0.0128 | 0.0423 |
| miR-132 | #121 | 0.0127 | −0.0418 |
| miR-136 | #130 | −0.0112 | 0.037 |
| let-7i | #10 | 0.0103 | −0.034 |
| miR-210 | #205 | 0.0074 | −0.0245 |
| miR-205 | #201 | 0.0073 | −0.024 |
| *miR-185 | #170 | 0.0071 | −0.0234 |
| miR-24-1 | #52 | 0.007 | −0.023 |
| miR-199b | #194 | 0.0064 | −0.021 |
| miR-125b-1 | #109 | 0.006 | −0.0199 |
| miR-206 prec | #203 | −0.005 | 0.0166 |
| miR-10a | #30 | 0.0045 | −0.015 |
| miR-95 | #84 | 0.0045 | −0.0149 |
| let-7c | #11 | −0.0039 | 0.013 |
| miR-124a-3 | #106 | −0.0028 | 0.0091 |
| miR-10b | #32 | 0.002 | −0.0066 |
| miR-185 prec | #171 | −0.0014 | 0.0047 |
| miR-92-1 | #81 | −2.00E−04 | 5.00E−04 |

*T = 1.5 and misclassification error = 0.176. Thirty six over-expressed miRs in cancer are indicated by positive cancer scores; 21 down-regulated miRs are indicated by negative cancer scores.

Example 2

Identification of microRNA Expression Signatures Associated with Various Human Solid Cancers Results To identify microRNAs that are prognostic for cancer status associated with solid tumors, without incurring bias due to tissue specificity, an alternative approach was used. First, six tissue-specific signatures, one for each cancer histotype, were obtained by performing independent PAM tests (summarized in Tables 6 and 7) Specific signatures for each cancer are shown in Tables 8-13: e.g., breast-Table 8; colon-Table 9; lung-Table 10; pancreas-Table 11; prostate-Table 12; stomach-Table 13. Using these data, deregulated microRNAs that were shared among the different histotype miRNA signatures were identified (Table 14). In order to compute the p-values for this comparative analysis, a re-sampling test with 1,000,000 random permutations on the miRNA identity was performed. The p-value was defined as the relative frequency of simulation scores exceeding the real score. Twenty-one misregulated microRNAs that were common to at least 3 types of solid cancers (p-value=2.5×10⁻³) were identified (Table 14).

TABLE 6

MicroRNAs used to classify human cancers and normal tissues*.

| Cancer | Up-regulated miRs | Down-regulated miRs | Misclassification error after 10 fold cross validation |
|---|---|---|---|
| Breast | 15 | 12 | 0.08 |
| Colon | 21 | 1 | 0.09 |
| Lung | 35 | 3 | 0.31 |
| Pancreas | 55 | 2 | 0.02 |
| Prostate | 39 | 6 | 0.11 |
| Stomach | 22 | 6 | 0.19 |

*Median normalization was performed and the method of the nearest shrunken centroids was used to select predictive miRNAs.

TABLE 7

Deregulated microRNAs in solid common cancers*.

| Cancer | PAM Up-regulated | SAM Up-regulated | PAM Down-regulated | SAM Down-regulated |
|---|---|---|---|---|
| Breast | 15 | 3 (FDR = 0.33) | 12 | 47 |
| Colon | 21 | 42 (FDR <= 0.06) | 1 | 5 |
| Lung | 35 | 38 (FDR <= 0.01) | 3 | 3 |
| Pancreas | 55 | 50 (FDR <= 0.01) | 2 | 8 |
| Stomach | 22 | 22 (FDR = 0.06) | 6 | 4 |
| Prostate | 39 | 49 (FDR = 0.06) | 6 | 3 |

*Prediction analysis of microarrays (PAM) identifies those genes which best characterize cancers and normal tissues, whilst significance analysis of microarrays (SAM) identifies all those which have differential expression in the two classes. False detection rates (FDR) computed in SAM are indicated in parenthesis.

TABLE 8

MicroRNAs selected by prediction analysis of microarray (PAM) in breast cancer (cancer vs. normal tissues) *.

| miR | Cancer score | Normal score |
|---|---|---|
| miR-21 (#47) | 0.0331 | −0.4364 |
| miR-29b-2 (#95) | 0.0263 | −0.3467 |
| miR-146 (#144) | 0.0182 | −0.2391 |
| miR-125b-2 (#111) | −0.0174 | 0.2286 |
| miR-125b-1 (#109) | −0.0169 | 0.222 |
| miR-10b (#32) | −0.0164 | 0.2166 |
| miR-145 (#143) | −0.0158 | 0.2076 |
| miR-181a (#158) | 0.0153 | −0.201 |
| miR-140 (#136) | −0.0122 | 0.1613 |
| miR-213 (#160) | 0.0116 | −0.1527 |
| miR-29a prec (#63) | 0.0109 | −0.1441 |
| miR-181b-1 (#210) | 0.0098 | −0.1284 |
| miR-199b (#194) | 0.0089 | −0.1172 |
| miR-29b-1 (#64) | 0.0084 | −0.1111 |
| miR-130a (#120) | −0.0076 | 0.1001 |
| miR-155 (#157) | 0.0072 | −0.0951 |
| let-7a-2 (#3) | −0.0042 | 0.0554 |
| miR-205 (#201) | −0.004 | 0.0533 |
| miR-29c (#65) | 0.0032 | −0.0423 |
| miR-224 (#228) | −0.003 | 0.0399 |
| miR-100 (#91) | −0.0021 | 0.0283 |
| miR-31 (#73) | 0.0017 | −0.022 |
| miR-30c (#70) | −7.00E−04 | 0.009 |
| miR-17-5p (#41) | 7.00E−04 | −0.0089 |
| miR-210 (#205) | 4.00E−04 | −0.0057 |
| miR-122a (#101) | 4.00E−04 | −0.005 |
| miR-16-2 (#39) | −1.00E−04 | 0.0013 |

* 27 miRs selected, misclassification error after cross validation of 0.008. Seventeen over-expressed miRs in cancer are indicated by positive cancer scores; 12 down-regulated miRs are indicated by negative cancer scores.

TABLE 9

MicroRNAs selected by prediction analysis of microarray (PAM) in colon (cancer vs. normal tissues)*.

| miR | Cancer score | Normal score |
|---|---|---|
| miR-24-1 (#52) | 0.0972 | −0.5589 |
| miR-29b-2 (#95) | 0.0669 | −0.3845 |
| miR-20a (#46) | 0.0596 | −0.3424 |
| miR-10a (#30) | 0.0511 | −0.2938 |
| miR-32 (#75) | 0.0401 | −0.2306 |
| miR-203 (#197) | 0.0391 | −0.2251 |
| miR-106a (#99) | 0.0364 | −0.2094 |
| miR-17-5p (#41) | 0.0349 | −0.2005 |
| miR-30c (#70) | 0.0328 | −0.1888 |
| miR-223 (#227) | 0.0302 | −0.1736 |
| miR-126* (#102) | 0.0199 | −0.1144 |
| miR-128b (#115) | 0.0177 | −0.102 |
| miR-21 (#47) | 0.0162 | −0.0929 |
| miR-24-2 (#54) | 0.0145 | −0.0835 |
| miR-99b prec (#88) | 0.0125 | −0.0721 |
| miR-155 (#157) | 0.0092 | −0.0528 |
| miR-213 (#160) | 0.0091 | −0.0522 |
| miR-150 (#148) | 0.0042 | −0.0243 |
| miR-107 (#100) | 0.003 | −0.0173 |
| miR-191 (#177) | 0.0028 | −0.0159 |
| miR-221 (#224) | 0.002 | −0.0116 |
| miR-9-3 (#28) | −0.0014 | 0.0083 |

*22 miRs selected, misclassification error after cross validation of 0.09. Twenty-one over-expressed miRs in cancer are indicated by positive cancer scores; 1 down-regulated miR is indicated by a negative cancer score.

TABLE 10

MicroRNAs selected by prediction analysis of microarray (PAM) in lung cancer (cancer vs. normal tissues)*.

| miR | Cancer score | Normal score |
|---|---|---|
| miR-21 (#47) | 0.175 | −0.175 |
| miR-205 (#201) | 0.1317 | −0.1317 |
| miR-200b (#195) | 0.1127 | −0.1127 |
| miR-9-1 (#24) | 0.1014 | −0.1014 |
| miR-210 (#205) | 0.0994 | −0.0994 |
| miR-148 (#146) | 0.0737 | −0.0737 |
| miR-141 (#137) | 0.0631 | −0.0631 |
| miR-132 (#121) | 0.0586 | −0.0586 |
| miR-215 (#213) | 0.0575 | −0.0575 |
| miR-128b (#115) | 0.0559 | −0.0559 |
| let-7g (#15) | 0.0557 | −0.0557 |
| miR-16-2 (#39) | 0.0547 | −0.0547 |
| miR-129-1/2 prec (#118) | 0.0515 | −0.0515 |
| miR-126* (#102) | −0.0406 | 0.0406 |
| miR-142-as (#139) | 0.0366 | −0.0366 |
| miR-30d (#72) | −0.0313 | 0.0313 |
| miR-30a-5p (#66) | −0.0297 | 0.0297 |
| miR-7-2 (#21) | 0.0273 | −0.0273 |
| miR-199a-1 (#191) | 0.0256 | −0.0256 |
| miR-127 (#112) | 0.0254 | −0.0254 |
| miR-34a prec (#79) | 0.0214 | −0.0214 |
| miR-34a (#78) | 0.0188 | −0.0188 |
| miR-136 (#130) | 0.0174 | −0.0174 |
| miR-202 (#196) | 0.0165 | −0.0165 |
| miR-196-2 (#188) | 0.0134 | −0.0134 |
| miR-199a-2 (#192) | 0.0126 | −0.0126 |
| let-7a-2 (#3) | 0.0109 | −0.0109 |
| miR-124a-1 (#104) | 0.0081 | −0.0081 |
| miR-149 (#147) | 0.0079 | −0.0079 |
| miR-17-5p (#41) | 0.0061 | −0.0061 |
| miR-196-1 prec (#186) | 0.0053 | −0.0053 |
| miR-10a (#30) | 0.0049 | −0.0049 |
| miR-99b prec (#88) | 0.0045 | −0.0045 |
| miR-196-1 (#185) | 0.0044 | −0.0044 |
| miR-199b (#194) | 0.0039 | −0.0039 |
| miR-191 (#177) | 0.0032 | −0.0032 |

TABLE 10-continued

MicroRNAs selected by prediction analysis of microarray (PAM) in lung cancer (cancer vs. normal tissues)*.

| miR | Cancer score | Normal score |
|---|---|---|
| miR-195 (#184) | 7.00E−04 | −7.00E−04 |
| miR-155 (#157) | 7.00E−04 | −7.00E−04 |

*38 miRs selected, misclassification error after cross validation of 0.31. Thirty-five over-expressed miRs in cancer are indicated by positive cancer scores; 3 down-regulated miRs are indicated by negative cancer scores.

TABLE 11

MicroRNAs selected by prediction analysis of microarray (PAM) in pancreatic cancer (cancer vs. normal tissues)*.

| miR | Cancer score | Normal score |
|---|---|---|
| miR-103-2 (#96) | 0.4746 | −1.582 |
| miR-103-1 (#97) | 0.4089 | −1.3631 |
| miR-24-2 (#54) | 0.4059 | −1.3529 |
| miR-107 (#100) | 0.3701 | −1.2336 |
| miR-100 (#91) | 0.3546 | −1.182 |
| miR-125b-2 (#111) | 0.3147 | −1.0489 |
| miR-125b-1 (#109) | 0.3071 | −1.0237 |
| miR-24-1 (#52) | 0.2846 | −0.9488 |
| miR-191 (#177) | 0.2661 | −0.887 |
| miR-23a (#50) | 0.2586 | −0.8619 |
| miR-26a-1 (#56) | 0.2081 | −0.6937 |
| miR-125a (#107) | 0.1932 | −0.644 |
| miR-130a (#120) | 0.1891 | −0.6303 |
| miR-26b (#58) | 0.1861 | −0.6203 |
| miR-145 (#143) | 0.1847 | −0.6158 |
| miR-221 (#224) | 0.177 | −0.59 |
| miR-126* (#102) | 0.1732 | −0.5772 |
| miR-16-2 (#39) | 0.1698 | −0.5659 |
| miR-146 (#144) | 0.1656 | −0.552 |
| miR-214 (#212) | 0.1642 | −0.5472 |
| miR-99b (#89) | 0.1636 | −0.5454 |
| miR-128b (#115) | 0.1536 | −0.512 |
| miR-155 (#157) | −0.1529 | 0.5098 |
| miR-29b-2 (#95) | 0.1487 | −0.4956 |
| miR-29a (#62) | 0.1454 | −0.4848 |
| miR-25 (#55) | 0.1432 | −0.4775 |
| miR-16-1 (#38) | 0.1424 | −0.4746 |
| miR-99a (#90) | 0.1374 | −0.4581 |
| miR-224 (#228) | 0.1365 | −0.4549 |
| miR-30d (#72) | 0.1301 | −0.4336 |
| miR-92-2 (#82) | 0.116 | −0.3865 |
| miR-199a-1 (#191) | 0.1158 | −0.3861 |
| miR-223 (#227) | 0.1141 | −0.3803 |
| miR-29c (#65) | 0.113 | −0.3768 |
| miR-30b (#68) | 0.1008 | −0.3361 |
| miR-129-1/2 (#117) | 0.1001 | −0.3337 |
| miR-197 (#189) | 0.0975 | −0.325 |
| miR-17-5p (#41) | 0.0955 | −0.3185 |
| miR-30c (#70) | 0.0948 | −0.316 |
| miR-7-1 (#19) | 0.0933 | −0.311 |
| miR-93-1 (#83) | 0.0918 | −0.3061 |
| miR-140 (#136) | 0.0904 | −0.3015 |
| miR-30a-5p (#66) | 0.077 | −0.2568 |
| miR-132 (#121) | 0.0654 | −0.2179 |
| miR-181b-1 (#210) | 0.0576 | −0.1918 |
| miR-152 prec (#151) | −0.0477 | 0.1591 |
| miR-23b (#51) | 0.0469 | −0.1562 |
| miR-20a (#46) | 0.0452 | −0.1507 |
| miR-222 (#225) | 0.0416 | −0.1385 |
| miR-27a (#59) | 0.0405 | −0.1351 |
| miR-92-1 (#81) | 0.0332 | −0.1106 |
| miR-21 (#47) | 0.0288 | −0.0959 |
| miR-129-1/2 prec (#118) | 0.0282 | −0.0939 |
| miR-150 (#148) | 0.0173 | −0.0578 |
| miR-32 (#75) | 0.0167 | −0.0558 |
| miR-106a (#99) | 0.0142 | −0.0473 |
| miR-29b-1 (#64) | 0.0084 | −0.028 |

*57 miRs selected, misclassification error after cross validation of 0.02. Fifty-seven miRs are over-expressed and 2 are down-regulated in cancer (indicated by positive and negative scores, respectively).

TABLE 12

MicroRNAs selected by prediction analysis of microarray (PAM) in prostate cancer (cancer vs. normal tissues) *.

| miR | Cancer score | Normal score |
|---|---|---|
| let-7d (#8) | 0.0528 | −0.4227 |
| miR-128a prec (#113) | −0.0412 | 0.3298 |
| miR-195 (#184) | 0.04 | −0.3199 |
| miR-203 (#197) | 0.0356 | −0.2851 |
| let-7a-2 prec (#2) | −0.0313 | 0.2504 |
| miR-34a (#78) | 0.0303 | −0.2428 |
| miR-20a (#46) | 0.029 | −0.2319 |
| miR-218-2 (#221) | −0.0252 | 0.2018 |
| miR-29a (#62) | 0.0247 | −0.1978 |
| miR-25 (#55) | 0.0233 | −0.1861 |
| miR-95 (#84) | 0.0233 | −0.1861 |
| miR-197 (#189) | 0.0198 | −0.1587 |
| miR-135-2 (#128) | 0.0198 | −0.1582 |
| miR-187 (#173) | 0.0192 | −0.1535 |
| miR-196-1 (#185) | 0.0176 | −0.1411 |
| miR-148 (#146) | 0.0175 | −0.1401 |
| miR-191 (#177) | 0.017 | −0.136 |
| miR-21 (#47) | 0.0169 | −0.1351 |
| let-7i (#10) | 0.0163 | −0.1303 |
| miR-198 (#190) | 0.0145 | −0.1161 |
| miR-199a-2 (#192) | 0.0136 | −0.1088 |
| miR-30c (#70) | 0.0133 | −0.1062 |
| miR-17-5p (#41) | 0.0132 | −0.1053 |
| miR-92-2 (#82) | 0.012 | −0.0961 |
| miR-146 (#144) | 0.0113 | −0.0908 |
| miR-181b-1 prec (#211) | 0.011 | −0.0878 |
| miR-32 (#75) | 0.0109 | −0.0873 |
| miR-206 (#202) | 0.0104 | −0.083 |
| miR-184 prec (#169) | 0.0096 | −0.0764 |
| miR-29a prec (#63) | −0.0095 | 0.076 |
| miR-29b-2 (#95) | 0.0092 | −0.0739 |
| miR-149 (#147) | −0.0084 | 0.0676 |
| miR-181b-1 (#210) | 0.0049 | −0.0392 |
| miR-196-1 prec (#186) | 0.0042 | −0.0335 |
| miR-93-1 (#83) | 0.0039 | −0.0312 |
| miR-223 (#227) | 0.0038 | −0.0308 |
| miR-16-1 (#38) | 0.0028 | −0.0226 |
| miR-101-1 prec (#92) | 0.0015 | −0.0123 |
| miR-124a-1 (#104) | 0.0015 | −0.0119 |
| miR-26a-1 (#56) | 0.0015 | −0.0119 |
| miR-214 (#212) | 0.0013 | −0.0105 |
| miR-27a (#59) | 0.0011 | −0.0091 |
| miR-24-1 (#53) | −8.00E−04 | 0.0067 |
| miR-106a (#99) | 7.00E−04 | −0.0057 |
| miR-199a-1 (#191) | 4.00E−04 | −0.0029 |

* T = 1, 45 miRs selected, misclassification error after cross validation of 0.11. Thirty-nine over-expressed miRs in cancer are indicated by positive cancer scores; 6 downregulated miRs are indicated by negative cancer scores.

TABLE 13

MicroRNAs selected by prediction analysis of microarray (PAM) in stomach cancer (cancer vs. normal tissues) *.

| miR | Cancer score | Normal score |
|---|---|---|
| miR-223 (#227) | 0.1896 | −0.1806 |
| miR-21 (#47) | 0.1872 | −0.1783 |
| miR-218-2 (#221) | −0.1552 | 0.1478 |
| miR-103-2 (#96) | 0.1206 | −0.1148 |
| miR-92-2 (#82) | 0.1142 | −0.1088 |
| miR-25 (#55) | 0.1097 | −0.1045 |
| miR-136 (#130) | −0.1097 | 0.1045 |
| miR-191 (#177) | 0.0946 | −0.0901 |
| miR-221 (#224) | 0.0919 | −0.0876 |
| miR-125b-2 (#111) | 0.0913 | −0.0869 |
| miR-103-1 (#97) | 0.0837 | −0.0797 |
| miR-214 (#212) | 0.0749 | −0.0713 |
| miR-222 (#225) | 0.0749 | −0.0713 |
| miR-212 prec (#209) | −0.054 | 0.0514 |
| miR-125b-1 (#109) | 0.0528 | −0.0503 |
| miR-100 (#91) | 0.0526 | −0.0501 |
| miR-107 (#100) | 0.0388 | −0.0369 |

TABLE 13-continued

MicroRNAs selected by prediction analysis of microarray (PAM) in stomach cancer (cancer vs. normal tissues) *.

| miR | Cancer score | Normal score |
|---|---|---|
| miR-92-1 (#81) | 0.0369 | −0.0351 |
| miR-96 (#86) | −0.0306 | 0.0291 |
| miR-192 (#178) | 0.0236 | −0.0224 |
| miR-23a (#50) | 0.022 | −0.021 |
| miR-215 (#213) | 0.0204 | −0.0194 |
| miR-7-2 (#21) | 0.0189 | −0.018 |
| miR-138-2 (#133) | −0.0185 | 0.0176 |
| miR-24-1 (#52) | 0.0151 | −0.0144 |
| miR-99b (#89) | 0.0098 | −0.0093 |
| miR-33b (#76) | −0.0049 | 0.0046 |
| miR-24-2 (#54) | 0.0041 | −0.0039 |

* T = 1, 28 miRs selected, misclassification error after cross validation of 0.19. Twenty-two over-expressed miRs in cancer are indicated by positive cancer scores; 6 down-regulated miRs are indicated by negative cancer scores.

TABLE 14

The microRNAs shared by the signatures of the 6 solid cancers*.

| miR | N | Tumor Type |
|---|---|---|
| miR-21 | 6 | Breast Colon Lung Pancreas Prostate Stomach |
| miR-17-5p | 5 | Breast Colon Lung Pancreas Prostate |
| miR-191 | 5 | Colon Lung Pancreas Prostate Stomach |
| miR-29b-2 | 4 | Breast Colon Pancreas Prostate |
| miR-223 | 4 | Colon Pancreas Prostate Stomach |
| miR-128b | 3 | Colon Lung Pancreas |
| miR-199a-1 | 3 | Lung Pancreas Prostate |
| miR-24-1 | 3 | Colon Pancreas Stomach |
| miR-24-2 | 3 | Colon Pancreas Stomach |
| miR-146 | 3 | Breast Pancreas Prostate |
| miR-155 | 3 | Breast Colon Lung |
| miR-181b-1 | 3 | Breast Pancreas Prostate |
| miR-20a | 3 | Colon Pancreas Prostate |
| miR-107 | 3 | Colon Pancreas Stomach |
| miR-32 | 3 | Colon Pancreas Prostate |
| miR-92-2 | 3 | Pancreas Prostate Stomach |
| miR-214 | 3 | Pancreas Prostate Stomach |
| miR-30c | 3 | Colon Pancreas Prostate |
| miR-25 | 3 | Pancreas Prostate Stomach |
| miR-221 | 3 | Colon Pancreas Stomach |
| miR-106a | 3 | Colon Pancreas Prostate |

*The list includes 21 commonly up-regulated microRNAs in 3 or more (N) types of solid cancers (p-value = $2.5 \times 10^{-3}$).

Figure 3:
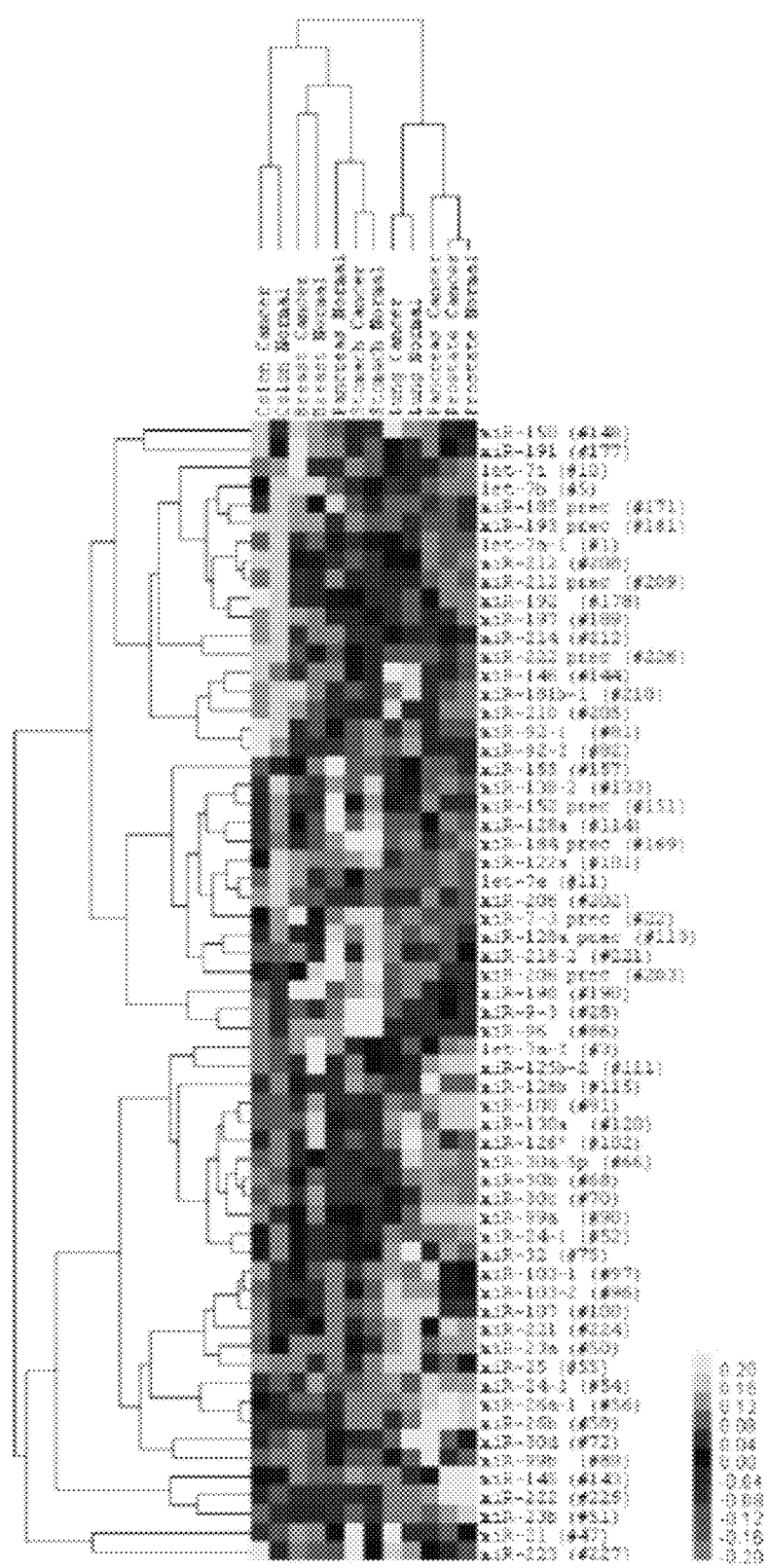
FIG. 3 depicts the expression of differentially-regulated miRNAs across solid cancers (top). Sixty-one microRNAs, which are present in at least 90% of the tissues solid cancers, are represented (right of panel). The tree displays the average absolute expression values for each of the listed microRNAs after $\log_2$ transformation. The mean was computed over all samples from the same tissue or tumor histotype. Genes were mean-centered and normalized using Gene Cluster 2.0. Average linkage clustering was performed using Euclidean distance.

To maximize concision, the mean absolute expression levels of the deregulated miRs for the 6 cancer/normal pairs were computed. Using the expression level of miRs in the comprehensive subset, the different tissues were correctly classified, irrespective of the disease status (FIG. 3).

Figure 4:
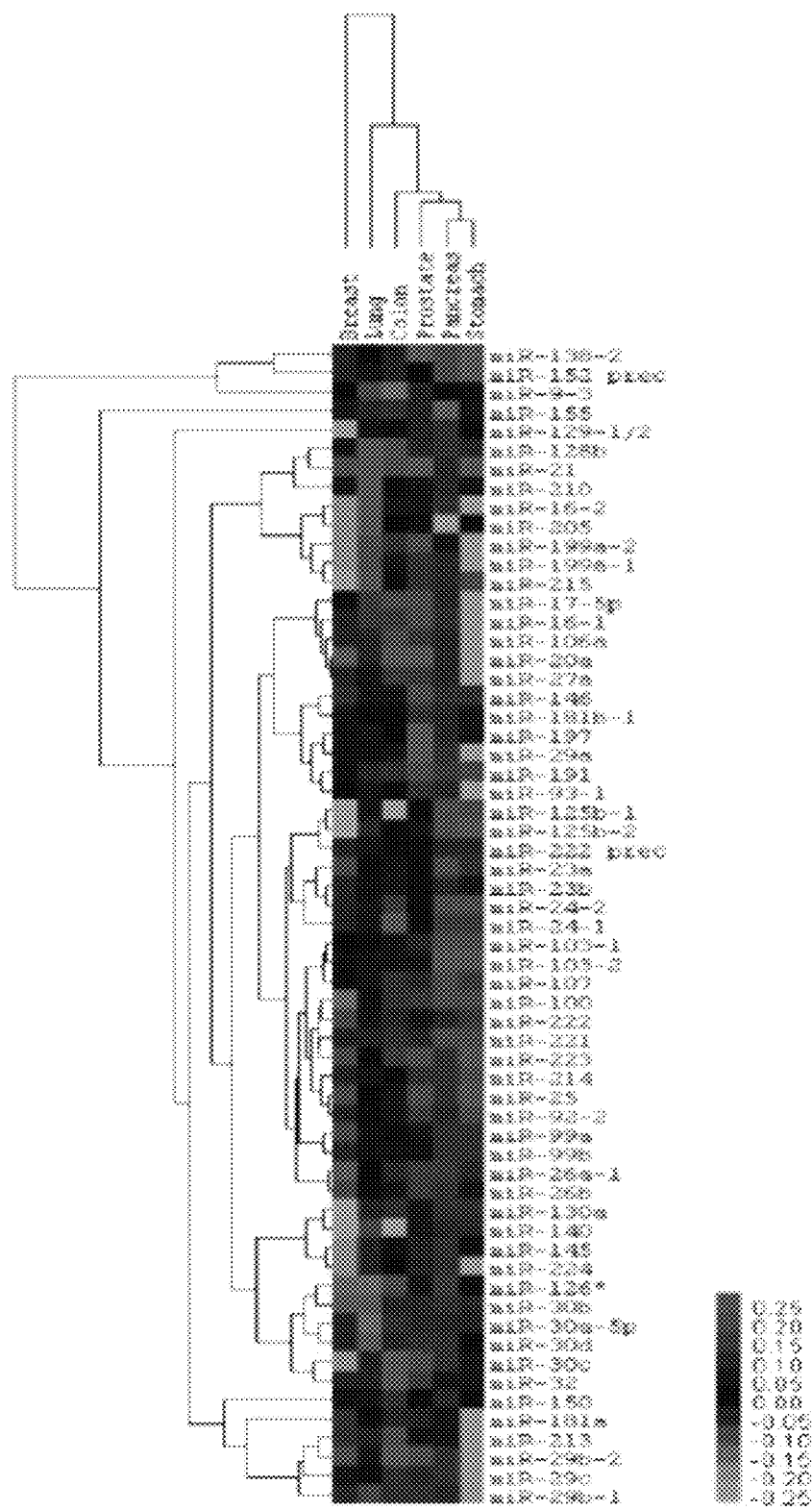
FIG. 4 depicts fold changes in the expression of miRNAs present in at least 75% of the solid tumors with at least 1 tumor absolute value higher than 2 in different cancer samples (top), relative to normal samples. The tree displays the $\log_2$ transformation of average fold changes (cancer vs. normal). The mean was computed over all samples from the same tissue or tumor histotype. Arrays were mean-centered and normalized using Gene Cluster 2.0. Average linkage clustering was performed using uncentered correlation metric.

FIG. 4 shows differential expression of the common microRNAs across the different tumor tissues, in relation to the normal tissues. The tree displays the different cancer types according to fold changes in the miRNA subset. Prostate, colon, stomach and pancreatic tissues are most similar among them, while lung and breast tissues were represented by a fairly different signature (FIG. 4). This tree clearly shows which miRNAs are associated with a particular cancer histotype.

Strikingly, miR-21, miR-191 and miR-17-5p are significantly over-expressed in all, or in 5 out of 6, of the tumor types that were considered. miR-21 was reported to be over-expressed in glioblastoma and to have anti-apoptotic properties (Chan, J. A., et al., Cancer Res. 65: 6029-6033 (2005)). Lung cancer shares a portion of its signature with breast cancer and a portion with the other solid tumors, including miR-17/20/92, all three of which are members of the microRNA cluster that actively cooperates with c-Myc to accelerate lymphoma-genesis (He, L., et al., Nature 435: 828-833 (2005)). The identification of these microRNAs as being over-expressed is an excellent confirmation of our approach. A second miRNA group that is activated includes miR-210 and miR-213, together with miR-155, which was already reported to be amplified in large cell lymphomas (E is, P. S., et al., Proc. Natl. Acad. Sci. USA 102: 3627-3632 (2005)), children with Burkitt lymphoma (Metzler, M., et al., Genes Chromosomes Cancer 39:167-169 (2004)) and various B cell lymphomas (Kluiver, J, et al., J. Pathol., e-published online, Jul. 22, 2005). These microRNAs are the only ones up-regulated in breast and lung cancer. miR-218-2 is consistently down-regulated in colon, stomach, prostate and pancreas cancers, but not in lung and breast carcinomas.

Several observations strengthen these results. First, in this study, the expression levels of both the precursor pre-miRNA and the mature miRNA were determined for the majority of genes. Of note, with the exception of miR-212 and miR-128a, in all other instances, the abnormally-expressed region was that corresponding to the active gene product. Second, as shown in FIG. 3, the expression variation of the miRNAs in the comprehensive subset was often univocal (namely, down- or up-regulation) across the different types of cancers, suggesting a common mechanism in human tumorigenesis. Third, the microarray data were validated by solution hybridization for 12 breast samples (miR-125b, miR-145 and miR-21; Iorio, M. V., et al., Cancer Res. 65: 7065-7070 (2005)) and 17 endocrine pancreatic and normal samples (miR-103, miR-155 and miR-204; data not shown), strongly confirming the accuracy of the microarray data.

Example 3

Identification of Predicted Targets for microRNAs that are Deregulated in Solid Tumors Materials and Methods:
Tumor Suppressor and Oncogene Target Predictions The most recent TargetScan predictions (April 2005) were used to identify putative microRNA targets. These include essentially the 3'UTR targets reported by Lewis et al. (Lewis, B. P., et al, Cell 120: 15-20 (2005)), with a few changes arising from updated gene boundary definitions from the April 2005 UCSC Genome Browser mapping of RefSeq mRNAs to the hg17 human genome assembly. Among the putative targets, known cancer genes (tumor suppressors and oncogenes) were specified according to their identification in the Cancer Gene Census as reported by OMIM.

Target In Vitro Assays

For luciferase reporter experiments, 3' UTR segments of Rb1, TGFBR2 and Plag1 that are predicted to interact with specific cancer-associated microRNAs were amplified by PCR from human genomic DNA and inserted into the pGL3 control vector (Promega) using the XbaI site immediately downstream from the stop codon of luciferase. The human megakaryocytic cell line, MEG-01, was grown in 10% FBS in RPMI medium 1640, supplemented with 1× nonessential amino acid and 1 mmol sodium pyruvate at 37° C. in a humified atmosphere of 5% $CO_2$. The cells were co-transfected in 12-well plates by using siPORT neoFX (Ambion, Austin, Tex.), according to the manufacturer's protocol, with 0.4 µg of the firefly luciferase reporter vector and 0.08 µg of the control vector containing Renilla luciferase, pRL-TK (Promega). For each well, microRNA oligonucleotides (Dharmacon Research, Lafayette, Colo.) and anti-sense or scrambled oligonucleotides (Ambion) were used at a concentration of 10 nM. Firefly and Renilla luciferase activities were measured consecutively at 24 h post transfection using dual-luciferase assays (Promega).

Western Blotting for RB1

Levels of RB1 protein were quantified using a mouse monoclonal anti-RB1 antibody (Santa Cruz, Calif.) using standard procedures for Western blotting. The normalization was performed with mouse monoclonal anti-Actin antibody (Sigma).

Results

The functional significance of microRNA deregulation in cancer needs to be understood. In solid tumors, it appears that the most common microRNA event is gain of expression, while loss of expression in cancer is a more limited event, and more tissue specific. We used a three-step consequential approach in the following order: first, "in silico" prediction of targets, then luciferase assay for first validation of cancer relevant targets and finally, ex vivo tumor correlation between miRNA expression (by microarray) and target protein expression (by Western blotting) for a specific miRNA:mRNA interactor pair. Relevant targets for cancer miRNAs could be either recessive (e.g., tumor suppressors) or dominant (e.g., oncogenes) cancer genes. To test the hypothesis that microRNAs that are deregulated in solid tumors target known oncogenes or tumor suppressors, the predicted targets for these miRNAs were determined using TargetScan, a database of conserved 3' UTR microRNA targets (Lewis, B. P., et al, *Cell* 120: 15-20 (2005)). TargetScan contained 5,121 predictions for 18 miRNAs that are dysregulated in solid tumors, in the total 22,402 (26.5%) predictions. One hundred fifteen out of 263 (44%), well-known cancer genes were predicted as targets for these 18 miRNAs (Table 15). Because a high percentage of cancer genes are targeted by miRs that are deregulated in solid tumors, it is unlikely that these predictions are due to chance ($P<0.0001$ at Fisher exact-test).

Figure 6A:
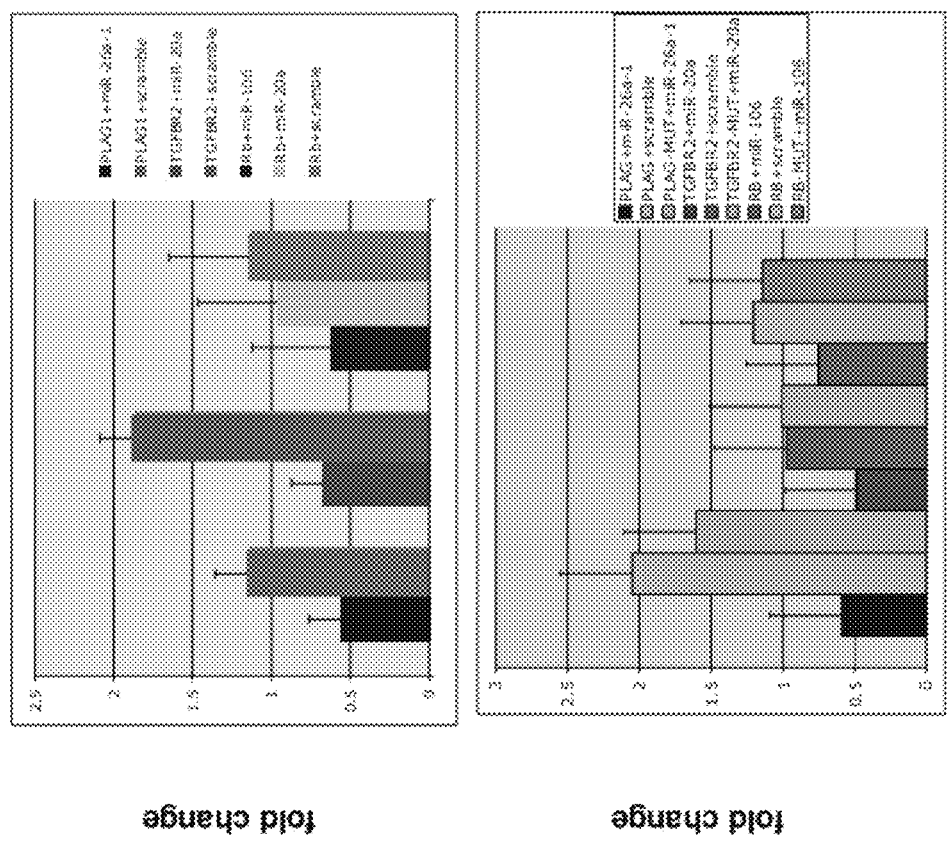
FIG. 6A depicts bar graphs indicating that the 3'UTR of different genes encoding cancer protein enables cancer regulation by microRNA. The relative repression of firefly luciferase expression (Fold Change) standardized to a renilla luciferase control. PLAG1, pleiomorphic adenoma gene 1; TGFBR2, transforming growth factor beta receptor II; Rb, retinoblastoma gene. pGL-3 (Promega) was used as the empty vector. miR-20a, miR-26a-1 and miR-106 oligoRNAs (sense and scrambled) were used for transfections. A second experiment using mutated versions of each target mRNA, which lack the 5' miRNA-end complementarity site (MUT), as controls is shown in the bottom panel. All the experiments were performed twice in triplicate (n=6).

In silico predictions for three different cancer genes, Retinoblastoma (Rb), TGF-beta-2 receptor (TGFBR2), and pleiomorphic adenoma gene 1 (PLAG1), were confirmed experimentally by in vitro assays. Using a luciferase reporter assay, three microRNAs tested (miR-106a, miR-20a and miR-26a-1) caused a significant reduction of protein translation relative to the scrambled control oligoRNAs in transfected MEG-01 cells (FIG. 6). Retinoblastoma 3'UTR, for example, was found to interact functionally with miR-106a. The biological significance of this miRNA:mRNA interaction is reinforced by previous reports showing that the Rb1 gene is normally transcribed in colon cancers, whilst various fractions of cells do not express Rb1 protein (Ali, A. A., et al., *FASEB J.* 7:931-937 (1993)). This finding suggests the existence of a post-transcriptional mechanism for regulating Rb1 that could be explained by concomitant miR-106a over-expression in colon carcinoma (FIG. 4). Furthermore, mir-20a is down-regulated in breast cancer (FIG. 4) and TFGBR2 protein is expressed in the epithelium of breast cancer cells (Buck, M. B., et al., *Clin. Cancer Res.* 10:491-498 (2004)). Conversely, the over-expression of mir-20a in colon cancer may represent a novel mechanism for down-regulating TGFBR2, in addition to mutational inactivation (Biswas, S., et al., *Cancer Res.* 64:687-692 (2004)).

Figure 5:
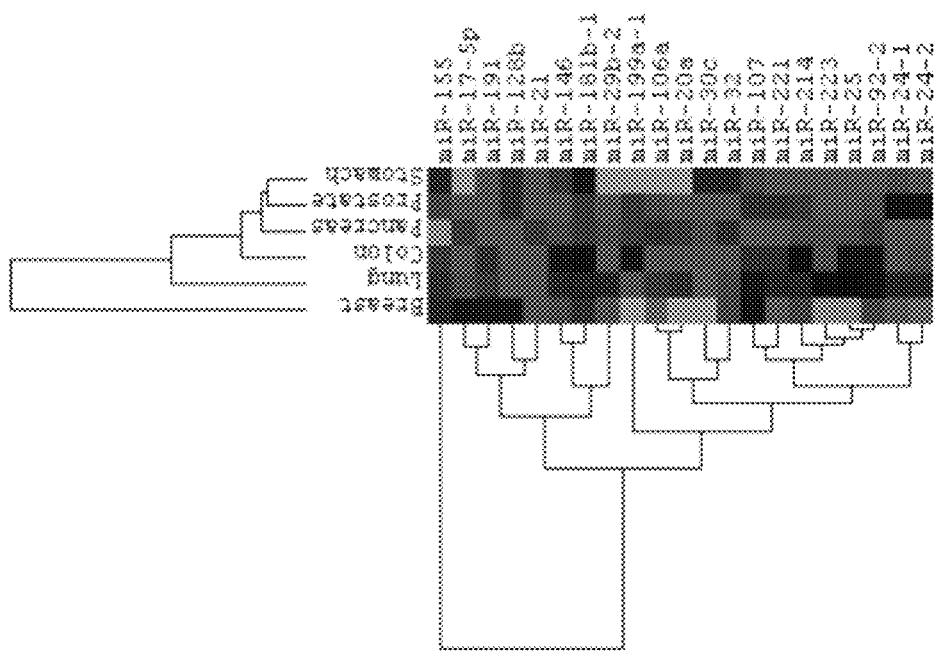
FIG. 5 depicts fold changes in the expression of miRNAs present in the signatures of at least 50% of the solid tumors in cancer vs. normal samples. The tree displays the $\log_2$ transformation of the average fold changes (cancer over normal). The mean was computed over all samples from the same tissue or tumor histotype. Arrays were mean centered and normalized using Gene Cluster 2.0. Average linkage clustering was performed using uncentered correlation metric.
Figure 6B:
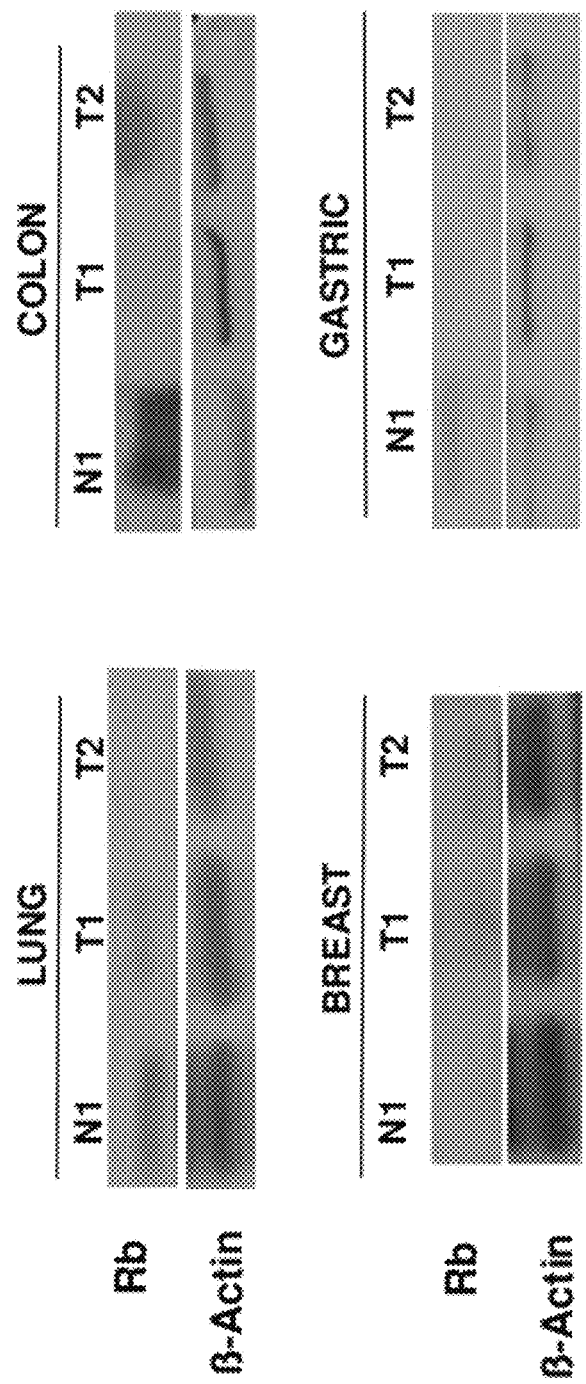
FIG. 6B depicts Western blots indicating that, in certain cancers (e.g., lung, breast, colon, gastric), the levels of RB1 (Rb) protein displays an inverse correlation with the level of miR-106a expression. β-Actin was used as a control for normalization. N1, normal sample; T1 and T2, tumor sample.
Figure 7:
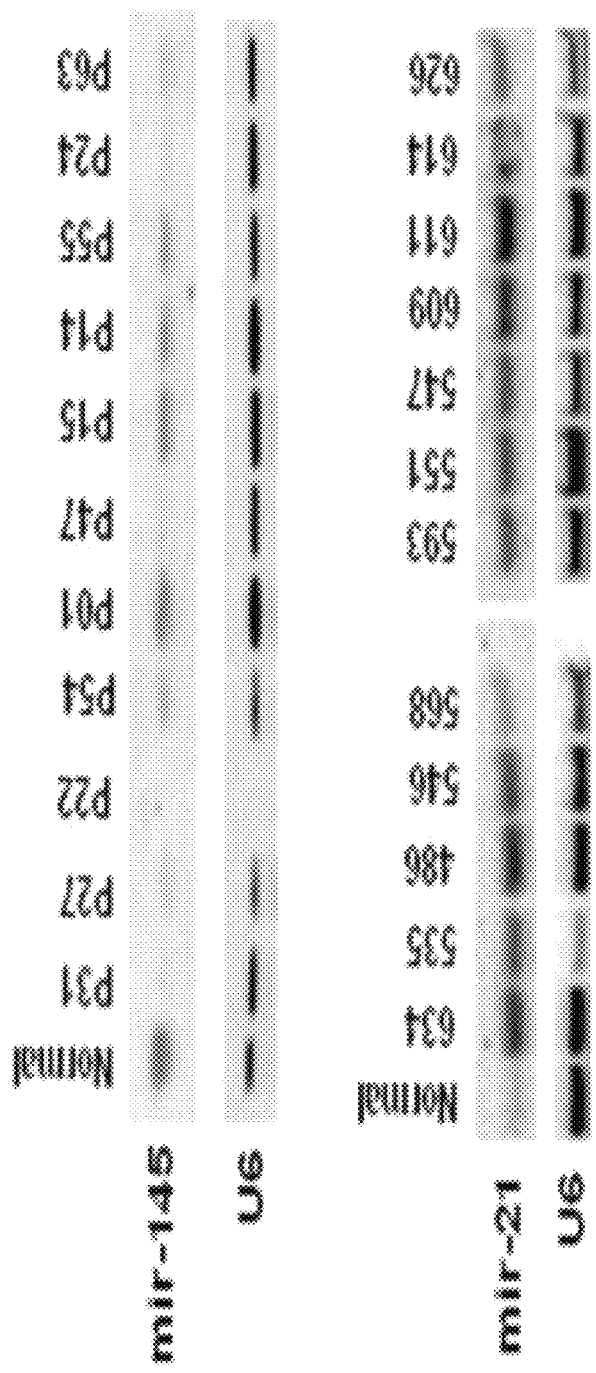
FIG. 7 depicts Northern blots showing down-regulation of miR-145 (top) and up-regulation of miR-21 (bottom) expression in breast cancer samples (P series and numbered series) relative to normal samples. Normalization was performed with a U6-specific probe.
Figure 8:
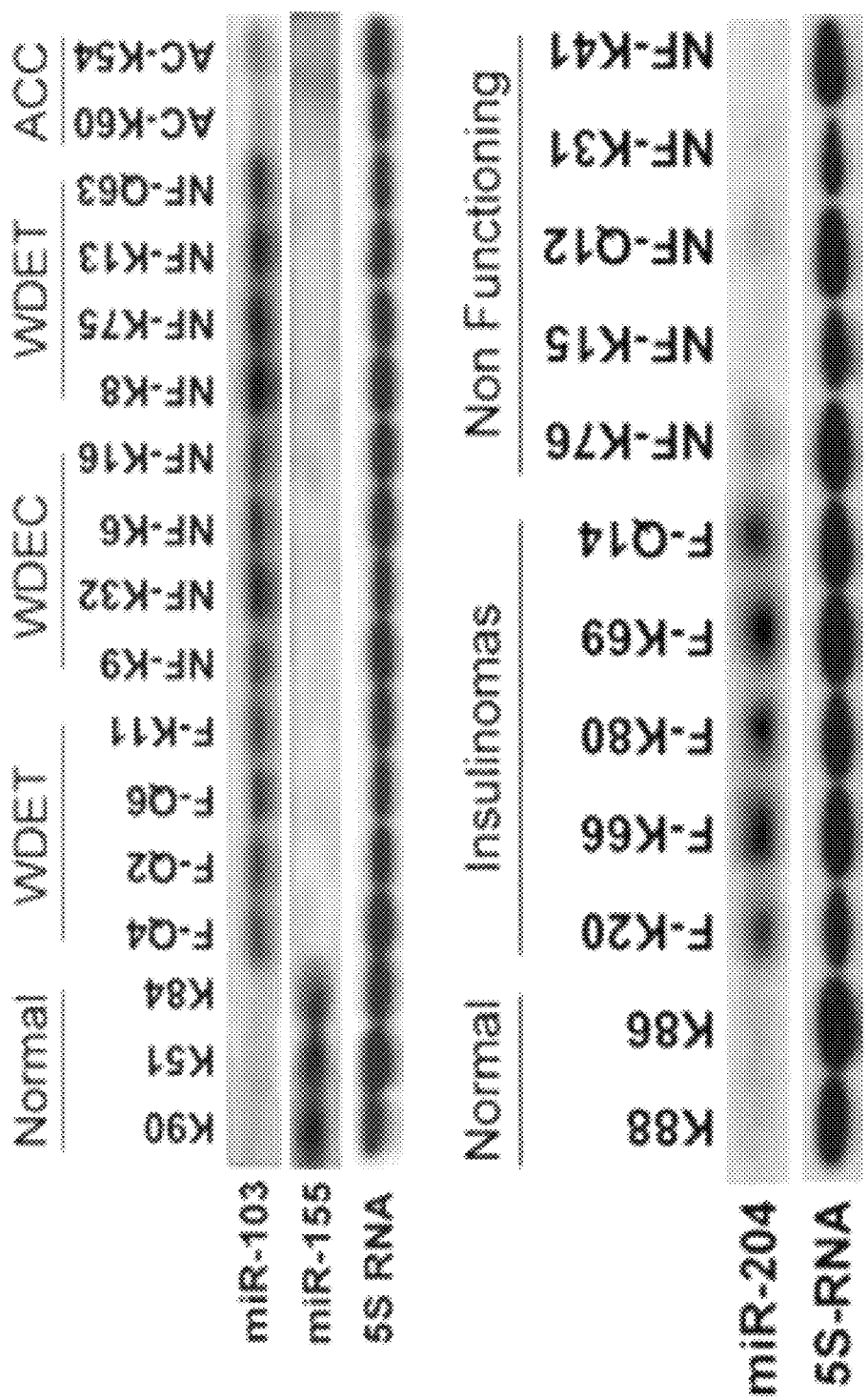
FIG. 8 depicts Northern blots showing up-regulation of miR-103 and down-regulation miR-155 (top) expression in different endocrine pancreatic cancer samples (WDET, well differentiated pancreatic endocrine tumors, WDEC, well differentiated pancreatic endocrine carcinomas and ACC, pancreatic acinar cell carcinomas) relative to normal samples (K series), as well as up-regulation of miR-204 (bottom) expression in insulinomas (F series) relative to normal samples (K series) and non secreting/non functioning (NF-series) samples. Normalization was performed with a probe specific to 5S RNA.

Finally, a set of patient samples was tested to verify whether RB1 protein expression correlates with miR-106a expression (FIG. 5 and FIG. 6B). As expected, in gastric, prostate and lung tumor samples RB1 was down-regulated (in respect to the paired normal) and miR-106a was found to be over-expressed, while in breast tumor samples, where miR-106a is slightly down-regulated (FIG. 5 and FIG. 6B), RB1 is expressed at slightly higher levels then in the paired normal control.

These experimental proofs reinforce the hypothesis that key cancer genes are regulated by aberrant expression of miRs in solid cancers. These data add novel examples to the list of microRNA with important cancer gene targets, as previously shown by Johnsson et al. (Johnson, S. M., et al., *Cell* 120: 635-647 (2005)) for the let-7:Ras interaction, O'Donnell et al. (O'Donnell, K. A., et al., *Nature* 435:839-843 (2005)) for the miR-17-5p:cMyc interaction, and Cimmino et al. (Cimmino, A., et al., *Proc. Natl. Acad. Sci. USA* 102:13944-13949 (2005)) for the mir-16:Bcl2 interaction. Notably, miR-17-5p and miR-16 are members of the miRNA solid cancer signature described herein.

TABLE 15

Oncogenes and tumor suppressor genes predicted by TargetScanS as targets or microRNAs from the comprehensive cancer subset.*

| miRNA gene | Gene Name | Gene description |
|---|---|---|
| miR-26a, miR-146 | ABL2 | v-abl Abelson murine leukemia viral oncogene homolog 2 (arg, Abelson-related gene) |
| miR-107 | AF5q31 | ALL1 fused gene from 5q31 |
| miR-20, miR-125b | AKT3 | v-akt murine thymoma viral oncogene homolog 3 |
| miR-26a, miR-155 miR-125b | APC | adenomatosis polyposis coli |
| miR-26a, miR-218 | ARHGEF12 | RHO guanine nucleotide exchange factor (GEF) 12 (LARG) |
| miR-107, miR-221 | ARNT | aryl hydrocarbon receptor nuclear translocator |
| miR-192 | ATF1 | activating transcription factor 1 |
| miR-26a | ATM | Ataxia telangiectasia mutated (includes complementation groups A, C and D) |
| miR-24 | AXL | AXL receptor tyrosine kinase |
| miR-26a, miR-107, miR-146, miR-155 miR-138, miR-92 | BCL11A | B-cell CLL/lymphoma 11A |
| miR-20 | BCL11B | B-cell CLL/lymphoma 11B (CTIP2) |
| miR-21 | BCL2 | B-cell CLL/lymphoma 2 |
| miR-26a, miR-26a miR-20, miR-92 | BCL6 | B-cell CLL/lymphoma 6 (zinc finger protein 51) |
| | BCL9 | B-cell CLL/lymphoma 9 |
| miR-26a, miR-223 miR-221, miR-125b | CBFB | core-binding factor, beta subunit |
| miR-218 | CCDC6 | coiled-coil domain containing 6 |

TABLE 15-continued

Oncogenes and tumor suppressor genes predicted by TargetScanS
as targets or microRNAs from the comprehensive cancer subset.*

| miRNA gene | Gene Name | Gene description |
|---|---|---|
| miR-20 | CCND1 | cyclin D1 (PRAD1: parathyroid adenomatosis 1) |
| miR-26a, miR-20 | CCND2 | cyclin D2 |
| miR-26a, miR-107, miR-92 | CDK6 | cyclin-dependent kinase 6 |
| miR-20 | CDKN1A | cyclin-dependent kinase inhibitor 1A (p21, Cip1) |
| miR-221, miR-92 | CDKN1C | cyclin-dependent kinase inhibitor 1C (p57, Kip2) |
| miR-24 | CDX2 | caudal type homeo box transcription factor 2 |
| miR-92 | CEBPA | CCAAT/enhancer binding protein (C/EBP), alpha |
| miR-26a | CLTC | clathrin, heavy polypeptide (Hc) |
| miR-218 | COL1A1 | collagen, type I, alpha 1 |
| miR-26a | CREBBP | CREB binding protein (CBP) |
| miR-20 | CRK | v-crk avian sarcoma virus CT10 oncogene homolog |
| miR-20 | CSF1 | colony stimulating factor 1 (macrophage) |
| miR-221, miR-192 | DDX6 | DEAD/H (Asp-Glu-Ala-Asp/His) box polypeptide 6 (RNA helicase, 54 kD) |
| miR-138 | DEK | DEK oncogene (DNA binding) |
| miR-20 | E2F1 | E2F transcription factor 1 |
| miR-20 | ELK3 | ELK3, ETS-domain protein (SRF accessory protein 2) |
| miR-24 | ELL | ELL gene (11-19 lysine-rich leukemia gene) |
| miR-26a, miR-138 | ERBB4 | v-erb-a avian erythroblastic leukemia viral oncogene homolog-like 4 |
| miR-221, miR-155, miR-125b | ETS1 | v-ets avian erythroblastosis virus E26 oncogene homolog 1 |
| miR-20 | ETV1 | ets variant gene 1 |
| miR-125b | ETV6 | ets variant gene 6 (TEL oncogene) |
| miR-223 | FAT | FAT tumor suppressor (*Drosophila*) homolog |
| miR-223, miR-125b, miR-218 | FGFR2 | fibroblast growth factor receptor 2 |
| miR-92 | FLI1 | Friend leukemia virus integration 1 |
| miR-24, miR-20 | FLT1 | fms-related tyrosine kinase 1 (vascular endothelial growth factor/vascular permeability factor receptor) |
| miR-221 | FOS | v-fos FBJ murine osteosarcoma viral oncogene homolog |
| miR-92 | FOXG1B | forkhead box G1B |
| miR-223 | FOXO3A | forkhead box O3A |
| miR-125b | GOLGA5 | golgi autoantigen, golgin subfamily a, 5 (PTC5) |
| miR-138 | GPHN | gephyrin (GPH) |
| miR-107, miR-223, miR-20, miR-218 | HLF | hepatic leukemia factor |
| miR-26a, miR-107 | HMGA1 | high mobility group AT-hook 1 |
| miR-20 | HOXA13 | homeo box A13 |
| miR-92 | HOXA9 | homeo box A9 |
| miR-125b | IRF4 | interferon regulatory factor 4 |
| miR-146, miR-20, miR-138 | JAZF1 | juxtaposed with another zinc finger gene 1 |
| miR-92 | JUN | v-jun avian sarcoma virus 17 oncogene homolog |
| miR-155 | KRAS | v-Ki-ras2 Kirsten rat sarcoma 2 viral oncogene homolog |
| miR-218 | LASP1 | LIM and SH3 protein 1 |
| miR-218 | LHFP | lipoma HMGIC fusion partner |
| miR-125b, miR-218 | LIFR | leukemia inhibitory factor receptor |
| miR-223 | LMO2 | LIM domain only 2 (rhombotin-like 1) (RBTN2) |
| miR-223, miR-155, miR-125b, miR-92 | MAF | v-maf musculoaponeurotic fibrosarcoma (avian) oncogene homolog |
| miR-92 | MAP2K4 | mitogen-activated protein kinase kinase 4 |
| miR-146, miR-20 | MAP3K8 | mitogen-activated protein kinase kinase kinase 8 |
| miR-125b | MAX | MAX protein |
| miR-218 | MCC | mutated in colorectal cancers |
| miR-24 | MEN1 | multiple endocrine neoplasia I |
| miR-138 | MLLT6 | myeloid/lymphoid or mixed-lineage leukemia (trithorax homolog, *Drosophila*); translocated to, 6 (AF17) |
| miR-192 | MSN | moesin |
| miR-24 | MYB | v-myb avian myeloblastosis viral oncogene homolog |
| miR-107, miR-223, miR-146, miR-221, miR-155, miR-218 | MYBL1 | v-myb avian myeloblastosis viral oncogene homolog-like 1 |

TABLE 15-continued

Oncogenes and tumor suppressor genes predicted by TargetScanS as targets or microRNAs from the comprehensive cancer subset.*

| miRNA gene | Gene Name | Gene description |
| --- | --- | --- |
| miR-107, miR-20 | MYCN | v-myc avian myelocytomatosis viral related oncogene, neuroblastoma derived |
| miR-107, miR-92 | MYH9 | myosin, heavy polypeptide 9, non-muscle |
| miR-24 | MYST4 | MYST histone acetyltransferase (monocytic leukemia) 4 (MORF) |
| miR-20 | NBL1 | neuroblastoma, suppression of tumorigenicity 1 |
| miR-125b | NIN | ninein (GSK3B interacting protein) |
| miR-26a, miR-107 | NKTR | natural killer-tumor recognition sequence |
| miR-92 | NOTCH1 | Notch homolog 1, translocation-associated (*Drosophila*) (TAN1) |
| miR-24 | NTRK3 | neurotrophic tyrosine kinase, receptor, type 3 |
| miR-125b | PCSK7 | proprotein convertase subtilisin/kexin type 7 |
| miR-24, miR-146 | PER1 | period homolog 1 (*Drosophila*) |
| miR-146, miR-125b, miR-138, | PHOX2B | paired-like homeobox 2b |
| miR-155 | PICALM | phosphatidylinositol binding clathrin assembly protein (CALM) |
| miR-24, miR-26a | PIM1 | pim-1 oncogene |
| miR-24, miR-26a, miR-21, miR-107, miR-20, miR-155 | PLAG1 | pleiomorphic adenoma gene 1 |
| miR-218 | RAB8A | RAB8A, member RAS oncogene family |
| miR-24, miR-221 | RALA | v-ral simian leukemia viral oncogene homolog A (ras related) |
| miR-138 | RARA | retinoic acid receptor, alpha |
| miR-20, miR-192 | RB1 | retinoblastoma 1 (including osteosarcoma) |
| miR-20, | RBL1 | retinoblastoma-like 1 (p107) |
| miR-20 | RBL2 | retinoblastoma-like 2 (p130) |
| miR-155, miR-138 | REL | v-rel avian reticuloendotheliosis viral oncogene homolog |
| miR-20, miR-138 | RHOC | ras homolog gene family, member C |
| miR-20, miR-192 | RUNX1 | runt-related transcription factor 1 (AML1) |
| miR-107, miR-223 | SEPT6 | septin 6 |
| miR-146, miR-20, miR-125b | SET | SET translocation |
| miR-21, miR-20, miR-155, miR-218 | SKI | v-ski avian sarcoma viral oncogene homolog |
| miR-26a, miR-146 | SMAD4 | SMAD, mothers against DPP homolog 4 (*Drosophila*) |
| miR-155 | SPI1 | spleen focus forming virus (SFFV) proviral integration oncogene spi1 |
| miR-125b | SS18 | synovial sarcoma translocation, chromosome 18 |
| miR-107, miR-155 | SUFU | suppressor of fused homolog (*Drosophila*) |
| miR-92 | TAF15 | TAF15 RNA polymerase II, TATA box binding protein (TBP)-associated factor, 68 kDa |
| miR-26a, miR-221, miR-138 | TCF12 | transcription factor 12 (HTF4, helix-loop-helix transcription factors 4) |
| miR-21, miR-20 | TGFBR2 | transforming growth factor, beta receptor II (70-80 kD) |
| miR-24, miR-26a, miR-92 | TOP1 | topoisomerase (DNA) I |
| miR-138 | TPM4 | tropomyosin 4 |
| miR-20 | TRIP11 | thyroid hormone receptor interactor 11 |
| miR-92 | TSC1 | Tuberous sclerosis 1 |
| miR-20 | TSG101 | Tumor susceptibility gene 101 |
| miR-20 | TUSC2 | Tumor suppressor candidate 2 |
| miR-24 | VAV1 | vav 1 oncogene |
| miR-125b | VAV2 | vav 2 oncogene |
| miR-107 | WHSC1 | Wolf-Hirschhorn syndrome candidate 1(MMSET) |
| miR-138 | WHSC1L1 | Wolf-Hirschhorn syndrome candidate 1-like 1 (NSD3) |
| miR-26a | WNT5A | wingless-type MMTV integration site family, member 5A |
| miR-26a, miR-20, miR-125b | YES1 | v-yes-1 Yamaguchi sarcoma viral oncogene homolog 1 |
| miR-107, miR-221 | ZNF198 | zinc finger protein 198 |
| miR-218 | ZNFN1A1 | zinc finger protein, subfamily 1A, 1 (Ikaros) |

*Known cancer genes (e.g., tumor suppressors, oncogenes) comprise those identified in the Cancer Gene Census or reported by OMIM.

The relevant teachings of all publications cited herein that have not explicitly been incorporated by reference, are incorporated herein by reference in their entirety. While this invention has been particularly shown and described with references to preferred embodiments thereof, it will be understood by those skilled in the art that various changes in form and details may be made therein without departing from the scope of the invention encompassed by the appended claims.

What is claimed is:

1. A method of diagnosing whether a subject has, or is at risk for developing, lung cancer, comprising:
   receiving a test sample of lung tissue extracted from a subject;
   measuring by Northern blot analysis the level of at least miR-205 gene product and at least one additional miR gene product in the test sample, wherein the Northern blot analysis comprises:
   extracting nucleic acids from the test sample;
   treating the extracted nucleic acids with DNase to remove DNA;
   separating RNA molecules in the extracted nucleic acids by gel electrophoresis;
   hybridizing the separated RNA molecules to labeled probes; and
   detecting and quantifying the hybridization to determine the level of at least miR-205 gene product and at least one additional miR gene product;
   comparing the level of at least miR-205 gene product and at least one additional miR gene product in the test sample to a control level of at least one corresponding miR-205 gene product and at least one additional miR gene product in normal lung tissue; and
   diagnosing whether the subject has, or is at risk for developing, lung cancer, if the level of the at least miR-205 gene product and at least one additional miR gene product in the test sample from the subject is greater than the control level of at least one miR-205 gene product and at least one corresponding additional miR gene product.

2. A method of claim 1, wherein the at least one additional miR gene product is miR-21.

3. A method of claim 1, wherein the at least one additional miR gene product is miR-200b.

4. A method of claim 1, wherein the at least one additional miR gene product is miR-9-1.

5. A method of claim 1, wherein the at least one additional miR gene product is miR-210.

6. A method of claim 1, wherein the at least one additional miR gene product is miR-148.

7. A method of claim 1, which further comprises: comparing the level of at least one additional miR gene product in a test sample from the subject to a control level of the miR gene product, wherein the at least one additional miR gene product is selected from the group consisting of: miR-21; miR-200b; miR-9-1; miR-210; miR-148; miR-141; miR-132; miR-215; miR-128b; let-7g; miR-16-2; miR-129-1/2 prec; miR-126; miR-142-as; miR-30d; miR-30a-5p; miR-7-2; miR-199a-1;

miR-127; miR-34a prec; miR-34a; miR-136; miR-202; miR-196-2; miR-199a-2; let-7a-2; miR-124a-1; miR-149; miR-17-5p; miR-196-1 prec; miR-10a; miR-99b prec; miR-196-1; miR-199b; miR-195; and miR-155.

8. A method of claim 1, which further comprises: comparing the level of at least one additional miR gene product in a test sample from the subject to a control level of the miR gene product, wherein the at least one additional miR gene product is selected from the group consisting of: miR-21; miR-17-5p; miR-29b-2; miR-223; miR-128b; miR-199a-1; miR-24-1; miR-24-2; miR-146; miR-155; miR-181b-1; miR-20a; miR-107; miR-32; miR-92-2; miR-214; miR-30c; miR-25; miR-221; and miR-106a.

\* \* \* \* \*

UNITED STATES PATENT AND TRADEMARK OFFICE
CERTIFICATE OF CORRECTION

PATENT NO. : 9,051,618 B2
APPLICATION NO. : 13/407894
DATED : June 9, 2015
INVENTOR(S) : Carlo M. Croce, George A. Calin and Stefano Volinia Page 1 of 1

It is certified that error appears in the above-identified patent and that said Letters Patent is hereby corrected as shown below:

In the Specification

Column 1, Lines 21-24 replace the Government Support Clause with:
--This invention was made with government support under grant numbers CA076259, CA081534, and CA056036 awarded by National Institutes of Health. The government has certain rights in the invention.--

Signed and Sealed this
Sixth Day of October, 2020

Andrei Iancu
*Director of the United States Patent and Trademark Office*